US009695172B2

(12) United States Patent
Bradner et al.

(10) Patent No.: US 9,695,172 B2
(45) Date of Patent: Jul. 4, 2017

(54) DIAZEPANE DERIVATIVES AND USES THEREOF

(71) Applicant: Dana-Farber Cancer Institute, Inc., Boston, MA (US)

(72) Inventors: James E. Bradner, Weston, MA (US); Nathanael S. Gray, Boston, MA (US); Jun Qi, Sharon, MA (US); Michael R. McKeown, Brookline, MA (US); Dennis Buckley, Boston, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 15/114,895

(22) PCT Filed: Feb. 2, 2015

(86) PCT No.: PCT/US2015/014109
§ 371 (c)(1),
(2) Date: Jul. 28, 2016

(87) PCT Pub. No.: WO2015/117083
PCT Pub. Date: Aug. 6, 2015

(65) Prior Publication Data
US 2016/0347749 A1   Dec. 1, 2016

Related U.S. Application Data

(60) Provisional application No. 61/934,668, filed on Jan. 31, 2014.

(51) Int. Cl.
C07D 471/04   (2006.01)
C07D 495/14   (2006.01)
C07D 487/04   (2006.01)

(52) U.S. Cl.
CPC ......... *C07D 471/04* (2013.01); *C07D 487/04* (2013.01); *C07D 495/14* (2013.01)

(58) Field of Classification Search
None
See application file for complete search history.

(56) References Cited

U.S. PATENT DOCUMENTS 5,712,274 A   1/1998   Sueoka et al.
5,721,231 A   2/1998   Moriwaki et al.
(Continued)

FOREIGN PATENT DOCUMENTS

EP   0 989 131 B1   11/2002
JP   2008-156311   7/2008
(Continued)

OTHER PUBLICATIONS

Database CAPLUS in STN, Acc. No. 2013:1979798, Deng et al., European Journal of Medicinal Chemistry (2013), 70, pp. 758-767 (abstract).*

International Search Report and Written Opinion for PCT/US2014/023386, mailed Jul. 9, 2014.
(Continued)

*Primary Examiner* — Brian J Davis
(74) *Attorney, Agent, or Firm* — Wolf, Greenfield & Sacks, P.C.

(57) ABSTRACT

The present invention provides compounds of any one of Formulae (I), (II-C) (e.g., Formula (II)), and (III), and pharmaceutically compositions thereof. Compounds of any one of Formulae (I), (II-C), and (III) are believed to be binders of bromodomains and/or bromodomain-containing proteins (e.g., bromo and extra terminal (BET) proteins). Also provided are methods, uses, and kits using the compounds and pharmaceutical compositions for inhibiting the activity (e.g., increased activity) of bromodomains and/or bromodomain-containing proteins and for treating and/or preventing in a subject diseases associated with bromodomains or bromodomain-containing proteins (e.g., proliferative diseases, cardiovascular diseases, viral infections, fibrotic diseases, metabolic diseases, endocrine diseases, and radiation poisoning). The compounds, pharmaceutical compositions, and kits are also useful for male contraception.

(Continued)

-continued

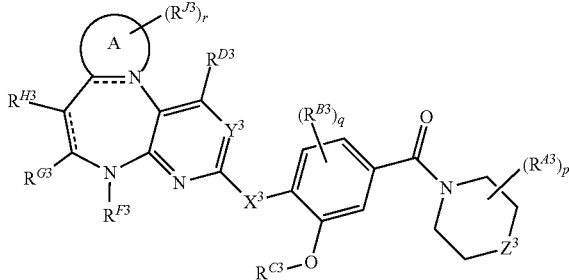
(III)

74 Claims, 1 Drawing Sheet

(56) References Cited

U.S. PATENT DOCUMENTS

| | | | |
|---|---|---|---|
| 5,846,972 | A | 12/1998 | Buckman et al. |
| 7,528,143 | B2 | 5/2009 | Noronha et al. |
| 7,750,152 | B2 | 7/2010 | Hoffman et al. |
| 7,786,299 | B2 | 8/2010 | Hoffmann et al. |
| 7,816,530 | B2 | 10/2010 | Grauert |
| 7,825,246 | B2 | 11/2010 | Noronha et al. |
| 8,003,786 | B2 | 8/2011 | Hoffmann et al. |
| 8,133,900 | B2 | 3/2012 | Hood et al. |
| 8,138,199 | B2 | 3/2012 | Noronha et al. |
| 8,604,042 | B2 | 12/2013 | Noronha et al. |
| 2002/0032200 | A1 | 3/2002 | Cai et al. |
| 2003/0216758 | A1 | 11/2003 | Signore |
| 2004/0176380 | A1 | 9/2004 | Hoffmann et al. |
| 2006/0074088 | A1 | 4/2006 | Munzert et al. |
| 2007/0105839 | A1 | 5/2007 | Imbach et al. |
| 2007/0179178 | A1 | 8/2007 | Buettelmann et al. |
| 2009/0238828 | A1 | 9/2009 | Munzert et al. |
| 2009/0280115 | A1 | 11/2009 | Maier et al. |
| 2009/0281191 | A1 | 11/2009 | Rangwala et al. |
| 2010/0041643 | A1 | 2/2010 | Adachi et al. |
| 2010/0249412 | A1 | 9/2010 | Linz et al. |
| 2010/0286127 | A1 | 11/2010 | Miyoshi et al. |
| 2011/0028405 | A1 | 2/2011 | Harrison et al. |
| 2011/0098288 | A1 | 4/2011 | Major et al. |
| 2011/0172231 | A1 | 7/2011 | Baenteli et al. |
| 2011/0201606 | A1 | 8/2011 | Garcia-Cheverria et al. |
| 2011/0212077 | A1 | 9/2011 | Noronha et al. |
| 2011/0245245 | A1 | 10/2011 | Mortensen et al. |
| 2012/0040961 | A1 | 2/2012 | Gray et al. |
| 2012/0329803 | A1 | 12/2012 | Linz et al. |
| 2013/0245013 | A1 | 9/2013 | Mohr et al. |
| 2013/0274239 | A1 | 10/2013 | Gangloff et al. |
| 2016/0033519 | A1 | 2/2016 | Bradner et al. |
| 2016/0332993 | A1 | 11/2016 | Bradner et al. |

FOREIGN PATENT DOCUMENTS

| | | |
|---|---|---|
| WO | WO 2007/095188 A2 | 8/2007 |
| WO | WO 2009/084693 A1 | 7/2009 |
| WO | WO 2011/054553 A1 | 5/2011 |
| WO | WO 2011/054841 A1 | 5/2011 |
| WO | WO 2011/054843 A1 | 5/2011 |
| WO | WO 2011/054844 A1 | 5/2011 |
| WO | WO 2011/054845 A1 | 5/2011 |
| WO | WO 2011/054846 A1 | 5/2011 |
| WO | WO 2011/054848 A1 | 5/2011 |
| WO | WO 2011/143669 A2 | 11/2011 |
| WO | WO 2011/161031 A1 | 12/2011 |
| WO | WO 2012/075383 A2 | 6/2012 |
| WO | WO 2012/116170 A1 | 8/2012 |
| WO | WO 2013/097601 A1 | 7/2013 |
| WO | WO 2014/071247 A1 | 5/2014 |

OTHER PUBLICATIONS

International Preliminary Report on Patentability for PCT/US2014/023386, mailed Sep. 24, 2015.
Invitation to Pay Additional Fees for PCT/US2014/48230, mailed Nov. 17, 2014.
International Search Report and Written Opinion for PCT/US2014/48230, mailed Jan. 30, 2015.
International Preliminary Report on Patentability for PCT/US2014/48230, mailed Feb. 4, 2016.
Invitation to Pay Additional Fees for PCT/US2015/14109, mailed Apr. 20, 2015.
International Search Report and Written Opinion for PCT/US2015/14109, mailed Jul. 6, 2015.
International Preliminary Report on Patentability for PCT/US2015/14109, mailed Aug. 11, 2016.
International Search Report and Written Opinion for PCT/US2015/14044, mailed Apr. 23, 2015.
International Preliminary Report on Patentability for PCT/US2015/14044, mailed Aug. 11, 2016.
International Search Report and Written Opinion for PCT/US2015/14039, mailed Apr. 23, 2015.
International Preliminary Report on Patentability for PCT/US2015/14039, mailed Aug. 11, 2016.
International Search Report and Written Opinion for PCT/US2015/14120, mailed Apr. 23, 2015.
International Preliminary Report on Patentability for PCT/US2015/14120, mailed Aug. 11, 2016.
International Search Report and Written Opinion for PCT/US2015/044180, mailed Nov. 5, 2015.
Invitation to Pay Additional Fees for PCT/US2015/44303, mailed Oct. 21, 2015.
International Search Report and Written Opinion for PCT/US2015/44303, mailed Dec. 31, 2015.
Invitation to Pay Additional Fees for PCT/US2016/051017, mailed Oct. 31, 2016.
International Search Report and Written Opinion for PCT/US2016051107, mailed Nov. 22, 2016.
[No Author Listed], PubChem SID 225027960. Available date/deposit date: Feb. 2, 2015. pubchem.ncbi.nlm.nih.gov/substance/225027960. Last accessed Nov. 28, 2016.
[No Author Listed], PubChem CID 5325760. Published Jan. 25, 2006 pubchem.ncbi.nlm.nih/gov//compound/5325760?from=summary#section=Top. Last accessed Oct. 20, 2014.
[No Author Listed], PubChem SID 235048169. Feb. 13, 2015. Retrieved on Oct. 24, 2016. Available at https://pubchem.ncbi.nlm.nih.gov/substance/235048169.
[No Author Listed], PubChem SID 235671906. Feb. 13, 2015. Retrieved on Oct. 24, 2016. Available at https://pubchem.ncbi.nlm.nih.gov/substance/235671906#section=Top>.
Anders et al., Genome-wide localization of small molecules. Nat Biotechnol. Jan. 2014;32(1):92-6. doi: 10.1038/nbt.2776. Epub Dec. 15, 2013.
Bartholomeeusen et al., Bromodomain and extra-terminal (BET) bromodomain inhibition activate transcription via transient release of positive transcription elongation factor b (P-TEFb) from 7SK small nuclear ribonucleoprotein. J Biol Chem. Oct. 19, 2012;287(43):36609-16. doi: 10.1074/jbc.M112.410746. Epub Sep. 5, 2012.
Baud et al., Chemical biology. A bump-and-hole approach to engineer controlled selectivity of BET bromodomain chemical probes. Science. Oct. 31, 2014;346(6209):638-41. doi: 10.1126/science.1249830. Epub Oct. 16, 2014.
Berge et al., Pharmaceutical salts. J Pharm Sci. Jan. 1977;66(1):1-19.

(56) References Cited

OTHER PUBLICATIONS

CAPLUS Database Result for Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013. Accession No. 2013:1979798. Abstract Only.

Chaidos et al., Potent antimyeloma activity of the novel bromodomain inhibitors I-BET151 and I-BET762. Blood. Jan. 30, 2014;123(5):697-705. doi: 10.1182/blood-2013-01-478420. Epub Dec. 13, 2013.

Dawson et al., Inhibition of BET recruitment to chromatin as an effective treatment for MLL-fusion leukaemia. Nature. Oct. 2, 2011;478(7370):529-33. doi: 10.1038/nature10509.

Delmore et al., BET bromodomain inhibition as a therapeutic strategy to target c-Myc. Cell Sep. 16, 2011;146(6):904-17. doi: 10.1016/j.cell.2011.08.017. Epub Sep. 1, 2011.

Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013.

Filippakopoulos et al., Targeting bromodomains: epigenetic readers of lysine acetylation Nat Rev Drug Discov. May 2014;13(5):337-56. doi: 10.1038/nrd4286. Epub Apr. 22, 2014.

French et al., BRD4-NUT fusion oncogene: a novel mechanism in aggressive carcinoma. Cancer Res. Jan. 15, 2003;63(2):304-7.

French et al., BRD-NUT oncoproteins: a family of closely related nuclear proteins that block epithelial differentiation and maintain the growth of carcinoma cells. Oncogene. Apr. 3, 2008;27(15):2237-42. Epub Oct. 15, 2007.

Krueger et al., The mechanism of release of P-TEFb and HEXIM1 from the 7SK snRNP by viral and cellular activators includes a conformational change in 7SK. PLoS One. Aug. 23, 2010;5(8):e12335. doi: 10.1371/journal.pone.0012335.

McKeown et al., Biased multicomponent reactions to develop novel bromodomain inhibitors. J Med Chem. Nov. 13, 2014;57(21):9019-27. doi: 10.1021/jm501120z. Epub Oct. 31, 2014.

Roberts et al., A Bead-Based Proximity Assay for BRD4 Ligand Discovery. Curr Protoc Chem Biol. Dec. 2, 2015;7(4):263-78. doi: 10.1002/9780470559277.ch150024.

Schroder et al., Two-pronged binding with bromodomain-containing protein 4 liberates positive transcription elongation factor b from inactive ribonucleoprotein complexes. J Biol Chem. Jan. 6, 2012;287(2):1090-9. doi: 10.1074/jbc.M111.282855. Epub Nov. 14, 2011.

Smith et al., The Bromodomain: A New Target in Emerging Epigenetic Medicine. ACS Chem Biol. Mar. 18, 2016;11(3):598-608. doi: 10.1021/acschembio.5b00831. Epub Dec. 3, 2015.

Tanaka et al., Inhibitors of emerging epigenetic targets for cancer therapy: a patent review (2010-2014). Pharm Pat Anal. 2015;4(4):261-84. doi: 10.4155/ppa.15.16.

Yang et al., Recruitment of P-TEFb for stimulation of transcriptional elongation by the bromodomain protein Brd4. Mol Cell. Aug. 19, 2005;19(4):535-45.

Zeng et al., Bromodomain: an acetyl-lysine binding domain. FEBS Lett. Feb. 20, 2002;513(1):124-8.

Zuber et al., RNAi screen identifies Brd4 as a therapeutic target in acute myeloid leukaemia. Nature. Aug. 3, 2011;478(7370):524-8. doi: 10.1038/nature10334.

Zuercher et al., Identification and structure-activity relationship of phenolic acyl hydrazones as selective agonists for the estrogen-related orphan nuclear receptors ERRbeta and ERRgamma.. J Med Chem. May 5, 2005;48(9):3107-9.

U.S. Appl. No. 14/774,958, filed Sep. 11, 2015, Bradner et al.
U.S. Appl. No. 14/907,339, filed Jan. 25, 2016, Bradner et al.
U.S. Appl. No. 15/114,989, filed Jul. 28, 2016, Bradner et al.
U.S. Appl. No. 15/115,038, filed Jul. 28, 2016, Bradner et al.
U.S. Appl. No. 15/115,085, filed Jul. 28, 2016, Bradner et al.
PCT/US2014/023386, Jul. 9, 2014, International Search Report and Written Opinion.
PCT/US2014/023386, Sep. 24, 2015, International Preliminary Report on Patentability.
PCT/US2014/048230, Nov. 17, 2014, Invitation to Pay Additional Fees.
PCT/US2014/048230, Jan. 30, 2015, International Search Report and Written Opinion.
PCT/US2014/048230, Feb. 4, 2016, International Preliminary Report on Patentability.
PCT/US2015/014109, Apr. 20, 2015, Invitation to Pay Additional Fees.
PCT/US2015/014109, Jul. 6, 2015, International Search Report and Written Opinion.
PCT/US2015/014109, Aug. 11, 2016, International Preliminary Report on Patentability.
PCT/US2015/014044, Apr. 23, 2015, International Search Report and Written Opinion.
PCT/US2015/014044, Aug. 11, 2016, International Preliminary Report on Patentability.
PCT/US2015/014039, Apr. 23, 2015, International Search Report and Written Opinion.
PCT/US2015/014039, Aug. 11, 2016, International Preliminary Report on Patentability.
PCT/US2015/014120, Apr. 23, 2015, International Search Report and Written Opinion.
PCT/US2015/014120, Aug. 11, 2016, International Preliminary Report on Patentability.
PCT/US2015/044180, Nov. 5, 2015, International Search Report and Written Opinion.
PCT/US2015/044303, Oct. 21, 2015, Invitation to Pay Additional Fees.
PCT/US2015/044303, Dec. 31, 2015, International Search Report and Written Opinion.
PCT/US2016/051017, Oct. 31, 2016, Invitation to Pay Additional Fees.
PCT/US2016/051107, Nov. 22, 2016, International Search Report and Written Opinion.

\* cited by examiner

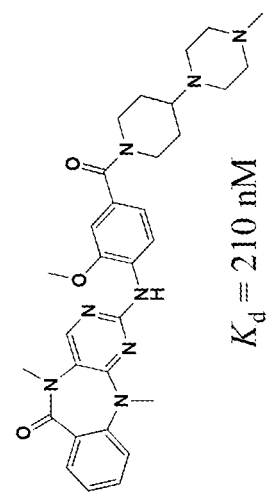
$K_d = 210$ nM
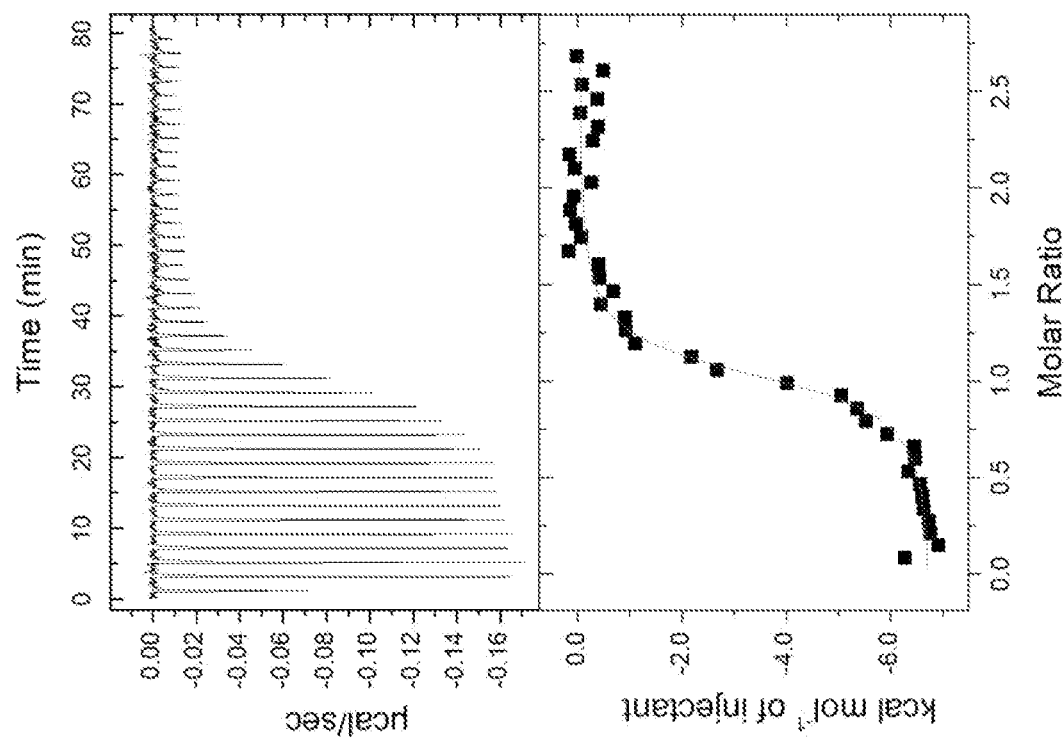

DIAZEPANE DERIVATIVES AND USES THEREOF

RELATED APPLICATIONS

The present application is a national stage filing under 35 U.S.C. §371 of international PCT application, PCT/US2015/014109, filed Feb. 2, 2015, which claims priority under 35 U.S.C. §119(e) to U.S. provisional patent application, U.S. Ser. No. 61/934,668, filed Jan. 31, 2014, each of which is incorporated herein by reference.

BACKGROUND OF THE INVENTION

Bromodomain-containing proteins are of substantial biological interest, as components of transcription factor complexes and determinants of epigenetic memory. For example, the bromo and extra terminal (BET) protein family (e.g., bromodomain-containing protein 2 (BRD2), bromodomain-containing protein 3 (BRD3), bromodomain-containing protein 4 (BRD4), and bromodomain testis-specific protein (BRDT)) shares a common domain architecture featuring two amino-terminal bromodomains that exhibit high levels of sequence conservation, and a more divergent carboxy-terminal recruitment domain (Filippakopoulos et al., Nature 2010, 468, 1067-1073). BRD2 and BRD3 are reported to associate with histones along actively transcribed genes and may be involved in facilitating transcriptional elongation (Leroy et al., Mol. Cell. 2008, 30, 51-60). It has also been reported that BRD4 or BRD3 may fuse with nuclear protein in testis (NUT), forming novel fusion oncogenes BRD4-NUT or BRD3-NUT, in a highly malignant form of epithelial neoplasia (French et al., Cancer Res., 2003, 63, 304-307; French et al., J. Clin. Oncol. 2004, 22, 4135-4139). Data suggests that BRD-NUT fusion proteins contribute to carcinogenesis (French et al., Oncogene 2008, 27, 2237-2242). BRDT is uniquely expressed in the testes and ovary. All family members of BET have been reported to have some function in controlling or executing aspects of the cell cycle and have been shown to remain in complex with chromosomes during cell division, suggesting a role in the maintenance of epigenetic memory. In addition, some viruses make use of BET proteins to tether their genomes to the host cell chromatin, as part of the process of viral replication (You et al., Cell 2004, 117, 349-360). BRD4 appears to be involved in the recruitment of the pTEF-b complex to inducible genes, resulting in phosphorylation of RNA polymerase and increased transcriptional output (Hargreaves et al., Cell 2009, 138, 129-145). In humans, BRD2, BRD3, BRD4, and BRDT exhibit similar gene arrangements, domain organizations, and some functional properties (Wu et al., J. Biol. Chem. 2007, 282, 13141-13145).

SUMMARY OF THE INVENTION

The present invention provides compounds of any one of Formulae (I), (II-C) (e.g., Formula (II)), and (III). The compounds described herein are thought to be binders of transcription factors, such as bromodomain-containing proteins (e.g., BET proteins) and may be useful in male contraception and in treating and/or preventing a wide range of diseases (e.g., diseases associated with bromodomains, diseases associated with the activity (e.g., aberrant activity) of bromodomains, diseases associated with bromodomain-containing proteins, and disease associated with the activity (e.g., aberrant activity) of bromodomain-containing proteins). Diseases that may be treated and/or prevented by the methods of the invention include, but are not limited to, proliferative diseases (e.g., cancers, benign neoplasms, angiogenesis, inflammatory diseases, and autoimmune diseases), cardiovascular diseases, viral infections, fibrotic diseases, metabolic diseases, endocrine diseases, and radiation poisoning. Also provided in the present invention are pharmaceutical compositions, kits, methods, and uses including or using a compound described herein.

In one aspect, the present invention provides compounds of Formula (I):

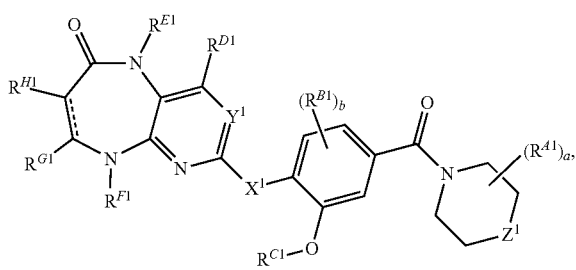

(I)

and pharmaceutically acceptable salts, solvates, hydrates, polymorphs, co-crystals, tautomers, stereoisomers, isotopically labeled derivatives, and prodrugs thereof, wherein ===, $Z^1$, $X^1$, $Y^1$, $R^{A1}$, $R^{B1}$, $R^{C1}$, $R^{D1}$, $R^{E1}$, $R^{F1}$, $R^{G1}$, $R^{H1}$, a, and b are as described herein.

Exemplary compounds of Formula (I) include, but are not limited to:

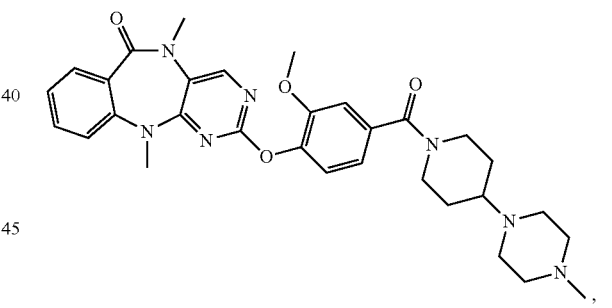

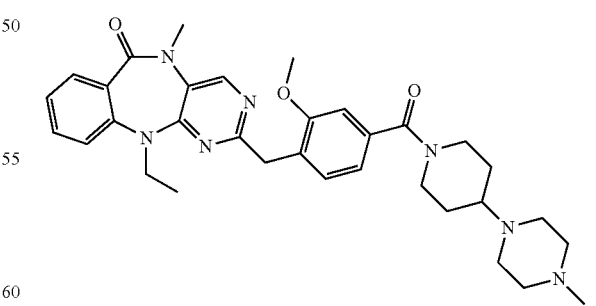

and pharmaceutically acceptable salts, solvates, hydrates, polymorphs, co-crystals, tautomers, stereoisomers, isotopically labeled derivatives, and prodrugs thereof.

In another aspect, the present invention provides compounds of Formula (II-C):

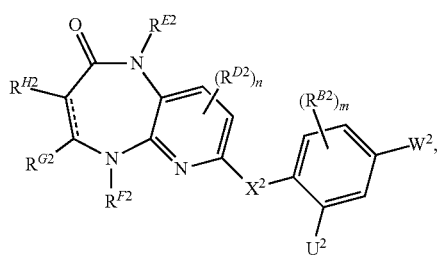
(II-C)

and pharmaceutically acceptable salts, solvates, hydrates, polymorphs, co-crystals, tautomers, stereoisomers, isotopically labeled derivatives, and prodrugs thereof, wherein ===, $W^2$, $U^2$, $X^2$, $R^{B2}$, $R^{D2}$, $R^{E2}$, $R^{F2}$, $R^{G2}$, $R^{H2}$, m, and n are as described herein.

In certain embodiments, a compound of Formula (II-C) is of Formula (II):

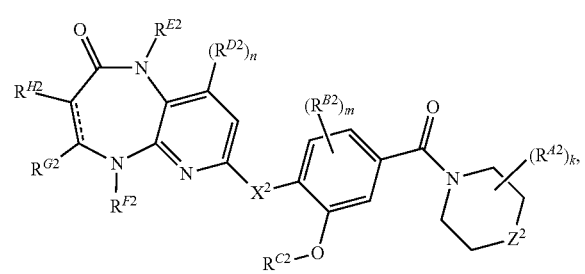
(II)

or a pharmaceutically acceptable salt, solvate, hydrate, polymorph, co-crystal, tautomer, stereoisomer, isotopically labeled derivative, or prodrug thereof, wherein $Z^2$, $R^{A2}$, $R^{C2}$, and k are as described herein.

Exemplary compounds of Formula (II-C) include, but are not limited to:

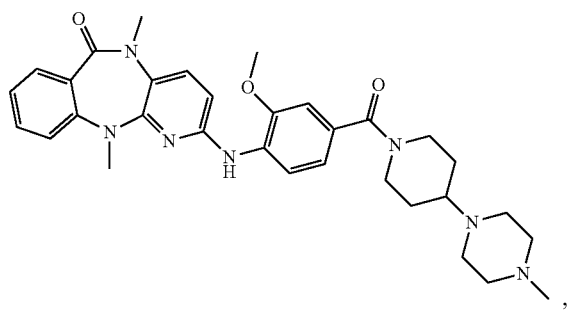
3 and pharmaceutically acceptable salts, solvates, hydrates, polymorphs, co-crystals, tautomers, stereoisomers, isotopically labeled derivatives, and prodrugs thereof.

Further exemplary compounds of Formula (II-C) include, but are not limited to:

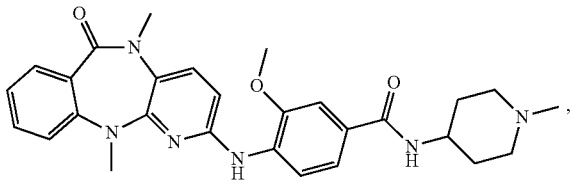
(2-227)

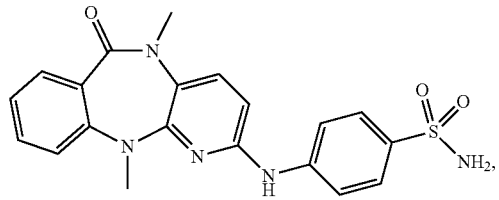
(2-221)

and pharmaceutically acceptable salts, solvates, hydrates, polymorphs, co-crystals, tautomers, stereoisomers, isotopically labeled derivatives, and prodrugs thereof.

In another aspect, the present invention provides compounds of Formula (III):

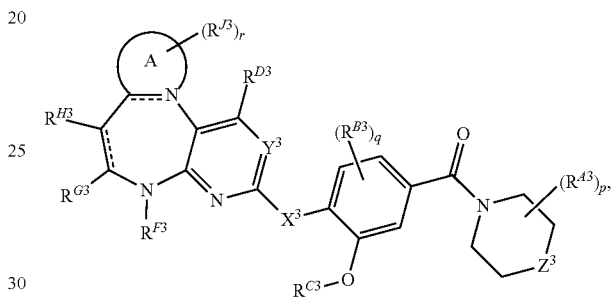
(III)

and pharmaceutically acceptable salts, solvates, hydrates, polymorphs, co-crystals, tautomers, stereoisomers, isotopically labeled derivatives, and prodrugs thereof, wherein ===, Ring A, $Z^3$, $X^3$, $Y^3$, $R^{A3}$, $R^{B3}$, $R^{C3}$, $R^{D3}$, $R^{F3}$, $R^{G3}$, $R^{H3}$, $R^{J3}$, p, q, and r are as described herein.

Exemplary compounds of Formula (III) include, but are not limited to:

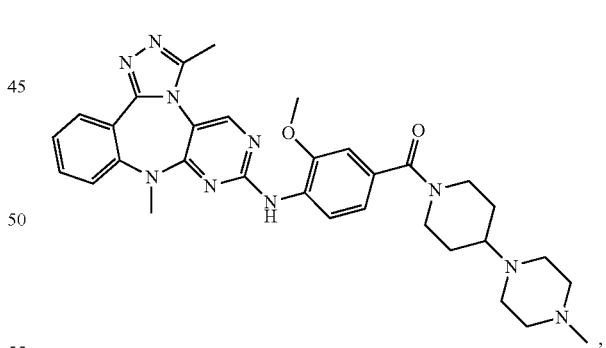
4 and pharmaceutically acceptable salts, solvates, hydrates, polymorphs, co-crystals, tautomers, stereoisomers, isotopically labeled derivatives, and prodrugs thereof.

The compounds described herein are thought to be able to bind bromodomain-containing proteins. In certain embodiments, the compounds described herein bind to a bromodomain (e.g., a bromodomain of a bromodomain-containing protein). The compounds described herein may inhibit the activity of the bromodomain-containing proteins. The compounds described herein may also inhibit the function of a bromodomain.

In still another aspect, the present invention provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating and/or preventing a disease in a subject in need thereof. The pharmaceutical composition may also be useful in inhibiting the replication of a virus, in killing a virus, in inhibiting the activity of a bromodomain-containing protein, in inhibiting the activity of a bromodomain, in inhibiting the binding of a bromodomain of a bromodomain-containing protein to an acetylated lysine residue of a histone or other protein, in modulating (e.g., inhibiting) transcriptional elongation, in modulating (e.g., reducing) the level of a bromodomain-containing protein, and/or in modulating (e.g., down-regulating or inhibiting) the expression (e.g., transcription) of a gene that is regulated by a bromodomain-containing protein in a subject or cell.

In certain embodiments, the disease described herein is a disease associated with the activity (e.g., aberrant activity (e.g., increased activity)) of a bromodomain-containing protein. In certain embodiments, the disease is a disease associated with the function of a bromodomain-containing protein. In certain embodiments, the disease is a disease associated with the activity (e.g., aberrant activity (e.g., increased activity)) of a bromodomain. In certain embodiments, the disease is a disease associated with the function of a bromodomain.

In certain embodiments, the disease is a proliferative disease (e.g., cancer, benign neoplasm, angiogenesis, an inflammatory disease, or an autoimmune disease), cardiovascular disease, viral infection, fibrotic disease, metabolic disease, endocrine disease, or radiation poisoning.

In certain embodiments, the subject is a human. In certain embodiments, the subject is a non-human animal. In certain embodiments, the cell is present in vitro. In certain embodiments, the cell is present in vivo.

Another aspect of the present invention relates to methods of treating a disease in a subject in need thereof.

In another aspect, the present invention provides methods of preventing a disease in a subject in need thereof.

Another aspect of the present invention relates to methods of reducing the risk of developing a disease in a subject in need thereof.

Another aspect of the present invention relates to methods of inhibiting the replication of a virus (e.g., human immunodeficiency virus (HIV), human papillomavirus (HPV), hepatitis C virus (HCV), herpes simplex virus (HSV), Ebola virus, and influenza virus).

Another aspect of the present invention relates to methods of killing a virus (e.g., human immunodeficiency virus (HIV), human papillomavirus (HPV), hepatitis C virus (HCV), herpes simplex virus (HSV), Ebola virus, and influenza virus).

In another aspect, the present invention provides methods of inhibiting the activity of a bromodomain-containing protein in a subject or cell. In certain embodiments, the activity of a bromodomain-containing protein is aberrant or unwanted activity (e.g., an increased activity) of the bromodomain-containing protein. In certain embodiments, the activity of the bromodomain-containing protein is selectively inhibited (e.g., when compared to the activity of a kinase that is different from the bromodomain-containing protein) by the methods.

In yet another aspect, the present invention provides methods of inhibiting the activity of a bromodomain in a subject or cell. In certain embodiments, the activity of a bromodomain being inhibited is aberrant or unwanted activity (e.g., an increased activity) of the bromodomain.

In yet another aspect, the present invention provides methods of inhibiting the binding of a bromodomain to an acetylated lysine residue of a second protein (e.g., histone (e.g., a histone described herein)) in a subject or cell. In certain embodiments, the second protein is a protein that includes at least one acetylated lysine residue.

In still another aspect, the present invention provides methods of modulating the expression (e.g., transcription) of a gene that is regulated by a bromodomain-containing protein in a subject or cell. In certain embodiments, the methods of modulating the expression (e.g., transcription) of a gene are methods of down-regulating or inhibiting the expression (e.g., transcription) of the gene. The method may result in decreased levels of a gene product (e.g., RNA, protein) in a cell.

In still another aspect, the present invention provides methods of modulating (e.g., inhibiting) transcriptional elongation in a subject or cell.

In still another aspect, the present invention provides methods of modulating (e.g., reducing) the level of a bromodomain-containing protein in a subject or cell.

The methods of the present invention include administering to the subject, contacting a cell with, or contacting a virus with an effective amount of a compound or pharmaceutical composition described herein. In certain embodiments, the effective amount is a therapeutically effective amount. In certain embodiments, the effective amount is a prophylactically effective amount. In certain embodiments, the methods of the present invention further include administering to the subject, contacting a cell with, or contacting a virus with an additional pharmaceutical agent in combination with a compound or pharmaceutical composition described herein. In certain embodiments, the combination of the pharmaceutical agent and the compound or pharmaceutical composition described herein is synergistic.

Another aspect of the invention relates to methods of screening a library of compounds to identify a compound that is useful in a method of the invention.

Another aspect of the present invention relates to kits comprising a container with a compound or pharmaceutical composition described herein. The kits described herein may include a single dose or multiple doses of the compound or pharmaceutical composition described herein. The provided kits may be useful in a method of the invention. In certain embodiments, the kit further includes instructions for using the kit.

In yet another aspect, the present invention provides compounds and pharmaceutical compositions described herein for use in a method of the invention.

In yet another aspect, the present invention provides uses of the compounds and pharmaceutical compositions described herein in a method of the invention.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents (e.g., halogen, such as F). In certain embodiments, the alkyl group is unsubstituted $C_{1-10}$ alkyl (e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is substituted $C_{1-10}$ alkyl (such as substituted $C_{1-6}$ alkyl, e.g., —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocylylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R, —OP(=O)$_2$R$^{aa}$, —P(=O) (R$^{aa}$)$_2$, —OP(=O)(R$^{aa}$)$_2$, —OP(=O)(OR$^{cc}$)$_2$, —P(=O)$_2$N (R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C (=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_3$-$C_{10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X, —N(OR$^{ee}$)R$^{ff}$, —SH, —SR$^{ee}$, —SSR$^{ee}$, —C(=O)R$^{ee}$, —C, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_1$-perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_6$10 aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$alkyl)$_2^+$X$^-$, —NH$_2$(C$_{1-6}$ alkyl)$^+$X$^-$, —NH$_3^+$X, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OC$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), BF$_4^-$, PF$_4^-$, PF$_6^-$, AsF$_6^-$, SbF$_6^-$, B[3,5-(CF$_3$)$_2$C$_6$H$_3$]$_4^-$, BPh$_4^-$, Al(OC(CF$_3$)$_3$)$_4^-$, carborane anions (e.g., CB$_{11}$H$_{12}^-$ or (HCB$_{11}$Me$_5$Br$_6$)$^-$), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group described herein is Bn, Boc, Cbz, Fmoc, trifluoroacetyl, triphenylmethyl, acetyl, or Ts.

Exemplary oxygen atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=$NR^{bb}$)R, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group described herein is silyl, TBDPS, TBDMS, TIPS, TES, TMS, MOM, THP, t-Bu, Bn, allyl, acetyl, pivaloyl, or benzoyl.

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=$NR^{bb}$)R, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. In certain embodiments, a sulfur protecting group described herein is acetamidomethyl, t-Bu, 3-nitro-2-pyridine sulfenyl, 2-pyridine-sulfenyl, or triphenylmethyl.

The invention is not intended to be limited in any manner by the above exemplary listing of substituents.

Other Definitions

The following definitions are more general terms used throughout the present application.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

A "protein," "peptide," or "polypeptide" comprises a polymer of amino acid residues linked together by peptide bonds and refers to proteins, polypeptides, and peptides of any size, structure, or function. Typically, a protein will be at least three amino acids long. A protein may refer to an individual protein or a collection of proteins. Proteins described herein preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The term "histone" refers to highly alkaline proteins found in eukaryotic cell nuclei that package and order the DNA into structural units called nucleosomes. They are the chief protein components of chromatin, acting as spools around which DNA winds, and play a role in gene regulation. In certain embodiments, the histone is histone H1 (e.g., histone H1F, histone H1H1). In certain embodiments, the histone is histone H2A (e.g., histone H2AF, histone H2A1, histone H2A2). In certain embodiments, the histone is histone H2B (e.g., histone H2BF, histone H2B1, histone H2B2). In certain embodiments, the histone is histone H3 (e.g., histone H3A1, histone H3A2, histone H3A3). In certain embodiments, the histone is histone H4 (e.g., histone H41, histone H44).

The term "bromodomain" refers to a protein domain that recognizes acetylated lysine residues such as those on the N-terminal tails of histones. In certain embodiments, a bromodomain of a BET protein comprises about 110 amino acids and shares a conserved fold comprising a left-handed bundle of four alpha helices linked by diverse loop regions that interact with chromatin. In certain embodiments, the bromodomain is ASH1L (GenBank ID: gi|8922081), ATAD2 (GenBank ID: gi|24497618), BAZ2B (GenBank ID: gi|7304923), BR$^{D1}$ (GenBank ID: gi|11321642), BRD2(1) (GenBank ID: gi|4826806), BRD2(2) (GenBank ID: gi|4826806), BRD3(1) (GenBank ID: gi|11067749), BRD3 (2) (GenBank ID: gi|11067749), BRD4(1) (GenBank ID: gi|19718731), BRD4(2) (GenBank ID: gi|19718731), BRD9 (GenBank ID: gi|57770383), BRDT(1) (GenBank ID: gi|46399198), BRPF1 (GenBank ID: gi|51173720), CECR2 (GenBank ID: gi|148612882), CREBBP (GenBank ID: gi|4758056), EP300 (GenBank ID: gi|50345997), FALZ (GenBank ID: gi|38788274), GCN5L2 (GenBank ID: gi|10835101), KIAA1240 (GenBank ID: gi|51460532), LOC93349 (GenBank ID: gi|134133279), PB1(1) (GenBank ID: gi|30794372), PB1(2) (GenBank ID: gi|30794372), PB1(3) (GenBank ID: gi|30794372), PB1(5) (GenBank ID: gi|30794372), PB1(6) (GenBank ID: gi|30794372), PCAF (GenBank ID: gi|40805843), PHIP(2) (GenBank ID: gi|34996489), SMARCA2 (GenBank ID: gi|48255900), SMARCA4 (GenBank ID: gi|21071056), SP140 (GenBank ID: gi|52487219), TAF1(1) (GenBank ID: gi|20357585), TAF1(2) (GenBank ID: gi|20357585), TAF1L(1) (GenBank ID: gi|24429572), TAF1L(2) (Gen- Bank ID: gi|24429572), TIF1 (GenBank ID: gi|14971415), TRIM28 (GenBank ID: gi|5032179), or WDR9(2) (GenBank ID: gi|116445436).

The term "bromodomain-containing protein" or "bromodomain protein" refers to a protein, whether wild-type or mutant, natural or synthetic, truncated or complete, or a variant thereof, that possesses the minimum amino acid sequence sufficient for a functional bromodomain capable of mediating molecular recognition of acetyl-lysine of acetylated lysine residues on a second protein (e.g., a histone), such as on the tails of histones. Bromodomain-containing proteins include, for example, fusion proteins comprising a bromodomain and an additional portion having desired functionality (e.g., a reporter portion). Exemplary bromodomains include, but are not limited to, bromodomains in The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is effective for inhibiting the activity of a bromodomain-containing protein. In certain embodiments, a therapeutically effective amount is effective for treating a disease described herein. In certain embodiments, a therapeutically effective amount is effective for inhibiting the activity of a bromodomain-containing protein and for treating a disease described herein.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for inhibiting the activity of a bromodomain-containing protein. In certain embodiments, a prophylactically effective amount is effective for preventing a disease described herein. In certain embodiments, a prophylactically effective amount is effective for inhibiting the activity of a bromodomain-containing protein and for preventing a disease described herein.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from preexisting vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrim's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK12, JAK2, JAK22, JAK3, JAK32, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKHlps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgKO50ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK, skM-LCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, ZC4/NRK.

BRIEF DESCRIPTION OF THE DRAWINGS

FIG. 1 shows the results of an exemplary measurement of $K_d$ values of an exemplary compound as measured by Isothermal Titration Calorimetery (ITC) at BRD4.1.

DETAILED DESCRIPTION OF CERTAIN EMBODIMENTS OF THE INVENTION

Recently, some compounds have been reported to be bromodomain binding agents, e.g., WO 2012/075383, WO 2011/054553, WO 2011/054841, WO 2011/054844, WO 2011/054845, WO 2011/054846, WO 2011/054848, WO 2011/143669, and WO 2011/161031. Moreover, Japanese patent application publication JP 2008/156311 discloses a benzimidazole derivative which is said to be a BRD2 bromodomain binding agent which has utility with respect to virus infection and/or proliferation. International PCT publication WO 2009/084693 discloses a series of thienotriazolodiazepine derivatives that are said to inhibit the binding between an acetylated histone and a bromodomain-containing protein which are said to be useful as anti-cancer agents. International PCT publication WO 2011/054843 suggests compounds which inhibit the binding of a bromodomain with its cognate acetylated proteins may have utility in the treatment of a range of autoimmune and inflammatory diseases or conditions. However, there remains a need for additional potent and safe bromodomain binders.

The present invention provides compounds of any one of Formulae (I), (II-C) (e.g., Formula (II)), and (III), which are binders of bromodomains and/or bromodomain-containing proteins. The compounds described herein may be able to bind to in a binding pocket of a bromodomain (e.g., a bromodomain of a bromodomain-containing protein). Without wishing to be bound by any particular theory, the compounds described herein may bind to the binding pocket of a bromodomain by mimicking the contact between an acetylated lysine residue of a second protein (e.g., a histone) and the binding pocket. In certain embodiments, the compounds described herein bind to the binding pocket of the bromodomain. The compound described herein may also be inhibitors of bromodomains and/or bromodomain-containing proteins. Also provided in the present invention are pharmaceutical compositions, methods, uses, and kits useful in inhibiting the activity of a bromodomain-containing protein (e.g., a transcription factor). The compounds, pharmaceutical compositions, methods, uses, and kits may be useful in treating and/or preventing diseases associated with a bromodomain, diseases associated with a bromodomain-containing protein, diseases associated with the activity (e.g., aberrant activity) of a bromodomain, and diseases associated with the activity (e.g., aberrant activity) of a bromodomain-containing protein. Exemplary diseases that maybe prevented and/or treated with compounds described herein include proliferative diseases (e.g., cancers, benign neoplasms, angiogenesis, inflammatory diseases, and autoimmune diseases), autoimmune diseases, cardiovascular diseases, viral infections, fibrotic diseases, metabolic diseases, endocrine diseases, and radiation poisoning. The compounds, pharmaceutical compositions, methods, uses, and kits may also be useful for male contraception and for inhibiting the replication of or killing a virus.

Compounds

Compounds of Formula (I)

In one aspect, the present invention provides compounds of Formula (I):

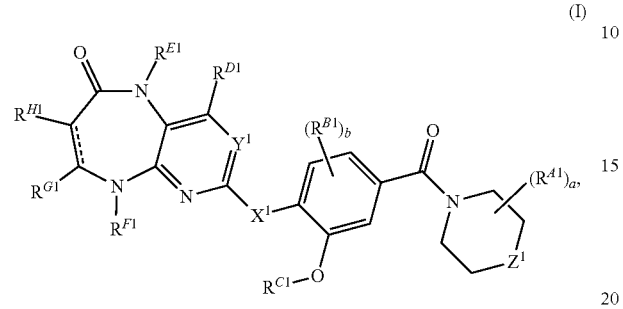

(I)

and pharmaceutically acceptable salts, solvates, hydrates, polymorphs, co-crystals, tautomers, stereoisomers, isotopically labeled derivatives, and prodrugs thereof, wherein:

is a single or double bond;

$X^1$ is —O—, —S—, or —C($R^{X1}$)$_2$—, wherein each instance of $R^{X1}$ is independently hydrogen, halogen, or substituted or unsubstituted $C_{1-6}$ alkyl;

$Y^1$ is N or $CR^{Y1}$, wherein $R^{Y1}$ is hydrogen, halogen, or substituted or unsubstituted $C_{1-6}$ alkyl;

$Z^1$ is —O—, —N($R^{Z1}$)— or —C($R^{Z1}$)$_2$—, wherein each instance of $R^{Z1}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or two instances of $R^{Z1}$ are joined to form a substituted or unsubstituted carbocyclic or substituted or unsubstituted heterocyclic ring;

each instance of $R^{A1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1a}$, —N($R^{A1a}$)$_2$, —$SR^{A1a}$, —CN, —SCN, —C(=N$R^{A1a}$)$R^{A1a}$, —C(=N$R^{A1a}$)O$R^{A1a}$, —C(=N$R^{A1a}$)N($R^{A1a}$)$_2$, —C(=O)$R^{A1a}$, —C(=O)O$R^{A1a}$, —C(=O)N($R^{A1a}$)$_2$, —NO$_2$, —N$R^{A1a}$C(=O)$R^{A1a}$, —N$R^{A1a}$C(=O)O$R^{A1a}$, —N$R^{A1a}$C(=O)N($R^{A1a}$)$_2$, —OC(=O)$R^{A1a}$, —OC(=O)O$R^{A1a}$, or —OC(=O)N($R^{A1a}$)$_2$, wherein each instance of $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1a}$ groups are joined to form a substituted or unsubstituted heterocyclic or substituted or unsubstituted heteroaryl ring;

a is 0, 1, 2, 3, 4, 5, 6, 7, or 8;

each instance of $R^{B1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1a}$, —N($R^{B1a}$)$_2$, —$SR^{B1a}$, —CN, —SCN, —C(=N$R^{B1a}$)$R^{B1a}$, —C(=N$R^{B1a}$)O$R^{B1a}$, —C(=N$R^{B1a}$)N($R^{B1a}$)$_2$, —C(=O)$R^{B1a}$, —C(=O)O$R^{B1a}$, —C(=O)N($R^{B1a}$)$_2$, —NO$_2$, —N$R^{B1a}$C(=O)$R^{B1a}$, —N$R^{B1a}$C(=O)O$R^{B1a}$, —N$R^{B1a}$C(=O)N($R^{B1a}$)$_2$, —OC(=O)$R^{B1a}$, —OC(=O)O$R^{B1a}$, or —OC(=O)N($R^{B1a}$)$_2$, wherein each instance of $R^{B1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1a}$ groups are joined to form a substituted or unsubstituted heterocyclic or substituted or unsubstituted heteroaryl ring;

b is 0, 1, 2, or 3;

$R^{C1}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

$R^{D1}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D1a}$, —N($R^{D1a}$)$_2$, —$SR^{D1a}$, —CN, —SCN, —C(=N$R^{D1a}$)$R^{D1a}$, —C(=N$R^{D1a}$)O$R^{D1a}$, —C(=N$R^{D1a}$)N($R^{D1a}$)$_2$, —C(=O)$R^{D1a}$, —C(=O)O$R^{D1a}$, —C(=O)N($R^{D1a}$)$_2$, —NO$_2$, —N$R^{D1a}$C(=O)$R^{D1a}$, —N$R^{D1a}$C(=O)O$R^{D1a}$, —N$R^{D1a}$C(=O)N($R^{D1a}$)$_2$, —OC(=O)$R^{D1a}$, —OC(=O)O$R^{D1a}$, or —OC(=O)N($R^{D1a}$)$_2$, wherein each instance of $R^{D1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{D1a}$ groups are joined to form a substituted or unsubstituted heterocyclic or substituted or unsubstituted heteroaryl ring;

$R^{E1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{F1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{G1}$ is hydrogen, halogen, or substituted or unsubstituted $C_{1-6}$ alkyl; and $R^{H1}$ is hydrogen, halogen, or substituted or unsubstituted $C_{1-6}$ alkyl;

or $R^{G1}$ and $R^{H1}$ are joined to form a substituted or unsubstituted phenyl ring.

Formula (I) includes a bond ⚌. In certain embodiments, ⚌ is a single bond. In certain embodiments, ⚌ is a double bond.

Formula (I) includes a divalent moiety $X^1$. In certain embodiments, $X^1$ is —O—. In certain embodiments, $X^1$ is —S—. In certain embodiments, $X^1$ is —C($R^{X1}$)$_2$—. In certain embodiments, $X^1$ is —CH($R^{X1}$)—. In certain embodiments, $X^1$ is —CH$_2$—.

In certain embodiments, at least one instance of $R^{X1}$ is H. In certain embodiments, each instance of $R^{X1}$ is H. In certain embodiments, at least one instance of $R^{X1}$ is halogen. In certain embodiments, at least one instance of $R^{X1}$ is F. In certain embodiments, at least one instance of $R^{X1}$ is Cl. In certain embodiments, at least one instance of $R^{X1}$ is Br. In certain embodiments, at least one instance of $R^{X1}$ is I (iodine). In certain embodiments, at least one instance of $R^{X1}$ is unsubstituted $C_{1-6}$ alkyl. In certain embodiments, each instance of $R^{X1}$ is unsubstituted $C_{1-6}$ alkyl. In certain embodiments, at least one instance of $R^{X1}$ is substituted $C_{1-6}$ alkyl. In certain embodiments, at least one instance of $R^{X1}$ is $C_{1-6}$ alkyl substituted with at least one halogen. In certain embodiments, at least one instance of $R^{X1}$ is —CH$_3$. In certain embodiments, each instance of $R^{X1}$ is —CH$_3$. In certain embodiments, at least one instance of $R^{X1}$ is substituted methyl. In certain embodiments, at least one instance of $R^{X1}$ is —CH$_2$F. In certain embodiments, at least one instance of $R^{X1}$ is —CHF$_2$. In certain embodiments, at least one instance of $R^{X1}$ is —CF$_3$. In certain embodiments, at least one instance of $R^{X1}$ is ethyl. In certain embodiments, at least one instance of $R^{X1}$ is propyl. In certain embodiments, at least one instance of $R^{X1}$ is butyl. In certain embodiments, at least one instance of $R^{X1}$ is pentyl. In certain embodiments, at least one instance of $R^{X1}$ is hexyl.

Formula (I) includes a divalent moiety $Y^1$. In certain embodiments, $Y^1$ is N. In certain embodiments, $Y^1$ is $CR^{Y1}$. In certain embodiments, $Y^1$ is CH. In certain embodiments, $Y^1$ is C (halogen). In certain embodiments, $Y^1$ is C(substituted or unsubstituted, $C_{1-6}$ alkyl).

In certain embodiments, $R^{Y1}$ is H. In certain embodiments, $R^{Y1}$ is halogen. In certain embodiments, $R^{Y1}$ is F. In certain embodiments, $R^{Y1}$ is Cl. In certain embodiments, $R^{Y1}$ is Br. In certain embodiments, $R^{Y1}$ is I (iodine). In certain embodiments, $R^{Y1}$ is unsubstituted $C_{1-6}$ alkyl. In certain embodiments, $R^{Y1}$ is substituted $C_{1-6}$ alkyl. In certain embodiments, $R^{Y1}$ is $C_{1-6}$ alkyl substituted with at least one halogen. In certain embodiments, $R^{Y1}$ is —CH$_3$. In certain embodiments, $R^{Y1}$ is substituted methyl. In certain embodiments, $R^{Y1}$ is —CH$_2$F. In certain embodiments, $R^{Y1}$ is —CHF$_2$. In certain embodiments, $R^{Y1}$ is —CF$_3$. In certain embodiments, $R^{Y1}$ is ethyl. In certain embodiments, $R^{Y1}$ is propyl. In certain embodiments, $R^{Y1}$ is butyl. In certain embodiments, $R^{Y1}$ is pentyl. In certain embodiments, $R^{Y1}$ is hexyl.

Formula (I) includes a divalent moiety $Z^1$. In certain embodiments, $Z^1$ is —O—. In certain embodiments, $Z^1$ is —N($R^{Z1}$)—. In certain embodiments, $Z^1$ is —NH—. In certain embodiments, $Z^1$ is —N(substituted or unsubstituted, $C_{1-6}$ alkyl)-. In certain embodiments, $Z^1$ is —N(substituted or unsubstituted, 4- to 7-membered, monocyclic heterocyclyl)-. In certain embodiments, $Z^1$ is —C($R^{Z1}$)$_2$—. In certain embodiments, $Z^1$ is —CH($R^{Z1}$)—. In certain embodiments, $Z^1$ is —CH(substituted or unsubstituted, $C_{1-6}$ alkyl)-. In certain embodiments, $Z^1$ is —CH(substituted or unsubstituted, 4- to 7-membered, monocyclic heterocyclyl)-.

Formula (I) may include one or more substituents $R^{Z1}$ on the divalent moiety $Z^1$. In certain embodiments, at least one instance of $R^{Z1}$ is H. In certain embodiments, at least one instance of $R^{Z1}$ is substituted acyl. In certain embodiments, at least one instance of $R^{Z1}$ is unsubstituted acyl. In certain embodiments, at least one instance of $R^{Z1}$ is acetyl. In certain embodiments, at least one instance of $R^{Z1}$ is substituted alkyl. In certain embodiments, at least one instance of $R^{Z1}$ is unsubstituted alkyl. In certain embodiments, at least one instance of $R^{Z1}$ is unsubstituted $C_{1-6}$ alkyl. In certain embodiments, at least one instance of $R^{Z1}$ is methyl. In certain embodiments, at least one instance of $R^{Z1}$ is ethyl. In certain embodiments, at least one instance of $R^{Z1}$ is propyl. In certain embodiments, at least one instance of $R^{Z1}$ is butyl. In certain embodiments, at least one instance of $R^{Z1}$ is pentyl. In certain embodiments, at least one instance of $R^{Z1}$ is hexyl. In certain embodiments, at least one instance of $R^{Z1}$ is substituted alkenyl. In certain embodiments, at least one instance of $R^{Z1}$ is unsubstituted alkenyl. In certain embodiments, at least one instance of $R^{Z1}$ is substituted alkynyl. In certain embodiments, at least one instance of $R^{Z1}$ is unsubstituted alkynyl. In certain embodiments, at least one instance of $R^{Z1}$ is substituted or unsubstituted carbocyclyl. In certain embodiments, at least one instance of $R^{Z1}$ is saturated carbocyclyl. In certain embodiments, at least one instance of $R^{Z1}$ is unsaturated carbocyclyl. In certain embodiments, at least one instance of $R^{Z1}$ is 3- to 7-membered, monocyclic carbocyclyl. In certain embodiments, at least one instance of $R^{Z1}$ is substituted or unsubstituted heterocyclyl. In certain embodiments, at least one instance of $R^{Z1}$ is saturated heterocyclyl. In certain embodiments, at least one instance of $R^{Z1}$ is unsaturated heterocyclyl. In certain embodiments, at least one instance of $R^{Z1}$ is substituted or unsubstituted, 4- to 7-membered, monocyclic heterocyclyl, wherein one, two, or three atoms in the heterocyclic ring system are independently nitrogen, oxygen, or sulfur. In certain embodiments, at least one instance of $R^{Z1}$ is substituted or unsubstituted, 6-membered, monocyclic heterocyclyl, wherein one or two atoms in the heterocyclic ring system are independently nitrogen, oxygen, or sulfur. In certain embodiments, at least one instance of $R^{Z1}$ is of the formula:

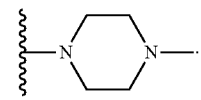 [SMILES: *N1CCN(C)CC1]

In certain embodiments, at least one instance of $R^{Z1}$ is of the formula:

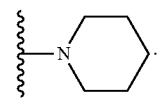

In certain embodiments, at least one instance of $R^{Z1}$ is of the formula:

In certain embodiments, at least one instance of $R^{Z1}$ is of the formula:

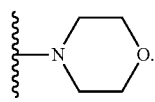

In certain embodiments, at least one instance of $R^{Z1}$ is of the formula:

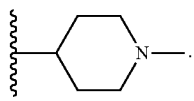

In certain embodiments, at least one instance of $R^{Z1}$ is of the formula:

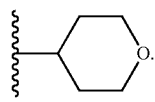 [SMILES: *C1CCOCC1]

In certain embodiments, at least one instance of $R^{Z1}$ is substituted or unsubstituted aryl. In certain embodiments, at least one instance of $R^{Z1}$ is 6- to 10-membered aryl. In certain embodiments, at least one instance of $R^{Z1}$ is monocyclic aryl. In certain embodiments, at least one instance of $R^{Z1}$ is substituted phenyl. In certain embodiments, at least one instance of $R^{Z1}$ is unsubstituted phenyl. In certain embodiments, at least one instance of $R^{Z1}$ is bicyclic aryl. In certain embodiments, at least one instance of $R^{Z1}$ is substituted or unsubstituted heteroaryl. In certain embodiments, at least one instance of $R^{Z1}$ is heteroaryl, wherein one, two, three, or four atoms in the heteroaryl ring system are independently selected from the group consisting of nitrogen, oxygen, and sulfur. In certain embodiments, at least one instance of $R^{Z1}$ is monocyclic heteroaryl. In certain embodiments, at least one instance of $R^{Z1}$ is 5- or 6-membered, monocyclic heteroaryl. In certain embodiments, at least one instance of $R^{Z1}$ is bicyclic heteroaryl, wherein the point of attachment may be on any atom of the bicyclic heteroaryl ring system, as valency permits. In certain embodiments, at least one instance of $R^{Z1}$ is a nitrogen protecting group when attached to a nitrogen atom. In certain embodiments, at least one instance of $R^{Z1}$ is Bn, Boc, Cbz, Fmoc, trifluoroacetyl, triphenylmethyl, acetyl, or Ts when attached to a nitrogen atom. In certain embodiments, two instances of $R^{Z1}$ are joined to form a substituted or unsubstituted carbocyclic ring. In certain embodiments, two instances of $R^{Z1}$ are joined to form a saturated or unsaturated carbocyclic ring. In certain embodiments, two instances of $R^{Z1}$ are joined to form a substituted or unsubstituted, 3- to 7-membered, monocyclic carbocyclic ring. In certain embodiments, two instances of $R^{Z1}$ are joined to form a substituted or unsubstituted heterocyclic ring. In certain embodiments, two instances of $R^{Z1}$ are joined to form a saturated or unsaturated heterocyclic ring. In certain embodiments, two instances of $R^{Z1}$ are joined to form a heterocyclic ring, wherein one, two, or three atoms in the heterocyclic ring system are independently selected from the group consisting of nitrogen, oxygen, and sulfur. In certain embodiments, two instances of $R^{Z1}$ are joined to form a 3- to 7-membered, monocyclic heterocyclic ring.

Formula (I) may include one or more substituents $R^{41}$. In certain embodiments, at least two instances of $R^{41}$ are different. In certain embodiments, all instances of $R^{41}$ are the same. In certain embodiments, at least one instance of $R^{41}$ is H. In certain embodiments, all instances of $R^{41}$ are H. In certain embodiments, at least one instance of $R^{41}$ is halogen. In certain embodiments, at least one instance of $R^{41}$ is F. In certain embodiments, at least one instance of $R^{41}$ is Cl. In certain embodiments, at least one instance of $R^{41}$ is Br. In certain embodiments, at least one instance of $R^{41}$ is I (iodine). In certain embodiments, at least one instance of $R^{41}$ is substituted alkyl. In certain embodiments, at least one instance of $R^{41}$ is unsubstituted alkyl. In certain embodiments, at least one instance of $R^{41}$ is unsubstituted $C_{1-6}$alkyl. In certain embodiments, all instances of $R^{41}$ are unsubstituted $C_{1-6}$ alkyl. In certain embodiments, at least one instance of $R^{41}$ is substituted $C_{1-6}$ alkyl. In certain embodiments, at least one instance of $R^{41}$ is $C_{1-6}$ alkyl substituted with at least one halogen. In certain embodiments, at least one instance of $R^{41}$ is —$CH_3$. In certain embodiments, all instances of $R^{41}$ are —$CH_3$. In certain embodiments, at least one instance of $R^{41}$ is substituted methyl. In certain embodiments, at least one instance of $R^{41}$ is —$CH_2F$. In certain embodiments, at least one instance of $R^{41}$ is —$CHF_2$. In certain embodiments, at least one instance of $R^{41}$ is —$CF_3$. In certain embodiments, at least one instance of $R^{41}$ is ethyl. In certain embodiments, at least one instance of $R^{41}$ is propyl. In certain embodiments, at least one instance of $R^{41}$ is butyl. In certain embodiments, at least one instance of $R^{41}$ is pentyl. In certain embodiments, at least one instance of $R^{41}$ is hexyl. In certain embodiments, at least one instance of $R^{41}$ is substituted alkenyl. In certain embodiments, at least one instance of $R^{41}$ is unsubstituted alkenyl. In certain embodiments, at least one instance of $R^{41}$ is substituted alkynyl. In certain embodiments, at least one instance of $R^{41}$ is unsubstituted alkynyl. In certain embodiments, at least one instance of $R^{41}$ is substituted carbocyclyl. In certain embodiments, at least one instance of $R^{41}$ is unsubstituted carbocyclyl. In certain embodiments, at least one instance of $R^{41}$ is saturated carbocyclyl. In certain embodiments, at least one instance of $R^{41}$ is unsaturated carbocyclyl. In certain embodiments, at least one instance of $R^{41}$ is monocyclic carbocyclyl. In certain embodiments, at least one instance of $R^{41}$ is 3- to 7-membered, monocyclic carbocyclyl. In certain embodiments, at least one instance of $R^{41}$ is substituted heterocyclyl. In certain embodiments, at least one instance of $R^{41}$ is unsubstituted heterocyclyl. In certain embodiments, at least one instance of $R^{41}$ is saturated heterocyclyl. In certain embodiments, at least one instance of $R^{41}$ is unsaturated heterocyclyl. In certain embodiments, at least one instance of $R^{41}$ is heterocyclyl, wherein one, two, or three atoms in the heterocyclic ring system are independently selected from the group consisting of nitrogen, oxygen, and sulfur. In certain embodiments, at least one instance of $R^{41}$ is monocyclic heterocyclyl. In certain embodiments, at least one instance of $R^{41}$ is 3- to 7-membered, monocyclic heterocyclyl. In certain embodiments, at least one instance of $R^{41}$ is substituted aryl. In certain embodiments, at least one instance of $R^{41}$ is unsubstituted aryl. In certain embodiments, at least one instance of $R^{41}$ is 6- to 10-membered aryl. In certain embodiments, at least one instance of $R^{41}$ is substituted phenyl. In certain embodiments, at least one instance of $R^{41}$ is unsubstituted phenyl. In certain embodiments, at least one instance of $R^{41}$ is substituted heteroaryl. In certain embodiments, at least one instance of $R^{41}$ is unsubstituted heteroaryl. In certain embodiments, at least one instance of $R^{41}$ is heteroaryl, wherein one, two, three, or four atoms in the heteroaryl ring system are independently selected from the group consisting of nitrogen, oxygen, and sulfur. In certain embodiments, at least one instance of $R^{A1}$ is monocyclic heteroaryl. In certain embodiments, at least one instance of $R^{A1}$ is 5-membered, monocyclic heteroaryl. In certain embodiments, at least one instance of $R^{A1}$ is 6-membered, monocyclic heteroaryl. In certain embodiments, at least one instance of $R^{A1}$ is bicyclic heteroaryl, wherein the point of attachment may be on any atom of the bicyclic heteroaryl ring system, as valency permits. In certain embodiments, at least one instance of $R^{A1}$ is 9- or 10-membered, bicyclic heteroaryl. In certain embodiments, at least one instance of $R^{A1}$ is $-OR^{A1a}$. In certain embodiments, at least one instance of $R^{A1}$ is $-OH$. In certain embodiments, at least one instance of $R^{A1}$ is $-OMe$. In certain embodiments, at least one instance of $R^{A1}$ is $-OEt$. In certain embodiments, at least one instance of $R^{A1}$ is $-OPr$. In certain embodiments, at least one instance of $R^{A1}$ is $-OBu$. In certain embodiments, at least one instance of $R^{A1}$ is $-OBn$. In certain embodiments, at least one instance of $R^{A1}$ is $-OPh$. In certain embodiments, at least one instance of $R^{A1}$ is $-SR^{A1a}$. In certain embodiments, at least one instance of $R^{A1}$ is $-SH$. In certain embodiments, at least one instance of $R^{A1}$ is $-SMe$. In certain embodiments, at least one instance of $R^{A1}$ is $-N(R^{A1a})_2$. In certain embodiments, at least one instance of $R^{A1}$ is $-NH_2$. In certain embodiments, at least one instance of $R^{A1}$ is $-NHMe$. In certain embodiments, at least one instance of $R^{A1}$ is $-NMe_2$. In certain embodiments, at least one instance of $R^{A1}$ is $-CN$. In certain embodiments, at least one instance of $R^{A1}$ is $-SCN$. In certain embodiments, at least one instance of $R^{A1}$ is $-C(=NR^{A1a})R^{A1a}$, $-C(=NR^{A1a})OR^{A1a}$, or $-C(=NR^{A1a})N(R^{A1a})_2$. In certain embodiments, at least one instance of $R^{A1}$ is $-C(=O)R^{A1a}$ or $-C(=O)OR^{A1a}$. In certain embodiments, at least one instance of $R^{A1}$ is $-C(=O)N(R^{A1a})_2$. In certain embodiments, at least one instance of $R^{A1}$ is $-C(=O)NMe_2$, $-C(=O)NHMe$, or $-C(=O)NH_2$. In certain embodiments, at least one instance of $R^{A1}$ is $-NO_2$. In certain embodiments, at least one instance of $R^{A1}$ is $-NR^{A1a}C(=O)R^{A1a}$, $-NR^{A1a}C(=O)OR^{A1a}$, or $-NR^{A1a}C(=O)N(R^{A1a})_2$. In certain embodiments, at least one instance of $R^{A1}$ is $-OC(=O)R^{A1a}$, $-OC(=O)OR^{A1a}$, or $-OC(=O)N(R^{A1a})_2$.

In certain embodiments, at least one instance of $R^{A1a}$ is H. In certain embodiments, at least one instance of $R^{A1a}$ is substituted acyl. In certain embodiments, at least one instance of $R^{A1a}$ is unsubstituted acyl. In certain embodiments, at least one instance of $R^{A1a}$ is acetyl. In certain embodiments, at least one instance of $R^{A1a}$ is substituted alkyl. In certain embodiments, at least one instance of $R^{A1a}$ is unsubstituted alkyl. In certain embodiments, at least one instance of $R^{A1a}$ is unsubstituted $C_{1-6}$ alkyl. In certain embodiments, at least one instance of $R^{A1a}$ is methyl. In certain embodiments, at least one instance of $R^{A1a}$ is ethyl. In certain embodiments, at least one instance of $R^{A1a}$ is propyl. In certain embodiments, at least one instance of $R^{A1a}$ is butyl. In certain embodiments, at least one instance of $R^{A1a}$ is pentyl. In certain embodiments, at least one instance of $R^{A1a}$ is hexyl. In certain embodiments, at least one instance of $R^{A1a}$ is substituted alkenyl. In certain embodiments, at least one instance of $R^{A1a}$ is unsubstituted alkenyl. In certain embodiments, at least one instance of $R^{A1a}$ is substituted alkynyl. In certain embodiments, at least one instance of $R^{A1a}$ is unsubstituted alkynyl. In certain embodiments, at least one instance of $R^{A1a}$ is substituted or unsubstituted carbocyclyl. In certain embodiments, at least one instance of $R^{A1a}$ is saturated carbocyclyl. In certain embodiments, at least one instance of $R^{A1a}$ is unsaturated carbocyclyl. In certain embodiments, at least one instance of $R^{A1a}$ is 3- to 7-membered, monocyclic carbocyclyl. In certain embodiments, at least one instance of $R^{A1a}$ is substituted or unsubstituted heterocyclyl. In certain embodiments, at least one instance of $R^{A1a}$ is saturated heterocyclyl. In certain embodiments, at least one instance of $R^{A1a}$ is unsaturated heterocyclyl. In certain embodiments, at least one instance of $R^{A1a}$ is heterocyclyl, wherein one, two, or three atoms in the heterocyclic ring system are independently selected from the group consisting of nitrogen, oxygen, and sulfur. In certain embodiments, at least one instance of $R^{A1a}$ is 3- to 7-membered, monocyclic heterocyclyl. In certain embodiments, at least one instance of $R^{A1a}$ is substituted or unsubstituted aryl. In certain embodiments, at least one instance of $R^{A1a}$ is 6- to 10-membered aryl. In certain embodiments, at least one instance of $R^{A1a}$ is monocyclic aryl. In certain embodiments, at least one instance of $R^{A1a}$ is substituted phenyl. In certain embodiments, at least one instance of $R^{A1a}$ is unsubstituted phenyl. In certain embodiments, at least one instance of $R^{A1a}$ is bicyclic aryl. In certain embodiments, at least one instance of $R^{A1a}$ is substituted or unsubstituted heteroaryl. In certain embodiments, at least one instance of $R^{A1a}$ is heteroaryl, wherein one, two, three, or four atoms in the heteroaryl ring system are independently selected from the group consisting of nitrogen, oxygen, and sulfur. In certain embodiments, at least one instance of $R^{A1a}$ is monocyclic heteroaryl. In certain embodiments, at least one instance of $R^{A1a}$ is 5- or 6-membered, monocyclic heteroaryl. In certain embodiments, at least one instance of $R^{A1a}$ is bicyclic heteroaryl, wherein the point of attachment may be on any atom of the bicyclic heteroaryl ring system, as valency permits. In certain embodiments, at least one instance of $R^{A1a}$ is a nitrogen protecting group when attached to a nitrogen atom. In certain embodiments, at least one instance of $R^{A1a}$ is Bn, Boc, Cbz, Fmoc, trifluoroacetyl, triphenylmethyl, acetyl, or Ts when attached to a nitrogen atom. In certain embodiments, $R^{A1a}$ is an oxygen protecting group when attached to an oxygen atom. In certain embodiments, $R^{A1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1a}$ is a sulfur protecting group when attached to a sulfur atom. In certain embodiments, $R^{A1a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{A1a}$ are joined to form a substituted or unsubstituted heterocyclic ring. In certain embodiments, two instances of $R^{A1a}$ are joined to form a saturated or unsaturated heterocyclic ring. In certain embodiments, two instances of $R^{A1a}$ are joined to form a heterocyclic ring, wherein one, two, or three atoms in the heterocyclic ring system are independently selected from the group consisting of nitrogen, oxygen, and sulfur. In certain embodiments, two instances of $R^{A1a}$ are joined to form a 3- to 7-membered, monocyclic heterocyclic ring. In certain embodiments, two instances of $R^{A1a}$ are joined to form a substituted or unsubstituted heteroaryl ring. In certain embodiments, two instances of $R^{A1a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, a is 0. In certain embodiments, a is 1. In certain embodiments, a is 2. In certain embodiments, a is 3. In certain embodiments, a is 4. In certain embodiments, a is 5. In certain embodiments, a is 6. In certain embodiments, a is 7. In certain embodiments, a is 8.

Formula (I) may include one or more substituents $R^{B1}$. In certain embodiments, at least two instances of $R^{B1}$ are different. In certain embodiments, all instances of $R^{B1}$ are the same. In certain embodiments, at least one instance of $R^{B1}$ is H. In certain embodiments, all instances of $R^{B1}$ are H. In certain embodiments, at least one instance of $R^{B1}$ is halogen. In certain embodiments, at least one instance of $R^{B1}$ is F. In certain embodiments, at least one instance of $R^{B1}$ is Cl. In certain embodiments, at least one instance of $R^{B1}$ is Br. In certain embodiments, at least one instance of $R^{B1}$ is I (iodine). In certain embodiments, at least one instance of $R^{B1}$ is substituted alkyl. In certain embodiments, at least one instance of $R^{B1}$ is unsubstituted alkyl. In certain embodiments, at least one instance of $R^{B1}$ is unsubstituted $C_{1-6}$ alkyl. In certain embodiments, all instances of $R^{B1}$ are unsubstituted $C_{1-6}$ alkyl. In certain embodiments, at least one instance of $R^{B1}$ is substituted $C_{1-6}$ alkyl. In certain embodiments, at least one instance of $R^{B1}$ is $C_{1-6}$ alkyl substituted with at least one halogen. In certain embodiments, at least one instance of $R^{B1}$ is —$CH_3$. In certain embodiments, all instances of $R^{B1}$ are —$CH_3$. In certain embodiments, at least one instance of $R^{B1}$ is substituted methyl. In certain embodiments, at least one instance of $R^{B1}$ is —$CH_2F$. In certain embodiments, at least one instance of $R^{B1}$ is —$CHF_2$. In certain embodiments, at least one instance of $R^{B1}$ is —$CF_3$. In certain embodiments, at least one instance of $R^{B1}$ is ethyl. In certain embodiments, at least one instance of $R^{B1}$ is propyl. In certain embodiments, at least one instance of $R^{B1}$ is butyl. In certain embodiments, at least one instance of $R^{B1}$ is pentyl. In certain embodiments, at least one instance of $R^{B1}$ is hexyl. In certain embodiments, at least one instance of $R^{B1}$ is substituted alkenyl. In certain embodiments, at least one instance of $R^{B1}$ is unsubstituted alkenyl. In certain embodiments, at least one instance of $R^{B1}$ is substituted alkynyl. In certain embodiments, at least one instance of $R^{B1}$ is unsubstituted alkynyl. In certain embodiments, at least one instance of $R^{B1}$ is substituted carbocyclyl. In certain embodiments, at least one instance of $R^{B1}$ is unsubstituted carbocyclyl. In certain embodiments, at least one instance of $R^{B1}$ is saturated carbocyclyl. In certain embodiments, at least one instance of $R^{B1}$ is unsaturated carbocyclyl. In certain embodiments, at least one instance of $R^{B1}$ is monocyclic carbocyclyl. In certain embodiments, at least one instance of $R^{B1}$ is 3- to 7-membered, monocyclic carbocyclyl. In certain embodiments, at least one instance of $R^{B1}$ is substituted heterocyclyl. In certain embodiments, at least one instance of $R^{B1}$ is unsubstituted heterocyclyl. In certain embodiments, at least one instance of $R^{B1}$ is saturated heterocyclyl. In certain embodiments, at least one instance of $R^{B1}$ is unsaturated heterocyclyl. In certain embodiments, at least one instance of $R^{B1}$ is heterocyclyl, wherein one, two, or three atoms in the heterocyclic ring system are independently selected from the group consisting of nitrogen, oxygen, and sulfur. In certain embodiments, at least one instance of $R^{B1}$ is monocyclic heterocyclyl. In certain embodiments, at least one instance of $R^{B1}$ is 3- to 7-membered, monocyclic heterocyclyl. In certain embodiments, at least one instance of $R^{B1}$ is substituted aryl. In certain embodiments, at least one instance of $R^{B1}$ is unsubstituted aryl. In certain embodiments, at least one instance of $R^{B1}$ is 6- to 10-membered aryl. In certain embodiments, at least one instance of $R^{B1}$ is substituted phenyl. In certain embodiments, at least one instance of $R^{B1}$ is unsubstituted phenyl. In certain embodiments, at least one instance of $R^{B1}$ is substituted heteroaryl. In certain embodiments, at least one instance of $R^{B1}$ is unsubstituted heteroaryl. In certain embodiments, at least one instance of $R^{B1}$ is heteroaryl, wherein one, two, three, or four atoms in the heteroaryl ring system are independently selected from the group consisting of nitrogen, oxygen, and sulfur. In certain embodiments, at least one instance of $R^{B1}$ is monocyclic heteroaryl. In certain embodiments, at least one instance of $R^{B1}$ is 5-membered, monocyclic heteroaryl. In certain embodiments, at least one instance of $R^{B1}$ is 6-membered, monocyclic heteroaryl. In certain embodiments, at least one instance of $R^{B1}$ is bicyclic heteroaryl, wherein the point of attachment may be on any atom of the bicyclic heteroaryl ring system, as valency permits. In certain embodiments, at least one instance of $R^{B1}$ is 9- or 10-membered, bicyclic heteroaryl. In certain embodiments, at least one instance of $R^{B1}$ is —$OR^{B1a}$. In certain embodiments, at least one instance of $R^{B1}$ is —OH. In certain embodiments, at least one instance of $R^{B1}$ is —OMe. In certain embodiments, at least one instance of $R^{B1}$ is —OEt. In certain embodiments, at least one instance of $R^{B1}$ is —OPr. In certain embodiments, at least one instance of $R^{B1}$ is —OBu. In certain embodiments, at least one instance of $R^{B1}$ is —OBn. In certain embodiments, at least one instance of $R^{B1}$ is —OPh. In certain embodiments, at least one instance of $R^{B1}$ is —$SR^{B1a}$. In certain embodiments, at least one instance of $R^{B1}$ is —SH. In certain embodiments, at least one instance of $R^{B1}$ is —SMe. In certain embodiments, at least one instance of $R^{B1}$ is —$N(R^{B1a})_2$. In certain embodiments, at least one instance of $R^{B1}$ is —$NH_2$. In certain embodiments, at least one instance of $R^{B1}$ is —NHMe. In certain embodiments, at least one instance of $R^{B1}$ is —$NMe_2$. In certain embodiments, at least one instance of $R^{B1}$ is —CN. In certain embodiments, at least one instance of $R^{B1}$ is —SCN. In certain embodiments, at least one instance of $R^{B1}$ is —$C(=NR^{B1a})R^{B1a}$, —$C(=NR^{B1a})OR^{B1a}$, or —$C(=NR^{B1a})N(R^{B1a})_2$. In certain embodiments, at least one instance of $R^{B1}$ is —$C(=O)R^{B1a}$ or —$C(=O)OR^{B1a}$. In certain embodiments, at least one instance of $R^{B1}$ is —$C(=O)N(R^{B1a})_2$. In certain embodiments, at least one instance of $R^{B1}$ is —$C(=O)NMe_2$, —$C(=O)NHMe$, or —$C(=O)NH_2$. In certain embodiments, at least one instance of $R^{B1}$ is —$NO_2$. In certain embodiments, at least one instance of $R^{B1}$ is —$NR^{B1a}C(=O)R^{B1a}$, —$NR^{B1a}C(=O)OR^{B1a}$, or —$NR^{B1a}C(=O)N(R^{B1a})_2$. In certain embodiments, at least one instance of $R^{B1}$ is —$OC(=O)R^{B1a}$, —$OC(=O)OR^{B1a}$, or —$OC(=O)N(R^{B1a})_2$.

In certain embodiments, at least one instance of $R^{B1a}$ is H. In certain embodiments, at least one instance of $R^{B1a}$ is substituted acyl. In certain embodiments, at least one instance of $R^{B1a}$ is unsubstituted acyl. In certain embodiments, at least one instance of $R^{B1a}$ is acetyl. In certain embodiments, at least one instance of $R^{B1a}$ is substituted alkyl. In certain embodiments, at least one instance of $R^{B1a}$ is unsubstituted alkyl. In certain embodiments, at least one instance of $R^{B1a}$ is unsubstituted $C_{1-6}$ alkyl. In certain embodiments, at least one instance of $R^{B1a}$ is methyl. In certain embodiments, at least one instance of $R^{B1a}$ is ethyl. In certain embodiments, at least one instance of $R^{B1a}$ is propyl. In certain embodiments, at least one instance of $R^{B1a}$ is butyl. In certain embodiments, at least one instance of $R^{B1a}$ is pentyl. In certain embodiments, at least one instance of $R^{B1a}$ is hexyl. In certain embodiments, at least one instance of $R^{B1a}$ is substituted alkenyl. In certain embodiments, at least one instance of $R^{B1a}$ is unsubstituted alkenyl. In certain embodiments, at least one instance of $R^{B1a}$ is substituted alkynyl. In certain embodiments, at least one instance of $R^{B1a}$ is unsubstituted alkynyl. In certain embodiments, at least one instance of $R^{B1a}$ is substituted or unsubstituted carbocyclyl. In certain embodiments, at least one instance of $R^{B1a}$ is saturated carbocyclyl. In certain embodiments, at least one instance of $R^{B1a}$ is unsaturated carbocyclyl. In certain embodiments, at least one instance of $R^{B1a}$ is 3- to 7-membered, monocyclic carbocyclyl. In certain embodiments, at least one instance of $R^{B1a}$ is substituted or unsubstituted heterocyclyl. In certain embodiments, at least one instance of $R^{B1a}$ is saturated heterocyclyl. In certain embodiments, at least one instance of $R^{B1a}$ is unsaturated heterocyclyl. In certain embodiments, at least one instance of $R^{B1a}$ is heterocyclyl, wherein one, two, or three atoms in the heterocyclic ring system are independently selected from the group consisting of nitrogen, oxygen, and sulfur. In certain embodiments, at least one instance of $R^{B1a}$ is 3- to 7-membered, monocyclic heterocyclyl. In certain embodiments, at least one instance of $R^{B1a}$ is substituted or unsubstituted aryl. In certain embodiments, at least one instance of $R^{B1a}$ is 6- to 10-membered aryl. In certain embodiments, at least one instance of $R^{B1a}$ is monocyclic aryl. In certain embodiments, at least one instance of $R^{B1a}$ is substituted phenyl. In certain embodiments, at least one instance of $R^{B1a}$ is unsubstituted phenyl. In certain embodiments, at least one instance of $R^{B1a}$ is bicyclic aryl. In certain embodiments, at least one instance of $R^{B1a}$ is substituted or unsubstituted heteroaryl. In certain embodiments, at least one instance of $R^{B1a}$ is heteroaryl, wherein one, two, three, or four atoms in the heteroaryl ring system are independently selected from the group consisting of nitrogen, oxygen, and sulfur. In certain embodiments, at least one instance of $R^{B1a}$ is monocyclic heteroaryl. In certain embodiments, at least one instance of $R^{B1a}$ is 5- or 6-membered, monocyclic heteroaryl. In certain embodiments, at least one instance of $R^{B1a}$ is bicyclic heteroaryl, wherein the point of attachment may be on any atom of the bicyclic heteroaryl ring system, as valency permits. In certain embodiments, at least one instance of $R^{B1a}$ is a nitrogen protecting group when attached to a nitrogen atom. In certain embodiments, at least one instance of $R^{B1a}$ is Bn, Boc, Cbz, Fmoc, trifluoroacetyl, triphenylmethyl, acetyl, or Ts when attached to a nitrogen atom. In certain embodiments, $R^{B1a}$ is an oxygen protecting group when attached to an oxygen atom. In certain embodiments, $R^{B1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1a}$ is a sulfur protecting group when attached to a sulfur atom. In certain embodiments, $R^{B1a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{B1a}$ are joined to form a substituted or unsubstituted heterocyclic ring. In certain embodiments, two instances of $R^{B1a}$ are joined to form a saturated or unsaturated heterocyclic ring. In certain embodiments, two instances of $R^{B1a}$ are joined to form a heterocyclic ring, wherein one, two, or three atoms in the heterocyclic ring system are independently selected from the group consisting of nitrogen, oxygen, and sulfur. In certain embodiments, two instances of $R^{B1a}$ are joined to form a 3- to 7-membered, monocyclic heterocyclic ring. In certain embodiments, two instances of $R^{B1a}$ are joined to form a substituted or unsubstituted heteroaryl ring. In certain embodiments, two instances of $R^{B1a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, b is 0. In certain embodiments, b is 1. In certain embodiments, b is 2. In certain embodiments, b is 3.

Formula (I) includes substituent $R^{C1}$. In certain embodiments, $R^{C1}$ is H. In certain embodiments, $R^{C1}$ is substituted acyl. In certain embodiments, $R^{C1}$ is unsubstituted acyl. In certain embodiments, $R^{C1}$ is acetyl. In certain embodiments, $R^{C1}$ is substituted alkyl. In certain embodiments, $R^{C1}$ is unsubstituted alkyl. In certain embodiments, $R^{C1}$ is unsubstituted $C_{1-6}$ alkyl. In certain embodiments, $R^{C1}$ is substituted $C_{1-6}$ alkyl. In certain embodiments, $R^{C1}$ is $C_{1-6}$ alkyl substituted with at least one halogen. In certain embodiments, $R^{C1}$ is —$CH_3$. In certain embodiments, $R^{C1}$ is substituted methyl. In certain embodiments, $R^{C1}$ is —$CH_2F$. In certain embodiments, $R^{C1}$ is —$CHF_2$. In certain embodiments, $R^{C1}$ is —$CF_3$. In certain embodiments, $R^{C1}$ is ethyl. In certain embodiments, $R^{C1}$ is propyl. In certain embodiments, $R^{C1}$ is butyl. In certain embodiments, $R^{C1}$ is pentyl. In certain embodiments, $R^{C1}$ is hexyl. In certain embodiments, $R^{C1}$ is substituted alkenyl. In certain embodiments, $R^{C1}$ is unsubstituted alkenyl. In certain embodiments, $R^{C1}$ is substituted alkynyl. In certain embodiments, $R^{C1}$ is unsubstituted alkynyl. In certain embodiments, $R^{C1}$ is substituted carbocyclyl. In certain embodiments, $R^{C1}$ is unsubstituted carbocyclyl. In certain embodiments, $R^{C1}$ is saturated carbocyclyl. In certain embodiments, $R^{C1}$ is unsaturated carbocyclyl. In certain embodiments, $R^{C1}$ is monocyclic carbocyclyl. In certain embodiments, $R^{C1}$ is 3- to 7-membered, monocyclic carbocyclyl. In certain embodiments, $R^{C1}$ is substituted heterocyclyl. In certain embodiments, $R^{C1}$ is unsubstituted heterocyclyl. In certain embodiments, $R^{C1}$ is saturated heterocyclyl. In certain embodiments, $R^{C1}$ is unsaturated heterocyclyl. In certain embodiments, $R^{C1}$ is heterocyclyl, wherein one, two, or three atoms in the heterocyclic ring system are independently selected from the group consisting of nitrogen, oxygen, and sulfur. In certain embodiments, $R^{C1}$ is monocyclic heterocyclyl. In certain embodiments, $R^{C1}$ is 3- to 7-membered, monocyclic heterocyclyl. In certain embodiments, $R^{C1}$ is substituted aryl. In certain embodiments, $R^{C1}$ is unsubstituted aryl. In certain embodiments, $R^{C1}$ is 6- to 10-membered aryl. In certain embodiments, $R^{C1}$ is substituted phenyl. In certain embodiments, $R^{C1}$ is unsubstituted phenyl. In certain embodiments, $R^{C1}$ is substituted heteroaryl. In certain embodiments, $R^{C1}$ is unsubstituted heteroaryl. In certain embodiments, $R^{C1}$ is heteroaryl, wherein one, two, three, or four atoms in the heteroaryl ring system are independently selected from the group consisting of nitrogen, oxygen, and sulfur. In certain embodiments, $R^{C1}$ is monocyclic heteroaryl. In certain embodiments, $R^{C1}$ is 5-membered, monocyclic heteroaryl. In certain embodiments, $R^{C1}$ is 6-membered, monocyclic heteroaryl. In certain embodiments, $R^{C1}$ is bicyclic heteroaryl, wherein the point of attachment may be on any atom of the bicyclic heteroaryl ring system, as valency permits. In certain embodiments, $R^{C1}$ is 9- or 10-membered, bicyclic heteroaryl. In certain embodiments, $R^{C1}$ is an oxygen protecting group. In certain embodiments, $R^{C1}$ is silyl, TBDPS, TBDMS, TIPS, TES, TMS, MOM, THP, t-Bu, Bn, allyl, acetyl, pivaloyl, or benzoyl.

Formula (I) includes substituent $R^{D1}$. In certain embodiments, $R^{D1}$ is H. In certain embodiments, $R^{D1}$ is halogen. In certain embodiments, $R^{D1}$ is F. In certain embodiments, $R^{D1}$ is Cl. In certain embodiments, $R^{D1}$ is Br. In certain embodiments, $R^{D1}$ is I (iodine). In certain embodiments, $R^{D1}$ is substituted alkyl. In certain embodiments, $R^{D1}$ is unsubstituted alkyl. In certain embodiments, $R^{D1}$ is unsubstituted $C_{1-6}$ alkyl. In certain embodiments, $R^{D1}$ is substituted $C_{1-6}$ alkyl. In certain embodiments, $R^{D1}$ is $C_{1-6}$ alkyl substituted with at least one halogen. In certain embodiments, $R^{D1}$ is —$CH_3$. In certain embodiments, $R^{D1}$ is substituted methyl.

In certain embodiments, $R^{D1}$ is —CH$_2$F. In certain embodiments, $R^{D1}$ is —CHF$_2$. In certain embodiments, $R^{D1}$ is —CF$_3$. In certain embodiments, $R^{D1}$ is ethyl. In certain embodiments, $R^{D1}$ is propyl. In certain embodiments, $R^{D1}$ is butyl. In certain embodiments, $R^{D1}$ is pentyl. In certain embodiments, $R^{D1}$ is hexyl. In certain embodiments, $R^{D1}$ is substituted alkenyl. In certain embodiments, $R^{D1}$ is unsubstituted alkenyl. In certain embodiments, $R^{D1}$ is substituted alkynyl. In certain embodiments, $R^{D1}$ is unsubstituted alkynyl. In certain embodiments, $R^{D1}$ is substituted carbocyclyl. In certain embodiments, $R^{D1}$ is unsubstituted carbocyclyl. In certain embodiments, $R^{D1}$ is saturated carbocyclyl. In certain embodiments, $R^{D1}$ is unsaturated carbocyclyl. In certain embodiments, $R^{D1}$ is monocyclic carbocyclyl. In certain embodiments, $R^{D1}$ is 3- to 7-membered, monocyclic carbocyclyl. In certain embodiments, $R^{D1}$ is substituted heterocyclyl. In certain embodiments, $R^{D1}$ is unsubstituted heterocyclyl. In certain embodiments, $R^{D1}$ is saturated heterocyclyl. In certain embodiments, $R^{D1}$ is unsaturated heterocyclyl. In certain embodiments, $R^{D1}$ is heterocyclyl, wherein one, two, or three atoms in the heterocyclic ring system are independently selected from the group consisting of nitrogen, oxygen, and sulfur. In certain embodiments, $R^{D1}$ is monocyclic heterocyclyl. In certain embodiments, $R^{D1}$ is 3- to 7-membered, monocyclic heterocyclyl. In certain embodiments, $R^{D1}$ is substituted aryl. In certain embodiments, $R^{D1}$ is unsubstituted aryl. In certain embodiments, $R^{D1}$ is 6- to 10-membered aryl. In certain embodiments, $R^{D1}$ is substituted phenyl. In certain embodiments, $R^{D1}$ is unsubstituted phenyl. In certain embodiments, $R^{D1}$ is substituted heteroaryl. In certain embodiments, $R^{D1}$ is unsubstituted heteroaryl. In certain embodiments, $R^{D1}$ is heteroaryl, wherein one, two, three, or four atoms in the heteroaryl ring system are independently selected from the group consisting of nitrogen, oxygen, and sulfur. In certain embodiments, $R^{D1}$ is monocyclic heteroaryl. In certain embodiments, $R^{D1}$ is 5-membered, monocyclic heteroaryl. In certain embodiments, $R^{D1}$ is 6-membered, monocyclic heteroaryl. In certain embodiments, $R^{D1}$ is bicyclic heteroaryl, wherein the point of attachment may be on any atom of the bicyclic heteroaryl ring system, as valency permits. In certain embodiments, $R^{D1}$ is 9- or 10-membered, bicyclic heteroaryl. In certain embodiments, $R^{D1}$ is —OR$^{D1a}$. In certain embodiments, $R^{D1}$ is —OH. In certain embodiments, $R^{D1}$ is —OMe. In certain embodiments, $R^{D1}$ is —OEt. In certain embodiments, $R^{D1}$ is —OPr. In certain embodiments, $R^{D1}$ is —OBu. In certain embodiments, $R^{D1}$ is —OBn. In certain embodiments, $R^{D1}$ is —OPh. In certain embodiments, $R^{D1}$ is —SR$^{D1a}$. In certain embodiments, $R^{D1}$ is —SH. In certain embodiments, $R^{D1}$ is —SMe. In certain embodiments, $R^{D1}$ is —N(R$^{D1a}$)$_2$. In certain embodiments, $R^{D1}$ is —NH$_2$. In certain embodiments, $R^{D1}$ is —NHMe. In certain embodiments, $R^{D1}$ is —NMe$_2$. In certain embodiments, $R^{D1}$ is —CN. In certain embodiments, $R^{D1}$ is —SCN. In certain embodiments, $R^{D1}$ is —C(=NR$^{D1a}$)R$^{D1a}$, —C(=NR$^{D1a}$)OR$^{D1a}$, or —C(=NR$^{D1a}$)N(R$^{D1a}$)$_2$. In certain embodiments, $R^{D1}$ is —C(=O)R$^{D1a}$ or —C(=O)OR$^{D1a}$. In certain embodiments, $R^{D1}$ is —C(=O)N(R$^{D1a}$)$_2$. In certain embodiments, $R^{D1}$ is —C(=O)NMe$_2$, —C(=O)NHMe, or —C(=O)NH$_2$. In certain embodiments, $R^{D1}$ is —NO$_2$. In certain embodiments, $R^{D1}$ is —NR$^{D1a}$C(=O)R$^{D1a}$, —NR$^{D1a}$C(=O)OR$^{D1a}$, or —NR$^{D1a}$C(=O)N(R$^{D1a}$)$_2$. In certain embodiments, $R^{D1}$ is —OC(=O)R$^{D1a}$, —OC(=O)OR$^{D1a}$, or —OC(=O)N(R$^{D1a}$)$_2$.

In certain embodiments, at least one instance of $R^{D1a}$ is H. In certain embodiments, at least one instance of $R^{D1a}$ is substituted acyl. In certain embodiments, at least one instance of $R^{D1a}$ is unsubstituted acyl. In certain embodiments, at least one instance of $R^{D1a}$ is acetyl. In certain embodiments, at least one instance of $R^{D1a}$ is substituted alkyl. In certain embodiments, at least one instance of $R^{D1a}$ is unsubstituted alkyl. In certain embodiments, at least one instance of $R^{D1a}$ is unsubstituted C$_{1-6}$ alkyl. In certain embodiments, at least one instance of $R^{D1a}$ is methyl. In certain embodiments, at least one instance of $R^{D1a}$ is ethyl. In certain embodiments, at least one instance of $R^{D1a}$ is propyl. In certain embodiments, at least one instance of $R^{D1a}$ is butyl. In certain embodiments, at least one instance of $R^{D1a}$ is pentyl. In certain embodiments, at least one instance of $R^{D1a}$ is hexyl. In certain embodiments, at least one instance of $R^{D1a}$ is substituted alkenyl. In certain embodiments, at least one instance of $R^{D1a}$ is unsubstituted alkenyl. In certain embodiments, at least one instance of $R^{D1a}$ is substituted alkynyl. In certain embodiments, at least one instance of $R^{D1a}$ is unsubstituted alkynyl. In certain embodiments, at least one instance of $R^{D1a}$ is substituted or unsubstituted carbocyclyl. In certain embodiments, at least one instance of $R^{D1a}$ is saturated carbocyclyl. In certain embodiments, at least one instance of $R^{D1a}$ is unsaturated carbocyclyl. In certain embodiments, at least one instance of $R^{D1a}$ is 3- to 7-membered, monocyclic carbocyclyl. In certain embodiments, at least one instance of $R^{D1a}$ is substituted or unsubstituted heterocyclyl. In certain embodiments, at least one instance of $R^{D1a}$ is saturated heterocyclyl. In certain embodiments, at least one instance of $R^{D1a}$ is saturated heterocyclyl. In certain embodiments, at least one instance of $R^{D1a}$ is heterocyclyl, wherein one, two, or three atoms in the heterocyclic ring system are independently selected from the group consisting of nitrogen, oxygen, and sulfur. In certain embodiments, at least one instance of $R^{D1a}$ is 3- to 7-membered, monocyclic heterocyclyl. In certain embodiments, at least one instance of $R^{D1a}$ is substituted or unsubstituted aryl. In certain embodiments, at least one instance of $R^{D1a}$ is 6- to 10-membered aryl. In certain embodiments, at least one instance of $R^{D1a}$ is monocyclic aryl. In certain embodiments, at least one instance of $R^{D1a}$ is substituted phenyl. In certain embodiments, at least one instance of $R^{D1a}$ is substituted phenyl. In certain embodiments, at least one instance of $R^{D1a}$ is bicyclic aryl. In certain embodiments, at least one instance of $R^{D1a}$ is substituted or unsubstituted heteroaryl. In certain embodiments, at least one instance of $R^{D1a}$ is heteroaryl, wherein one, two, three, or four atoms in the heteroaryl ring system are independently selected from the group consisting of nitrogen, oxygen, and sulfur. In certain embodiments, at least one instance of $R^{D1a}$ is monocyclic heteroaryl. In certain embodiments, at least one instance of $R^{D1a}$ is 5- or 6-membered, monocyclic heteroaryl. In certain embodiments, at least one instance of $R^{D1a}$ is bicyclic heteroaryl, wherein the point of attachment may be on any atom of the bicyclic heteroaryl ring system, as valency permits. In certain embodiments, at least one instance of $R^{D1a}$ is a nitrogen protecting group when attached to a nitrogen atom. In certain embodiments, at least one instance of $R^{D1a}$ is Bn, Boc, Cbz, Fmoc, trifluoroacetyl, triphenylmethyl, acetyl, or Ts when attached to a nitrogen atom. In certain embodiments, at least one instance of $R^{D1a}$ is an oxygen protecting group when attached to an oxygen atom. In certain embodiments, at least one instance of $R^{D1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, at least one instance of $R^{D1a}$ is a sulfur protecting group when attached to a sulfur atom. In certain embodiments, at least one instance of $R^{D1a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{D1a}$ are joined to form a substituted or unsubstituted heterocyclic ring. In certain embodiments, two instances of $R^{D1a}$ are joined to form a saturated or unsaturated heterocyclic ring. In certain embodiments, two instances of $R^{D1a}$ are joined to form a heterocyclic ring, wherein one, two, or three atoms in the heterocyclic ring system are independently selected from the group consisting of nitrogen, oxygen, and sulfur. In certain embodiments, two instances of $R^{D1a}$ are joined to form a 3- to 7-membered, monocyclic heterocyclic ring. In certain embodiments, two instances of $R^{D1a}$ are joined to form a substituted or unsubstituted heteroaryl ring. In certain embodiments, two instances of $R^{D1a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

Formula (I) includes substituent $R^{E1}$. In certain embodiments, $R^{E1}$ is H. In certain embodiments, $R^{E1}$ is substituted alkyl. In certain embodiments, $R^{E1}$ is unsubstituted alkyl. In certain embodiments, $R^{E1}$ is unsubstituted $C_{1-6}$ alkyl. In certain embodiments, $R^{E1}$ is substituted $C_{1-6}$ alkyl. In certain embodiments, $R^{E1}$ is $C_{1-6}$ alkyl substituted with at least one halogen. In certain embodiments, $R^{E1}$ is —$CH_3$. In certain embodiments, $R^{E1}$ is substituted methyl. In certain embodiments, $R^{E1}$ is —$CH_2F$. In certain embodiments, $R^{E1}$ is —$CHF_2$. In certain embodiments, $R^{E1}$ is —$CF_3$. In certain embodiments, $R^{E1}$ is ethyl. In certain embodiments, $R^{E1}$ is propyl. In certain embodiments, $R^{E1}$ is butyl. In certain embodiments, $R^{E1}$ is pentyl. In certain embodiments, $R^{E1}$ is hexyl. In certain embodiments, $R^{E1}$ is substituted alkenyl. In certain embodiments, $R^{E1}$ is unsubstituted alkenyl. In certain embodiments, $R^{E1}$ is substituted alkynyl. In certain embodiments, $R^{E1}$ is unsubstituted alkynyl. In certain embodiments, $R^{E1}$ is substituted carbocyclyl. In certain embodiments, $R^{E1}$ is unsubstituted carbocyclyl. In certain embodiments, $R^{E1}$ is saturated carbocyclyl. In certain embodiments, $R^{E1}$ is unsaturated carbocyclyl. In certain embodiments, $R^{E1}$ is monocyclic carbocyclyl. In certain embodiments, $R^{E1}$ is 3- to 7-membered, monocyclic carbocyclyl. In certain embodiments, $R^{E1}$ is substituted heterocyclyl. In certain embodiments, $R^{E1}$ is unsubstituted heterocyclyl. In certain embodiments, $R^{E1}$ is saturated heterocyclyl. In certain embodiments, $R^{E1}$ is unsaturated heterocyclyl. In certain embodiments, $R^{E1}$ is heterocyclyl, wherein one, two, or three atoms in the heterocyclic ring system are independently selected from the group consisting of nitrogen, oxygen, and sulfur. In certain embodiments, $R^{E1}$ is monocyclic heterocyclyl. In certain embodiments, $R^{E1}$ is 3- to 7-membered, monocyclic heterocyclyl. In certain embodiments, $R^{E1}$ is substituted aryl. In certain embodiments, $R^{E1}$ is unsubstituted aryl. In certain embodiments, $R^{E1}$ is 6- to 10-membered aryl. In certain embodiments, $R^{E1}$ is substituted phenyl. In certain embodiments, $R^{E1}$ is unsubstituted phenyl. In certain embodiments, $R^{E1}$ is substituted heteroaryl. In certain embodiments, $R^{E1}$ is unsubstituted heteroaryl. In certain embodiments, $R^{E1}$ is heteroaryl, wherein one, two, three, or four atoms in the heteroaryl ring system are independently selected from the group consisting of nitrogen, oxygen, and sulfur. In certain embodiments, $R^{E1}$ is monocyclic heteroaryl. In certain embodiments, $R^{E1}$ is 5-membered, monocyclic heteroaryl. In certain embodiments, $R^{E1}$ is 6-membered, monocyclic heteroaryl. In certain embodiments, $R^{E1}$ is bicyclic heteroaryl, wherein the point of attachment may be on any atom of the bicyclic heteroaryl ring system, as valency permits. In certain embodiments, $R^{E1}$ is 9- or 10-membered, bicyclic heteroaryl. In certain embodiments, $R^{E1}$ is a nitrogen protecting group. In certain embodiments, $R^{E1}$ is Bn, Boc, Cbz, Fmoc, trifluoroacetyl, triphenylmethyl, acetyl, or Ts.

Formula (I) includes substituent $R^{F1}$. In certain embodiments, $R^{F1}$ is H. In certain embodiments, $R^{F1}$ is substituted alkyl. In certain embodiments, $R^{F1}$ is unsubstituted alkyl. In certain embodiments, $R^{F1}$ is unsubstituted $C_{1-6}$ alkyl. In certain embodiments, $R^{F1}$ is substituted $C_{1-6}$ alkyl. In certain embodiments, $R^{F1}$ is $C_{1-6}$ alkyl substituted with at least one halogen. In certain embodiments, $R^{F1}$ is —$CH_3$. In certain embodiments, $R^{F1}$ is substituted methyl. In certain embodiments, $R^{F1}$ is —$CH_2F$. In certain embodiments, $R^{F1}$ is —$CHF_2$. In certain embodiments, $R^{F1}$ is —$CF_3$. In certain embodiments, $R^{F1}$ is ethyl. In certain embodiments, $R^{F1}$ is propyl. In certain embodiments, $R^{F1}$ is butyl. In certain embodiments, $R^{F1}$ is pentyl. In certain embodiments, $R^{F1}$ is hexyl. In certain embodiments, $R^{F1}$ is substituted alkenyl. In certain embodiments, $R^{F1}$ is unsubstituted alkenyl. In certain embodiments, $R^{F1}$ is substituted alkynyl. In certain embodiments, $R^{F1}$ is unsubstituted alkynyl. In certain embodiments, $R^{F1}$ is substituted carbocyclyl. In certain embodiments, $R^{F1}$ is unsubstituted carbocyclyl. In certain embodiments, $R^{F1}$ is saturated carbocyclyl. In certain embodiments, $R^{F1}$ is unsaturated carbocyclyl. In certain embodiments, $R^{F1}$ is monocyclic carbocyclyl. In certain embodiments, $R^{F1}$ is 3- to 7-membered, monocyclic carbocyclyl. In certain embodiments, $R^{F1}$ is substituted heterocyclyl. In certain embodiments, $R^{F1}$ is unsubstituted heterocyclyl. In certain embodiments, $R^{F1}$ is saturated heterocyclyl. In certain embodiments, $R^{F1}$ is unsaturated heterocyclyl. In certain embodiments, $R^{F1}$ is heterocyclyl, wherein one, two, or three atoms in the heterocyclic ring system are independently selected from the group consisting of nitrogen, oxygen, and sulfur. In certain embodiments, $R^{F1}$ is monocyclic heterocyclyl. In certain embodiments, $R^{F1}$ is 3- to 7-membered, monocyclic heterocyclyl. In certain embodiments, $R^{F1}$ is substituted aryl. In certain embodiments, $R^{F1}$ is unsubstituted aryl. In certain embodiments, $R^{F1}$ is 6- to 10-membered aryl. In certain embodiments, $R^{F1}$ is substituted phenyl. In certain embodiments, $R^{F1}$ is unsubstituted phenyl. In certain embodiments, $R^{F1}$ is substituted heteroaryl. In certain embodiments, $R^{F1}$ is unsubstituted heteroaryl. In certain embodiments, $R^{F1}$ is heteroaryl, wherein one, two, three, or four atoms in the heteroaryl ring system are independently selected from the group consisting of nitrogen, oxygen, and sulfur. In certain embodiments, $R^{F1}$ is monocyclic heteroaryl. In certain embodiments, $R^{F1}$ is 5-membered, monocyclic heteroaryl. In certain embodiments, $R^{F1}$ is 6-membered, monocyclic heteroaryl. In certain embodiments, $R^{F1}$ is bicyclic heteroaryl, wherein the point of attachment may be on any atom of the bicyclic heteroaryl ring system, as valency permits. In certain embodiments, $R^{F1}$ is 9- or 10-membered, bicyclic heteroaryl. In certain embodiments, $R^{F1}$ is a nitrogen protecting group. In certain embodiments, $R^{F1}$ is Bn, Boc, Cbz, Fmoc, trifluoroacetyl, triphenylmethyl, acetyl, or Ts.

Formula (I) includes substituent $R^{G1}$. In certain embodiments, $R^{G1}$ is H. In certain embodiments, $R^{G1}$ is halogen. In certain embodiments, $R^{G1}$ is F. In certain embodiments, $R^{G1}$ is Cl. In certain embodiments, $R^{G1}$ is Br. In certain embodiments, $R^{G1}$ is I (iodine). In certain embodiments, $R^{G1}$ is unsubstituted $C_{1-6}$ alkyl. In certain embodiments, $R^{G1}$ is substituted $C_{1-6}$ alkyl. In certain embodiments, $R^{G1}$ is $C_{1-6}$ alkyl substituted with at least one halogen. In certain embodiments, $R^{G1}$ is —$CH_3$. In certain embodiments, $R^{G1}$ is substituted methyl. In certain embodiments, $R^{G1}$ is —CH$_2$F. In certain embodiments, R$^{G1}$ is —CHF$_2$. In certain embodiments, R$^{G1}$ is —CF$_3$. In certain embodiments, R$^{G1}$ is ethyl. In certain embodiments, R$^{G1}$ is propyl. In certain embodiments, R$^{G1}$ is butyl. In certain embodiments, R$^{G1}$ is pentyl. In certain embodiments, R$^{G1}$ is hexyl.

Formula (I) includes substituent R$^{H1}$. In certain embodiments, R$^{H1}$ is H. In certain embodiments, R$^{H1}$ is halogen. In certain embodiments, R$^{H1}$ is F. In certain embodiments, R$^{H1}$ is Cl. In certain embodiments, R$^{H1}$ is Br. In certain embodiments, R$^{H1}$ is I (iodine). In certain embodiments, R$^{H1}$ is unsubstituted C$_{1-6}$ alkyl. In certain embodiments, R$^{H1}$ is substituted C$_{1-6}$alkyl. In certain embodiments, R$^{H1}$ is C$_{1-6}$ alkyl substituted with at least one halogen. In certain embodiments, R$^{H1}$ is —CH$_3$. In certain embodiments, R$^{H1}$ is substituted methyl. In certain embodiments, R$^{H1}$ is —CH$_2$F. In certain embodiments, R$^{H1}$ is —CHF$_2$. In certain embodiments, R$^{H1}$ is —CF$_3$. In certain embodiments, R$^{H1}$ is ethyl. In certain embodiments, R$^{H1}$ is propyl. In certain embodiments, R$^{H1}$ is butyl. In certain embodiments, R$^{H1}$ is pentyl. In certain embodiments, R$^{H1}$ is hexyl.

In certain embodiments, each of R$^{G1}$ and R$^{H1}$ is hydrogen.

In certain embodiments, R$^{G1}$ and R$^{H1}$ are joined to form a substituted phenyl ring. In certain embodiments, R$^{G1}$ and R$^{H1}$ are joined to form a unsubstituted phenyl ring. In certain embodiments, a compound described herein is of Formula (I-A):

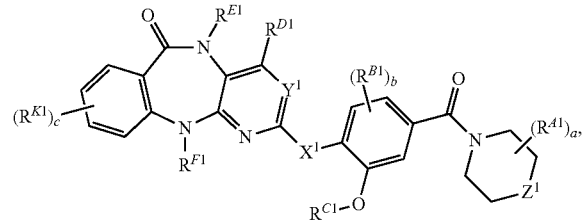

(I-A)

or a pharmaceutically acceptable salt, solvate, hydrate, polymorph, co-crystal, tautomer, stereoisomer, isotopically labeled derivative, or prodrug thereof, wherein:

each instance of R$^{K1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{K1a}$, —N(R$^{K1a}$)$_2$, —SR$^{K1a}$, —CN, —SCN, —C(=NR$^{K1a}$)R$^{K1a}$, —C(=NR$^{K1a}$)OR$^{K1a}$, —C(=NR$^{K1a}$)N(R$^{K1a}$)$_2$, —C(=O)R$^{K1a}$, —C(=O)OR$^{K1a}$, —C(=O)N(R$^{K1a}$)$_2$, —NO$_2$, —NR$^{K1a}$C(=O)R$^{K1a}$, —NR$^{K1a}$C(=O)OR$^{K1a}$, —NR$^{K1a}$C(=O)N(R$^{K1a}$)$_2$, —OC(=O)R$^{K1a}$, —OC(=O)OR$^{K1a}$, or —OC(=O)N(R$^{K1a}$)$_2$, wherein each instance of R$^{K1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{K1a}$ groups are joined to form a substituted or unsubstituted heterocyclic or substituted or unsubstituted heteroaryl ring; and c is 0, 1, 2, 3, or 4.

Formula (I-A) may include one or more substituents R$^{K1}$. In certain embodiments, at least two instances of R$^{K1}$ are different. In certain embodiments, all instances of R$^{K1}$ are the same. In certain embodiments, at least one instance of R$^{K1}$ is H. In certain embodiments, all instances of R$^{K1}$ are H. In certain embodiments, at least one instance of R$^{K1}$ is halogen. In certain embodiments, at least one instance of R$^{K1}$ is F. In certain embodiments, at least one instance of R$^{K1}$ is Cl. In certain embodiments, at least one instance of R$^{K1}$ is Br. In certain embodiments, at least one instance of R$^{K1}$ is I (iodine). In certain embodiments, at least one instance of R$^{K1}$ is substituted alkyl. In certain embodiments, at least one instance of R$^{K1}$ is unsubstituted alkyl. In certain embodiments, at least one instance of R$^{K1}$ is unsubstituted C$_{1-6}$alkyl. In certain embodiments, all instances of R$^{K1}$ are unsubstituted C$_{1-6}$ alkyl. In certain embodiments, at least one instance of R$^{K1}$ is substituted C$_{1-6}$ alkyl. In certain embodiments, at least one instance of R$^{K1}$ is C$_{1-6}$ alkyl substituted with at least one halogen. In certain embodiments, at least one instance of R$^{K1}$ is —CH$_3$. In certain embodiments, all instances of R$^{K1}$ are —CH$_3$. In certain embodiments, at least one instance of R$^{K1}$ is substituted methyl. In certain embodiments, at least one instance of R$^{K1}$ is —CH$_2$F. In certain embodiments, at least one instance of R$^{K1}$ is —CHF$_2$. In certain embodiments, at least one instance of R$^{K1}$ is —CF$_3$. In certain embodiments, at least one instance of R$^{K1}$ is ethyl. In certain embodiments, at least one instance of R$^{K1}$ is propyl. In certain embodiments, at least one instance of R$^{K1}$ is butyl. In certain embodiments, at least one instance of R$^{K1}$ is pentyl. In certain embodiments, at least one instance of R$^{K1}$ is hexyl. In certain embodiments, at least one instance of R$^{K1}$ is substituted alkenyl. In certain embodiments, at least one instance of R$^{K1}$ is unsubstituted alkenyl. In certain embodiments, at least one instance of R$^{K1}$ is substituted alkynyl. In certain embodiments, at least one instance of R$^{K1}$ is unsubstituted alkynyl. In certain embodiments, at least one instance of R$^{K1}$ is substituted carbocyclyl. In certain embodiments, at least one instance of R$^{K1}$ is unsubstituted carbocyclyl. In certain embodiments, at least one instance of R$^{K1}$ is saturated carbocyclyl. In certain embodiments, at least one instance of R$^{K1}$ is unsaturated carbocyclyl. In certain embodiments, at least one instance of R$^{K1}$ is monocyclic carbocyclyl. In certain embodiments, at least one instance of R$^{K1}$ is 3- to 7-membered, monocyclic carbocyclyl. In certain embodiments, at least one instance of R$^{K1}$ is substituted heterocyclyl. In certain embodiments, at least one instance of R$^{K1}$ is unsubstituted heterocyclyl. In certain embodiments, at least one instance of R$^{K1}$ is saturated heterocyclyl. In certain embodiments, at least one instance of R$^{K1}$ is unsaturated heterocyclyl. In certain embodiments, at least one instance of R$^{K1}$ is heterocyclyl, wherein one, two, or three atoms in the heterocyclic ring system are independently selected from the group consisting of nitrogen, oxygen, and sulfur. In certain embodiments, at least one instance of R$^{K1}$ is monocyclic heterocyclyl. In certain embodiments, at least one instance of R$^{K1}$ is 3- to 7-membered, monocyclic heterocyclyl. In certain embodiments, at least one instance of R$^{K1}$ is substituted aryl. In certain embodiments, at least one instance of R$^{K1}$ is unsubstituted aryl. In certain embodiments, at least one instance of R$^{K1}$ is 6- to 10-membered aryl. In certain embodiments, at least one instance of R$^{K1}$ is substituted phenyl. In certain embodiments, at least one instance of R$^{K1}$ is unsubstituted phenyl. In certain embodiments, at least one instance of $R^{K1}$ is substituted heteroaryl. In certain embodiments, at least one instance of $R^{K1}$ is unsubstituted heteroaryl. In certain embodiments, at least one instance of $R^{K1}$ is heteroaryl, wherein one, two, three, or four atoms in the heteroaryl ring system are independently selected from the group consisting of nitrogen, oxygen, and sulfur. In certain embodiments, at least one instance of $R^{K1}$ is monocyclic heteroaryl. In certain embodiments, at least one instance of $R^{K1}$ is 5-membered, monocyclic heteroaryl. In certain embodiments, at least one instance of $R^{K1}$ is 6-membered, monocyclic heteroaryl. In certain embodiments, at least one instance of $R^{K1}$ is bicyclic heteroaryl, wherein the point of attachment may be on any atom of the bicyclic heteroaryl ring system, as valency permits. In certain embodiments, at least one instance of $R^{K1}$ is 9- or 10-membered, bicyclic heteroaryl. In certain embodiments, at least one instance of $R^{K1}$ is —$OR^{K1a}$. In certain embodiments, at least one instance of $R^{K1}$ is —OH. In certain embodiments, at least one instance of $R^{K1}$ is —OMe. In certain embodiments, at least one instance of $R^{K1}$ is —OEt. In certain embodiments, at least one instance of $R^{K1}$ is —OPr. In certain embodiments, at least one instance of $R^{K1}$ is —OBu. In certain embodiments, at least one instance of $R^{K1}$ is —OBn. In certain embodiments, at least one instance of $R^{K1}$ is —OPh. In certain embodiments, at least one instance of $R^{K1}$ is —$SR^{K1a}$. In certain embodiments, at least one instance of $R^{K1}$ is —SH. In certain embodiments, at least one instance of $R^{K1}$ is —SMe. In certain embodiments, at least one instance of $R^{K1}$ is —$N(R^{K1a})_2$. In certain embodiments, at least one instance of $R^{K1}$ is —$NH_2$. In certain embodiments, at least one instance of $R^{K1}$ is —NHMe. In certain embodiments, at least one instance of $R^{K1}$ is —$NMe_2$. In certain embodiments, at least one instance of $R^{K1}$ is —CN. In certain embodiments, at least one instance of $R^{K1}$ is —SCN. In certain embodiments, at least one instance of $R^{K1}$ is —$C(=NR^{K1a})R^{K1a}$, —$C(=NR^{K1a})OR^{K1a}$, or —$C(=NR^{K1a})N(R^{K1a})_2$. In certain embodiments, at least one instance of $R^{K1}$ is —$C(=O)R^{K1a}$ or —$C(=O)OR^{K1a}$. In certain embodiments, at least one instance of $R^{K1}$ is —$C(=O)N(R^{K1a})_2$. In certain embodiments, at least one instance of $R^{K1}$ is —$C(=O)NMe_2$, —$C(=O)NHMe$, or —$C(=O)NH_2$. In certain embodiments, at least one instance of $R^{K1}$ is —$NO_2$. In certain embodiments, at least one instance of $R^{K1}$ is —$NR^{K1a}C(=O)R^{K1a}$, —$NR^{K1a}C(=O)OR^{K1a}$, or —$NR^{K1a}C(=O)N(R^{K1a})_2$. In certain embodiments, at least one instance of $R^{K1}$ is —$OC(=O)R^{K1a}$, —$OC(=O)OR^{K1a}$, or —$OC(=O)N(R^{K1a})_2$.

In certain embodiments, at least one instance of $R^{K1a}$ is H. In certain embodiments, at least one instance of $R^{K1a}$ is substituted acyl. In certain embodiments, at least one instance of $R^{K1a}$ is unsubstituted acyl. In certain embodiments, at least one instance of $R^{K1a}$ is acetyl. In certain embodiments, at least one instance of $R^{K1a}$ is substituted alkyl. In certain embodiments, at least one instance of $R^{K1a}$ is unsubstituted alkyl. In certain embodiments, at least one instance of $R^{K1a}$ is unsubstituted $C_{1-6}$ alkyl. In certain embodiments, at least one instance of $R^{K1a}$ is methyl. In certain embodiments, at least one instance of $R^{K1a}$ is ethyl. In certain embodiments, at least one instance of $R^{K1a}$ is propyl. In certain embodiments, at least one instance of $R^{K1a}$ is butyl. In certain embodiments, at least one instance of $R^{K1a}$ is pentyl. In certain embodiments, at least one instance of $R^{K1a}$ is hexyl. In certain embodiments, at least one instance of $R^{K1a}$ is substituted alkenyl. In certain embodiments, at least one instance of $R^{K1a}$ is unsubstituted alkenyl. In certain embodiments, at least one instance of $R^{K1a}$ is substituted alkynyl. In certain embodiments, at least one instance of $R^{K1a}$ is unsubstituted alkynyl. In certain embodiments, at least one instance of $R^{K1a}$ is substituted or unsubstituted carbocyclyl. In certain embodiments, at least one instance of $R^{K1a}$ is saturated carbocyclyl. In certain embodiments, at least one instance of $R^{K1a}$ is unsaturated carbocyclyl. In certain embodiments, at least one instance of $R^{K1a}$ is 3- to 7-membered, monocyclic carbocyclyl. In certain embodiments, at least one instance of $R^{K1a}$ is substituted or unsubstituted heterocyclyl. In certain embodiments, at least one instance of $R^{K1}$ is saturated heterocyclyl. In certain embodiments, at least one instance of $R^{K1a}$ is unsaturated heterocyclyl. In certain embodiments, at least one instance of $R^{K1a}$ is heterocyclyl, wherein one, two, or three atoms in the heterocyclic ring system are independently selected from the group consisting of nitrogen, oxygen, and sulfur. In certain embodiments, at least one instance of $R^{K1a}$ is 3- to 7-membered, monocyclic heterocyclyl. In certain embodiments, at least one instance of $R^{K1a}$ is substituted or unsubstituted aryl. In certain embodiments, at least one instance of $R^{K1a}$ is 6- to 10-membered aryl. In certain embodiments, at least one instance of $R^{K1a}$ is monocyclic aryl. In certain embodiments, at least one instance of $R^{K1a}$ is substituted phenyl. In certain embodiments, at least one instance of $R^{K1a}$ is unsubstituted phenyl. In certain embodiments, at least one instance of $R^{K1a}$ is bicyclic aryl. In certain embodiments, at least one instance of $R^{K1a}$ is substituted or unsubstituted heteroaryl. In certain embodiments, at least one instance of $R^{K1a}$ is heteroaryl, wherein one, two, three, or four atoms in the heteroaryl ring system are independently selected from the group consisting of nitrogen, oxygen, and sulfur. In certain embodiments, at least one instance of $R^{K1a}$ is monocyclic heteroaryl. In certain embodiments, at least one instance of $R^{K1a}$ is 5- or 6-membered, monocyclic heteroaryl. In certain embodiments, at least one instance of $R^{K1a}$ is bicyclic heteroaryl, wherein the point of attachment may be on any atom of the bicyclic heteroaryl ring system, as valency permits. In certain embodiments, at least one instance of $R^{K1a}$ is a nitrogen protecting group when attached to a nitrogen atom. In certain embodiments, at least one instance of $R^{K1a}$ is Bn, Boc, Cbz, Fmoc, trifluoroacetyl, triphenylmethyl, acetyl, or Ts when attached to a nitrogen atom. In certain embodiments, $R^{K1a}$ is an oxygen protecting group when attached to an oxygen atom. In certain embodiments, $R^{K1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{K1a}$ is a sulfur protecting group when attached to a sulfur atom. In certain embodiments, $R^{K1a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{K1a}$ are joined to form a substituted or unsubstituted heterocyclic ring. In certain embodiments, two instances of $R^{K1a}$ are joined to form a saturated or unsaturated heterocyclic ring. In certain embodiments, two instances of $R^{K1a}$ are joined to form a heterocyclic ring, wherein one, two, or three atoms in the heterocyclic ring system are independently selected from the group consisting of nitrogen, oxygen, and sulfur. In certain embodiments, two instances of $R^{K1a}$ are joined to form a 3- to 7-membered, monocyclic heterocyclic ring. In certain embodiments, two instances of $R^{K1a}$ are joined to form a substituted or unsubstituted heteroaryl ring. In certain embodiments, two instances of $R^{K1a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, c is 0. In certain embodiments, c is 1. In certain embodiments, c is 2. In certain embodiments, c is 3. In certain embodiments, c is 4.

In certain embodiments, a compound described herein is of Formula (I-B):

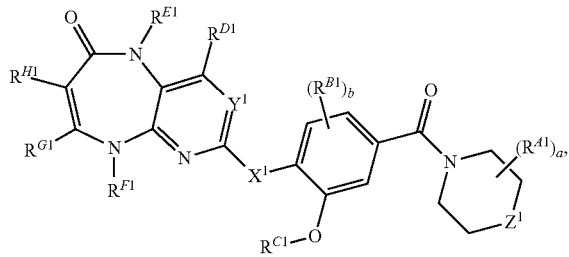

(I-B)

or a pharmaceutically acceptable salt, solvate, hydrate, polymorph, co-crystal, tautomer, stereoisomer, isotopically labeled derivative, or prodrug thereof.

In certain embodiments, a compound described herein is of the formula:

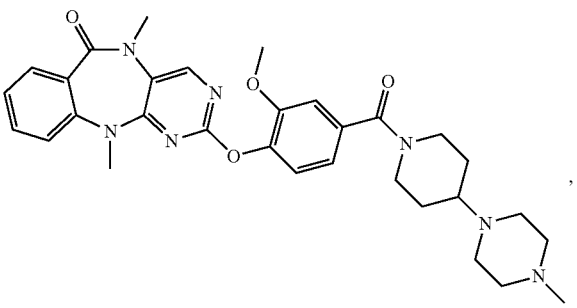

1 or a pharmaceutically acceptable salt, solvate, hydrate, polymorph, co-crystal, tautomer, stereoisomer, isotopically labeled derivative, or prodrug thereof.

In certain embodiments, a compound described herein is of the formula:

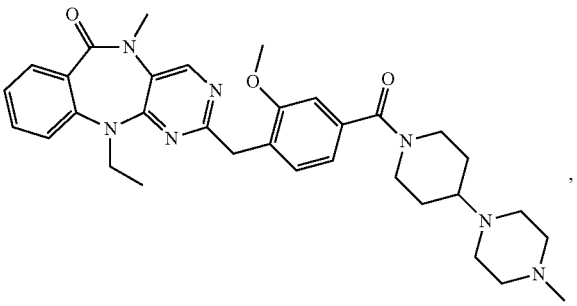

2 or a pharmaceutically acceptable salt, solvate, hydrate, polymorph, co-crystal, tautomer, stereoisomer, isotopically labeled derivative, or prodrug thereof.

Compounds of Formula (II-C)

In another aspect, the present invention provides compounds of Formula (II-C):

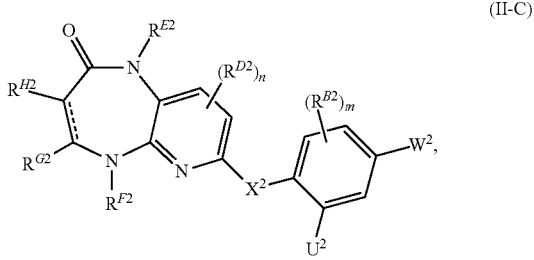

(II-C)

and pharmaceutically acceptable salts, solvates, hydrates, polymorphs, co-crystals, tautomers, stereoisomers, isotopically labeled derivatives, and prodrugs thereof, wherein:

≡≡≡ is a single or double bond;

$W^2$ is —S(=O)O$R^{W2}$, —S(=O)N($R^{W2}$)$_2$, —S(=O)$_2$O$R^{W2}$, —S(=O)$_2$N($R^{W2}$)$_2$,

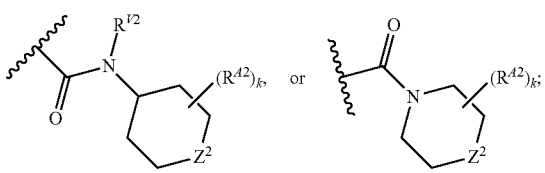

each instance of $R^{W2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two instances of $R^{W2}$ are joined to form a substituted or unsubstituted heterocyclic or substituted or unsubstituted heteroaryl ring; and $R^{V2}$ is hydrogen, substituted or unsubstituted $C_{1-6}$ alkyl, or a nitrogen protecting group;

$U^2$ is $R^{B2}$ or —O$R^{C2}$;

$X^2$ is —O—, —S—, —N($R^{X2}$)—, or —C($R^{X2}$)$_2$—, wherein each instance of $R^{X2}$ is independently hydrogen, halogen, substituted or unsubstituted $C_{1-6}$ alkyl, or a nitrogen protecting group when attached to a nitrogen atom;

$Z^2$ is —O—, —N($R^{Z2}$)— or —C($R^{Z2}$)$_2$—, wherein each instance of $R^{Z2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or two instances of $R^{Z2}$ are joined to form a substituted or unsubstituted carbocyclic or substituted or unsubstituted heterocyclic ring;

each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A2a}$, —N(R$^{A2a}$)$_2$, —SR$^{A2a}$, —CN, —SCN, —C(=NR$^{A2a}$)R$^{A2a}$, —C(=NR$^{A2a}$)OR$^{A2a}$, —C(=NR$^{A2a}$)N(R$^{A2a}$)$_2$, —C(=O)R$^{A2a}$, —C(=O)OR$^{A2a}$, —C(=O)N(R$^{A2a}$)$_2$, —NO$_2$, —NR$^{A2a}$C(=O)R$^{A2a}$, —NR$^{A2a}$C(=O)OR$^{A2a}$, —NR$^{A2a}$C(=O)N(R$^{A2a}$)$_2$, —OC(=O)R$^{A2a}$, —OC(=O)OR$^{A2a}$, or —OC(=O)N(R$^{A2a}$)$_2$, wherein each instance of R$^{A2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A2a}$ groups are joined to form a substituted or unsubstituted heterocyclic or substituted or unsubstituted heteroaryl ring;

k is 0, 1, 2, 3, 4, 5, 6, 7, 8, or 9;

each instance of R$^{B2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B2a}$, —N(R$^{B2a}$)$_2$, —SR$^{B2a}$, —CN, —SCN, —C(=NR$^{B2a}$)R$^{B2a}$, —C(=NR$^{B2a}$)OR$^{B2a}$, —C(=NR$^{B2a}$)N(R$^{B2a}$)$_2$, —C(=O)R$^{B2a}$, —C(=O)OR$^{B2a}$, —C(=O)N(R$^{B2a}$)$_2$, —NO$_2$, —NR$^{B2a}$C(=O)R$^{B2a}$, —NR$^{B2a}$C(=O)OR$^{B2a}$, —NR$^{B2a}$C(=O)N(R$^{B2a}$)$_2$, —OC(=O)R$^{B2a}$, —OC(=O)OR$^{B2a}$, or —OC(=O)N(R$^{B2a}$)$_2$, wherein each instance of R$^{B2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{B2a}$ groups are joined to form a substituted or unsubstituted heterocyclic or substituted or unsubstituted heteroaryl ring;

m is 0, 1, 2, or 3;

R$^{C2}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

each instance of R$^{D2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D2a}$, —N(R$^{D2a}$)$_2$, —SR$^{D2a}$, —CN, —SCN, —C(=NR$^{D2a}$)R$^{D2a}$, —C(=NR$^{D2a}$)OR$^{D2a}$, —C(=NR$^{D2a}$)N(R$^{D2a}$)$_2$, —C(=O)R$^{D2a}$, —C(=O)OR$^{D2a}$, —C(=O)N(R$^{D2a}$)$_2$, —NO$_2$, —NR$^{D2a}$C(=O)R$^{D2a}$, —NR$^{D2a}$C(=O)OR$^{D2a}$, —NR$^{D2a}$C(=O)N(R$^{D2a}$)$_2$, —OC(=O)R$^{D2a}$, —OC(=O)OR$^{D2a}$, or —OC(=O)N(R$^{D2a}$)$_2$, wherein each instance of R$^{D2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{D2a}$ groups are joined to form a substituted or unsubstituted heterocyclic or substituted or unsubstituted heteroaryl ring;

n is 0, 1, or 2;

R$^{E2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

R$^{F2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

R$^{G2}$ is hydrogen, halogen, or substituted or unsubstituted C$_{1-6}$ alkyl; and R$^{H2}$ is hydrogen, halogen, or substituted or unsubstituted C$_{1-6}$ alkyl;

or R$^{G2}$ and R$^{H2}$ are joined to form a substituted or unsubstituted phenyl ring.

Formula (II-C) includes a bond ═══. In certain embodiments ═══ is a single bond. In certain embodiments, ═══ is a double bond.

Formula (II-C) includes moiety W$^2$ on the phenyl ring. In certain embodiments, W$^2$ is —S(=O)OR$^{W2}$ or —S(=O)N(R$^{W2}$)$_2$, optionally wherein each instance of R$^{W2}$ is independently substituted or unsubstituted C$_{1-6}$ alkyl (e.g., Me), substituted or unsubstituted phenyl, an oxygen protecting group when attached to an oxygen atom, or a nitrogen protecting group when attached to a nitrogen atom, or optionally wherein two instances of R$^{W2}$ are joined to form a substituted or unsubstituted heterocyclic ring or substituted or unsubstituted heteroaryl ring. In certain embodiments, W$^2$ is —S(=O)OH. In certain embodiments, W$^2$ is —S(=O)NH(R$^{W2}$), optionally wherein R$^{W2}$ is substituted or unsubstituted C$_{1-6}$ alkyl (e.g., Me), substituted or unsubstituted phenyl, or a nitrogen protecting group. In certain embodiments, W$^2$ is —S(=O)NH$_2$. In certain embodiments, W$^2$ is —S(=O)$_2$OR$^{W2}$, optionally wherein R$^{W2}$ is substituted or unsubstituted C$_{1-6}$ alkyl (e.g., Me), substituted or unsubstituted phenyl, or an oxygen protecting group. In certain embodiments, W$^2$ is —S(=O)$_2$OH. In certain embodiments, W$^2$ is —S(=O)$_2$N(R$^2$)$_2$, optionally wherein each instance of R$^{W2}$ is independently substituted or unsubstituted C$_{1-6}$ alkyl (e.g., Me), substituted or unsubstituted phenyl, or a nitrogen protecting group, or optionally wherein two instances of R$^{W2}$ are joined to form a substituted or unsubstituted heterocyclic ring or substituted or unsubstituted heteroaryl ring. In certain embodiments, W$^2$ is —S(=O)$_2$NH(R$^{W2}$), optionally wherein R$^{W2}$ is substituted or unsubstituted C$_{1-6}$ alkyl (e.g., Me), substituted or unsubstituted phenyl, or a nitrogen protecting group. In certain embodiments, W$^2$ is —S(=O)$_2$NH$_2$.

In certain embodiments, $W^2$ is of the formula:

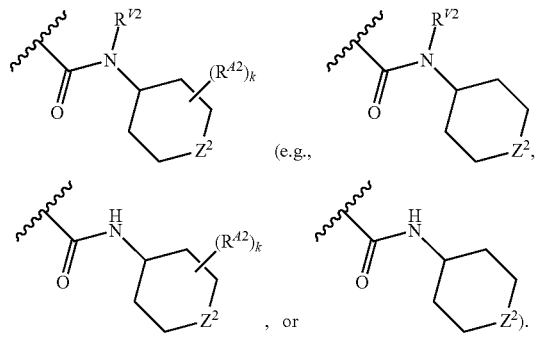

In certain embodiments, $W^2$ is of the formula:

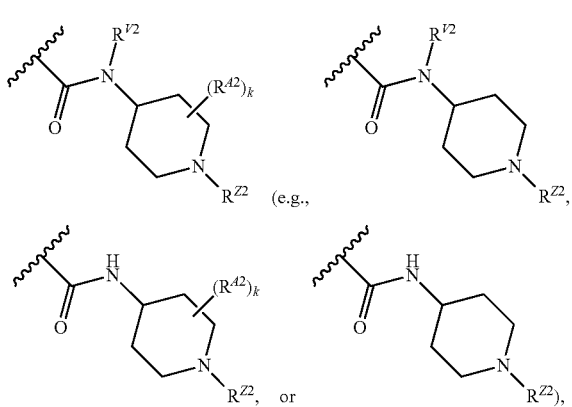

optionally wherein $R^{Z2}$ is substituted or unsubstituted $C_{1-6}$ alkyl or substituted or unsubstituted, 4- to 7-membered, monocyclic heterocyclyl, wherein one, two, or three atoms in the heterocyclic ring system are independently nitrogen, oxygen, or sulfur. In certain embodiments, $W^2$ is of the formula:

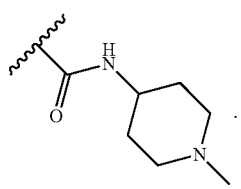 [SMILES: *C(=O)NC1CCN(C)CC1].

In certain embodiments, $W^2$ is of the formula:

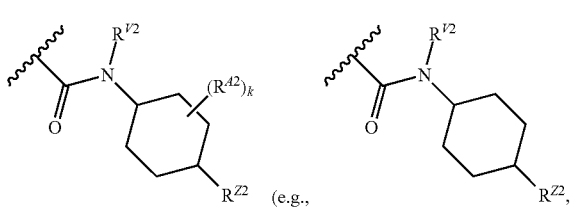

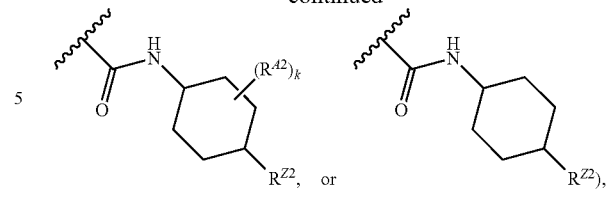

optionally wherein $R^{Z2}$ is substituted or unsubstituted $C_{1-6}$ alkyl or substituted or unsubstituted, 4- to 7-membered, monocyclic heterocyclyl, wherein one, two, or three atoms in the heterocyclic ring system are independently nitrogen, oxygen, or sulfur.

In certain embodiments, $W^2$ is of the formula:

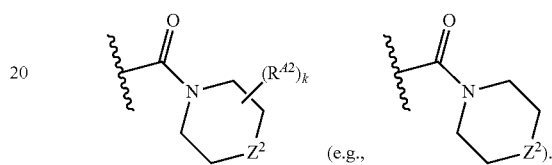

In certain embodiments, $W^2$ is of the formula

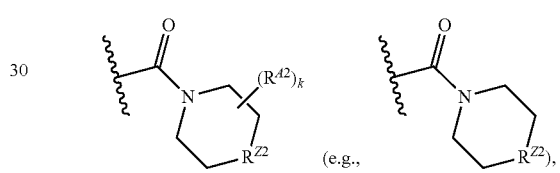

optionally wherein $R^{Z2}$ is substituted or unsubstituted $C_{1-6}$ alkyl or substituted or unsubstituted, 4- to 7-membered, monocyclic heterocyclyl, wherein one, two, or three atoms in the heterocyclic ring system are independently nitrogen, oxygen, or sulfur. In certain embodiments, $W^2$ s of the formula:

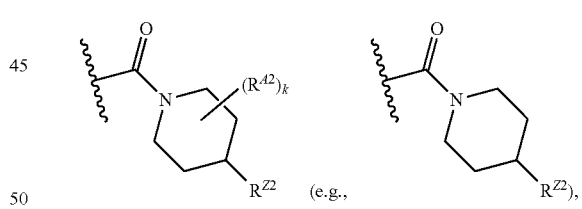

wherein $R^{Z2}$ is substituted or unsubstituted, 6-membered, monocyclic heterocyclyl, wherein one or two atoms in the heterocyclic ring system are independently nitrogen, oxygen, or sulfur. In certain embodiments, $W^2$ is of the formula:

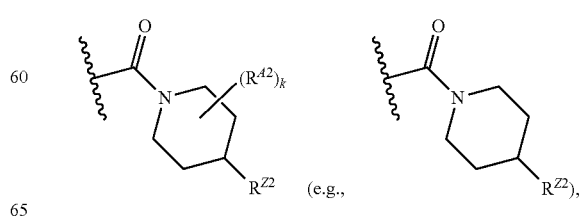

wherein $R^{Z2}$ is substituted or unsubstituted tetrahydropyranyl, substituted or unsubstituted piperidinyl, substituted or unsubstituted morpholinyl, or substituted or unsubstituted piperazinyl. In certain embodiments, $W^2$ is of the formula:

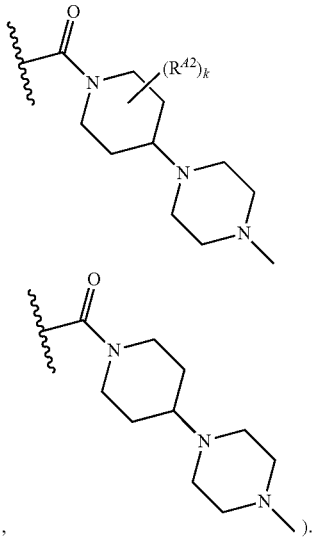

(e.g., ).

In certain embodiments, $W^2$ is of the formula:

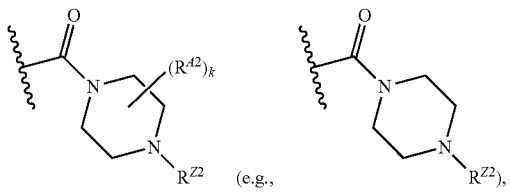

optionally wherein $R^{Z2}$ is substituted or unsubstituted $C_{1-6}$ alkyl or substituted or unsubstituted, 4- to 7-membered, monocyclic heterocyclyl, wherein one, two, or three atoms in the heterocyclic ring system are independently nitrogen, oxygen, or sulfur. In certain embodiments, $W^2$ is of the formula:

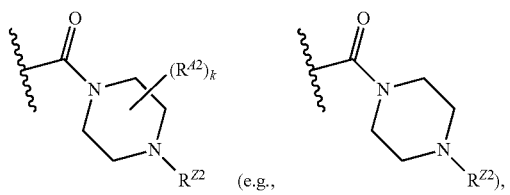

wherein $R^{Z2}$ is substituted or unsubstituted, 6-membered, monocyclic heterocyclyl, wherein one or two atoms in the heterocyclic ring system are independently nitrogen, oxygen, or sulfur. In certain embodiments, $W^2$ is of the formula:

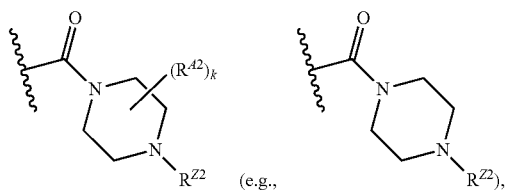

wherein $R^{Z2}$ is substituted or unsubstituted tetrahydropyranyl, substituted or unsubstituted piperidinyl, substituted or unsubstituted morpholinyl, or substituted or unsubstituted piperazinyl.

Formula (II-C) may include one or two substituents $R^{W2}$. When Formula (II-C) includes two instances of $R^{W2}$, the two instances of $R^{W2}$ may be the same or different from each other. In certain embodiments, at least one instance of $R^{W2}$ is H. In certain embodiments, each instance of $R^{W2}$ is H. In certain embodiments, at least one instance of $R^{W2}$ is substituted acyl. In certain embodiments, at least one instance of $R^{W2}$ is unsubstituted acyl. In certain embodiments, at least one instance of $R^{W2}$ is acetyl. In certain embodiments, at least one instance of $R^{W2}$ is substituted alkyl. In certain embodiments, at least one instance of $R^{W2}$ is unsubstituted alkyl. In certain embodiments, at least one instance of $R^{W2}$ is unsubstituted $C_{1-6}$ alkyl. In certain embodiments, at least one instance of $R^{W2}$ is methyl. In certain embodiments, at least one instance of $R^{W2}$ is ethyl, propyl, butyl, pentyl, or hexyl. In certain embodiments, at least one instance of $R^{W2}$ is substituted $C_{1-6}$ alkyl. In certain embodiments, at least one instance of $R^{W2}$ is substituted alkenyl. In certain embodiments, at least one instance of $R^{W2}$ is unsubstituted alkenyl. In certain embodiments, at least one instance of $R^{W2}$ is substituted alkynyl. In certain embodiments, at least one instance of $R^{W2}$ is unsubstituted alkynyl. In certain embodiments, at least one instance of $R^{W2}$ is substituted or unsubstituted carbocyclyl. In certain embodiments, at least one instance of $R^{W2}$ is saturated carbocyclyl. In certain embodiments, at least one instance of $R^{W2}$ is unsaturated carbocyclyl. In certain embodiments, at least one instance of $R^{W2}$ is 3- to 7-membered, monocyclic carbocyclyl. In certain embodiments, at least one instance of $R^{W2}$ is substituted or unsubstituted heterocyclyl. In certain embodiments, at least one instance of $R^{W2}$ is saturated heterocyclyl. In certain embodiments, at least one instance of $R^{W2}$ is unsaturated heterocyclyl. In certain embodiments, at least one instance of $R^{W2}$ is substituted or unsubstituted, 4- to 7-membered, monocyclic heterocyclyl, wherein one, two, or three atoms in the heterocyclic ring system are independently nitrogen, oxygen, or sulfur. In certain embodiments, at least one instance of $R^{W2}$ is substituted or unsubstituted, 6-membered, monocyclic heterocyclyl, wherein one or two atoms in the heterocyclic ring system are independently nitrogen, oxygen, or sulfur. In certain embodiments, at least one instance of $R^{W2}$ is substituted or unsubstituted aryl. In certain embodiments, at least one instance of $R^{W2}$ is 6- to 10-membered aryl. In certain embodiments, at least one instance of $R^{W2}$ is monocyclic aryl. In certain embodiments, at least one instance of $R^{W2}$ is substituted phenyl. In certain embodiments, at least one instance of $R^{W2}$ is unsubstituted phenyl. In certain embodiments, at least one instance of $R^{W2}$ is bicyclic aryl. In certain embodiments, at least one instance of $R^{W2}$ is substituted or unsubstituted heteroaryl. In certain embodiments, at least one instance of $R^{W2}$ is heteroaryl, wherein one, two, three, or four atoms in the heteroaryl ring system are independently selected from the group consisting of nitrogen, oxygen, and sulfur. In certain embodiments, at least one instance of $R^{W2}$ is monocyclic heteroaryl. In certain embodiments, at least one instance of $R^{W2}$ is 5- or 6-membered, monocyclic heteroaryl. In certain embodiments, at least one instance of $R^{W2}$ is bicyclic heteroaryl, wherein the point of attachment may be on any atom of the bicyclic heteroaryl ring system, as valency permits. In certain embodiments, $R^{W2}$ is an oxygen protecting group when attached to an oxygen atom. In certain embodiments, $R^{W2}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, at least one instance of $R^{W2}$ is a nitrogen protecting group when attached to a nitrogen atom. In certain embodiments, at least one instance of $R^{W2}$ is Bn, Boc, Cbz, Fmoc, trifluoroacetyl, triphenylmethyl, acetyl, or Ts when attached to a nitrogen atom. In certain embodiments, two instances of $R^{W2}$ are joined to form a substituted or unsubstituted heterocyclic ring. In certain embodiments, two instances of $R^{W2}$ are joined to form a saturated or unsaturated heterocyclic ring. In certain embodiments, two instances of $R^{W2}$ are joined to form a 3- to 7-membered, monocyclic heterocyclic ring, wherein one, two, or three atoms in the heterocyclic ring system are independently selected from the group consisting of nitrogen, oxygen, and sulfur. In certain embodiments, two instances of $R^{W2}$ are joined to form a substituted or unsubstituted heteroaryl ring (e.g., substituted or unsubstituted, 5- to 6-membered, monocyclic heteroaryl ring, wherein one, two, three, or four atoms in the heteroaryl ring system are independently selected from the group consisting of nitrogen, oxygen, and sulfur).

Formula (II-C) may include substituent $R^{V2}$ on a nitrogen atom. In certain embodiments, $R^{V2}$ is H. In certain embodiments, $R^{V2}$ is substituted or unsubstituted $C_{1-6}$ alkyl. In certain embodiments, $R^{V2}$ is Me. In certain embodiments, $R^{V2}$ is substituted methyl (e.g., —$CF_3$ or Bn). In certain embodiments, $R^{V2}$ is Et, substituted ethyl (e.g., perfluoroethyl), Pr, substituted propyl (e.g., perfluoropropyl or —$(CH_2)_3NH_2$), Bu, or substituted butyl (e.g., perfluorobutyl). In certain embodiments, $R^{V2}$ is a nitrogen protecting group (e.g., Bn, Boc, Cbz, Fmoc, trifluoroacetyl, triphenylmethyl, acetyl, or Ts).

Formula (II-C) includes moiety $U^2$ on the phenyl ring. In certain embodiments, $U^2$ is $R^{B2}$. In certain embodiments, $U^2$ is H. In certain embodiments, $U^2$ is —$OR^{C2}$, optionally wherein $R^{C2}$ is substituted or unsubstituted $C_{1-6}$ alkyl. In certain embodiments, $U^2$ is —OMe.

In certain embodiments, $W^2$ is of the formula:

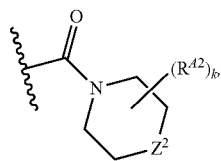

and $U^2$ is —$OR^{C2}$, and thus a compound of Formula (II-C) is of Formula (II):

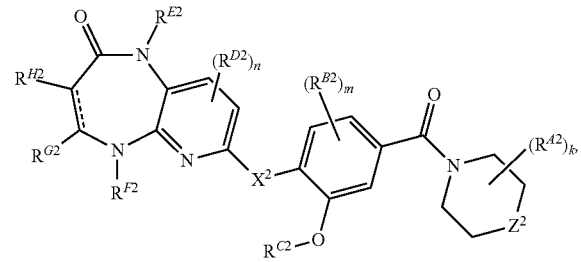

(II)

or a pharmaceutically acceptable salt, solvate, hydrate, polymorph, co-crystal, tautomer, stereoisomer, isotopically labeled derivative, or prodrug thereof.

In certain embodiments, $W^2$ is of the formula:

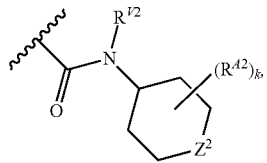

and $U^2$ is —$OR^{C2}$, and thus a compound of Formula (II-C) is of the formula:

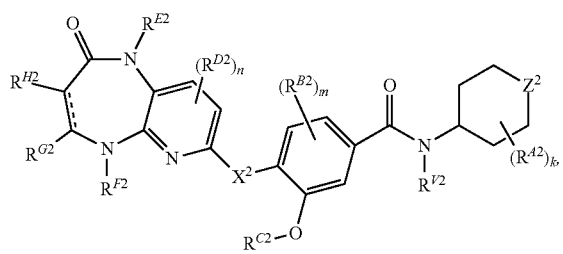

or a pharmaceutically acceptable salt, solvate, hydrate, polymorph, co-crystal, tautomer, stereoisomer, isotopically labeled derivative, or prodrug thereof.

In certain embodiments, $W^2$ is —S(=O)$OR^{W2}$, —S(=O)N($R^{W2}$)$_2$, —S(=O)$_2OR^{W2}$, —S(=O)$_2$N($R^{W2}$)$_2$, and $U^2$ is $R^{B2}$ (e.g., H). In certain embodiments, $W^2$ is —S(=O)$_2$N($R^2$)$_2$ (e.g., —S(=O)$_2NH_2$), and $U^2$ is $R^{B2}$ (e.g., H).

Formula (II-C) includes a divalent moiety $X^2$. In certain embodiments, $X^2$ is —O—. In certain embodiments, $X^2$ is —S—. In certain embodiments, $X^2$ is —N($R^{X2}$)—. In certain embodiments, $X^2$ is —NH—. In certain embodiments, $X^2$ is —N(substituted or unsubstituted, $C_{1-6}$ alkyl)-. In certain embodiments, $X^2$ is —N($CH_3$)—. In certain embodiments, $X^2$ is —C($R^{X2}$)$_2$—. In certain embodiments, $X^2$ is —CH($R^{X2}$)—. In certain embodiments, $X^2$ is —$CH_2$—.

In certain embodiments, at least one instance of $R^{X2}$ is H. In certain embodiments, each instance of $R^{X2}$ is H. In certain embodiments, at least one instance of $R^{X2}$ is halogen. In certain embodiments, at least one instance of $R^{X2}$ is F. In certain embodiments, at least one instance of $R^{X2}$ is Cl. In certain embodiments, at least one instance of $R^{X2}$ is Br. In certain embodiments, at least one instance of $R^{X2}$ is I (iodine). In certain embodiments, at least one instance of $R^{X2}$ is unsubstituted $C_{1-6}$ alkyl. In certain embodiments, each instance of $R^{X2}$ is unsubstituted $C_{1-6}$ alkyl. In certain embodiments, at least one instance of $R^{X2}$ is substituted $C_{1-6}$ alkyl. In certain embodiments, at least one instance of $R^{X2}$ is $C_{1-6}$ alkyl substituted with at least one halogen. In certain embodiments, at least one instance of $R^{X2}$ is —$CH_3$. In certain embodiments, each instance of $R^{X2}$ is —$CH_3$. In certain embodiments, at least one instance of $R^{X2}$ is substituted methyl. In certain embodiments, at least one instance of $R^{X2}$ is —$CH_2F$. In certain embodiments, at least one instance of $R^{X2}$ is —$CHF_2$. In certain embodiments, at least one instance of $R^{X2}$ is —$CF_3$. In certain embodiments, at least one instance of $R^{X2}$ is ethyl. In certain embodiments, at least one instance of $R^{X2}$ is propyl. In certain embodiments, at least one instance of $R^{X2}$ is butyl. In certain embodiments, at least one instance of $R^{X2}$ is pentyl. In certain embodiments, at least one instance of $R^{X2}$ is hexyl.

Formula (II-C) includes a divalent moiety $Z^2$. In certain embodiments, $Z^2$ is —O—. In certain embodiments, $Z^2$ is —N($R^{Z2}$)—. In certain embodiments, $Z^2$ is —NH—. In certain embodiments, $Z^2$ is —N(substituted or unsubstituted, $C_{1-6}$ alkyl)-. In certain embodiments, $Z^2$ is —N(substituted or unsubstituted, 4- to 7-membered, monocyclic heterocyclyl)-. In certain embodiments, $Z^2$ is —C($R^{Z2}$)$_2$—. In certain embodiments, $Z^2$ is —CH($R^{Z2}$)—. In certain embodiments, $Z^2$ is —CH(substituted or unsubstituted, $C_{1-6}$ alkyl)-. In certain embodiments, $Z^2$ is —CH(substituted or unsubstituted, 4- to 7-membered, monocyclic heterocyclyl)-.

Formula (II-C) may include one or more substituents $R^{Z2}$ on the divalent moiety $Z^2$. In certain embodiments, at least one instance of $R^{Z2}$ is H. In certain embodiments, at least one instance of $R^{Z2}$ is substituted acyl. In certain embodiments, at least one instance of $R^{Z2}$ is unsubstituted acyl. In certain embodiments, at least one instance of $R^{Z2}$ is acetyl. In certain embodiments, at least one instance of $R^{Z2}$ is substituted alkyl. In certain embodiments, at least one instance of $R^{Z2}$ is unsubstituted alkyl. In certain embodiments, at least one instance of $R^{Z2}$ is unsubstituted $C_{1-6}$ alkyl. In certain embodiments, at least one instance of $R^{Z2}$ is methyl. In certain embodiments, at least one instance of $R^{Z2}$ is ethyl. In certain embodiments, at least one instance of $R^{Z2}$ is propyl. In certain embodiments, at least one instance of $R^{Z2}$ is butyl. In certain embodiments, at least one instance of $R^{Z2}$ is pentyl. In certain embodiments, at least one instance of $R^{Z2}$ is hexyl. In certain embodiments, at least one instance of $R^{Z2}$ is substituted alkenyl. In certain embodiments, at least one instance of $R^{Z2}$ is unsubstituted alkenyl. In certain embodiments, at least one instance of $R^{Z2}$ is substituted alkynyl. In certain embodiments, at least one instance of $R^{Z2}$ is unsubstituted alkynyl. In certain embodiments, at least one instance of $R^{Z2}$ is substituted or unsubstituted carbocyclyl. In certain embodiments, at least one instance of $R^{Z2}$ is saturated carbocyclyl. In certain embodiments, at least one instance of $R^2$ is unsaturated carbocyclyl. In certain embodiments, at least one instance of $R^{Z2}$ is 3- to 7-membered, monocyclic carbocyclyl. In certain embodiments, at least one instance of $R^{Z2}$ is substituted or unsubstituted heterocyclyl. In certain embodiments, at least one instance of $R^{Z2}$ is saturated heterocyclyl. In certain embodiments, at least one instance of $R^{Z2}$ is unsaturated heterocyclyl. In certain embodiments, at least one instance of $R^{Z2}$ is substituted or unsubstituted, 4- to 7-membered, monocyclic heterocyclyl, wherein one, two, or three atoms in the heterocyclic ring system are independently nitrogen, oxygen, or sulfur. In certain embodiments, at least one instance of $R^{Z2}$ is substituted or unsubstituted, 6-membered, monocyclic heterocyclyl, wherein one or two atoms in the heterocyclic ring system are independently nitrogen, oxygen, or sulfur. In certain embodiments, at least one instance of $R^{Z2}$ is of the formula:

In certain embodiments, at least one instance of $R^{Z2}$ is of the formula:

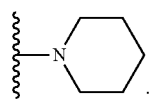

In certain embodiments, at least one instance of $R^{Z2}$ is of the formula:

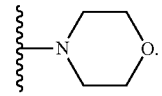

In certain embodiments, at least one instance of $R^{Z2}$ is of the formula:

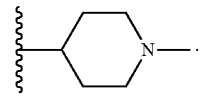

In certain embodiments, at least one instance of $R^{Z2}$ is of the formula:

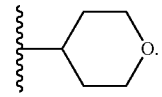

In certain embodiments, at least one instance of $R^{Z2}$ is substituted or unsubstituted aryl. In certain embodiments, at least one instance of $R^{Z2}$ is 6- to 10-membered aryl. In certain embodiments, at least one instance of $R^{Z2}$ is monocyclic aryl. In certain embodiments, at least one instance of $R^{Z2}$ is substituted phenyl. In certain embodiments, at least one instance of $R^{Z2}$ is unsubstituted phenyl. In certain embodiments, at least one instance of $R^{Z2}$ is bicyclic aryl. In certain embodiments, at least one instance of $R^{Z2}$ is substituted or unsubstituted heteroaryl. In certain embodiments, at least one instance of $R^{Z2}$ is heteroaryl, wherein one, two, three, or four atoms in the heteroaryl ring system are independently selected from the group consisting of nitrogen, oxygen, and sulfur. In certain embodiments, at least one instance of $R^{Z2}$ is monocyclic heteroaryl. In certain embodiments, at least one instance of $R^{Z2}$ is 5- or 6-membered, monocyclic heteroaryl. In certain embodiments, at least one instance of $R^{Z2}$ is bicyclic heteroaryl, wherein the point of attachment may be on any atom of the bicyclic heteroaryl ring system, as valency permits. In certain embodiments, at least one instance of $R^{Z2}$ is a nitrogen protecting group when attached to a nitrogen atom. In certain embodiments, at least one instance of $R^{Z2}$ is Bn, Boc, Cbz, Fmoc, trifluoroacetyl, triphenylmethyl, acetyl, or Ts when attached to a nitrogen atom. In certain embodiments, two instances of $R^{Z2}$ are joined to form a substituted or unsubstituted carbocyclic ring. In certain embodiments, two instances of $R^{Z2}$ are joined to form a saturated or unsaturated carbocyclic ring. In certain embodiments, two instances of $R^{Z2}$ are joined to form a substituted or unsubstituted, 3- to 7-membered, monocyclic carbocyclic ring. In certain embodiments, two instances of $R^{Z2}$ are joined to form a substituted or unsubstituted heterocyclic ring. In certain embodiments, two instances of $R^{Z2}$ are joined to form a saturated or unsaturated heterocyclic ring. In certain embodiments, two instances of $R^{Z2}$ are joined to form a heterocyclic ring, wherein one, two, or three atoms in the heterocyclic ring system are independently selected from the group consisting of nitrogen, oxygen, and sulfur. In certain embodiments, two instances of $R^{Z2}$ are joined to form a 3- to 7-membered, monocyclic heterocyclic ring.

Formula (II-C) may include one or more substituents $R^{A2}$. In certain embodiments, at least two instances of $R^{A2}$ are different. In certain embodiments, all instances of $R^{A2}$ are the same. In certain embodiments, at least one instance of $R^{A2}$ is H. In certain embodiments, all instances of $R^{A2}$ are H. In certain embodiments, at least one instance of $R^{A2}$ is halogen. In certain embodiments, at least one instance of $R^{A2}$ is F. In certain embodiments, at least one instance of $R^{A2}$ is Cl. In certain embodiments, at least one instance of $R^{A2}$ is Br. In certain embodiments, at least one instance of $R^{A2}$ is I (iodine). In certain embodiments, at least one instance of $R^{A2}$ is substituted alkyl. In certain embodiments, at least one instance of $R^{A2}$ is unsubstituted alkyl. In certain embodiments, at least one instance of $R^{A2}$ is unsubstituted $C_{1-6}$ alkyl. In certain embodiments, all instances of $R^{A2}$ are unsubstituted $C_{1-6}$ alkyl. In certain embodiments, at least one instance of $R^{A2}$ is substituted $C_{1-6}$ alkyl. In certain embodiments, at least one instance of $R^{A2}$ is $C_{1-6}$ alkyl substituted with at least one halogen. In certain embodiments, at least one instance of $R^{A2}$ is —$CH_3$. In certain embodiments, all instances of $R^{A2}$ are —$CH_3$. In certain embodiments, at least one instance of $R^{A2}$ is substituted methyl. In certain embodiments, at least one instance of $R^{A2}$ is —$CH_2F$. In certain embodiments, at least one instance of $R^{A2}$ is —$CHF_2$. In certain embodiments, at least one instance of $R^{A2}$ is —$CF_3$. In certain embodiments, at least one instance of $R^{A2}$ is ethyl. In certain embodiments, at least one instance of $R^{A2}$ is propyl. In certain embodiments, at least one instance of $R^{A2}$ is butyl. In certain embodiments, at least one instance of $R^{A2}$ is pentyl. In certain embodiments, at least one instance of $R^{A2}$ is hexyl. In certain embodiments, at least one instance of $R^{A2}$ is substituted alkenyl. In certain embodiments, at least one instance of $R^{A2}$ is unsubstituted alkenyl. In certain embodiments, at least one instance of $R^{A2}$ is substituted alkynyl. In certain embodiments, at least one instance of $R^{A2}$ is unsubstituted alkynyl. In certain embodiments, at least one instance of $R^{A2}$ is substituted carbocyclyl. In certain embodiments, at least one instance of $R^{A2}$ is unsubstituted carbocyclyl. In certain embodiments, at least one instance of $R^{A2}$ is saturated carbocyclyl. In certain embodiments, at least one instance of $R^{A2}$ is unsaturated carbocyclyl. In certain embodiments, at least one instance of $R^{A2}$ is monocyclic carbocyclyl. In certain embodiments, at least one instance of $R^{A2}$ is 3- to 7-membered, monocyclic carbocyclyl. In certain embodiments, at least one instance of $R^{A2}$ is substituted heterocyclyl. In certain embodiments, at least one instance of $R^{A2}$ is unsubstituted heterocyclyl. In certain embodiments, at least one instance of $R^{A2}$ is saturated heterocyclyl. In certain embodiments, at least one instance of $R^{A2}$ is unsaturated heterocyclyl. In certain embodiments, at least one instance of $R^{A2}$ is heterocyclyl, wherein one, two, or three atoms in the heterocyclic ring system are independently selected from the group consisting of nitrogen, oxygen, and sulfur. In certain embodiments, at least one instance of $R^{A2}$ is monocyclic heterocyclyl. In certain embodiments, at least one instance of $R^{A2}$ is 3- to 7-membered, monocyclic heterocyclyl. In certain embodiments, at least one instance of $R^{A2}$ is substituted aryl. In certain embodiments, at least one instance of $R^{A2}$ is unsubstituted aryl. In certain embodiments, at least one instance of $R^{A2}$ is 6- to 10-membered aryl. In certain embodiments, at least one instance of $R^{A2}$ is substituted phenyl. In certain embodiments, at least one instance of $R^{A2}$ is unsubstituted phenyl. In certain embodiments, at least one instance of $R^{A2}$ is substituted heteroaryl. In certain embodiments, at least one instance of $R^{A2}$ is unsubstituted heteroaryl. In certain embodiments, at least one instance of $R^{A2}$ is heteroaryl, wherein one, two, three, or four atoms in the heteroaryl ring system are independently selected from the group consisting of nitrogen, oxygen, and sulfur. In certain embodiments, at least one instance of $R^{A2}$ is monocyclic heteroaryl. In certain embodiments, at least one instance of $R^{A2}$ is 5-membered, monocyclic heteroaryl. In certain embodiments, at least one instance of $R^{A2}$ is 6-membered, monocyclic heteroaryl. In certain embodiments, at least one instance of $R^{A2}$ is bicyclic heteroaryl, wherein the point of attachment may be on any atom of the bicyclic heteroaryl ring system, as valency permits. In certain embodiments, at least one instance of $R^{A2}$ is 9- or 10-membered, bicyclic heteroaryl. In certain embodiments, at least one instance of $R^{A2}$ is —$OR^{A2a}$. In certain embodiments, at least one instance of $R^{A2}$ is —OH. In certain embodiments, at least one instance of $R^{A2}$ is —OMe. In certain embodiments, at least one instance of $R^{A2}$ is —OEt. In certain embodiments, at least one instance of $R^{A2}$ is —OPr. In certain embodiments, at least one instance of $R^{A2}$ is —OBu. In certain embodiments, at least one instance of $R^{A2}$ is —OBn. In certain embodiments, at least one instance of $R^{A2}$ is —OPh. In certain embodiments, at least one instance of $R^{A2}$ is —$SR^{A2a}$. In certain embodiments, at least one instance of $R^{A2}$ is —SH. In certain embodiments, at least one instance of $R^{A2}$ is —SMe. In certain embodiments, at least one instance of $R^{A2}$ is —$N(R^{A2a})_2$. In certain embodiments, at least one instance of $R^{A2}$ is —$NH_2$. In certain embodiments, at least one instance of $R^{A2}$ is —NHMe. In certain embodiments, at least one instance of $R^{A2}$ is —$NMe_2$. In certain embodiments, at least one instance of $R^{A2}$ is —CN. In certain embodiments, at least one instance of $R^{A2}$ is —SCN. In certain embodiments, at least one instance of $R^{A2}$ is —$C(=NR^{A2a})R^{A2a}$, —$C(=NR^{A2a})OR^{A2a}$, or —$C(=NR^{A2a})N(R^{A2a})_2$. In certain embodiments, at least one instance of $R^{A2}$ is —$C(=O)R^{A2a}$ or —$C(=O)OR^{A2a}$. In certain embodiments, at least one instance of $R^{A2}$ is —$C(=O)N(R^{A2a})_2$. In certain embodiments, at least one instance of $R^{A2}$ is —$C(=O)NMe_2$, —$C(=O)NHMe$, or —$C(=O)NH_2$. In certain embodiments, at least one instance of $R^{A2}$ is —$NO_2$. In certain embodiments, at least one instance of $R^{A2}$ is —$NR^{A2a}C(=O)R^{A2a}$, —$NR^{A2a}C(=O)OR^{A2a}$, or —$NR^{A2a}C(=O)N(R^{A2a})_2$. In certain embodiments, at least one instance of $R^{A2}$ is —$OC(=O)R^{A2a}$, —$OC(=O)OR^{A2a}$, or —$OC(=O)N(R^{A2a})_2$.

In certain embodiments, at least one instance of $R^{A2a}$ is H. In certain embodiments, at least one instance of $R^{A2a}$ is substituted acyl. In certain embodiments, at least one instance of $R^{A2a}$ is unsubstituted acyl. In certain embodiments, at least one instance of $R^{A2a}$ is acetyl. In certain embodiments, at least one instance of $R^{A2a}$ is substituted alkyl. In certain embodiments, at least one instance of $R^{A2a}$ is unsubstituted alkyl. In certain embodiments, at least one instance of $R^{A2a}$ is unsubstituted $C_{1-6}$ alkyl. In certain embodiments, at least one instance of $R^{A2a}$ is methyl. In certain embodiments, at least one instance of $R^{A2a}$ is ethyl. In certain embodiments, at least one instance of $R^{A2a}$ is propyl. In certain embodiments, at least one instance of $R^{A2a}$ is butyl. In certain embodiments, at least one instance of $R^{A2a}$ is pentyl. In certain embodiments, at least one instance of $R^{A2a}$ is hexyl. In certain embodiments, at least one instance of $R^{A2a}$ is substituted alkenyl. In certain embodiments, at least one instance of $R^{A2a}$ is unsubstituted alkenyl. In certain embodiments, at least one instance of $R^{A2a}$ is substituted alkynyl. In certain embodiments, at least one instance of $R^{A2a}$ is unsubstituted alkynyl. In certain embodiments, at least one instance of $R^{A2a}$ is substituted or unsubstituted carbocyclyl. In certain embodiments, at least one instance of $R^{A2a}$ is saturated carbocyclyl. In certain embodiments, at least one instance of $R^{A2a}$ is unsaturated carbocyclyl. In certain embodiments, at least one instance of $R^{A2a}$ is 3- to 7-membered, monocyclic carbocyclyl. In certain embodiments, at least one instance of $R^{A2a}$ is substituted or unsubstituted heterocyclyl. In certain embodiments, at least one instance of $R^{A2a}$ is saturated heterocyclyl. In certain embodiments, at least one instance of $R^{A2a}$ is unsaturated heterocyclyl. In certain embodiments, at least one instance of $R^{A2a}$ is heterocyclyl, wherein one, two, or three atoms in the heterocyclic ring system are independently selected from the group consisting of nitrogen, oxygen, and sulfur. In certain embodiments, at least one instance of $R^{A2a}$ is 3- to 7-membered, monocyclic heterocyclyl. In certain embodiments, at least one instance of $R^{A2a}$ is substituted or unsubstituted aryl. In certain embodiments, at least one instance of $R^{A2a}$ is 6- to 10-membered aryl. In certain embodiments, at least one instance of $R^{A2a}$ is monocyclic aryl. In certain embodiments, at least one instance of $R^{A2a}$ is substituted phenyl. In certain embodiments, at least one instance of $R^{A2a}$ is unsubstituted phenyl. In certain embodiments, at least one instance of $R^{A2a}$ is bicyclic aryl. In certain embodiments, at least one instance of $R^{A2}$a Is substituted or unsubstituted heteroaryl. In certain embodiments, at least one instance of $R^{A2}$a is heteroaryl, wherein one, two, three, or four atoms in the heteroaryl ring system are independently selected from the group consisting of nitrogen, oxygen, and sulfur. In certain embodiments, at least one instance of $R^{A2}$a is monocyclic heteroaryl. In certain embodiments, at least one instance of $R^{A2}$a is 5- or 6-membered, monocyclic heteroaryl. In certain embodiments, at least one instance of $R^{A2a}$ is bicyclic heteroaryl, wherein the point of attachment may be on any atom of the bicyclic heteroaryl ring system, as valency permits. In certain embodiments, at least one instance of $R^{A2a}$ is a nitrogen protecting group when attached to a nitrogen atom. In certain embodiments, at least one instance of $R^{A2a}$ is Bn, Boc, Cbz, Fmoc, trifluoroacetyl, triphenylmethyl, acetyl, or Ts when attached to a nitrogen atom. In certain embodiments, $R^{A2a}$ is an oxygen protecting group when attached to an oxygen atom. In certain embodiments, $R^{A2}$a is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A2a}$ is a sulfur protecting group when attached to a sulfur atom. In certain embodiments, $R^{A2a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{A2a}$ are joined to form a substituted or unsubstituted heterocyclic ring. In certain embodiments, two instances of $R^{A2a}$ are joined to form a saturated or unsaturated heterocyclic ring. In certain embodiments, two instances of $R^{A2a}$ are joined to form a heterocyclic ring, wherein one, two, or three atoms in the heterocyclic ring system are independently selected from the group consisting of nitrogen, oxygen, and sulfur. In certain embodiments, two instances of $R^{A2a}$ are joined to form a 3- to 7-membered, monocyclic heterocyclic ring. In certain embodiments, two instances of $R^{A2a}$ are joined to form a substituted or unsubstituted heteroaryl ring. In certain embodiments, two instances of $R^{A2a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, k is 0. In certain embodiments, k is 1. In certain embodiments, k is 2. In certain embodiments, k is 3. In certain embodiments, k is 4. In certain embodiments, k is 5. In certain embodiments, k is 6. In certain embodiments, k is 7. In certain embodiments, k is 8. In certain embodiments, k is 9.

Formula (II-C) may include one or more substituents $R^{B2}$. In certain embodiments, at least two instances of $R^{B2}$ are different. In certain embodiments, all instances of $R^{B2}$ are the same. In certain embodiments, at least one instance of $R^{B2}$ is H. In certain embodiments, all instances of $R^{B2}$ are H. In certain embodiments, at least one instance of $R^{B2}$ is halogen. In certain embodiments, at least one instance of $R^{B2}$ is F. In certain embodiments, at least one instance of $R^{B2}$ is Cl. In certain embodiments, at least one instance of $R^{B2}$ is Br. In certain embodiments, at least one instance of $R^{B2}$ is I (iodine). In certain embodiments, at least one instance of $R^{B2}$ is substituted alkyl. In certain embodiments, at least one instance of $R^{B2}$ is unsubstituted alkyl. In certain embodiments, at least one instance of $R^{B2}$ is unsubstituted $C_{1-6}$ alkyl. In certain embodiments, all instances of $R^{B2}$ are unsubstituted $C_{1-6}$ alkyl. In certain embodiments, at least one instance of $R^{B2}$ is substituted $C_{1-6}$ alkyl. In certain embodiments, at least one instance of $R^{B2}$ is $C_{1-6}$ alkyl substituted with at least one halogen. In certain embodiments, at least one instance of $R^{B2}$ is —$CH_3$. In certain embodiments, all instances of $R^{B2}$ are —$CH_3$. In certain embodiments, at least one instance of $R^{B2}$ is substituted methyl. In certain embodiments, at least one instance of $R^{B2}$ is —$CH_2F$. In certain embodiments, at least one instance of $R^{B2}$ is —$CHF_2$. In certain embodiments, at least one instance of $R^{B2}$ is —$CF_3$. In certain embodiments, at least one instance of $R^{B2}$ is ethyl. In certain embodiments, at least one instance of $R^{B2}$ is propyl. In certain embodiments, at least one instance of $R^{B2}$ is butyl. In certain embodiments, at least one instance of $R^{B2}$ is pentyl. In certain embodiments, at least one instance of $R^{B2}$ is hexyl. In certain embodiments, at least one instance of $R^{B2}$ is substituted alkenyl. In certain embodiments, at least one instance of $R^{B2}$ is unsubstituted alkenyl. In certain embodiments, at least one instance of $R^{B2}$ is unsubstituted alkynyl. In certain embodiments, at least one instance of $R^{B2}$ is unsubstituted alkynyl. In certain embodiments, at least one instance of $R^{B2}$ is unsubstituted carbocyclyl. In certain embodiments, at least one instance of $R^{B2}$ is substituted carbocyclyl. In certain embodiments, at least one instance of $R^{B2}$ instance of saturated carbocyclyl. In certain embodiments, at least one instance of $R^{B2}$ is unsaturated carbocyclyl. In certain embodiments, at least one instance of $R^{B2}$ is monocyclic carbocyclyl. In certain embodiments, at least one instance of $R^{B2}$ is 3- to 7-membered, monocyclic carbocyclyl. In certain embodiments, at least one instance of $R^{B2}$ is substituted heterocyclyl. In certain embodiments, at least one instance of $R^{B2}$ is unsubstituted heterocyclyl. In certain embodiments, at least one instance of $R^{B2}$ is saturated heterocyclyl. In certain embodiments, at least one instance of $R^{B2}$ is unsaturated heterocyclyl. In certain embodiments, at least one instance of $R^{B2}$ is heterocyclyl, wherein one, two, or three atoms in the heterocyclic ring system are independently selected from the group consisting of nitrogen, oxygen, and sulfur. In certain embodiments, at least one instance of $R^{B2}$ is monocyclic heterocyclyl. In certain embodiments, at least one instance of $R^{B2}$ is 3- to 7-membered, monocyclic heterocyclyl. In certain embodiments, at least one instance of $R^{B2}$ is substituted aryl. In certain embodiments, at least one instance of $R^{B2}$ is unsubstituted aryl. In certain embodiments, at least one instance of $R^{B2}$ is 6- to 10-membered aryl. In certain embodiments, at least one instance of $R^{B2}$ is substituted phenyl. In certain embodiments, at least one instance of $R^{B2}$ is unsubstituted phenyl. In certain embodiments, at least one instance of $R^{B2}$ is substituted heteroaryl. In certain embodiments, at least one instance of $R^{B2}$ is unsubstituted heteroaryl. In certain embodiments, at least one instance of $R^{B2}$ is heteroaryl, wherein one, two, three, or four atoms in the heteroaryl ring system are independently selected from the group consisting of nitrogen, oxygen, and sulfur. In certain embodiments, at least one instance of $R^{B2}$ is monocyclic heteroaryl. In certain embodiments, at least one instance of $R^{B2}$ is 5-membered, monocyclic heteroaryl. In certain embodiments, at least one instance of $R^{B2}$ is 6-membered, monocyclic heteroaryl. In certain embodiments, at least one instance of $R^{B2}$ is bicyclic heteroaryl, wherein the point of attachment may be on any atom of the bicyclic heteroaryl ring system, as valency permits. In certain embodiments, at least one instance of $R^{B2}$ is 9- or 10-membered, bicyclic heteroaryl. In certain embodiments, at least one instance of $R^{B2}$ is —$OR^{B2a}$. In certain embodiments, at least one instance of $R^{B2}$ is —OH. In certain embodiments, at least one instance of $R^{B2}$ is —OMe. In certain embodiments, at least one instance of $R^{B2}$ is —OEt. In certain embodiments, at least one instance of $R^{B2}$ is —OPr. In certain embodiments, at least one instance of $R^{B2}$ is —OBu. In certain embodiments, at least one instance of $R^{B2}$ is —OBn. In certain embodiments, at least one instance of $R^{B2}$ is —OPh. In certain embodiments, at least one instance of $R^{B2}$ is —$SR^{B2a}$. In certain embodiments, at least one instance of $R^{B2}$ is —SH. In certain embodiments, at least one instance of $R^{B2}$ is —SMe. In certain embodiments, at least one instance of $R^{B2}$ is —$N(R^{B2a})_2$. In certain embodiments, at least one instance of $R^{B2}$ is —$NH_2$. In certain embodiments, at least one instance of $R^{B2}$ is —NHMe. In certain embodiments, at least one instance of $R^{B2}$ is —$NMe_2$. In certain embodiments, at least one instance of $R^{B2}$ is —CN. In certain embodiments, at least one instance of $R^{B2}$ is —SCN. In certain embodiments, at least one instance of $R^{B2}$ is —$C(=NR^{B2a})R^{B2a}$, —$C(=NR^{B2a})OR^{B2a}$, or —$C(=NR^{B2a})N(R^{B2a})_2$. In certain embodiments, at least one instance of $R^{B2}$ is —$C(=O)R^{B2a}$ or —$C(=O)OR^{B2a}$. In certain embodiments, at least one instance of $R^{B2}$ is —$C(=O)N(R^{B2a})_2$. In certain embodiments, at least one instance of $R^{B2}$ is —$C(=O)NMe_2$, —$C(=O)NHMe$, or —$C(=O)NH_2$. In certain embodiments, at least one instance of $R^{B2}$ is —$NO_2$. In certain embodiments, at least one instance of $R^{B2}$ is —$NR^{B2a}C(=O)R^{B2a}$, —$NR^{B2a}C(=O)OR^{B2a}$, or —$NR^{B2a}C(=O)N(R^{B2a})_2$. In certain embodiments, at least one instance of $R^{B2}$ is —$OC(=O)R^{B2a}$, —$OC(=O)OR^{B2a}$, or —$OC(=O)N(R^{B2a})_2$.

In certain embodiments, at least one instance of $R^{B2a}$ is H. In certain embodiments, at least one instance of $R^{B2a}$ is substituted acyl. In certain embodiments, at least one instance of $R^{B2a}$ is unsubstituted acyl. In certain embodiments, at least one instance of $R^{B2a}$ is acetyl. In certain embodiments, at least one instance of $R^{B2a}$ is substituted alkyl. In certain embodiments, at least one instance of $R^{B2a}$ is unsubstituted alkyl. In certain embodiments, at least one instance of $R^{B2a}$ is unsubstituted $C_{1-6}$ alkyl. In certain embodiments, at least one instance of $R^{B2a}$ is methyl. In certain embodiments, at least one instance of $R^{B2a}$ is ethyl. In certain embodiments, at least one instance of $R^{B2a}$ is propyl. In certain embodiments, at least one instance of $R^{B2a}$ is butyl. In certain embodiments, at least one instance of $R^{B2a}$ is pentyl. In certain embodiments, at least one instance of $R^{B2a}$ is hexyl. In certain embodiments, at least one instance of $R^{B2a}$ is substituted alkenyl. In certain embodiments, at least one instance of $R^{B1a}$ is unsubstituted alkenyl. In certain embodiments, at least one instance of $R^{B2a}$ is substituted alkynyl. In certain embodiments, at least one instance of $R^{B2a}$ is unsubstituted alkynyl. In certain embodiments, at least one instance of $R^{B2a}$ is substituted or unsubstituted carbocyclyl. In certain embodiments, at least one instance of $R^{B2a}$ is saturated carbocyclyl. In certain embodiments, at least one instance of $R^{B2a}$ is unsaturated carbocyclyl. In certain embodiments, at least one instance of $R^{B2a}$ is 3- to 7-membered, monocyclic carbocyclyl. In certain embodiments, at least one instance of $R^{B2a}$ is substituted or unsubstituted heterocyclyl. In certain embodiments, at least one instance of $R^{B2a}$ is saturated heterocyclyl. In certain embodiments, at least one instance of $R^{B2a}$ is unsaturated heterocyclyl. In certain embodiments, at least one instance of $R^{B2a}$ is heterocyclyl, wherein one, two, or three atoms in the heterocyclic ring system are independently selected from the group consisting of nitrogen, oxygen, and sulfur. In certain embodiments, at least one instance of $R^{B2a}$ is 3- to 7-membered, monocyclic heterocyclyl. In certain embodiments, at least one instance of $R^{B2a}$ is substituted or unsubstituted aryl. In certain embodiments, at least one instance of $R^{B2a}$ is 6- to 10-membered aryl. In certain embodiments, at least one instance of $R^{B2a}$ is monocyclic aryl. In certain embodiments, at least one instance of $R^{B2a}$ is substituted phenyl. In certain embodiments, at least one instance of $R^{B2a}$ is unsubstituted phenyl. In certain embodiments, at least one instance of $R^{B2a}$ is bicyclic aryl. In certain embodiments, at least one instance of $R^{B2a}$ is substituted or unsubstituted heteroaryl. In certain embodiments, at least one instance of $R^{B2a}$ is heteroaryl, wherein one, two, three, or four atoms in the heteroaryl ring system are independently selected from the group consisting of nitrogen, oxygen, and sulfur. In certain embodiments, at least one instance of $R^{B2a}$ is monocyclic heteroaryl. In certain embodiments, at least one instance of $R^{B2a}$ is 5- or 6-membered, monocyclic heteroaryl. In certain embodiments, at least one instance of $R^{B2a}$ is bicyclic heteroaryl, wherein the point of attachment may be on any atom of the bicyclic heteroaryl ring system, as valency permits. In certain embodiments, at least one instance of $R^{B2a}$ is a nitrogen protecting group when attached to a nitrogen atom. In certain embodiments, at least one instance of $R^{B2a}$ is Bn, Boc, Cbz, Fmoc, trifluoroacetyl, triphenylmethyl, acetyl, or Ts when attached to a nitrogen atom. In certain embodiments, $R^{B2a}$ is an oxygen protecting group when attached to an oxygen atom. In certain embodiments, $R^{B2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B2a}$ is a sulfur protecting group when attached to a sulfur atom. In certain embodiments, $R^{B2a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{B2a}$ are joined to form a substituted or unsubstituted heterocyclic ring. In certain embodiments, two instances of $R^{B2a}$ are joined to form a saturated or unsaturated heterocyclic ring. In certain embodiments, two instances of $R^{B2a}$ are joined to form a heterocyclic ring, wherein one, two, or three atoms in the heterocyclic ring system are independently selected from the group consisting of nitrogen, oxygen, and sulfur. In certain embodiments, two instances of $R^{B2a}$ are joined to form a 3- to 7-membered, monocyclic heterocyclic ring. In certain embodiments, two instances of $R^{B2a}$ are joined to form a substituted or unsubstituted heteroaryl ring. In certain embodiments, two instances of $R^{B2a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, m is 0. In certain embodiments, m is 1. In certain embodiments, m is 2. In certain embodiments, m is 3.

Formula (II-C) includes substituent $R^{C2}$. In certain embodiments, $R^{C2}$ is H. In certain embodiments, $R^{C2}$ is substituted acyl. In certain embodiments, $R^{C2}$ is unsubstituted acyl. In certain embodiments, $R^{C2}$ is acetyl. In certain embodiments, $R^{C2}$ is substituted alkyl. In certain embodiments, $R^{C2}$ is unsubstituted alkyl. In certain embodiments, $R^{C2}$ is unsubstituted $C_{1-6}$ alkyl. In certain embodiments, $R^{C2}$ is substituted $C_{1-6}$ alkyl. In certain embodiments, $R^{C2}$ is $C_{1-6}$ alkyl substituted with at least one halogen. In certain embodiments, $R^{C2}$ is —$CH_3$. In certain embodiments, $R^{C2}$ is substituted methyl. In certain embodiments, $R^{C2}$ is —$CH_2F$. In certain embodiments, $R^{C2}$ is —$CHF_2$. In certain embodiments, $R^{C2}$ is —$CF_3$. In certain embodiments, $R^{C2}$ is ethyl. In certain embodiments, $R^{C2}$ is propyl. In certain embodiments, $R^{C2}$ is butyl. In certain embodiments, $R^{C2}$ is pentyl. In certain embodiments, $R^{C2}$ is hexyl. In certain embodiments, $R^{C2}$ is substituted alkenyl. In certain embodiments, $R^{C2}$ is unsubstituted alkenyl. In certain embodiments, $R^{C2}$ is substituted alkynyl. In certain embodiments, $R^{C2}$ is unsubstituted alkynyl. In certain embodiments, $R^{C2}$ is substituted carbocyclyl. In certain embodiments, $R^{C2}$ is unsubstituted carbocyclyl. In certain embodiments, $R^{C2}$ is saturated carbocyclyl. In certain embodiments, $R^{C2}$ is unsaturated carbocyclyl. In certain embodiments, $R^{C2}$ is monocyclic carbocyclyl. In certain embodiments, $R^{C2}$ is 3- to 7-membered, monocyclic carbocyclyl. In certain embodiments, $R^{C2}$ is substituted heterocyclyl. In certain embodiments, $R^{C2}$ is unsubstituted heterocyclyl. In certain embodiments, $R^{C2}$ is saturated heterocyclyl. In certain embodiments, $R^{C2}$ is unsaturated heterocyclyl. In certain embodiments, $R^{C2}$ is heterocyclyl, wherein one, two, or three atoms in the heterocyclic ring system are independently selected from the group consisting of nitrogen, oxygen, and sulfur. In certain embodiments, $R^{C2}$ is monocyclic heterocyclyl. In certain embodiments, $R^{C2}$ is 3- to 7-membered, monocyclic heterocyclyl. In certain embodiments, $R^{C2}$ is substituted aryl. In certain embodiments, $R^{C2}$ is unsubstituted aryl. In certain embodiments, $R^{C2}$ is 6- to 10-membered aryl. In certain embodiments, $R^{C2}$ is substituted phenyl. In certain embodiments, $R^{C2}$ is unsubstituted phenyl. In certain embodiments, $R^{C2}$ is substituted heteroaryl. In certain embodiments, $R^{C2}$ is unsubstituted heteroaryl. In certain embodiments, $R^{C2}$ is heteroaryl, wherein one, two, three, or four atoms in the heteroaryl ring system are independently selected from the group consisting of nitrogen, oxygen, and sulfur. In certain embodiments, $R^{C2}$ is monocyclic heteroaryl. In certain embodiments, $R^{C2}$ is 5-membered, monocyclic heteroaryl. In certain embodiments, $R^{C2}$ is 6-membered, monocyclic heteroaryl. In certain embodiments, $R^{C2}$ is bicyclic heteroaryl, wherein the point of attachment may be on any atom of the bicyclic heteroaryl ring system, as valency permits. In certain embodiments, $R^{C2}$ is 9- or 10-membered, bicyclic heteroaryl. In certain embodiments, $R^{C2}$ is an oxygen protecting group. In certain embodiments, $R^{C2}$ is silyl, TBDPS, TBDMS, TIPS, TES, TMS, MOM, THP, t-Bu, Bn, allyl, acetyl, pivaloyl, or benzoyl.

Formula (II-C) may include one or two substituents $R^{D2}$. In certain embodiments, two instances of $R^{D2}$ are different. In certain embodiments, two instances of $R^{D2}$ are the same. In certain embodiments, at least one instance of $R^{D2}$ is H. In certain embodiments, both instances of $R^{D2}$ are H. In certain embodiments, at least one instance of $R^{D2}$ is halogen. In certain embodiments, at least one instance of $R^{D2}$ is F. In certain embodiments, at least one instance of $R^{D2}$ is Cl. In certain embodiments, at least one instance of $R^{D2}$ is Br. In certain embodiments, at least one instance of $R^{D2}$ is I (iodine). In certain embodiments, at least one instance of $R^{D2}$ is substituted alkyl. In certain embodiments, at least one instance of $R^{D2}$ is unsubstituted alkyl. In certain embodiments, at least one instance of $R^{D2}$ is unsubstituted $C_{1-6}$alkyl. In certain embodiments, each instance of $R^{D2}$ is unsubstituted $C_{1-6}$ alkyl. In certain embodiments, at least one instance of $R^{D2}$ is substituted $C_{1-6}$ alkyl. In certain embodiments, at least one instance of $R^{D2}$ is $C_{1-6}$ alkyl substituted with at least one halogen. In certain embodiments, at least one instance of $R^{D2}$ is —$CH_3$. In certain embodiments, each instance of $R^{D2}$ is —$CH_3$. In certain embodiments, at least one instance of $R^{D2}$ is substituted methyl. In certain embodiments, at least one instance of $R^{D2}$ is —$CH_2F$. In certain embodiments, at least one instance of $R^{D2}$ is —$CHF_2$. In certain embodiments, at least one instance of $R^{D2}$ is —$CF_3$. In certain embodiments, at least one instance of $R^{D2}$ is ethyl. In certain embodiments, at least one instance of $R^{D2}$ is propyl. In certain embodiments, at least one instance of $R^{D2}$ is butyl. In certain embodiments, at least one instance of $R^{D2}$ is pentyl. In certain embodiments, at least one instance of $R^{D2}$ is hexyl. In certain embodiments, at least one instance of $R^{D2}$ is substituted alkenyl. In certain embodiments, at least one instance of $R^{D2}$ is unsubstituted alkenyl. In certain embodiments, at least one instance of $R^{D2}$ is substituted alkynyl. In certain embodiments, at least one instance of $R^{D2}$ is unsubstituted alkynyl. In certain embodiments, at least one instance of $R^{D2}$ is substituted carbocyclyl. In certain embodiments, at least one instance of $R^{D2}$ is unsubstituted carbocyclyl. In certain embodiments, at least one instance of $R^{D2}$ is saturated carbocyclyl. In certain embodiments, at least one instance of $R^{D2}$ is unsaturated carbocyclyl. In certain embodiments, at least one instance of $R^{D2}$ is monocyclic carbocyclyl. In certain embodiments, at least one instance of $R^{D2}$ is 3- to 7-membered, monocyclic carbocyclyl. In certain embodiments, at least one instance of $R^{D2}$ is substituted heterocyclyl. In certain embodiments, at least one instance of $R^{D2}$ is unsubstituted heterocyclyl. In certain embodiments, at least one instance of $R^{D2}$ is saturated heterocyclyl. In certain embodiments, at least one instance of $R^{D2}$ is unsaturated heterocyclyl. In certain embodiments, at least one instance of $R^{D2}$ is heterocyclyl, wherein one, two, or three atoms in the heterocyclic ring system are independently selected from the group consisting of nitrogen, oxygen, and sulfur. In certain embodiments, at least one instance of $R^{D2}$ is monocyclic heterocyclyl. In certain embodiments, at least one instance of $R^{D2}$ is 3- to 7-membered, monocyclic heterocyclyl. In certain embodiments, at least one instance of $R^{D2}$ is substituted aryl. In certain embodiments, at least one instance of $R^{D2}$ is unsubstituted aryl. In certain embodiments, at least one instance of $R^{D2}$ is 6- to 10-membered aryl. In certain embodiments, at least one instance of $R^{D2}$ is substituted phenyl. In certain embodiments, at least one instance of $R^{D2}$ is unsubstituted phenyl. In certain embodiments, at least one instance of $R^{D2}$ is substituted heteroaryl. In certain embodiments, at least one instance of $R^{D2}$ is unsubstituted heteroaryl. In certain embodiments, at least one instance of $R^{D2}$ is heteroaryl, wherein one, two, three, or four atoms in the heteroaryl ring system are independently selected from the group consisting of nitrogen, oxygen, and sulfur. In certain embodiments, at least one instance of $R^{D2}$ is monocyclic heteroaryl. In certain embodiments, at least one instance of $R^{D2}$ is 5-membered, monocyclic heteroaryl. In certain embodiments, at least one instance of $R^{D2}$ is 6-membered, monocyclic heteroaryl. In certain embodiments, at least one instance of $R^{D2}$ is bicyclic heteroaryl, wherein the point of attachment may be on any atom of the bicyclic heteroaryl ring system, as valency permits. In certain embodiments, at least one instance of $R^{D2}$ is 9- or 10-membered, bicyclic heteroaryl. In certain embodiments, at least one instance of $R^{D2}$ is —$OR^{D2a}$. In certain embodiments, at least one instance of $R^{D2}$ is —OH. In certain embodiments, at least one instance of $R^{D2}$ is —OMe. In certain embodiments, at least one instance of $R^{D2}$ is —OEt. In certain embodiments, at least one instance of $R^{D2}$ is —OPr. In certain embodiments, at least one instance of $R^{D2}$ is —OBu. In certain embodiments, at least one instance of $R^{D2}$ is —OBn. In certain embodiments, at least one instance of $R^{D2}$ is —OPh. In certain embodiments, at least one instance of $R^{D2}$ is —$S^{R2a}$. In certain embodiments, at least one instance of $R^{D2}$ is —SH. In certain embodiments, at least one instance of $R^{D2}$ is —SMe. In certain embodiments, at least one instance of $R^{D2}$ is —$N(R^{D2a})_2$. In certain embodiments, at least one instance of $R^{D2}$ is —$NH_2$. In certain embodiments, at least one instance of $R^{D2}$ is —NHMe. In certain embodiments, at least one instance of $R^{D2}$ is —$NMe_2$. In certain embodiments, at least one instance of $R^{D2}$ is —CN. In certain embodiments, at least one instance of $R^{D2}$ is —SCN. In certain embodiments, at least one instance of $R^{D2}$ is —$C(=NR^{D2a})R^{D2a}$, —$C(=NR^{D2a})OR^{D2a}$, or —$C(=NR^{D2a})N(R^{D2a})_2$. In certain embodiments, at least one instance of $R^{D2}$ is —$C(=O)R^{D2a}$ or —$C(=O)OR^{D2a}$. In certain embodiments, at least one instance of $R^{D2}$ is —$C(=O)N(R^{D2a})_2$. In certain embodiments, at least one instance of $R^{D2}$ is —$C(=O)NMe_2$, —$C(=O)NHMe$, or —$C(=O)NH_2$. In certain embodiments, at least one instance of $R^{D2}$ is —$NO_2$. In certain embodiments, at least one instance of $R^{D2}$ is —$NR^{D2a}C(=O)R^{D2a}$, —$NR^{D2a}C(=O)OR^{D2a}$, or —$NR^{D2a}C(=O)N(R^{D2a})_2$. In certain embodiments, at least one instance of $R^{D2}$ is —$OC(=O)R^{D2a}$, —$OC(=O)OR^{D2a}$, or —$OC(=O)N(R^{D2a})_2$.

In certain embodiments, at least one instance of $R^{D2a}$ is H. In certain embodiments, at least one instance of $R^{D2a}$ is substituted acyl. In certain embodiments, at least one instance of $R^{D2a}$ is unsubstituted acyl. In certain embodiments, at least one instance of $R^{D2a}$ is acetyl. In certain embodiments, at least one instance of $R^{D2a}$ is substituted alkyl. In certain embodiments, at least one instance of $R^{D2a}$ is unsubstituted alkyl. In certain embodiments, at least one instance of $R^{D2a}$ is unsubstituted $C_{1-6}$ alkyl. In certain embodiments, at least one instance of $R^{D2a}$ is methyl. In certain embodiments, at least one instance of $R^{D2a}$ is ethyl. In certain embodiments, at least one instance of $R^{D2a}$ is propyl. In certain embodiments, at least one instance of $R^{D2a}$ is butyl. In certain embodiments, at least one instance of $R^{D2a}$ is pentyl. In certain embodiments, at least one instance of $R^{D2a}$ is hexyl. In certain embodiments, at least one instance of $R^{D2a}$ is substituted alkenyl. In certain embodiments, at least one instance of $R^{D2a}$ is unsubstituted alkenyl. In certain embodiments, at least one instance of $R^{D2a}$ is substituted alkynyl. In certain embodiments, at least one instance of $R^{D2a}$ is unsubstituted alkynyl. In certain embodiments, at least one instance of $R^{D2a}$ is substituted or unsubstituted carbocyclyl. In certain embodiments, at least one instance of $R^{D2a}$ is saturated carbocyclyl. In certain embodiments, at least one instance of $R^{D2a}$ is unsaturated carbocyclyl. In certain embodiments, at least one instance of $R^{D2a}$ is 3- to 7-membered, monocyclic carbocyclyl. In certain embodiments, at least one instance of $R^{D2a}$ is substituted or unsubstituted heterocyclyl. In certain embodiments, at least one instance of $R^{D2a}$ is saturated heterocyclyl. In certain embodiments, at least one instance of $R^{D2a}$ is unsaturated heterocyclyl. In certain embodiments, at least one instance of $R^{D2a}$ is heterocyclyl, wherein one, two, or three atoms in the heterocyclic ring system are independently selected from the group consisting of nitrogen, oxygen, and sulfur. In certain embodiments, at least one instance of $R^{D2a}$ is 3- to 7-membered, monocyclic heterocyclyl. In certain embodiments, at least one instance of $R^{D2a}$ is substituted or unsubstituted aryl. In certain embodiments, at least one instance of $R^{D2a}$ is 6- to 10-membered aryl. In certain embodiments, at least one instance of $R^{D2a}$ is monocyclic aryl. In certain embodiments, at least one instance of $R^{D2a}$ is substituted phenyl. In certain embodiments, at least one instance of $R^{D2a}$ is unsubstituted phenyl. In certain embodiments, at least one instance of $R^{D2a}$ is bicyclic aryl. In certain embodiments, at least one instance of $R^{D2a}$ is substituted or unsubstituted heteroaryl. In certain embodiments, at least one instance of $R^{D2a}$ is heteroaryl, wherein one, two, three, or four atoms in the heteroaryl ring system are independently selected from the group consisting of nitrogen, oxygen, and sulfur. In certain embodiments, at least one instance of $R^{D2a}$ is monocyclic heteroaryl. In certain embodiments, at least one instance of $R^{D2a}$ is 5- or 6-membered, monocyclic heteroaryl. In certain embodiments, at least one instance of $R^{D2a}$ is bicyclic heteroaryl, wherein the point of attachment may be on any atom of the bicyclic heteroaryl ring system, as valency permits. In certain embodiments, at least one instance of $R^{D2a}$ is a nitrogen protecting group when attached to a nitrogen atom. In certain embodiments, at least one instance of $R^{D2a}$ is Bn, Boc, Cbz, Fmoc, trifluoroacetyl, triphenylmethyl, acetyl, or Ts when attached to a nitrogen atom. In certain embodiments, $R^{D2a}$ is an oxygen protecting group when attached to an oxygen atom. In certain embodiments, $R^{D2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D2}$ is a sulfur protecting group when attached to a sulfur atom. In certain embodiments, $R^{D2a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{D2a}$ are joined to form a substituted or unsubstituted heterocyclic ring. In certain embodiments, two instances of $R^{D2a}$ are joined to form a saturated or unsaturated heterocyclic ring. In certain embodiments, two instances of $R^{D2a}$ are joined to form a heterocyclic ring, wherein one, two, or three atoms in the heterocyclic ring system are independently selected from the group consisting of nitrogen, oxygen, and sulfur. In certain embodiments, two instances of $R^{D2a}$ are joined to form a 3- to 7-membered, monocyclic heterocyclic ring. In certain embodiments, two instances of $R^{D2a}$ are joined to form a substituted or unsubstituted heteroaryl ring. In certain embodiments, two instances of $R^{D2a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, n is 0. In certain embodiments, n is 1. In certain embodiments, n is 2.

Formula (II-C) includes substituent $R^{E2}$. In certain embodiments, $R^{E2}$ is H. In certain embodiments, $R^{E2}$ is substituted alkyl. In certain embodiments, $R^{E2}$ is unsubstituted alkyl. In certain embodiments, $R^{E2}$ is unsubstituted $C_{1-6}$ alkyl. In certain embodiments, $R^{E2}$ is substituted $C_{1-6}$ alkyl. In certain embodiments, $R^{E2}$ is $C_{1-6}$ alkyl substituted with at least one halogen. In certain embodiments, $R^{E2}$ is —CH$_3$. In certain embodiments, $R^{E2}$ is substituted methyl. In certain embodiments, $R^{E2}$ is —CH$_2$F. In certain embodiments, $R^{E2}$ is —CHF$_2$. In certain embodiments, $R^{E2}$ is —CF$_3$. In certain embodiments, $R^{E2}$ is ethyl. In certain embodiments, $R^{E2}$ is propyl. In certain embodiments, $R^{E2}$ is butyl. In certain embodiments, $R^{E2}$ is pentyl. In certain embodiments, $R^{E2}$ is hexyl. In certain embodiments, $R^{E2}$ is substituted alkenyl. In certain embodiments, $R^{E2}$ is unsubstituted alkenyl. In certain embodiments, $R^{E2}$ is substituted alkynyl. In certain embodiments, $R^{E2}$ is unsubstituted alkynyl. In certain embodiments, $R^{E2}$ is substituted carbocyclyl. In certain embodiments, $R^{E2}$ is unsubstituted carbocyclyl. In certain embodiments, $R^{E2}$ is saturated carbocyclyl. In certain embodiments, $R^{E2}$ is unsaturated carbocyclyl. In certain embodiments, $R^{E2}$ is monocyclic carbocyclyl. In certain embodiments, $R^{E2}$ is 3- to 7-membered, monocyclic carbocyclyl. In certain embodiments, $R^{E2}$ is substituted heterocyclyl. In certain embodiments, $R^{E2}$ is unsubstituted heterocyclyl. In certain embodiments, $R^{E2}$ is saturated heterocyclyl. In certain embodiments, $R^{E2}$ is unsaturated heterocyclyl. In certain embodiments, $R^{E2}$ is heterocyclyl, wherein one, two, or three atoms in the heterocyclic ring system are independently selected from the group consisting of nitrogen, oxygen, and sulfur. In certain embodiments, $R^{E2}$ is monocyclic heterocyclyl. In certain embodiments, $R^{E2}$ is 3- to 7-membered, monocyclic heterocyclyl. In certain embodiments, $R^{E2}$ is substituted aryl. In certain embodiments, $R^{E2}$ is unsubstituted aryl. In certain embodiments, $R^{E2}$ is 6- to 10-membered aryl. In certain embodiments, $R^{E2}$ is substituted phenyl. In certain embodiments, $R^{E2}$ is unsubstituted phenyl. In certain embodiments, $R^{E2}$ is substituted heteroaryl. In certain embodiments, $R^{E2}$ is unsubstituted heteroaryl. In certain embodiments, $R^{E2}$ is heteroaryl, wherein one, two, three, or four atoms in the heteroaryl ring system are independently selected from the group consisting of nitrogen, oxygen, and sulfur. In certain embodiments, $R^{E2}$ is monocyclic heteroaryl. In certain embodiments, $R^{E2}$ is 5-membered, monocyclic heteroaryl. In certain embodiments, $R^{E2}$ is 6-membered, monocyclic heteroaryl. In certain embodiments, $R^{E2}$ is bicyclic heteroaryl, wherein the point of attachment may be on any atom of the bicyclic heteroaryl ring system, as valency permits. In certain embodiments, $R^{E2}$ is 9- or 10-membered, bicyclic heteroaryl. In certain embodiments, $R^{E2}$ is a nitrogen protecting group. In certain embodiments, $R^{E2}$ is Bn, Boc, Cbz, Fmoc, trifluoroacetyl, triphenylmethyl, acetyl, or Ts.

Formula (II-C) includes substituent $R^{F2}$. In certain embodiments, $R^{F2}$ is H. In certain embodiments, $R^{F2}$ is substituted alkyl. In certain embodiments, $R^{F2}$ is unsubstituted alkyl. In certain embodiments, $R^{F2}$ is unsubstituted $C_{1-6}$ alkyl. In certain embodiments, $R^{F2}$ is substituted $C_{1-6}$ alkyl. In certain embodiments, $R^{F2}$ is $C_{1-6}$ alkyl substituted with at least one halogen. In certain embodiments, $R^{F2}$ is —CH$_3$. In certain embodiments, $R^{F2}$ is substituted methyl. In certain embodiments, $R^{F2}$ is —CH$_2$F. In certain embodiments, $R^{F2}$ is —CHF$_2$. In certain embodiments, $R^{F2}$ is —CF$_3$. In certain embodiments, $R^{F2}$ is ethyl. In certain embodiments, $R^{F2}$ is propyl. In certain embodiments, $R^{F2}$ is butyl. In certain embodiments, $R^{F2}$ is pentyl. In certain embodiments, $R^{F2}$ is hexyl. In certain embodiments, $R^{F2}$ is substituted alkenyl. In certain embodiments, $R^{F2}$ is unsubstituted alkenyl. In certain embodiments, $R^{F2}$ is substituted alkynyl. In certain embodiments, $R^{F2}$ is unsubstituted alkynyl. In certain embodiments, $R^{F2}$ is substituted carbocyclyl. In certain embodiments, $R^{F2}$ is unsubstituted carbocyclyl. In certain embodiments, $R^{F2}$ is saturated carbocyclyl. In certain embodiments, $R^{F2}$ is unsaturated carbocyclyl. In certain embodiments, $R^{F2}$ is monocyclic carbocyclyl. In certain embodiments, $R^{F2}$ is 3- to 7-membered, monocyclic carbocyclyl. In certain embodiments, $R^{F2}$ is substituted heterocyclyl. In certain embodiments, $R^{F2}$ is unsubstituted heterocyclyl. In certain embodiments, $R^{F2}$ is saturated heterocyclyl. In certain embodiments, $R^{F2}$ is unsaturated heterocyclyl. In certain embodiments, $R^{F2}$ is heterocyclyl, wherein one, two, or three atoms in the heterocyclic ring system are independently selected from the group consisting of nitrogen, oxygen, and sulfur. In certain embodiments, $R^{F2}$ is monocyclic heterocyclyl. In certain embodiments, $R^{F2}$ is 3- to 7-membered, monocyclic heterocyclyl. In certain embodiments, $R^{F2}$ is substituted aryl. In certain embodiments, $R^{F2}$ is unsubstituted aryl. In certain embodiments, $R^{F2}$ is 6- to 10-membered aryl. In certain embodiments, $R^{F2}$ is substituted phenyl. In certain embodiments, $R^{F2}$ is unsubstituted phenyl. In certain embodiments, $R^{F2}$ is substituted heteroaryl. In certain embodiments, $R^{F2}$ is unsubstituted heteroaryl. In certain embodiments, $R^{F2}$ is heteroaryl, wherein one, two, three, or four atoms in the heteroaryl ring system are independently selected from the group consisting of nitrogen, oxygen, and sulfur. In certain embodiments, $R^{F2}$ is monocyclic heteroaryl. In certain embodiments, $R^{F2}$ is 5-membered, monocyclic heteroaryl. In certain embodiments, $R^{F2}$ is 6-membered, monocyclic heteroaryl. In certain embodiments, $R^{F2}$ is bicyclic heteroaryl, wherein the point of attachment may be on any atom of the bicyclic heteroaryl ring system, as valency permits. In certain embodiments, $R^{F2}$ is 9- or 10-membered, bicyclic heteroaryl. In certain embodiments, $R^{F2}$ is a nitrogen protecting group. In certain embodiments, $R^{F2}$ is Bn, Boc, Cbz, Fmoc, trifluoroacetyl, triphenylmethyl, acetyl, or Ts.

Formula (II-C) includes substituent $R^{G2}$. In certain embodiments, $R^{G2}$ is H. In certain embodiments, $R^{G2}$ is halogen. In certain embodiments, $R^{G2}$ is F. In certain embodiments, $R^{G2}$ is Cl. In certain embodiments, $R^{G2}$ is Br. In certain embodiments, $R^{G2}$ is I (iodine). In certain embodiments, $R^{G2}$ is unsubstituted $C_{1-6}$ alkyl. In certain embodiments, $R^{G2}$ is substituted $C_{1-6}$ alkyl. In certain embodiments, $R^{G2}$ is $C_{1-6}$ alkyl substituted with at least one halogen. In certain embodiments, $R^{G2}$ is —CH$_3$. In certain embodiments, $R^{G2}$ is substituted methyl. In certain embodiments, $R^{G2}$ is —CH$_2$F. In certain embodiments, $R^{G2}$ is —CHF$_2$. In certain embodiments, $R^{G2}$ is —CF$_3$. In certain embodiments, $R^{G2}$ is ethyl. In certain embodiments, $R^{G2}$ is propyl. In certain embodiments, $R^{G2}$ is butyl. In certain embodiments, $R^{G2}$ is pentyl. In certain embodiments, $R^{G2}$ is hexyl.

Formula (II-C) includes substituent $R^{H2}$. In certain embodiments, $R^{H2}$ is H. In certain embodiments, $R^{H2}$ is halogen. In certain embodiments, $R^{H2}$ is F. In certain embodiments, $R^{H2}$ is Cl. In certain embodiments, $R^{H2}$ is Br. In certain embodiments, $R^{H2}$ is I (iodine). In certain embodiments, $R^{H2}$ is unsubstituted $C_{1-6}$ alkyl. In certain embodiments, $R^{H2}$ is substituted $C_{1-6}$ alkyl. In certain embodiments, $R^{H2}$ is $C_{1-6}$ alkyl substituted with at least one halogen. In certain embodiments, $R^{H2}$ is —CH$_3$. In certain embodiments, $R^{H2}$ is substituted methyl. In certain embodiments, $R^{H2}$ is —CH$_2$F. In certain embodiments, $R^{H2}$ is —CHF$_2$. In certain embodiments, $R^{H2}$ is —CF$_3$. In certain embodiments, $R^{H2}$ is ethyl. In certain embodiments, $R^{H2}$ is propyl. In certain embodiments, $R^{H2}$ is butyl. In certain embodiments, $R^{H2}$ is pentyl. In certain embodiments, $R^{H2}$ is hexyl.

In certain embodiments, each of $R^{G2}$ and $R^{H2}$ is hydrogen.

In certain embodiments, $R^{G2}$ and $R^{H2}$ are joined to form a substituted phenyl ring. In certain embodiments, $R^{G2}$ and $R^{H2}$ are joined to form a unsubstituted phenyl ring. In certain embodiments, a compound described herein is of the formula:

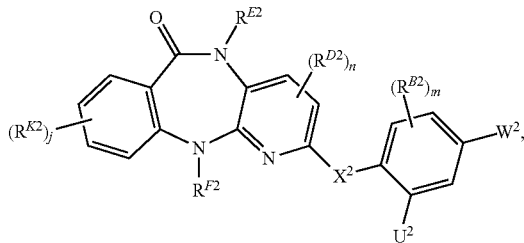

or a pharmaceutically acceptable salt, solvate, hydrate, polymorph, co-crystal, tautomer, stereoisomer, isotopically labeled derivative, or prodrug thereof, wherein:

each instance of $R^{K2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{K2a}$, —$N(R^{K2a})_2$, —$SR^{K2a}$, —CN, —SCN, —$C(=NR^{K2a})R^{K2a}$, —$C(=NR^{K2a})OR^{K2a}$, —$C(=NR^{K2a})N(R^{K2a})_2$, —$C(=O)R^{K2a}$, —$C(=O)OR^{K2a}$, —$C(=O)N(R^{K2a})_2$, —$NO_2$, —$NR^{K2a}C(=O)R^{K2a}$, —$NR^{K2a}C(=O)OR^{K2a}$, —$NR^{K2a}C(=O)N(R^{K2a})_2$, —$OC(=O)R^{K2a}$, —$OC(=O)OR^{K2a}$, or —$OC(=O)N(R^{K2a})_2$, wherein each instance of $R^{K2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{K2a}$ groups are joined to form a substituted or unsubstituted heterocyclic or substituted or unsubstituted heteroaryl ring; and j is 0, 1, 2, 3, or 4.

Formula (II-A) may include one or more substituents $R^{K2}$. In certain embodiments, at least two instances of $R^{K2}$ are different. In certain embodiments, all instances of $R^{K2}$ are the same. In certain embodiments, at least one instance of $R^{K2}$ is H. In certain embodiments, all instances of $R^{K2}$ are H. In certain embodiments, at least one instance of $R^{K2}$ is halogen. In certain embodiments, at least one instance of $R^{K2}$ is F. In certain embodiments, at least one instance of $R^{K2}$ is Cl. In certain embodiments, at least one instance of $R^{K2}$ is Br. In certain embodiments, at least one instance of $R^{K2}$ is I (iodine). In certain embodiments, at least one instance of $R^{K2}$ is substituted alkyl. In certain embodiments, at least one instance of $R^{K2}$ is unsubstituted alkyl. In certain embodiments, at least one instance of $R^{K2}$ is unsubstituted $C_{1-6}$ alkyl. In certain embodiments, all instances of $R^{K2}$ are unsubstituted $C_{1-6}$ alkyl. In certain embodiments, at least one instance of $R^{K2}$ is substituted $C_{1-6}$ alkyl. In certain embodiments, at least one instance of $R^{K2}$ is $C_{1-6}$ alkyl substituted with at least one halogen. In certain embodiments, at least one instance of $R^{K2}$ is —$CH_3$. In certain embodiments, all instances of $R^{K2}$ are —$CH_3$. In certain embodiments, at least one instance of $R^{K2}$ is substituted methyl. In certain embodiments, at least one instance of $R^{K2}$ is —$CH_2F$. In certain embodiments, at least one instance of $R^{K2}$ is —$CHF_2$. In certain embodiments, at least one instance of $R^{K2}$ is —$CF_3$. In certain embodiments, at least one instance of $R^{K2}$ is ethyl. In certain embodiments, at least one instance of $R^{K2}$ is propyl. In certain embodiments, at least one instance of $R^{K2}$ is butyl. In certain embodiments, at least one instance of $R^{K2}$ is pentyl. In certain embodiments, at least one instance of $R^{K2}$ is hexyl. In certain embodiments, at least one instance of $R^{K2}$ is substituted alkenyl. In certain embodiments, at least one instance of $R^{K2}$ is unsubstituted alkenyl. In certain embodiments, at least one instance of $R^{K2}$ is substituted alkynyl. In certain embodiments, at least one instance of $R^{K2}$ is unsubstituted alkynyl. In certain embodiments, at least one instance of $R^{K2}$ is substituted carbocyclyl. In certain embodiments, at least one instance of $R^{K2}$ is unsubstituted carbocyclyl. In certain embodiments, at least one instance of $R^{K2}$ instance of saturated carbocyclyl. In certain embodiments, at least one instance of $R^{K2}$ is unsaturated carbocyclyl. In certain embodiments, at least one instance of $R^{K2}$ is monocyclic carbocyclyl. In certain embodiments, at least one instance of $R^{K2}$ is 3- to 7-membered, monocyclic carbocyclyl. In certain embodiments, at least one instance of $R^{K2}$ is substituted heterocyclyl. In certain embodiments, at least one instance of $R^{K2}$ is unsubstituted heterocyclyl. In certain embodiments, at least one instance of $R^{K2}$ is saturated heterocyclyl. In certain embodiments, at least one instance of $R^{K2}$ is unsaturated heterocyclyl. In certain embodiments, at least one instance of $R^{K2}$ is heterocyclyl, wherein one, two, or three atoms in the heterocyclic ring system are independently selected from the group consisting of nitrogen, oxygen, and sulfur. In certain embodiments, at least one instance of $R^{K2}$ is monocyclic heterocyclyl. In certain embodiments, at least one instance of $R^{K2}$ is 3- to 7-membered, monocyclic heterocyclyl. In certain embodiments, at least one instance of $R^{K2}$ is substituted aryl. In certain embodiments, at least one instance of $R^{K2}$ is unsubstituted aryl. In certain embodiments, at least one instance of $R^{K2}$ is 6- to 10-membered aryl. In certain embodiments, at least one instance of $R^{K2}$ is substituted phenyl. In certain embodiments, at least one instance of $R^{K2}$ is unsubstituted phenyl. In certain embodiments, at least one instance of $R^{K2}$ is substituted heteroaryl. In certain embodiments, at least one instance of $R^{K2}$ is unsubstituted heteroaryl. In certain embodiments, at least one instance of $R^{K2}$ is heteroaryl, wherein one, two, three, or four atoms in the heteroaryl ring system are independently selected from the group consisting of nitrogen, oxygen, and sulfur. In certain embodiments, at least one instance of $R^{K2}$ is monocyclic heteroaryl. In certain embodiments, at least one instance of $R^{K2}$ is 5-membered, monocyclic heteroaryl. In certain embodiments, at least one instance of $R^{K2}$ is 6-membered, monocyclic heteroaryl. In certain embodiments, at least one instance of $R^{K2}$ is bicyclic heteroaryl, wherein the point of attachment may be on any atom of the bicyclic heteroaryl ring system, as valency permits. In certain embodiments, at least one instance of $R^{K2}$ is 9- or 10-membered, bicyclic heteroaryl. In certain embodiments, at least one instance of $R^{K2}$ is —$OR^{K2a}$. In certain embodiments, at least one instance of $R^{K2}$ is —OH. In certain embodiments, at least one instance of $R^{K2}$ is —OMe. In certain embodiments, at least one instance of $R^{K2}$ is —OEt. In certain embodiments, at least one instance of $R^{K2}$ is —OPr. In certain embodiments, at least one instance of $R^{K2}$ is —OBu. In certain embodiments, at least one instance of $R^{K2}$ is —OBn. In certain embodiments, at least one instance of $R^{K2}$ is —OPh. In certain embodiments, at least one instance of $R^{K2}$ is —$SR^{K2a}$. In certain embodiments, at least one instance of $R^{K2}$ is —SH. In certain embodiments, at least one instance of $R^{K2}$ is —SMe. In certain embodiments, at least one instance of $R^{K2}$ is —$N(R^{K2a})_2$. In certain embodiments, at least one instance of $R^{K2}$ is —$NH_2$. In certain embodiments, at least one instance of $R^{K2}$ is —NHMe. In certain embodiments, at least one instance of $R^{K2}$ is —$NMe_2$. In certain embodiments, at least one instance of $R^{K2}$ is —CN. In certain embodiments, at least one instance of $R^{K2}$ is —SCN. In certain embodiments, at least one instance of $R^{K2}$ is —$C(=NR^{K2a})R^{K2a}$, —$C(=NR^{K2a})OR^{K2a}$, or —$C(=NR^{K2a})N(R^{K2a})_2$. In certain embodiments, at least one instance of $R^{K2}$ is —$C(=O)R^{K2a}$ or —$C(=O)OR^{K2a}$. In certain embodiments, at least one instance of $R^{K2}$ is —$C(=O)N(R^{K2a})_2$. In certain embodiments, at least one instance of $R^{K2}$ is —$C(=O)NMe_2$, —$C(=O)NHMe$, or —$C(=O)NH_2$. In certain embodiments, at least one instance of $R^{K2}$ is —$NO_2$. In certain embodiments, at least one instance of $R^{K2}$ is —$NR^{K2a}C(=O)R^{K2a}$, —$NR^{K2a}C(=O)OR^{K2a}$, or —$NR^{K2a}C(=O)N(R^{K2a})_2$. In certain embodiments, at least one instance of $R^{K2}$ is —$OC(=O)R^{K2a}$, —$OC(=O)OR^{K2a}$, or —$OC(=O)N(R^{K2a})_2$.

In certain embodiments, at least one instance of $R^{K2a}$ is H. In certain embodiments, at least one instance of $R^{K2a}$ is substituted acyl. In certain embodiments, at least one instance of $R^{K2a}$ is unsubstituted acyl. In certain embodiments, at least one instance of $R^{K2a}$ is acetyl. In certain embodiments, at least one instance of $R^{K2a}$ is substituted alkyl. In certain embodiments, at least one instance of $R^{K2a}$ is unsubstituted alkyl. In certain embodiments, at least one instance of $R^{K2a}$ is unsubstituted $C_{1-6}$ alkyl. In certain embodiments, at least one instance of $R^{K2a}$ is methyl. In certain embodiments, at least one instance of $R^{K2a}$ is ethyl. In certain embodiments, at least one instance of $R^{K2a}$ is propyl. In certain embodiments, at least one instance of $R^{K2a}$ is butyl. In certain embodiments, at least one instance of $R^{K2a}$ is pentyl. In certain embodiments, at least one instance of $R^{K2a}$ is hexyl. In certain embodiments, at least one instance of $R^{K2a}$ is substituted alkenyl. In certain embodiments, at least one instance of $R^{K2a}$ is unsubstituted alkenyl. In certain embodiments, at least one instance of $R^{K2a}$ is substituted alkynyl. In certain embodiments, at least one instance of $R^{K1a}$ is unsubstituted alkynyl. In certain embodiments, at least one instance of $R^{K2a}$ is substituted or unsubstituted carbocyclyl. In certain embodiments, at least one instance of $R^{K2a}$ is saturated carbocyclyl. In certain embodiments, at least one instance of $R^{K2a}$ is unsaturated carbocyclyl. In certain embodiments, at least one instance of $R^{K2a}$ is 3- to 7-membered, monocyclic carbocyclyl. In certain embodiments, at least one instance of $R^{K2a}$ is substituted or unsubstituted heterocyclyl. In certain embodiments, at least one instance of $R^{K2a}$ is saturated heterocyclyl. In certain embodiments, at least one instance of $R^{K2a}$ is unsaturated heterocyclyl. In certain embodiments, at least one instance of $R^{K2a}$ is heterocyclyl, wherein one, two, or three atoms in the heterocyclic ring system are independently selected from the group consisting of nitrogen, oxygen, and sulfur. In certain embodiments, at least one instance of $R^{K2a}$ is 3- to 7-membered, monocyclic heterocyclyl. In certain embodiments, at least one instance of $R^{K2a}$ is substituted or unsubstituted aryl. In certain embodiments, at least one instance of $R^{K2a}$ is 6- to 10-membered aryl. In certain embodiments, at least one instance of $R^{K2a}$ is monocyclic aryl. In certain embodiments, at least one instance of $R^{K2a}$ is substituted phenyl. In certain embodiments, at least one instance of $R^{K2a}$ is unsubstituted phenyl. In certain embodiments, at least one instance of $R^{K2a}$ is bicyclic aryl. In certain embodiments, at least one instance of $R^{K2a}$ is substituted or unsubstituted heteroaryl. In certain embodiments, at least one instance of $R^{K2}$ is heteroaryl, wherein one, two, three, or four atoms in the heteroaryl ring system are independently selected from the group consisting of nitrogen, oxygen, and sulfur. In certain embodiments, at least one instance of $R^{K2a}$ is monocyclic heteroaryl. In certain embodiments, at least one instance of $R^{K2a}$ is 5- or 6-membered, monocyclic heteroaryl. In certain embodiments, at least one instance of $R^{K2a}$ is bicyclic heteroaryl, wherein the point of attachment may be on any atom of the bicyclic heteroaryl ring system, as valency permits. In certain embodiments, at least one instance of $R^{K2a}$ is a nitrogen protecting group when attached to a nitrogen atom. In certain embodiments, at least one instance of $R^{K2a}$ is Bn, Boc, Cbz, Fmoc, trifluoroacetyl, triphenylmethyl, acetyl, or Ts when attached to a nitrogen atom. In certain embodiments, $R^{K2a}$ is an oxygen protecting group when attached to an oxygen atom. In certain embodiments, $R^{K2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{K2a}$ is a sulfur protecting group when attached to a sulfur atom. In certain embodiments, $R^{K2a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{K2a}$ are joined to form a substituted or unsubstituted heterocyclic ring. In certain embodiments, two instances of $R^{K2a}$ are joined to form a saturated or unsaturated heterocyclic ring. In certain embodiments, two instances of $R^{K2a}$ are joined to form a heterocyclic ring, wherein one, two, or three atoms in the heterocyclic ring system are independently selected from the group consisting of nitrogen, oxygen, and sulfur. In certain embodiments, two instances of $R^{K2a}$ are joined to form a 3- to 7-membered, monocyclic heterocyclic ring. In certain embodiments, two instances of $R^{K2a}$ are joined to form a substituted or unsubstituted heteroaryl ring. In certain embodiments, two instances of $R^{K2a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, j is 0. In certain embodiments, j is 1. In certain embodiments, j is 2. In certain embodiments, j is 3. In certain embodiments, j is 4.

In certain embodiments, a compound described herein is of Formula (II-A):

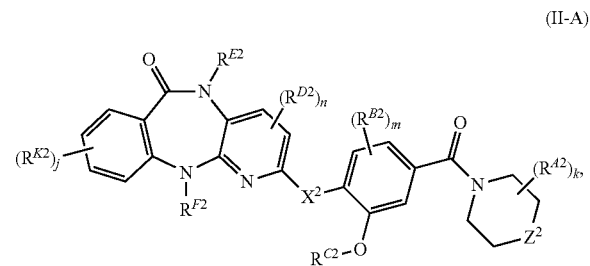

(II-A)

or a pharmaceutically acceptable salt, solvate, hydrate, polymorph, co-crystal, tautomer, stereoisomer, isotopically labeled derivative, or prodrug thereof.

In certain embodiments, a compound described herein is of the formula:

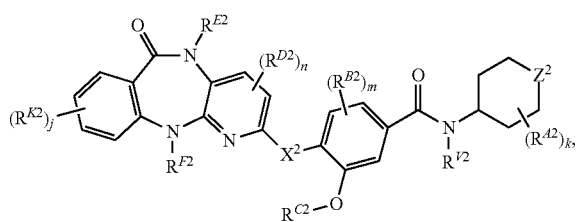

or a pharmaceutically acceptable salt, solvate, hydrate, polymorph, co-crystal, tautomer, stereoisomer, isotopically labeled derivative, or prodrug thereof.

In certain embodiments, a compound described herein is of the formula:

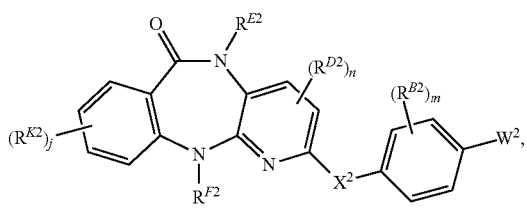

or a pharmaceutically acceptable salt, solvate, hydrate, polymorph, co-crystal, tautomer, stereoisomer, isotopically labeled derivative, or prodrug thereof, wherein $W^2$ is $-S(=O)OR^2$, $-S(=O)N(R^{W2})_2$, $-S(=O)_2OR^{W2}$, $-S(=O)_2N(R^{W2})_2$ (e.g., wherein $W^2$ is $-S(=O)_2NH_2$).

In certain embodiments, a compound described herein is of Formula (II-B):

(II-B)

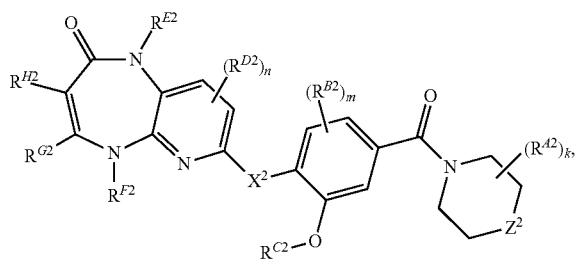

or a pharmaceutically acceptable salt, solvate, hydrate, polymorph, co-crystal, tautomer, stereoisomer, isotopically labeled derivative, or prodrug thereof.

In certain embodiments, a compound described herein is of the formula:

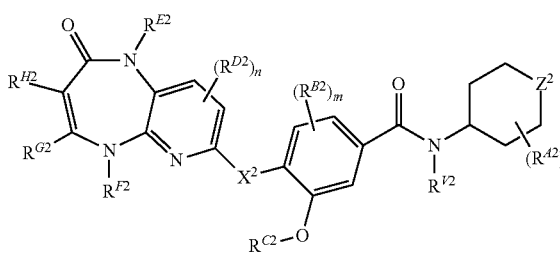

or a pharmaceutically acceptable salt, solvate, hydrate, polymorph, co-crystal, tautomer, stereoisomer, isotopically labeled derivative, or prodrug thereof.

In certain embodiments, a compound described herein is of the formula: 3,

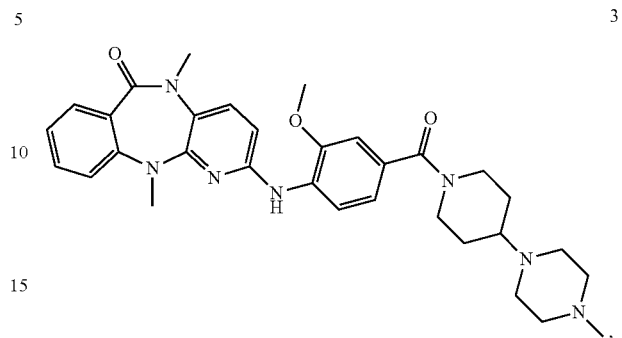

or a pharmaceutically acceptable salt, solvate, hydrate, polymorph, co-crystal, tautomer, stereoisomer, isotopically labeled derivative, or prodrug thereof.

In certain embodiments, a compound described herein is of the formula:

(2-227)

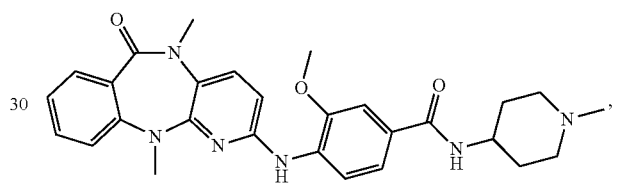

(2-221)

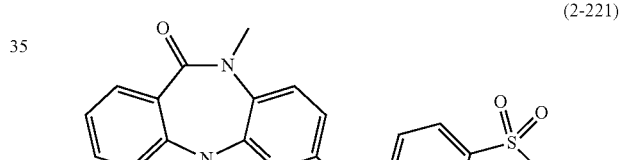

or a pharmaceutically acceptable salt, solvate, hydrate, polymorph, co-crystal, tautomer, stereoisomer, isotopically labeled derivative, or prodrug thereof.

Compounds of Formula (III)

In another aspect, the present invention provides compounds of Formula (III):

(III)

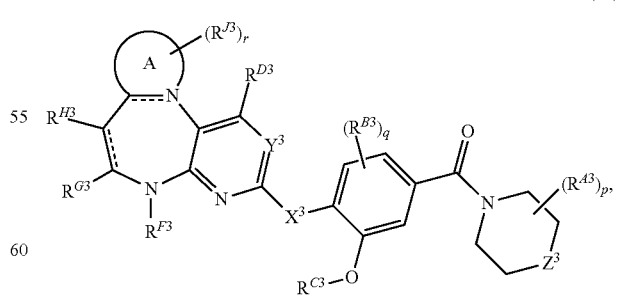

and pharmaceutically acceptable salts, solvates, hydrates, polymorphs, co-crystals, tautomers, stereoisomers, isotopically labeled derivatives, and prodrugs thereof, wherein:

each instance of === is independently a single or double bond;

$X^3$ is —O—, —S—, —N($R^{X3}$)—, or —C($R^{X3}$)$_2$—, wherein each instance of $R^{X3}$ is independently hydrogen, halogen, substituted or unsubstituted $C_{1-6}$ alkyl, or a nitrogen protecting group when attached to a nitrogen atom;

$Y^3$ is N or $CR^{Y3}$, wherein $R^{Y3}$ is hydrogen, halogen, or substituted or unsubstituted $C_{1-6}$ alkyl; $Z^3$ is —O—, —N($R^{Z3}$)— or —C($R^{Z3}$)$_2$—, wherein each instance of $R^{Z3}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or two instances of $R^{Z3}$ are joined to form a substituted or unsubstituted carbocyclic or substituted or unsubstituted heterocyclic ring;

each instance of $R^{A3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A3a}$, —N($R^{A3a}$)$_2$, —$SR^{A3a}$, —CN, —SCN, —C(=N$R^{A3a}$)$R^{A3a}$, —C(=N$R^{A3a}$)O$R^{A3a}$, —C(=N$R^{A3a}$)N($R^{A3a}$)$_2$, —C(=O)$R^{A3a}$, —C(=O)O$R^{A3a}$, —C(=O)N($R^{A3a}$)$_2$, —NO$_2$, —N$R^{A3a}$C(=O)$R^{A3a}$, —N$R^{A3a}$C(=O)O$R^{A3a}$, —N$R^{A3a}$C(=O)N($R^{A3a}$)$_2$, —OC(=O)$R^{A3a}$, —OC(=O)O$R^{A3a}$, or —OC(=O)N($R^{A3a}$)$_2$, wherein each instance of $R^{A3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A3a}$ groups are joined to form a substituted or unsubstituted heterocyclic or substituted or unsubstituted heteroaryl ring;

p is 0, 1, 2, 3, 4, 5, 6, 7, or 8;

each instance of $R^{B3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B3a}$, —N($R^{B3a}$)$_2$, —$SR^{B3a}$, —CN, —SCN, —C(=N$R^{B3a}$)$R^{B3a}$, —C(=N$R^{B3a}$)O$R^{B3a}$, —C(=N$R^{B3a}$)N($R^{B3a}$)$_2$, —C(=O)$R^{B3a}$, —C(=O)O$R^{B3a}$, —C(=O)N($R^{B3a}$)$_2$, —NO$_2$, —N$R^{B3a}$C(=O)$R^{B3a}$, —N$R^{B3a}$C(=O)O$R^{B3a}$, —N$R^{B3a}$C(=O)N($R^{B3a}$)$_2$, —OC(=O)$R^{B3a}$, —OC(=O)O$R^{B3a}$, or —OC(=O)N($R^{B3a}$)$_2$, wherein each instance of $R^{B3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B3a}$ groups are joined to form a substituted or unsubstituted heterocyclic or substituted or unsubstituted heteroaryl ring;

q is 0, 1, 2, or 3;

$R^{C3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

$R^{D3}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D3a}$, —N($R^{D3a}$)$_2$, —$SR^{D3a}$, —CN, —SCN, —C(=N$R^{D3a}$)$R^{D3a}$, —C(=N$R^{D3a}$)O$R^{D3a}$, —C(=N$R^{D3a}$)N($R^{D3a}$)$_2$, —C(=O)$R^{D3a}$, —C(=O)O$R^{D3a}$, —C(=O)N($R^{D3a}$)$_2$, —NO$_2$, —N$R^{D3a}$C(=O)$R^{D3a}$, —N$R^{D3a}$C(=O)O$R^{D3a}$, —N$R^{D3a}$C(=O)N($R^{D3a}$)$_2$, —OC(=O)$R^{D3a}$, —OC(=O)O$R^{D3a}$, or —OC(=O)N($R^{D3a}$)$_2$, wherein each instance of $R^{D3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{D3a}$ groups are joined to form a substituted or unsubstituted heterocyclic or substituted or unsubstituted heteroaryl ring;

Ring A is substituted or unsubstituted, 5- to 6-membered, monocyclic, heterocyclic or heteroaryl ring;

each instance of $R^{J3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{J3a}$, —N($R^{J3a}$)$_2$, —$SR^{J3a}$, —CN, —SCN, —C(=N$R^{J3a}$)$R^{J3a}$, —C(=N$R^{J3a}$)O$R^{J3a}$, —C(=N$R^{J3a}$)N($R^{J3a}$)$_2$, —C(=O)$R^{J3a}$, —C(=O)O$R^{J3a}$, —C(=O)N($R^{J3a}$)$_2$, —NO$_2$, —N$R^{J3a}$C(=O)$R^{J3a}$, —N$R^{J3a}$C(=O)O$R^{J3a}$, —N$R^{J3a}$C(=O)N($R^{J3a}$)$_2$, —OC(=O)$R^{J3a}$, —OC(=O)O$R^{J3a}$, —OC(=O)N($R^{J3a}$)$_2$, or a nitrogen protecting group when attached to a nitrogen atom, wherein each instance of $R^{J3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{J3a}$ groups are joined to form a substituted or unsubstituted heterocyclic or substituted or unsubstituted heteroaryl ring;

r is 0, 1, 2, 3, 4, 5, 6, 7, or 8;

$R^{F3}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{G3}$ is hydrogen, halogen, or substituted or unsubstituted $C_{1-6}$ alkyl; and $R^{H3}$ is hydrogen, halogen, or substituted or unsubstituted $C_{1-6}$ alkyl;

or $R^{G3}$ and $R^{H3}$ are joined to form a substituted or unsubstituted phenyl ring.

Formula (III) includes two bonds ⚌. In certain embodiments, at least one instance of ⚌ is a single bond. In certain embodiments, at least one instance of ⚌ is a double bond. In certain embodiments, each instance of ⚌ is a single bond. In certain embodiments, each instance of ⚌ is a double bond. In certain embodiments, one instance of ⚌ is a single bond, and the other instance of ⚌ is a double bond.

Formula (III) includes a divalent moiety $X^3$. In certain embodiments, $X^3$ is —O—. In certain embodiments, $X^3$ is —S—. In certain embodiments, $X^3$ is —N($R^{X3}$)—. In certain embodiments, $X^3$ is —NH—. In certain embodiments, $X^3$ is —N(substituted or unsubstituted, $C_{1-6}$alkyl)-. In certain embodiments, $X^3$ is —N(CH$_3$)—. In certain embodiments, $X^3$ is —C($R^{X3}$)$_2$—. In certain embodiments, $X^3$ is —CH($R^{X3}$)—. In certain embodiments, $X^3$ is —CH$_2$—.

In certain embodiments, at least one instance of $R^{X3}$ is H. In certain embodiments, each instance of $R^{X3}$ is H. In certain embodiments, at least one instance of $R^{X3}$ is halogen. In certain embodiments, at least one instance of $R^{X3}$ is F. In certain embodiments, at least one instance of $R^{X3}$ is Cl. In certain embodiments, at least one instance of $R^{X3}$ is Br. In certain embodiments, at least one instance of $R^{X3}$ is I (iodine). In certain embodiments, at least one instance of $R^{X3}$ is unsubstituted $C_{1-6}$ alkyl. In certain embodiments, each instance of $R^{X3}$ is unsubstituted $C_{1-6}$ alkyl. In certain embodiments, at least one instance of $R^{X3}$ is substituted $C_{1-6}$ alkyl. In certain embodiments, at least one instance of $R^{X3}$ is $C_{1-6}$ alkyl substituted with at least one halogen. In certain embodiments, at least one instance of $R^{X3}$ is —CH$_3$. In certain embodiments, each instance of $R^{X3}$ is —CH$_3$. In certain embodiments, at least one instance of $R^{X3}$ is substituted methyl. In certain embodiments, at least one instance of $R^{X3}$ is —CH$_2$F. In certain embodiments, at least one instance of $R^{X3}$ is —CHF$_2$. In certain embodiments, at least one instance of $R^{X3}$ is —CF$_3$. In certain embodiments, at least one instance of $R^{X3}$ is ethyl. In certain embodiments, at least one instance of $R^{X3}$ is propyl. In certain embodiments, at least one instance of $R^{X3}$ is butyl. In certain embodiments, at least one instance of $R^{X3}$ is pentyl. In certain embodiments, at least one instance of $R^{X3}$ is hexyl.

Formula (III) includes a divalent moiety $Y^3$. In certain embodiments, $Y^3$ is N. In certain embodiments, $Y^3$ is $CR^{Y3}$. In certain embodiments, $Y^3$ is CH. In certain embodiments, $Y^3$ is C (halogen). In certain embodiments, $Y^3$ is C(substituted or unsubstituted, $C_{1-6}$ alkyl).

In certain embodiments, $R^{Y3}$ is H. In certain embodiments, $R^{Y3}$ is halogen. In certain embodiments, $R^{Y3}$ is F. In certain embodiments, $R^{Y3}$ is Cl. In certain embodiments, $R^{Y3}$ is Br. In certain embodiments, $R^{Y3}$ is I (iodine). In certain embodiments, $R^{Y3}$ is unsubstituted $C_{1-6}$ alkyl. In certain embodiments, $R^{Y3}$ is substituted $C_{1-6}$ alkyl. In certain embodiments, $R^{Y3}$ is $C_{1-6}$ alkyl substituted with at least one halogen. In certain embodiments, $R^{Y3}$ is —CH$_3$. In certain embodiments, $R^{Y3}$ is substituted methyl. In certain embodiments, $R^{Y3}$ is —CH$_2$F. In certain embodiments, $R^{Y3}$ is —CHF$_2$. In certain embodiments, $R^{Y3}$ is —CF$_3$. In certain embodiments, $R^{Y3}$ is ethyl. In certain embodiments, $R^{Y3}$ is propyl. In certain embodiments, $R^{Y3}$ is butyl. In certain embodiments, $R^{Y3}$ is pentyl. In certain embodiments, $R^{Y3}$ is hexyl.

Formula (III) includes a divalent moiety $Z^3$. In certain embodiments, $Z^3$ is —O—. In certain embodiments, $Z^3$ is —N($R^{Z3}$)—. In certain embodiments, $Z^3$ is —NH—. In certain embodiments, $Z^3$ is —N(substituted or unsubstituted, $C_{1-6}$ alkyl)-. In certain embodiments, $Z^3$ is —N(substituted or unsubstituted, 4- to 7-membered, monocyclic heterocyclyl)-. In certain embodiments, $Z^3$ is —C($R^{Z3}$)$_2$—. In certain embodiments, $Z^3$ is —CH($R^{Z3}$)—. In certain embodiments, $Z^3$ is —CH(substituted or unsubstituted, $C_{1-6}$ alkyl)-. In certain embodiments, $Z^3$ is —CH(substituted or unsubstituted, 4- to 7-membered, monocyclic heterocyclyl)-.

Formula (III) may include one or more substituents $R^{Z3}$ on the divalent moiety $Z^3$. In certain embodiments, at least one instance of $R^{Z3}$ is H. In certain embodiments, at least one instance of $R^{Z3}$ is substituted acyl. In certain embodiments, at least one instance of $R^{Z3}$ is unsubstituted acyl. In certain embodiments, at least one instance of $R^{Z3}$ is acetyl. In certain embodiments, at least one instance of $R^{Z3}$ is substituted alkyl. In certain embodiments, at least one instance of $R^{Z3}$ is unsubstituted alkyl. In certain embodiments, at least one instance of $R^{Z3}$ is unsubstituted $C_{1-6}$ alkyl. In certain embodiments, at least one instance of $R^{Z3}$ is methyl. In certain embodiments, at least one instance of $R^{Z3}$ is ethyl. In certain embodiments, at least one instance of $R^{Z3}$ is propyl. In certain embodiments, at least one instance of $R^{Z3}$ is butyl. In certain embodiments, at least one instance of $R^{Z3}$ is pentyl. In certain embodiments, at least one instance of $R^{Z3}$ is hexyl. In certain embodiments, at least one instance of $R^{Z3}$ is substituted alkenyl. In certain embodiments, at least one instance of $R^{Z3}$ is unsubstituted alkenyl. In certain embodiments, at least one instance of $R^{Z3}$ is substituted alkynyl. In certain embodiments, at least one instance of $R^{Z3}$ is unsubstituted alkynyl. In certain embodiments, at least one instance of $R^{Z3}$ is substituted or unsubstituted carbocyclyl. In certain embodiments, at least one instance of $R^{Z3}$ is saturated carbocyclyl. In certain embodiments, at least one instance of $R^3$ is unsaturated carbocyclyl. In certain embodiments, at least one instance of $R^{Z3}$ is 3- to 7-membered, monocyclic carbocyclyl. In certain embodiments, at least one instance of $R^{Z3}$ is substituted or unsubstituted heterocyclyl. In certain embodiments, at least one instance of $R^{Z3}$ is saturated heterocyclyl. In certain embodiments, at least one instance of $R^{Z3}$ is unsaturated heterocyclyl. In certain embodiments, at least one instance of $R^{Z3}$ is substituted or unsubstituted, 4- to 7-membered, monocyclic heterocyclyl, wherein one, two, or three atoms in the heterocyclic ring system are independently nitrogen, oxygen, or sulfur. In certain embodiments, at least one instance of $R^{Z3}$ is substituted or unsubstituted, 6-membered, monocyclic heterocyclyl, wherein one or two atoms in the heterocyclic ring system are independently nitrogen, oxygen, or sulfur. In certain embodiments, at least one instance of $R^{Z3}$ is of the formula:

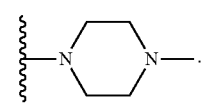

In certain embodiments, at least one instance of $R^{Z3}$ is of the formula:

In certain embodiments, at least one instance of $R^{Z3}$ is of the formula:

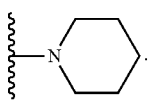

In certain embodiments, at least one instance of $R^{Z3}$ is of the formula:

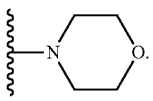 [SMILES: *N1CCOCC1]

In certain embodiments, at least one instance of $R^{Z3}$ is of the formula:

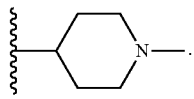

In certain embodiments, at least one instance of $R^{Z3}$ is of the formula:

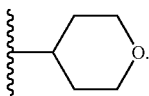

In certain embodiments, at least one instance of $R^{Z3}$ is substituted or unsubstituted aryl. In certain embodiments, at least one instance of $R^3$ is 6- to 10-membered aryl. In certain embodiments, at least one instance of $R^3$ is monocyclic aryl. In certain embodiments, at least one instance of $R^{Z3}$ is substituted phenyl. In certain embodiments, at least one instance of $R^{Z3}$ is unsubstituted phenyl. In certain embodiments, at least one instance of $R^{Z3}$ is bicyclic aryl. In certain embodiments, at least one instance of $R^3$ is substituted or unsubstituted heteroaryl. In certain embodiments, at least one instance of $R^3$ is heteroaryl, wherein one, two, three, or four atoms in the heteroaryl ring system are independently selected from the group consisting of nitrogen, oxygen, and sulfur. In certain embodiments, at least one instance of $R^{Z3}$ is monocyclic heteroaryl. In certain embodiments, at least one instance of $R^{Z3}$ is 5- or 6-membered, monocyclic heteroaryl. In certain embodiments, at least one instance of $R^{Z3}$ is bicyclic heteroaryl, wherein the point of attachment may be on any atom of the bicyclic heteroaryl ring system, as valency permits. In certain embodiments, at least one instance of $R^Z$ is a nitrogen protecting group when attached to a nitrogen atom. In certain embodiments, at least one instance of $R^Z$ is Bn, Boc, Cbz, Fmoc, trifluoroacetyl, triphenylmethyl, acetyl, or Ts when attached to a nitrogen atom. In certain embodiments, two instances of $R^3$ are joined to form a substituted or unsubstituted carbocyclic ring. In certain embodiments, two instances of $R^3$ are joined to form a saturated or unsaturated carbocyclic ring. In certain embodiments, two instances of $R^3$ are joined to form a substituted or unsubstituted, 3- to 7-membered, monocyclic carbocyclic ring. In certain embodiments, two instances of $R^{Z3}$ are joined to form a substituted or unsubstituted heterocyclic ring. In certain embodiments, two instances of $R^{Z3}$ are joined to form a saturated or unsaturated heterocyclic ring. In certain embodiments, two instances of $R^{Z3}$ are joined to form a heterocyclic ring, wherein one, two, or three atoms in the heterocyclic ring system are independently selected from the group consisting of nitrogen, oxygen, and sulfur. In certain embodiments, two instances of $R^{Z3}$ are joined to form a 3- to 7-membered, monocyclic heterocyclic ring.

Formula (III) may include one or more substituents $R^{43}$. In certain embodiments, at least two instances of $R^{43}$ are different. In certain embodiments, all instances of $R^{43}$ are the same. In certain embodiments, at least one instance of $R^{43}$ is H. In certain embodiments, all instances of $R^{43}$ are H. In certain embodiments, at least one instance of $R^{43}$ is halogen. In certain embodiments, at least one instance of $R^{43}$ is F. In certain embodiments, at least one instance of $R^{43}$ is Cl. In certain embodiments, at least one instance of $R^{43}$ is Br. In certain embodiments, at least one instance of $R^{43}$ is I (iodine). In certain embodiments, at least one instance of $R^{43}$ is substituted alkyl. In certain embodiments, at least one instance of $R^{43}$ is unsubstituted alkyl. In certain embodiments, at least one instance of $R^{43}$ is unsubstituted $C_{1-6}$ alkyl. In certain embodiments, all instances of $R^{43}$ are unsubstituted $C_{1-6}$ alkyl. In certain embodiments, at least one instance of $R^{43}$ is substituted $C_{1-6}$ alkyl. In certain embodiments, at least one instance of $R^{43}$ is $C_{1-6}$ alkyl substituted with at least one halogen. In certain embodiments, at least one instance of $R^{43}$ is —$CH_3$. In certain embodiments, all instances of $R^{43}$ are —$CH_3$. In certain embodiments, at least one instance of $R^{43}$ is substituted methyl. In certain embodiments, at least one instance of $R^{43}$ is —$CH_2F$. In certain embodiments, at least one instance of $R^{43}$ is —$CHF_2$. In certain embodiments, at least one instance of $R^{43}$ is —$CF_3$. In certain embodiments, at least one instance of $R^{43}$ is ethyl. In certain embodiments, at least one instance of $R^{43}$ is propyl. In certain embodiments, at least one instance of $R^{43}$ is butyl. In certain embodiments, at least one instance of $R^{43}$ is pentyl. In certain embodiments, at least one instance of $R^{43}$ is hexyl. In certain embodiments, at least one instance of $R^{43}$ is substituted alkenyl. In certain embodiments, at least one instance of $R^{43}$ is unsubstituted alkenyl. In certain embodiments, at least one instance of $R^{43}$ is substituted alkynyl. In certain embodiments, at least one instance of $R^{43}$ is unsubstituted alkynyl. In certain embodiments, at least one instance of $R^{43}$ is substituted carbocyclyl. In certain embodiments, at least one instance of $R^{43}$ is unsubstituted carbocyclyl. In certain embodiments, at least one instance of $R^{43}$ is saturated carbocyclyl. In certain embodiments, at least one instance of $R^{43}$ is unsaturated carbocyclyl. In certain embodiments, at least one instance of $R^{43}$ is monocyclic carbocyclyl. In certain embodiments, at least one instance of $R^{43}$ is 3- to 7-membered, monocyclic carbocyclyl. In certain embodiments, at least one instance of $R^{43}$ is substituted heterocyclyl. In certain embodiments, at least one instance of $R^{43}$ is unsubstituted heterocyclyl. In certain embodiments, at least one instance of $R^{43}$ is saturated heterocyclyl. In certain embodiments, at least one instance of $R^{43}$ is unsaturated heterocyclyl. In certain embodiments, at least one instance of $R^{43}$ is heterocyclyl, wherein one, two, or three atoms in the heterocyclic ring system are independently selected from the group consisting of nitrogen, oxygen, and sulfur. In certain embodiments, at least one instance of $R^{43}$ is monocyclic heterocyclyl. In certain embodiments, at least one instance of $R^{43}$ is 3- to 7-membered, monocyclic heterocyclyl. In certain embodiments, at least one instance of $R^{43}$ is substituted aryl. In certain embodiments, at least one instance of $R^{43}$ is unsubstituted aryl. In certain embodiments, at least one instance of $R^{43}$ is 6- to 10-membered aryl. In certain embodiments, at least one instance of $R^{A3}$ is substituted phenyl. In certain embodiments, at least one instance of $R^{A3}$ is unsubstituted phenyl. In certain embodiments, at least one instance of $R^{A3}$ is substituted heteroaryl. In certain embodiments, at least one instance of $R^{A3}$ is unsubstituted heteroaryl. In certain embodiments, at least one instance of $R^{A3}$ is heteroaryl, wherein one, two, three, or four atoms in the heteroaryl ring system are independently selected from the group consisting of nitrogen, oxygen, and sulfur. In certain embodiments, at least one instance of $R^{A3}$ is monocyclic heteroaryl. In certain embodiments, at least one instance of $R^{A3}$ is 5-membered, monocyclic heteroaryl. In certain embodiments, at least one instance of $R^{A3}$ is 6-membered, monocyclic heteroaryl. In certain embodiments, at least one instance of $R^{A3}$ is bicyclic heteroaryl, wherein the point of attachment may be on any atom of the bicyclic heteroaryl ring system, as valency permits. In certain embodiments, at least one instance of $R^{A3}$ is 9- or 10-membered, bicyclic heteroaryl. In certain embodiments, at least one instance of $R^{A3}$ is —$OR^{A3a}$. In certain embodiments, at least one instance of $R^{A3}$ is —OH. In certain embodiments, at least one instance of $R^{A3}$ is —OMe. In certain embodiments, at least one instance of $R^{A3}$ is —OEt. In certain embodiments, at least one instance of $R^{A3}$ is —OPr. In certain embodiments, at least one instance of $R^{A3}$ is —OBu. In certain embodiments, at least one instance of $R^{A3}$ is —OBn. In certain embodiments, at least one instance of $R^{A3}$ is —OPh. In certain embodiments, at least one instance of $R^{A3}$ is —$SR^{A3a}$. In certain embodiments, at least one instance of $R^{A3}$ is —SH. In certain embodiments, at least one instance of $R^{A3}$ is —SMe. In certain embodiments, at least one instance of $R^{A3}$ is —$N(R^{A3a})_2$. In certain embodiments, at least one instance of $R^{A3}$ is —$NH_2$. In certain embodiments, at least one instance of $R^{A3}$ is —NHMe. In certain embodiments, at least one instance of $R^{A3}$ is —$NMe_2$. In certain embodiments, at least one instance of $R^{A3}$ is —CN. In certain embodiments, at least one instance of $R^{A3}$ is —SCN. In certain embodiments, at least one instance of $R^{A3}$ is —$C(=NR^{A3a})R^{A3a}$, —$C(=NR^{A3a})OR^{A3a}$, or —$C(=NR^{A3a})N(R^{A3a})_2$. In certain embodiments, at least one instance of $R^{A3}$ is —$C(=O)R^{A3a}$ or —$C(=O)OR^{A3a}$. In certain embodiments, at least one instance of $R^{A3}$ is —$C(=O)N(R^{A3a})_2$. In certain embodiments, at least one instance of $R^{A3}$ is —$C(=O)NMe_2$, —$C(=O)NHMe$, or —$C(=O)NH_2$. In certain embodiments, at least one instance of $R^{A3}$ is —$NO_2$. In certain embodiments, at least one instance of $R^{A3}$ is —$NR^{A3a}C(=O)R^{A3a}$, —$NR^{A3a}C(=O)OR^{A3a}$, or —$NR^{A3a}C(=O)N(R^{A3a})_2$. In certain embodiments, at least one instance of $R^{A3}$ is —$OC(=O)R^{A3a}$, —$OC(=O)OR^{A3a}$, or —$OC(=O)N(R^{A3a})_2$.

In certain embodiments, at least one instance of $R^{A3a}$ is H. In certain embodiments, at least one instance of $R^{A3a}$ is substituted acyl. In certain embodiments, at least one instance of $R^{A3a}$ is unsubstituted acyl. In certain embodiments, at least one instance of $R^{A3a}$ is acetyl. In certain embodiments, at least one instance of $R^{A3a}$ is substituted alkyl. In certain embodiments, at least one instance of $R^{A3a}$ is unsubstituted alkyl. In certain embodiments, at least one instance of $R^{A3a}$ is unsubstituted $C_{1-6}$ alkyl. In certain embodiments, at least one instance of $R^{A3a}$ is methyl. In certain embodiments, at least one instance of $R^{A3a}$ is ethyl. In certain embodiments, at least one instance of $R^{A3a}$ is propyl. In certain embodiments, at least one instance of $R^{A3a}$ is butyl. In certain embodiments, at least one instance of $R^{A3a}$ is pentyl. In certain embodiments, at least one instance of $R^{A3a}$ is hexyl. In certain embodiments, at least one instance of $R^{A3a}$ is substituted alkenyl. In certain embodiments, at least one instance of $R^{A3a}$ is unsubstituted alkenyl. In certain embodiments, at least one instance of $R^{A3a}$ is substituted alkynyl. In certain embodiments, at least one instance of $R^{A3a}$ is unsubstituted alkynyl. In certain embodiments, at least one instance of $R^{A3a}$ is substituted or unsubstituted carbocyclyl. In certain embodiments, at least one instance of $R^{A3a}$ is saturated carbocyclyl. In certain embodiments, at least one instance of $R^{A3a}$ is unsaturated carbocyclyl. In certain embodiments, at least one instance of $R^{A3a}$ is 3- to 7-membered, monocyclic carbocyclyl. In certain embodiments, at least one instance of $R^{A3a}$ is substituted or unsubstituted heterocyclyl. In certain embodiments, at least one instance of $R^{A3a}$ is saturated heterocyclyl. In certain embodiments, at least one instance of $R^{A3a}$ is unsaturated heterocyclyl. In certain embodiments, at least one instance of $R^{A3a}$ is heterocyclyl, wherein one, two, or three atoms in the heterocyclic ring system are independently selected from the group consisting of nitrogen, oxygen, and sulfur. In certain embodiments, at least one instance of $R^{A3a}$ is 3- to 7-membered, monocyclic heterocyclyl. In certain embodiments, at least one instance of $R^{A3a}$ is substituted or unsubstituted aryl. In certain embodiments, at least one instance of $R^{A3a}$ is 6- to 10-membered aryl. In certain embodiments, at least one instance of $R^{A3a}$ is monocyclic aryl. In certain embodiments, at least one instance of $R^{A3a}$ is substituted phenyl. In certain embodiments, at least one instance of $R^{A3a}$ is unsubstituted phenyl. In certain embodiments, at least one instance of $R^{A3a}$ is bicyclic aryl. In certain embodiments, at least one instance of $R^{A3a}$ is substituted or unsubstituted heteroaryl. In certain embodiments, at least one instance of $R^{A3a}$ is heteroaryl, wherein one, two, three, or four atoms in the heteroaryl ring system are independently selected from the group consisting of nitrogen, oxygen, and sulfur. In certain embodiments, at least one instance of $R^{A3a}$ is monocyclic heteroaryl. In certain embodiments, at least one instance of $R^{A3a}$ is 5- or 6-membered, monocyclic heteroaryl. In certain embodiments, at least one instance of $R^{A3a}$ is bicyclic heteroaryl, wherein the point of attachment may be on any atom of the bicyclic heteroaryl ring system, as valency permits. In certain embodiments, at least one instance of $R^{A3a}$ is a nitrogen protecting group when attached to a nitrogen atom. In certain embodiments, at least one instance of $R^{A3a}$ is Bn, Boc, Cbz, Fmoc, trifluoroacetyl, triphenylmethyl, acetyl, or Ts when attached to a nitrogen atom. In certain embodiments, $R^{A3a}$ is an oxygen protecting group when attached to an oxygen atom. In certain embodiments, $R^{A3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A3a}$ is a sulfur protecting group when attached to a sulfur atom. In certain embodiments, $R^{A3a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{A3a}$ are joined to form a substituted or unsubstituted heterocyclic ring. In certain embodiments, two instances of $R^{A3a}$ are joined to form a saturated or unsaturated heterocyclic ring. In certain embodiments, two instances of $R^{A3a}$ are joined to form a heterocyclic ring, wherein one, two, or three atoms in the heterocyclic ring system are independently selected from the group consisting of nitrogen, oxygen, and sulfur. In certain embodiments, two instances of $R^{A3a}$ are joined to form a 3- to 7-membered, monocyclic heterocyclic ring. In certain embodiments, two instances of $R^{A3a}$ are joined to form a substituted or unsubstituted heteroaryl ring. In certain embodiments, two instances of $R^{A3a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, p is 0. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8.

Formula (III) may include one or more substituents $R^{B3}$. In certain embodiments, at least two instances of $R^{B3}$ are different. In certain embodiments, all instances of $R^{B3}$ are the same. In certain embodiments, at least one instance of $R^{B3}$ is H. In certain embodiments, all instances of $R^{B3}$ are H. In certain embodiments, at least one instance of $R^{B3}$ is halogen. In certain embodiments, at least one instance of $R^{B3}$ is F. In certain embodiments, at least one instance of $R^{B3}$ is Cl. In certain embodiments, at least one instance of $R^{B3}$ is Br. In certain embodiments, at least one instance of $R^{B3}$ is I (iodine). In certain embodiments, at least one instance of $R^{B3}$ is substituted alkyl. In certain embodiments, at least one instance of $R^{B3}$ is unsubstituted alkyl. In certain embodiments, at least one instance of $R^{B3}$ is unsubstituted $C_{1-6}$alkyl. In certain embodiments, all instances of $R^{B3}$ are unsubstituted $C_{1-6}$ alkyl. In certain embodiments, at least one instance of $R^{B3}$ is substituted $C_{1-6}$ alkyl. In certain embodiments, at least one instance of $R^{B3}$ is $C_{1-6}$ alkyl substituted with at least one halogen. In certain embodiments, at least one instance of $R^{B3}$ is —$CH_3$. In certain embodiments, all instances of $R^{B3}$ are —$CH_3$. In certain embodiments, at least one instance of $R^{B3}$ is substituted methyl. In certain embodiments, at least one instance of $R^{B3}$ is —$CH_2F$. In certain embodiments, at least one instance of $R^{B3}$ is —$CHF_2$. In certain embodiments, at least one instance of $R^{B3}$ is —$CF_3$. In certain embodiments, at least one instance of $R^{B3}$ is ethyl. In certain embodiments, at least one instance of $R^{B3}$ is propyl. In certain embodiments, at least one instance of $R^{B3}$ is butyl. In certain embodiments, at least one instance of $R^{B3}$ is pentyl. In certain embodiments, at least one instance of $R^{B3}$ is hexyl. In certain embodiments, at least one instance of $R^{B3}$ is substituted alkenyl. In certain embodiments, at least one instance of $R^{B3}$ is unsubstituted alkenyl. In certain embodiments, at least one instance of $R^{B3}$ is substituted alkynyl. In certain embodiments, at least one instance of $R^{B3}$ is unsubstituted alkynyl. In certain embodiments, at least one instance of $R^{B3}$ is substituted carbocyclyl. In certain embodiments, at least one instance of $R^{B3}$ is unsubstituted carbocyclyl. In certain embodiments, at least one instance of $R^{B3}$ is saturated carbocyclyl. In certain embodiments, at least one instance of $R^{B3}$ is unsaturated carbocyclyl. In certain embodiments, at least one instance of $R^{B3}$ is monocyclic carbocyclyl. In certain embodiments, at least one instance of $R^{B3}$ is 3- to 7-membered, monocyclic carbocyclyl. In certain embodiments, at least one instance of $R^{B3}$ is substituted heterocyclyl. In certain embodiments, at least one instance of $R^{B3}$ is unsubstituted heterocyclyl. In certain embodiments, at least one instance of $R^{B3}$ is saturated heterocyclyl. In certain embodiments, at least one instance of $R^{B3}$ is unsaturated heterocyclyl. In certain embodiments, at least one instance of $R^{B3}$ is heterocyclyl, wherein one, two, or three atoms in the heterocyclic ring system are independently selected from the group consisting of nitrogen, oxygen, and sulfur. In certain embodiments, at least one instance of $R^{B3}$ is monocyclic heterocyclyl. In certain embodiments, at least one instance of $R^{B3}$ is 3- to 7-membered, monocyclic heterocyclyl. In certain embodiments, at least one instance of $R^{B3}$ is substituted aryl. In certain embodiments, at least one instance of $R^{B3}$ is unsubstituted aryl. In certain embodiments, at least one instance of $R^{B3}$ is 6- to 10-membered aryl. In certain embodiments, at least one instance of $R^{B3}$ is substituted phenyl. In certain embodiments, at least one instance of $R^{B3}$ is unsubstituted phenyl. In certain embodiments, at least one instance of $R^{B3}$ is substituted heteroaryl. In certain embodiments, at least one instance of $R^{B3}$ is unsubstituted heteroaryl. In certain embodiments, at least one instance of $R^{B3}$ is heteroaryl, wherein one, two, three, or four atoms in the heteroaryl ring system are independently selected from the group consisting of nitrogen, oxygen, and sulfur. In certain embodiments, at least one instance of $R^{B3}$ is monocyclic heteroaryl. In certain embodiments, at least one instance of $R^{B3}$ is 5-membered, monocyclic heteroaryl. In certain embodiments, at least one instance of $R^{B3}$ is 6-membered, monocyclic heteroaryl. In certain embodiments, at least one instance of $R^{B3}$ is bicyclic heteroaryl, wherein the point of attachment may be on any atom of the bicyclic heteroaryl ring system, as valency permits. In certain embodiments, at least one instance of $R^{B3}$ is 9- or 10-membered, bicyclic heteroaryl. In certain embodiments, at least one instance of $R^{B3}$ is —$OR^{B3a}$. In certain embodiments, at least one instance of $R^{B3}$ is —OH. In certain embodiments, at least one instance of $R^{B3}$ is —OMe. In certain embodiments, at least one instance of $R^{B3}$ is —OEt. In certain embodiments, at least one instance of $R^{B3}$ is —OPr. In certain embodiments, at least one instance of $R^{B3}$ is —OBu. In certain embodiments, at least one instance of $R^{B3}$ is —OBn. In certain embodiments, at least one instance of $R^{B3}$ is —OPh. In certain embodiments, at least one instance of $R^{B3}$ is —$SR^{B3a}$. In certain embodiments, at least one instance of $R^{B3}$ is —SH. In certain embodiments, at least one instance of $R^{B3}$ is —SMe. In certain embodiments, at least one instance of $R^{B3}$ is —$N(R^{B3a})_2$. In certain embodiments, at least one instance of $R^{B3}$ is —$NH_2$. In certain embodiments, at least one instance of $R^{B3}$ is —NHMe. In certain embodiments, at least one instance of $R^{B3}$ is —$NMe_2$. In certain embodiments, at least one instance of $R^{B3}$ is —CN. In certain embodiments, at least one instance of $R^{B3}$ is —SCN. In certain embodiments, at least one instance of $R^{B3}$ is —$C(=NR^{B3a})R^{B3a}$, —$C(=NR^{B3a})OR^{B3a}$, or —$C(=NR^{B3a})N(R^{B3a})_2$. In certain embodiments, at least one instance of $R^{B3}$ is —$C(=O)R^{B3a}$ or —$C(=O)OR^{B3a}$. In certain embodiments, at least one instance of $R^{B3}$ is —$C(=O)N(R^{B3a})_2$. In certain embodiments, at least one instance of $R^{B3}$ is —$C(=O)NMe_2$, —$C(=O)NHMe$, or —$C(=O)NH_2$. In certain embodiments, at least one instance of $R^{B3}$ is —$NO_2$. In certain embodiments, at least one instance of $R^{B3}$ is —$NR^{B3a}C(=O)R^{B3a}$, —$NR^{B3a}C(=O)OR^{B3a}$, or —$NR^{B3a}C(=O)N(R^{B3a})_2$. In certain embodiments, at least one instance of $R^{B3}$ is —$OC(=O)R^{B3a}$, —$OC(=O)OR^{B3a}$, or —$OC(=O)N(R^{B3a})_2$.

In certain embodiments, at least one instance of $R^{B3a}$ is H. In certain embodiments, at least one instance of $R^{B3a}$ is substituted acyl. In certain embodiments, at least one instance of $R^{B3a}$ is unsubstituted acyl. In certain embodiments, at least one instance of $R^{B3a}$ is acetyl. In certain embodiments, at least one instance of $R^{B3a}$ is substituted alkyl. In certain embodiments, at least one instance of $R^{B3a}$ is unsubstituted alkyl. In certain embodiments, at least one instance of $R^{B3a}$ is unsubstituted $C_{1-6}$ alkyl. In certain embodiments, at least one instance of $R^{B3a}$ is methyl. In certain embodiments, at least one instance of $R^{B3a}$ is ethyl. In certain embodiments, at least one instance of $R^{B3a}$ is propyl. In certain embodiments, at least one instance of $R^{B3a}$ is butyl. In certain embodiments, at least one instance of $R^{B3a}$ is pentyl. In certain embodiments, at least one instance of $R^{B3a}$ is hexyl. In certain embodiments, at least one instance of $R^{B3a}$ is substituted alkenyl. In certain embodiments, at least one instance of $R^{B3a}$ is unsubstituted alkenyl. In certain embodiments, at least one instance of $R^{B3a}$ is substituted alkynyl. In certain embodiments, at least one instance of $R^{B3a}$ is unsubstituted alkynyl. In certain embodiments, at least one instance of $R^{B3a}$ is substituted or unsubstituted carbocyclyl. In certain embodiments, at least one instance of $R^{B3a}$ is saturated carbocyclyl. In certain embodiments, at least one instance of $R^{B3a}$ is unsaturated carbocyclyl. In certain embodiments, at least one instance of $R^{B3a}$ is 3- to 7-membered, monocyclic carbocyclyl. In certain embodiments, at least one instance of $R^{B3a}$ is substituted or unsubstituted heterocyclyl. In certain embodiments, at least one instance of $R^{B3a}$ is saturated heterocyclyl. In certain embodiments, at least one instance of $R^{B3a}$ is unsaturated heterocyclyl. In certain embodiments, at least one instance of $R^{B3a}$ is heterocyclyl, wherein one, two, or three atoms in the heterocyclic ring system are independently selected from the group consisting of nitrogen, oxygen, and sulfur. In certain embodiments, at least one instance of $R^{B3a}$ is 3- to 7-membered, monocyclic heterocyclyl. In certain embodiments, at least one instance of $R^{B3a}$ is substituted or unsubstituted aryl. In certain embodiments, at least one instance of $R^{B3a}$ is 6- to 10-membered aryl. In certain embodiments, at least one instance of $R^{B3a}$ is monocyclic aryl. In certain embodiments, at least one instance of $R^{B3a}$ is substituted phenyl. In certain embodiments, at least one instance of $R^{B3a}$ is unsubstituted phenyl. In certain embodiments, at least one instance of $R^{B3a}$ is bicyclic aryl. In certain embodiments, at least one instance of $R^{B3a}$ is substituted or unsubstituted heteroaryl. In certain embodiments, at least one instance of $R^{B3a}$ is heteroaryl, wherein one, two, three, or four atoms in the heteroaryl ring system are independently selected from the group consisting of nitrogen, oxygen, and sulfur. In certain embodiments, at least one instance of $R^{B3a}$ is monocyclic heteroaryl. In certain embodiments, at least one instance of $R^{B3a}$ is 5- or 6-membered, monocyclic heteroaryl. In certain embodiments, at least one instance of $R^{B3a}$ is bicyclic heteroaryl, wherein the point of attachment may be on any atom of the bicyclic heteroaryl ring system, as valency permits. In certain embodiments, at least one instance of $R^{B3a}$ is a nitrogen protecting group when attached to a nitrogen atom. In certain embodiments, at least one instance of $R^{B3a}$ is Bn, Boc, Cbz, Fmoc, trifluoroacetyl, triphenylmethyl, acetyl, or Ts when attached to a nitrogen atom. In certain embodiments, $R^{B3a}$ is an oxygen protecting group when attached to an oxygen atom. In certain embodiments, $R^{B3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B3a}$ is a sulfur protecting group when attached to a sulfur atom. In certain embodiments, $R^{B3a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{B3a}$ are joined to form a substituted or unsubstituted heterocyclic ring. In certain embodiments, two instances of $R^{B3a}$ are joined to form a saturated or unsaturated heterocyclic ring. In certain embodiments, two instances of $R^{B3a}$ are joined to form a heterocyclic ring, wherein one, two, or three atoms in the heterocyclic ring system are independently selected from the group consisting of nitrogen, oxygen, and sulfur. In certain embodiments, two instances of $R^{B3a}$ are joined to form a 3- to 7-membered, monocyclic heterocyclic ring. In certain embodiments, two instances of $R^{B3a}$ are joined to form a substituted or unsubstituted heteroaryl ring. In certain embodiments, two instances of $R^{B3a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, q is 0. In certain embodiments, q is 1. In certain embodiments, q is 2. In certain embodiments, q is 3.

Formula (III) includes substituent $R^{C3}$. In certain embodiments, $R^{C3}$ is H. In certain embodiments, $R^{C3}$ is substituted acyl. In certain embodiments, $R^{C3}$ is unsubstituted acyl. In certain embodiments, $R^{C3}$ is acetyl. In certain embodiments, $R^{C3}$ is substituted alkyl. In certain embodiments, $R^{C3}$ is unsubstituted alkyl. In certain embodiments, $R^{C3}$ is unsubstituted $C_{1-6}$ alkyl. In certain embodiments, $R^{C3}$ is substituted $C_{1-6}$ alkyl. In certain embodiments, $R^{C3}$ is $C_{1-6}$ alkyl substituted with at least one halogen. In certain embodiments, $R^{C3}$ is —$CH_3$. In certain embodiments, $R^{C3}$ is substituted methyl. In certain embodiments, $R^{C3}$ is —$CH_2F$. In certain embodiments, $R^{C3}$ is —$CHF_2$. In certain embodiments, $R^{C3}$ is —$CF_3$. In certain embodiments, $R^{C3}$ is ethyl. In certain embodiments, $R^{C3}$ is propyl. In certain embodiments, $R^{C3}$ is butyl. In certain embodiments, $R^{C3}$ is pentyl. In certain embodiments, $R^{C3}$ is hexyl. In certain embodiments, $R^{C3}$ is substituted alkenyl. In certain embodiments, $R^{C3}$ is unsubstituted alkenyl. In certain embodiments, $R^{C3}$ is substituted alkynyl. In certain embodiments, $R^{C3}$ is unsubstituted alkynyl. In certain embodiments, $R^{C3}$ is substituted carbocyclyl. In certain embodiments, $R^{C3}$ is unsubstituted carbocyclyl. In certain embodiments, $R^{C3}$ is saturated carbocyclyl. In certain embodiments, $R^{C3}$ is unsaturated carbocyclyl. In certain embodiments, $R^{C3}$ is monocyclic carbocyclyl. In certain embodiments, $R^{C3}$ is 3- to 7-membered, monocyclic carbocyclyl. In certain embodiments, $R^{C3}$ is substituted heterocyclyl. In certain embodiments, $R^C$ is unsubstituted heterocyclyl. In certain embodiments, $R^{C3}$ is saturated heterocyclyl. In certain embodiments, $R^{C3}$ is unsaturated heterocyclyl. In certain embodiments, $R^C$ is heterocyclyl, wherein one, two, or three atoms in the heterocyclic ring system are independently selected from the group consisting of nitrogen, oxygen, and sulfur. In certain embodiments, $R^{C3}$ is monocyclic heterocyclyl. In certain embodiments, $R^{C3}$ is 3- to 7-membered, monocyclic heterocyclyl. In certain embodiments, $R^{C3}$ is substituted aryl. In certain embodiments, $R^{C3}$ is unsubstituted aryl. In certain embodiments, $R^{C3}$ is 6- to 10-membered aryl. In certain embodiments, $R^{C3}$ is substituted phenyl. In certain embodiments, $R^C$ is unsubstituted phenyl. In certain embodiments, $R^{C3}$ is substituted heteroaryl. In certain embodiments, $R^C$ is unsubstituted heteroaryl. In certain embodiments, $R^{C3}$ is heteroaryl, wherein one, two, three, or four atoms in the heteroaryl ring system are independently selected from the group consisting of nitrogen, oxygen, and sulfur. In certain embodiments, $R^{C3}$ is monocyclic heteroaryl. In certain embodiments, $R^{C3}$ is 5-membered, monocyclic heteroaryl. In certain embodiments, $R^{C3}$ is 6-membered, monocyclic heteroaryl. In certain embodiments, $R^{C3}$ is bicyclic heteroaryl, wherein the point of attachment may be on any atom of the bicyclic heteroaryl ring system, as valency permits. In certain embodiments, $R^{C3}$ is 9- or 10-membered, bicyclic heteroaryl. In certain embodiments, $R^{C3}$ is an oxygen protecting group. In certain embodiments, $R^C$ is silyl, TBDPS, TBDMS, TIPS, TES, TMS, MOM, THP, t-Bu, Bn, allyl, acetyl, pivaloyl, or benzoyl.

Formula (III) includes substituent $R^{D3}$. In certain embodiments, $R^{D3}$ is H. In certain embodiments, $R^{D3}$ is halogen. In certain embodiments, $R^{D3}$ is F. In certain embodiments, $R^{D3}$ is Cl. In certain embodiments, $R^{D3}$ is Br. In certain embodiments, $R^{D3}$ is I (iodine). In certain embodiments, $R^{D3}$ is substituted alkyl. In certain embodiments, $R^{D3}$ is unsubstituted alkyl. In certain embodiments, $R^{D3}$ is unsubstituted $C_{1-6}$ alkyl. In certain embodiments, $R^{D3}$ is substituted $C_{1-6}$ alkyl. In certain embodiments, $R^{D3}$ is $C_{1-6}$ alkyl substituted with at least one halogen. In certain embodiments, $R^{D3}$ is —CH$_3$. In certain embodiments, $R^{D3}$ is substituted methyl. In certain embodiments, $R^{D3}$ is —CH$_2$F. In certain embodiments, $R^{D3}$ is —CHF$_2$. In certain embodiments, $R^{D3}$ is —CF$_3$. In certain embodiments, $R^{D3}$ is ethyl. In certain embodiments, $R^{D3}$ is propyl. In certain embodiments, $R^{D3}$ is butyl. In certain embodiments, $R^{D3}$ is pentyl. In certain embodiments, $R^{D3}$ is hexyl. In certain embodiments, $R^{D3}$ is substituted alkenyl. In certain embodiments, $R^{D3}$ is unsubstituted alkenyl. In certain embodiments, $R^{D3}$ is substituted alkynyl. In certain embodiments, $R^{D3}$ is unsubstituted alkynyl. In certain embodiments, $R^{D3}$ is substituted carbocyclyl. In certain embodiments, $R^{D3}$ is unsubstituted carbocyclyl. In certain embodiments, $R^{D3}$ is saturated carbocyclyl. In certain embodiments, $R^{D3}$ is unsaturated carbocyclyl. In certain embodiments, $R^{D3}$ is monocyclic carbocyclyl. In certain embodiments, $R^{D3}$ is 3- to 7-membered, monocyclic carbocyclyl. In certain embodiments, $R^{D3}$ is substituted heterocyclyl. In certain embodiments, $R^{D3}$ is unsubstituted heterocyclyl. In certain embodiments, $R^{D3}$ is saturated heterocyclyl. In certain embodiments, $R^{D3}$ is unsaturated heterocyclyl. In certain embodiments, $R^{D3}$ is heterocyclyl, wherein one, two, or three atoms in the heterocyclic ring system are independently selected from the group consisting of nitrogen, oxygen, and sulfur. In certain embodiments, $R^{D3}$ is monocyclic heterocyclyl. In certain embodiments, $R^{D3}$ is 3- to 7-membered, monocyclic heterocyclyl. In certain embodiments, $R^{D3}$ is substituted aryl. In certain embodiments, $R^{D3}$ is unsubstituted aryl. In certain embodiments, $R^{D3}$ is 6- to 10-membered aryl. In certain embodiments, $R^{D3}$ is substituted phenyl. In certain embodiments, $R^{D3}$ is unsubstituted phenyl. In certain embodiments, $R^{D3}$ is substituted heteroaryl. In certain embodiments, $R^{D3}$ is unsubstituted heteroaryl. In certain embodiments, $R^{D3}$ is heteroaryl, wherein one, two, three, or four atoms in the heteroaryl ring system are independently selected from the group consisting of nitrogen, oxygen, and sulfur. In certain embodiments, $R^{D3}$ is monocyclic heteroaryl. In certain embodiments, $R^{D3}$ is 5-membered, monocyclic heteroaryl. In certain embodiments, $R^{D3}$ is 6-membered, monocyclic heteroaryl. In certain embodiments, $R^{D3}$ is bicyclic heteroaryl, wherein the point of attachment may be on any atom of the bicyclic heteroaryl ring system, as valency permits. In certain embodiments, $R^{D3}$ is 9- or 10-membered, bicyclic heteroaryl. In certain embodiments, $R^{D3}$ is —OR$^{D3a}$. In certain embodiments, $R^{D3}$ is —OH. In certain embodiments, $R^{D3}$ is —OMe. In certain embodiments, $R^{D3}$ is —OEt. In certain embodiments, $R^{D3}$ is —OPr. In certain embodiments, $R^{D3}$ is —OBu. In certain embodiments, $R^{D3}$ is —OBn. In certain embodiments, $R^{D3}$ is —OPh. In certain embodiments, $R^{D3}$ is —SR$^{D3a}$. In certain embodiments, $R^{D3}$ is —SH. In certain embodiments, $R^{D3}$ is —SMe. In certain embodiments, $R^{D3}$ is —N(R$^{D3a}$)$_2$. In certain embodiments, $R^{D3}$ is —NH$_2$. In certain embodiments, $R^{D3}$ is —NHMe. In certain embodiments, $R^{D3}$ is —NMe$_2$. In certain embodiments, $R^{D3}$ is —CN. In certain embodiments, $R^{D3}$ is —SCN. In certain embodiments, $R^{D3}$ is —C(=NR$^{D3a}$)R$^{D3a}$, —C(=NR$^{D3a}$)OR$^{D3a}$, or —C(=NR$^{D3a}$)N(R$^{D3a}$)$_2$. In certain embodiments, $R^{D3}$ is —C(=O)R$^{D3a}$ or —C(=O)OR$^{D3a}$. In certain embodiments, $R^{D3}$ is —C(=O)N(R$^{D3a}$)$_2$. In certain embodiments, $R^{D3}$ is —C(=O)NMe$_2$, —C(=O)NHMe, or —C(=O)NH$_2$. In certain embodiments, $R^{D3}$ is —NO$_2$. In certain embodiments, $R^{D3}$ is —NR$^{D3a}$C(=O)R$^{D3a}$, —NR$^{D3a}$C(=O)OR$^{D3a}$, or —NR$^{D3a}$C(=O)N(R$^{D3a}$)$_2$. In certain embodiments, $R^{D3}$ is —OC(=O)R$^{D3a}$, —OC(=O)OR$^{D3a}$, or —OC(=O)N(R$^{D3a}$)$_2$.

In certain embodiments, at least one instance of $R^{D3a}$ is H. In certain embodiments, at least one instance of $R^{D3a}$ is substituted acyl. In certain embodiments, at least one instance of $R^{D3a}$ is unsubstituted acyl. In certain embodiments, at least one instance of $R^{D3a}$ is acetyl. In certain embodiments, at least one instance of $R^{D3a}$ is substituted alkyl. In certain embodiments, at least one instance of $R^{D3a}$ is unsubstituted alkyl. In certain embodiments, at least one instance of $R^{D3a}$ is unsubstituted $C_{1-6}$ alkyl. In certain embodiments, at least one instance of $R^{D3a}$ is methyl. In certain embodiments, at least one instance of $R^{D3a}$ is ethyl. In certain embodiments, at least one instance of $R^{D3a}$ is propyl. In certain embodiments, at least one instance of $R^{D3a}$ is butyl. In certain embodiments, at least one instance of $R^{D3a}$ is pentyl. In certain embodiments, at least one instance of $R^{D3a}$ is hexyl. In certain embodiments, at least one instance of $R^{D3a}$ is substituted alkenyl. In certain embodiments, at least one instance of $R^{D3a}$ is unsubstituted alkenyl. In certain embodiments, at least one instance of $R^{D3a}$ is substituted alkynyl. In certain embodiments, at least one instance of $R^{D3a}$ is unsubstituted alkynyl. In certain embodiments, at least one instance of $R^{D3a}$ is substituted or unsubstituted carbocyclyl. In certain embodiments, at least one instance of $R^{D3a}$ is saturated carbocyclyl. In certain embodiments, at least one instance of $R^{D3a}$ is unsaturated carbocyclyl. In certain embodiments, at least one instance of $R^{D3a}$ is 3- to 7-membered, monocyclic carbocyclyl. In certain embodiments, at least one instance of $R^{D3a}$ is substituted or unsubstituted heterocyclyl. In certain embodiments, at least one instance of $R^{D3a}$ is saturated heterocyclyl. In certain embodiments, at least one instance of $R^{D3a}$ is unsaturated heterocyclyl. In certain embodiments, at least one instance of $R^{D3a}$ is heterocyclyl, wherein one, two, or three atoms in the heterocyclic ring system are independently selected from the group consisting of nitrogen, oxygen, and sulfur. In certain embodiments, at least one instance of $R^{D3a}$ is 3- to 7-membered, monocyclic heterocyclyl. In certain embodiments, at least one instance of $R^{D3a}$ is substituted or unsubstituted aryl. In certain embodiments, at least one instance of $R^{D3a}$ is 6- to 10-membered aryl. In certain embodiments, at least one instance of $R^{D3a}$ is monocyclic aryl. In certain embodiments, at least one instance of $R^{D3a}$ is substituted phenyl. In certain embodiments, at least one instance of $R^{D3a}$ is unsubstituted phenyl. In certain embodiments, at least one instance of $R^{D3a}$ is bicyclic aryl. In certain embodiments, at least one instance of $R^{D3a}$ is substituted or unsubstituted heteroaryl. In certain embodiments, at least one instance of $R^{D3a}$ is heteroaryl, wherein one, two, three, or four atoms in the heteroaryl ring system are independently selected from the group consisting of nitrogen, oxygen, and sulfur. In certain embodiments, at least one instance of $R^{D3a}$ is monocyclic heteroaryl. In certain embodiments, at least one instance of $R^{D3a}$ is 5- or 6-membered, monocyclic heteroaryl. In certain embodiments, at least one instance of $R^{D3a}$ is bicyclic heteroaryl, wherein the point of attachment may be on any atom of the bicyclic heteroaryl ring system, as valency permits. In certain embodiments, at least one instance of $R^{D3a}$ is a nitrogen protecting group when attached to a nitrogen atom. In certain embodiments, at least one instance of $R^{D3a}$ is Bn, Boc, Cbz, Fmoc, trifluoroacetyl, triphenylmethyl, acetyl, or Ts when attached to a nitrogen atom. In certain embodiments, at least one instance of $R^{D3a}$ is an oxygen protecting group when attached to an oxygen atom. In certain embodiments, at least one instance of $R^{D3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, at least one instance of $R^{D3}$a is a sulfur protecting group when attached to a sulfur atom. In certain embodiments, at least one instance of $R^{D3}$a is acetamidomethyl, t-Bu, 3-nitro-2-pyridine sulfenyl, 2-pyridine-sulfenyl, or triphenylmethyl when attached to a sulfur atom. In certain embodiments, two instances of $R^{D3}$a are joined to form a substituted or unsubstituted heterocyclic ring. In certain embodiments, two instances of $R^{D3}$a are joined to form a saturated or unsaturated heterocyclic ring. In certain embodiments, two instances of $R^{D3a}$ are joined to form a heterocyclic ring, wherein one, two, or three atoms in the heterocyclic ring system are independently selected from the group consisting of nitrogen, oxygen, and sulfur. In certain embodiments, two instances of $R^{D3}$a are joined to form a 3- to 7-membered, monocyclic heterocyclic ring. In certain embodiments, two instances of $R^{D3}$a are joined to form a substituted or unsubstituted heteroaryl ring. In certain embodiments, two instances of $R^{D3}$a are joined to form a substituted or unsubstituted, 5- to 6-membered, monocyclic heteroaryl ring, wherein one, two, three, or four atoms in the heteroaryl ring system are independently nitrogen, oxygen, or sulfur.

Formula (III) include Ring A. In certain embodiments, Ring A is substituted 5-membered monocyclic heterocyclic ring. In certain embodiments, Ring A is unsubstituted 5-membered monocyclic heterocyclic ring. In certain embodiments, Ring A is substituted 6-membered monocyclic heterocyclic ring. In certain embodiments, Ring A is unsubstituted 6-membered monocyclic heterocyclic ring. In certain embodiments, when Ring A is a substituted or unsubstituted, 5- to 6-membered, monocyclic heterocyclic ring, one, two, or three atoms in the heterocyclic ring system are independently nitrogen, oxygen, or sulfur. In certain embodiments, when Ring A is a substituted or unsubstituted, 5- to 6-membered, monocyclic heterocyclic ring, the heterocyclic ring system includes zero, one, or two double bonds.

In certain embodiments, Ring A is substituted 5-membered monocyclic heteroaryl ring. In certain embodiments, Ring A is unsubstituted 5-membered monocyclic heteroaryl ring. In certain embodiments, Ring A is substituted 6-membered monocyclic heteroaryl ring. In certain embodiments, Ring A is unsubstituted 6-membered monocyclic heteroaryl ring. In certain embodiments, when Ring A is a substituted or unsubstituted, 5- to 6-membered, monocyclic heteroaryl ring, one, two, three, or four atoms in the heteroaryl ring system are independently nitrogen, oxygen, or sulfur.

Formula (III) may include one or more substituents $R^{J3}$ on Ring A. In certain embodiments, at least two instances of $R^{J3}$ are different. In certain embodiments, all instances of $R^{J3}$ are the same. In certain embodiments, at least one instance of $R^{J3}$ is H. In certain embodiments, all instances of $R^{J3}$ are H. In certain embodiments, at least one instance of $R^{J3}$ is halogen. In certain embodiments, at least one instance of $R^{J3}$ is F. In certain embodiments, at least one instance of $R^{J3}$ is Cl. In certain embodiments, at least one instance of $R^{J3}$ is Br. In certain embodiments, at least one instance of $R^{J3}$ is I (iodine). In certain embodiments, at least one instance of $R^{J3}$ is substituted alkyl. In certain embodiments, at least one instance of $R^{J3}$ is unsubstituted alkyl. In certain embodiments, at least one instance of $R^{J3}$ is unsubstituted $C_{1-6}$alkyl. In certain embodiments, all instances of $R^{J3}$ are unsubstituted $C_{1-6}$ alkyl. In certain embodiments, at least one instance of $R^{J3}$ is substituted $C_{1-6}$ alkyl. In certain embodiments, at least one instance of $R^{J3}$ is $C_{1-6}$ alkyl substituted with at least one halogen. In certain embodiments, at least one instance of $R^{J3}$ is —$CH_3$. In certain embodiments, all instances of $R^{J3}$ are —$CH_3$. In certain embodiments, at least one instance of $R^{J3}$ is substituted methyl. In certain embodiments, at least one instance of $R^3$ is —$CH_2F$. In certain embodiments, at least one instance of $R^{J3}$ is —$CHF_2$. In certain embodiments, at least one instance of $R^{J3}$ is —$CF_3$. In certain embodiments, at least one instance of $R^{J3}$ is ethyl. In certain embodiments, at least one instance of $R^{J3}$ is propyl. In certain embodiments, at least one instance of $R^{J3}$ is butyl. In certain embodiments, at least one instance of $R^{J3}$ is pentyl. In certain embodiments, at least one instance of $R^{J3}$ is hexyl. In certain embodiments, at least one instance of $R^{J3}$ is substituted alkenyl. In certain embodiments, at least one instance of $R^{J3}$ is unsubstituted alkenyl. In certain embodiments, at least one instance of $R^{J3}$ is substituted alkynyl. In certain embodiments, at least one instance of $R^{J3}$ is unsubstituted alkynyl. In certain embodiments, at least one instance of $R^{J3}$ is substituted carbocyclyl. In certain embodiments, at least one instance of $R^{J3}$ is unsubstituted carbocyclyl. In certain embodiments, at least one instance of $R^{J3}$ is saturated carbocyclyl. In certain embodiments, at least one instance of $R^{J3}$ is unsaturated carbocyclyl. In certain embodiments, at least one instance of $R^{J3}$ is monocyclic carbocyclyl. In certain embodiments, at least one instance of $R^{J3}$ is 3- to 7-membered, monocyclic carbocyclyl. In certain embodiments, at least one instance of $R^{J3}$ is substituted heterocyclyl. In certain embodiments, at least one instance of $R^{J3}$ is unsubstituted heterocyclyl. In certain embodiments, at least one instance of $R^{J3}$ is saturated heterocyclyl. In certain embodiments, at least one instance of $R^{J3}$ is unsaturated heterocyclyl. In certain embodiments, at least one instance of $R^{J3}$ is heterocyclyl, wherein one, two, or three atoms in the heterocyclic ring system are independently selected from the group consisting of nitrogen, oxygen, and sulfur. In certain embodiments, at least one instance of $R^{J3}$ is monocyclic heterocyclyl. In certain embodiments, at least one instance of $R^{J3}$ is 3- to 7-membered, monocyclic heterocyclyl. In certain embodiments, at least one instance of $R^{J3}$ is substituted aryl. In certain embodiments, at least one instance of $R^{J3}$ is unsubstituted aryl. In certain embodiments, at least one instance of $R^{J3}$ is 6- to 10-membered aryl. In certain embodiments, at least one instance of $R^{J3}$ is substituted phenyl. In certain embodiments, at least one instance of $R^{J3}$ is unsubstituted phenyl. In certain embodiments, at least one instance of $R^{J3}$ is substituted heteroaryl. In certain embodiments, at least one instance of $R^{J3}$ is unsubstituted heteroaryl. In certain embodiments, at least one instance of $R^{J3}$ is heteroaryl, wherein one, two, three, or four atoms in the heteroaryl ring system are independently selected from the group consisting of nitrogen, oxygen, and sulfur. In certain embodiments, at least one instance of $R^{J3}$ is monocyclic heteroaryl. In certain embodiments, at least one instance of $R^{J3}$ is 5-membered, monocyclic heteroaryl. In certain embodiments, at least one instance of $R^{J3}$ is 6-membered, monocyclic heteroaryl. In certain embodiments, at least one instance of $R^{J3}$ is bicyclic heteroaryl, wherein the point of attachment may be on any atom of the bicyclic heteroaryl ring system, as valency permits. In certain embodiments, at least one instance of $R^{J3}$ is 9- or 10-membered, bicyclic heteroaryl. In certain embodiments, at least one instance of $R^{J3}$ is —$OR^{J3a}$. In certain embodiments, at least one instance of $R^{J3}$ is —OH. In certain embodiments, at least one instance of $R^{J3}$ is —OMe. In certain embodiments, at least one instance of $R^{J3}$ is —OEt.

In certain embodiments, at least one instance of $R^{J3}$ is —OPr. In certain embodiments, at least one instance of $R^{J3}$ is —OBu. In certain embodiments, at least one instance of $R^{J3}$ is —OBn. In certain embodiments, at least one instance of $R^{J3}$ is —OPh. In certain embodiments, at least one instance of $R^{J3}$ is —$SR^{J3a}$. In certain embodiments, at least one instance of $R^{J3}$ is —SH. In certain embodiments, at least one instance of $R^{J3}$ is —SMe. In certain embodiments, at least one instance of $R^{J3}$ is —$N(R^{J3a})_2$. In certain embodiments, at least one instance of $R^{J3}$ is —$NH_2$. In certain embodiments, at least one instance of $R^{J3}$ is —NHMe. In certain embodiments, at least one instance of $R^{J3}$ is —$NMe_2$. In certain embodiments, at least one instance of $R^{J3}$ is —CN. In certain embodiments, at least one instance of $R^{J3}$ is —SCN. In certain embodiments, at least one instance of $R^{J3}$ is —$C(=NR^{J3a})R^{J3a}$, —$C(=NR^{J3a})OR^{J3a}$, or —$C(=NR^{J3a})N(R^{J3a})_2$. In certain embodiments, at least one instance of $R^{J3}$ is —$C(=O)R^{J3a}$ or —$C(=O)OR^{J3}a$. In certain embodiments, at least one instance of $R^{J3}$ is —$C(=O)N(R^{J3a})_2$. In certain embodiments, at least one instance of $R^{J3}$ is —$C(=O)NMe_2$, —$C(=O)NHMe$, or —$C(=O)NH_2$. In certain embodiments, at least one instance of $R^{J3}$ is —$NO_2$. In certain embodiments, at least one instance of $R^{J3}$ is —$NR^{J3a}C(=O)R^{J3a}$, —$NR^{J3a}C(=O)OR^{J3a}$, or —$NR^{J3a}C(=O)N(R^{J3a})_2$. In certain embodiments, at least one instance of $R^{J3}$ is —$OC(=O)R^{J3a}$, —$OC(=O)OR^{J3a}$, or —$OC(=O)N(R^{J3a})_2$.

In certain embodiments, at least one instance of $R^{J3a}$ is H. In certain embodiments, at least one instance of $R^{J3a}$ is substituted acyl. In certain embodiments, at least one instance of $R^{J3a}$ is unsubstituted acyl. In certain embodiments, at least one instance of $R^{J3a}$ is acetyl. In certain embodiments, at least one instance of $R^{J3a}$ is substituted alkyl. In certain embodiments, at least one instance of $R^{J3a}$ is unsubstituted alkyl. In certain embodiments, at least one instance of $R^{J3a}$ is unsubstituted $C_{1-6}$ alkyl. In certain embodiments, at least one instance of $R^{J3a}$ is methyl. In certain embodiments, at least one instance of $R^{J3a}$ is ethyl. In certain embodiments, at least one instance of $R^{J3a}$ is propyl. In certain embodiments, at least one instance of $R^{J3a}$ is butyl. In certain embodiments, at least one instance of $R^{J3a}$ is pentyl. In certain embodiments, at least one instance of $R^{J3a}$ is hexyl. In certain embodiments, at least one instance of $R^{J3a}$ is substituted alkenyl. In certain embodiments, at least one instance of $R^{J3a}$ is unsubstituted alkenyl. In certain embodiments, at least one instance of $R^{J3a}$ is substituted alkynyl. In certain embodiments, at least one instance of $R^{J3a}$ is unsubstituted alkynyl. In certain embodiments, at least one instance of $R^{J3a}$ is substituted or unsubstituted carbocyclyl. In certain embodiments, at least one instance of $R^{J3a}$ is saturated carbocyclyl. In certain embodiments, at least one instance of $R^{J3a}$ is unsaturated carbocyclyl. In certain embodiments, at least one instance of $R^{J3a}$ is 3- to 7-membered, monocyclic carbocyclyl. In certain embodiments, at least one instance of $R^{J3a}$ is substituted or unsubstituted heterocyclyl. In certain embodiments, at least one instance of $R^{J3a}$ is saturated heterocyclyl. In certain embodiments, at least one instance of $R^{J3a}$ is unsaturated heterocyclyl. In certain embodiments, at least one instance of $R^{J3a}$ is heterocyclyl, wherein one, two, or three atoms in the heterocyclic ring system are independently selected from the group consisting of nitrogen, oxygen, and sulfur. In certain embodiments, at least one instance of $R^{J3a}$ is 3- to 7-membered, monocyclic heterocyclyl. In certain embodiments, at least one instance of $R^{J3a}$ is substituted or unsubstituted aryl. In certain embodiments, at least one instance of $R^{J3a}$ is 6- to 10-membered aryl. In certain embodiments, at least one instance of $R^{J3a}$ is monocyclic aryl. In certain embodiments, at least one instance of $R^{J3a}$ is substituted phenyl. In certain embodiments, at least one instance of $R^{J3a}$ is unsubstituted phenyl. In certain embodiments, at least one instance of $R^{J3a}$ is bicyclic aryl. In certain embodiments, at least one instance of $R^{J3a}$ is substituted or unsubstituted heteroaryl. In certain embodiments, at least one instance of $R^{J3a}$ is heteroaryl, wherein one, two, three, or four atoms in the heteroaryl ring system are independently selected from the group consisting of nitrogen, oxygen, and sulfur. In certain embodiments, at least one instance of $R^{J3a}$ is monocyclic heteroaryl. In certain embodiments, at least one instance of $R^{J3a}$ is 5- or 6-membered, monocyclic heteroaryl. In certain embodiments, at least one instance of $R^{J3a}$ is bicyclic heteroaryl, wherein the point of attachment may be on any atom of the bicyclic heteroaryl ring system, as valency permits. In certain embodiments, at least one instance of $R^{J3a}$ is a nitrogen protecting group when attached to a nitrogen atom. In certain embodiments, at least one instance of $R^{J3a}$ is Bn, Boc, Cbz, Fmoc, trifluoroacetyl, triphenylmethyl, acetyl, or Ts when attached to a nitrogen atom. In certain embodiments, $R^{J3a}$ is an oxygen protecting group when attached to an oxygen atom. In certain embodiments, $R^{J3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{J3a}$ is a sulfur protecting group when attached to a sulfur atom. In certain embodiments, $R^{J3a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{J3a}$ are joined to form a substituted or unsubstituted heterocyclic ring. In certain embodiments, two instances of $R^{J3a}$ are joined to form a saturated or unsaturated heterocyclic ring. In certain embodiments, two instances of $R^{J3a}$ are joined to form a heterocyclic ring, wherein one, two, or three atoms in the heterocyclic ring system are independently selected from the group consisting of nitrogen, oxygen, and sulfur. In certain embodiments, two instances of $R^{J3a}$ are joined to form a 3- to 7-membered, monocyclic heterocyclic ring. In certain embodiments, two instances of $R^{J3a}$ are joined to form a substituted or unsubstituted heteroaryl ring. In certain embodiments, two instances of $R^{J3a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, r is 0. In certain embodiments, r is 1. In certain embodiments, r is 2. In certain embodiments, r is 3. In certain embodiments, r is 4. In certain embodiments, r is 5. In certain embodiments, r is 6. In certain embodiments, r is 7. In certain embodiments, r is 8.

Formula (III) includes substituent $R^{F3}$. In certain embodiments, $R^{F3}$ is H. In certain embodiments, $R^{F3}$ is substituted alkyl. In certain embodiments, $R^{F3}$ is unsubstituted alkyl. In certain embodiments, $R^{F3}$ is unsubstituted $C_{1-6}$ alkyl. In certain embodiments, $R^{F3}$ is substituted $C_{1-6}$ alkyl. In certain embodiments, $R^{F3}$ is $C_{1-6}$ alkyl substituted with at least one halogen. In certain embodiments, $R^{F3}$ is —$CH_3$. In certain embodiments, $R^{F3}$ is substituted methyl. In certain embodiments, $R^{F3}$ is —$CH_2F$. In certain embodiments, $R^{F3}$ is —$CHF_2$. In certain embodiments, $R^{F3}$ is —$CF_3$. In certain embodiments, $R^{F3}$ is ethyl. In certain embodiments, $R^{F3}$ is propyl. In certain embodiments, $R^{F3}$ is butyl. In certain embodiments, $R^{F3}$ is pentyl. In certain embodiments, $R^{F3}$ is hexyl. In certain embodiments, $R^{F3}$ is substituted alkenyl. In certain embodiments, $R^{F3}$ is unsubstituted alkenyl. In certain embodiments, $R^{F3}$ is substituted alkynyl. In certain embodiments, $R^{F3}$ is unsubstituted alkynyl. In certain embodiments, $R^{F3}$ is substituted carbocyclyl. In certain embodiments, $R^{F3}$ is unsubstituted carbocyclyl. In certain embodiments, $R^{F3}$ is saturated carbocyclyl. In certain embodiments, $R^{F3}$ is unsaturated carbocyclyl. In certain embodiments, $R^{F3}$ is monocyclic carbocyclyl. In certain embodiments, $R^{F3}$ is 3- to 7-membered, monocyclic carbocyclyl. In certain embodiments, $R^{F3}$ is substituted heterocyclyl. In certain embodiments, $R^{F3}$ is unsubstituted heterocyclyl. In certain embodiments, $R^{F3}$ is saturated heterocyclyl. In certain embodiments, $R^{F3}$ is unsaturated heterocyclyl. In certain embodiments, $R^{F3}$ is heterocyclyl, wherein one, two, or three atoms in the heterocyclic ring system are independently selected from the group consisting of nitrogen, oxygen, and sulfur. In certain embodiments, $R^{F3}$ is monocyclic heterocyclyl. In certain embodiments, $R^{F3}$ is 3- to 7-membered, monocyclic heterocyclyl. In certain embodiments, $R^{F3}$ is substituted aryl. In certain embodiments, $R^{F3}$ is unsubstituted aryl. In certain embodiments, $R^{F3}$ is 6- to 10-membered aryl. In certain embodiments, $R^{F3}$ is substituted phenyl. In certain embodiments, $R^{F3}$ is unsubstituted phenyl. In certain embodiments, $R^{F3}$ is substituted heteroaryl. In certain embodiments, $R^{F3}$ is unsubstituted heteroaryl. In certain embodiments, $R^{F3}$ is heteroaryl, wherein one, two, three, or four atoms in the heteroaryl ring system are independently selected from the group consisting of nitrogen, oxygen, and sulfur. In certain embodiments, $R^{F3}$ is monocyclic heteroaryl. In certain embodiments, $R^{F3}$ is 5-membered, monocyclic heteroaryl. In certain embodiments, $R^{F3}$ is 6-membered, monocyclic heteroaryl. In certain embodiments, $R^{F3}$ is bicyclic heteroaryl, wherein the point of attachment may be on any atom of the bicyclic heteroaryl ring system, as valency permits. In certain embodiments, $R^{F3}$ is 9- or 10-membered, bicyclic heteroaryl. In certain embodiments, $R^{F3}$ is a nitrogen protecting group. In certain embodiments, $R^{F3}$ is Bn, Boc, Cbz, Fmoc, trifluoroacetyl, triphenylmethyl, acetyl, or Ts.

Formula (III) includes substituent $R^{G3}$. In certain embodiments, $R^{G3}$ is H. In certain embodiments, $R^{G3}$ is halogen. In certain embodiments, $R^{G3}$ is F. In certain embodiments, $R^{G3}$ is Cl. In certain embodiments, $R^{G3}$ is Br. In certain embodiments, $R^{G3}$ is I (iodine). In certain embodiments, $R^{G3}$ is unsubstituted $C_{1-6}$ alkyl. In certain embodiments, $R^{G3}$ is substituted $C_{1-6}$ alkyl. In certain embodiments, $R^{G3}$ is $C_{1-6}$ alkyl substituted with at least one halogen. In certain embodiments, $R^{G3}$ is —$CH_3$. In certain embodiments, $R^{G3}$ is substituted methyl. In certain embodiments, $R^{G3}$ is —$CH_2F$. In certain embodiments, $R^{G3}$ is —$CHF_2$. In certain embodiments, $R^{G3}$ is —$CF_3$. In certain embodiments, $R^{G3}$ is ethyl. In certain embodiments, $R^{G3}$ is propyl. In certain embodiments, $R^{G3}$ is butyl. In certain embodiments, $R^{G3}$ is pentyl. In certain embodiments, $R^{G3}$ is hexyl.

Formula (III) includes substituent $R^{H3}$. In certain embodiments, $R^{H3}$ is H. In certain embodiments, $R^{H3}$ is halogen. In certain embodiments, $R^{H3}$ is F. In certain embodiments, $R^{H3}$ is Cl. In certain embodiments, $R^{H3}$ is Br. In certain embodiments, $R^{H3}$ is I (iodine). In certain embodiments, $R^{H3}$ is unsubstituted $C_{1-6}$ alkyl. In certain embodiments, $R^{H3}$ is substituted $C_{1-6}$ alkyl. In certain embodiments, $R^{H3}$ is $C_{1-6}$ alkyl substituted with at least one halogen. In certain embodiments, $R^{H3}$ is —$CH_3$. In certain embodiments, $R^{H3}$ is substituted methyl. In certain embodiments, $R^{H3}$ is —$CH_2F$. In certain embodiments, $R^{H3}$ is —$CHF_2$. In certain embodiments, $R^{H3}$ is —$CF_3$. In certain embodiments, $R^{H3}$ is ethyl. In certain embodiments, $R^{H3}$ is propyl. In certain embodiments, $R^{H3}$ is butyl. In certain embodiments, $R^{H3}$ is pentyl. In certain embodiments, $R^{H3}$ is hexyl.

In certain embodiments, each of $R^{G3}$ and $R^{H3}$ is hydrogen.

In certain embodiments, $R^{G3}$ and $R^{H3}$ are joined to form a substituted phenyl ring. In certain embodiments, $R^{G3}$ and $R^{H3}$ are joined to form a unsubstituted phenyl ring. In certain embodiments, a compound described herein is of Formula (III-A):

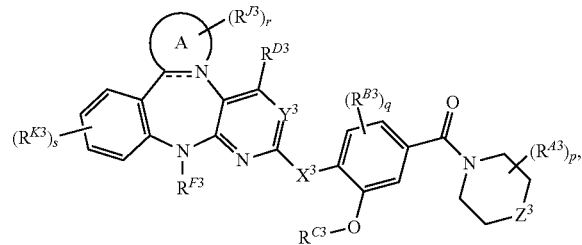

(III-A)

or a pharmaceutically acceptable salt, solvate, hydrate, polymorph, co-crystal, tautomer, stereoisomer, isotopically labeled derivative, or prodrug thereof, wherein:

each instance of $R^{K3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{K3a}$, —$N(R^{K3a})_2$, —$SR^{K3a}$, —CN, —SCN, —C(=$NR^{K3a}$)$R^{K3a}$, —C(=$NR^{K3a}$)$OR^{K3a}$, —C(=$NR^{K3a}$)N($R^{K3a}$)$_2$, —C(=O)$R^{K3a}$, —C(=O)$OR^{K3a}$, —C(=O)N($R^{K3a}$)$_2$, —$NO_2$, —$NR^{K3a}$C(=O)$R^{K3a}$, —$NR^{K3a}$C(=O)$OR^{K3a}$, —$NR^{K3a}$C(=O)N($R^{K3a}$)$_2$, —OC(=O)$R^{K3a}$, —OC(=O)$OR^{K3a}$, or —OC(=O)N($R^{K3a}$)$_2$, wherein each instance of $R^{K3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{K3a}$ groups are joined to form a substituted or unsubstituted heterocyclic or substituted or unsubstituted heteroaryl ring; and s is 0, 1, 2, 3, or 4.

Formula (III-A) may include one or more substituents $R^{K3}$. In certain embodiments, at least two instances of $R^{K3}$ are different. In certain embodiments, all instances of $R^{K3}$ are the same. In certain embodiments, at least one instance of $R^{K3}$ is H. In certain embodiments, all instances of $R^{K3}$ are H. In certain embodiments, at least one instance of $R^{K3}$ is halogen. In certain embodiments, at least one instance of $R^{K3}$ is F. In certain embodiments, at least one instance of $R^{K3}$ is Cl. In certain embodiments, at least one instance of $R^{K3}$ is Br. In certain embodiments, at least one instance of $R^{K3}$ is I (iodine). In certain embodiments, at least one instance of $R^{K3}$ is substituted alkyl. In certain embodiments, at least one instance of $R^{K3}$ is unsubstituted alkyl. In certain embodiments, at least one instance of $R^{K3}$ is unsubstituted $C_{1-6}$alkyl. In certain embodiments, all instances of $R^{K3}$ are unsubstituted $C_{1-6}$ alkyl. In certain embodiments, at least one instance of $R^{K3}$ is substituted $C_{1-6}$ alkyl. In certain embodiments, at least one instance of $R^{K3}$ is $C_{1-6}$ alkyl substituted with at least one halogen. In certain embodiments, at least one instance of $R^{K3}$ is —$CH_3$. In certain embodiments, all instances of $R^{K3}$ are —$CH_3$. In certain embodiments, at least one instance of $R^{K3}$ is substituted methyl. In certain embodiments, at least one instance of $R^{K3}$ is —$CH_2F$. In certain embodiments, at least one instance of $R^{K3}$ is —$CHF_2$. In certain embodiments, at least one instance of $R^{K3}$ is —$CF_3$. In certain embodiments, at least one instance of $R^{K3}$ is ethyl. In certain embodiments, at least one instance of $R^{K3}$ is propyl. In certain embodiments, at least one instance of $R^{K3}$ is butyl. In certain embodiments, at least one instance of $R^{K3}$ is pentyl. In certain embodiments, at least one instance of $R^{K3}$ is hexyl. In certain embodiments, at least one instance of $R^{K3}$ is substituted alkenyl. In certain embodiments, at least one instance of $R^{K3}$ is unsubstituted alkenyl. In certain embodiments, at least one instance of $R^{K3}$ is substituted alkynyl. In certain embodiments, at least one instance of $R^{K3}$ is unsubstituted alkynyl. In certain embodiments, at least one instance of $R^{K3}$ is substituted carbocyclyl. In certain embodiments, at least one instance of $R^{K3}$ is unsubstituted carbocyclyl. In certain embodiments, at least one instance of $R^{K3}$ instance of saturated carbocyclyl. In certain embodiments, at least one instance of $R^{K3}$ is unsaturated carbocyclyl. In certain embodiments, at least one instance of $R^{K3}$ is monocyclic carbocyclyl. In certain embodiments, at least one instance of $R^{K3}$ is 3- to 7-membered, monocyclic carbocyclyl. In certain embodiments, at least one instance of $R^{K3}$ is substituted heterocyclyl. In certain embodiments, at least one instance of $R^{K3}$ is unsubstituted heterocyclyl. In certain embodiments, at least one instance of $R^{K3}$ is saturated heterocyclyl. In certain embodiments, at least one instance of $R^{K3}$ is unsaturated heterocyclyl. In certain embodiments, at least one instance of $R^{K3}$ is heterocyclyl, wherein one, two, or three atoms in the heterocyclic ring system are independently selected from the group consisting of nitrogen, oxygen, and sulfur. In certain embodiments, at least one instance of $R^{K3}$ is monocyclic heterocyclyl. In certain embodiments, at least one instance of $R^{K3}$ is 3- to 7-membered, monocyclic heterocyclyl. In certain embodiments, at least one instance of $R^{K3}$ is substituted aryl. In certain embodiments, at least one instance of $R^{K3}$ is unsubstituted aryl. In certain embodiments, at least one instance of $R^{K3}$ is 6- to 10-membered aryl. In certain embodiments, at least one instance of $R^{K3}$ is substituted phenyl. In certain embodiments, at least one instance of $R^{K3}$ is unsubstituted phenyl. In certain embodiments, at least one instance of $R^{K3}$ is substituted heteroaryl. In certain embodiments, at least one instance of $R^{K3}$ is unsubstituted heteroaryl. In certain embodiments, at least one instance of $R^{K3}$ is heteroaryl, wherein one, two, three, or four atoms in the heteroaryl ring system are independently selected from the group consisting of nitrogen, oxygen, and sulfur. In certain embodiments, at least one instance of $R^{K3}$ is monocyclic heteroaryl. In certain embodiments, at least one instance of $R^{K3}$ is 5-membered, monocyclic heteroaryl. In certain embodiments, at least one instance of $R^{K3}$ is 6-membered, monocyclic heteroaryl. In certain embodiments, at least one instance of $R^{K3}$ is bicyclic heteroaryl, wherein the point of attachment may be on any atom of the bicyclic heteroaryl ring system, as valency permits. In certain embodiments, at least one instance of $R^{K3}$ is 9- or 10-membered, bicyclic heteroaryl. In certain embodiments, at least one instance of $R^{K3}$ is —$OR^{K3a}$. In certain embodiments, at least one instance of $R^{K3}$ is —OH. In certain embodiments, at least one instance of $R^{K3}$ is —OMe. In certain embodiments, at least one instance of $R^{K3}$ is —OEt. In certain embodiments, at least one instance of $R^{K3}$ is —OPr. In certain embodiments, at least one instance of $R^{K3}$ is —OBu. In certain embodiments, at least one instance of $R^{K3}$ is —OBn. In certain embodiments, at least one instance of $R^{K3}$ is —OPh. In certain embodiments, at least one instance of $R^{K3}$ is —$SR^{K3a}$. In certain embodiments, at least one instance of $R^{K3}$ is —SH. In certain embodiments, at least one instance of $R^{K3}$ is —SMe. In certain embodiments, at least one instance of $R^{K3}$ is —$N(R^{K3a})_2$. In certain embodiments, at least one instance of $R^{K3}$ is —$NH_2$. In certain embodiments, at least one instance of $R^{K3}$ is —NHMe. In certain embodiments, at least one instance of $R^{K3}$ is —$NMe_2$. In certain embodiments, at least one instance of $R^{K3}$ is —CN. In certain embodiments, at least one instance of $R^{K3}$ is —SCN. In certain embodiments, at least one instance of $R^{K3}$ is —$C(=NR^{K3a})R^{K3a}$, —$C(=NR^{K3a})OR^{K3a}$, or —$C(=NR^{K3a})N(R^{K3a})_2$. In certain embodiments, at least one instance of $R^{K3}$ is —$C(=O)R^{K3a}$ or —$C(=O)OR^{K3a}$. In certain embodiments, at least one instance of $R^{K3}$ is —$C(=O)N(R^{K3a})_2$. In certain embodiments, at least one instance of $R^{K3}$ is —$C(=O)NMe_2$, —$C(=O)NHMe$, or —$C(=O)NH_2$. In certain embodiments, at least one instance of $R^{K3}$ is —$NO_2$. In certain embodiments, at least one instance of $R^{K3}$ is —$NR^{K3a}C(=O)R^{K3a}$, —$NR^{K3a}C(=O)OR^{K3a}$, or —$NR^{K3a}C(=O)N(R^{K3a})_2$. In certain embodiments, at least one instance of $R^{K3}$ is —$OC(=O)R^{K3a}$, —$OC(=O)OR^{K3a}$, or —$OC(=O)N(R^{K3a})_2$.

In certain embodiments, at least one instance of $R^{K3a}$ is H. In certain embodiments, at least one instance of $R^{K3a}$ is substituted acyl. In certain embodiments, at least one instance of $R^{K3a}$ is unsubstituted acyl. In certain embodiments, at least one instance of $R^{K3a}$ is acetyl. In certain embodiments, at least one instance of $R^{K3a}$ is substituted alkyl. In certain embodiments, at least one instance of $R^{K3a}$ is unsubstituted alkyl. In certain embodiments, at least one instance of $R^{K3a}$ is unsubstituted $C_{1-6}$ alkyl. In certain embodiments, at least one instance of $R^{K3a}$ is methyl. In certain embodiments, at least one instance of $R^{K3a}$ is ethyl. In certain embodiments, at least one instance of $R^{K3a}$ is propyl. In certain embodiments, at least one instance of $R^{K3a}$ is butyl. In certain embodiments, at least one instance of $R^{K3a}$ is pentyl. In certain embodiments, at least one instance of $R^{K3a}$ is hexyl. In certain embodiments, at least one instance of $R^{K3a}$ is substituted alkenyl. In certain embodiments, at least one instance of $R^{K3a}$ is unsubstituted alkenyl. In certain embodiments, at least one instance of $R^{K3a}$ is substituted alkynyl. In certain embodiments, at least one instance of $R^{K3a}$ is unsubstituted alkynyl. In certain embodiments, at least one instance of $R^{K3a}$ is substituted or unsubstituted carbocyclyl. In certain embodiments, at least one instance of $R^{K3a}$ is saturated carbocyclyl. In certain embodiments, at least one instance of $R^{K3a}$ is unsaturated carbocyclyl. In certain embodiments, at least one instance of $R^{K3a}$ is 3- to 7-membered, monocyclic carbocyclyl. In certain embodiments, at least one instance of $R^{K3a}$ is substituted or unsubstituted heterocyclyl. In certain embodiments, at least one instance of $R^{K3a}$ is saturated heterocyclyl. In certain embodiments, at least one instance of $R^{K3a}$ is unsaturated heterocyclyl. In certain embodiments, at least one instance of $R^{K3a}$ is heterocyclyl, wherein one, two, or three atoms in the heterocyclic ring system are independently selected from the group consisting of nitrogen, oxygen, and sulfur. In certain embodiments, at least one instance of $R^{K3a}$ is 3- to 7-membered, monocyclic heterocyclyl. In certain embodiments, at least one instance of $R^{K3a}$ is substituted or unsubstituted aryl. In certain embodiments, at least one instance of $R^{K3a}$ is 6- to 10-membered aryl. In certain embodiments, at least one instance of $R^{K3a}$ is monocyclic aryl. In certain embodiments, at least one instance of $R^{K3a}$ is substituted phenyl. In certain embodiments, at least one instance of $R^{K3a}$ is unsubstituted phenyl. In certain embodiments, at least one instance of $R^{K3a}$ is bicyclic aryl. In certain embodiments, at least one instance of $R^{K3a}$ is substituted or unsubstituted heteroaryl. In certain embodiments, at least one instance of $R^{K3a}$ is heteroaryl, wherein one, two, three, or four atoms in the heteroaryl ring system are independently selected from the group consisting of nitrogen, oxygen, and sulfur. In certain embodiments, at least one instance of $R^{K3a}$ is monocyclic heteroaryl. In certain embodiments, at least one instance of $R^{K3a}$ is 5- or 6-membered, monocyclic heteroaryl. In certain embodiments, at least one instance of $R^{K3a}$ is bicyclic heteroaryl, wherein the point of attachment may be on any atom of the bicyclic heteroaryl ring system, as valency permits. In certain embodiments, at least one instance of $R^{K3a}$ is a nitrogen protecting group when attached to a nitrogen atom. In certain embodiments, at least one instance of $R^{K3a}$ is Bn, Boc, Cbz, Fmoc, trifluoroacetyl, triphenylmethyl, acetyl, or Ts when attached to a nitrogen atom. In certain embodiments, $R^{K3a}$ is an oxygen protecting group when attached to an oxygen atom. In certain embodiments, $R^{K3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{K3a}$ is a sulfur protecting group when attached to a sulfur atom. In certain embodiments, $R^{K3a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{K3a}$ are joined to form a substituted or unsubstituted heterocyclic ring. In certain embodiments, two instances of $R^{K3a}$ are joined to form a saturated or unsaturated heterocyclic ring. In certain embodiments, two instances of $R^{K3a}$ are joined to form a heterocyclic ring, wherein one, two, or three atoms in the heterocyclic ring system are independently selected from the group consisting of nitrogen, oxygen, and sulfur. In certain embodiments, two instances of $R^{K3a}$ are joined to form a 3- to 7-membered, monocyclic heterocyclic ring. In certain embodiments, two instances of $R^{K3a}$ are joined to form a substituted or unsubstituted heteroaryl ring. In certain embodiments, two instances of $R^{K3a}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, s is 0. In certain embodiments, s is 1. In certain embodiments, s is 2. In certain embodiments, s is 3. In certain embodiments, s is 4.

In certain embodiments, a compound described herein is of Formula (III-B):

(III-B)

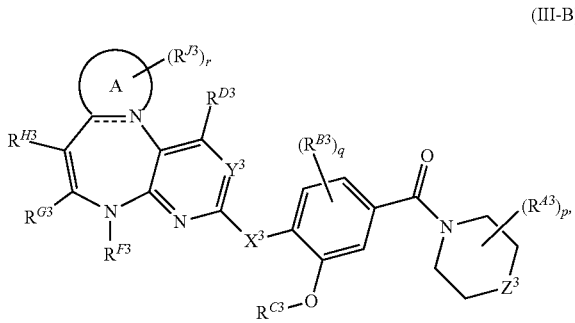

or a pharmaceutically acceptable salt, solvate, hydrate, polymorph, co-crystal, tautomer, stereoisomer, isotopically labeled derivative, or prodrug thereof.

In certain embodiments, a compound described herein is of Formula (III-C):

(III-C)

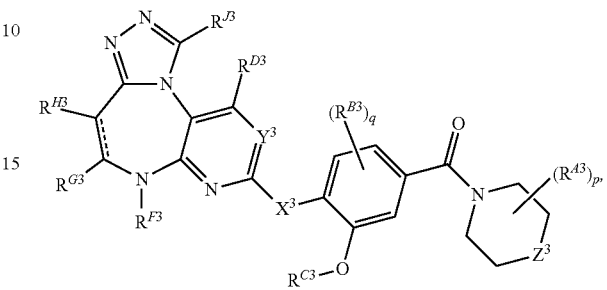

or a pharmaceutically acceptable salt, solvate, hydrate, polymorph, co-crystal, tautomer, stereoisomer, isotopically labeled derivative, or prodrug thereof.

In certain embodiments, a compound described herein is of the formula:

4

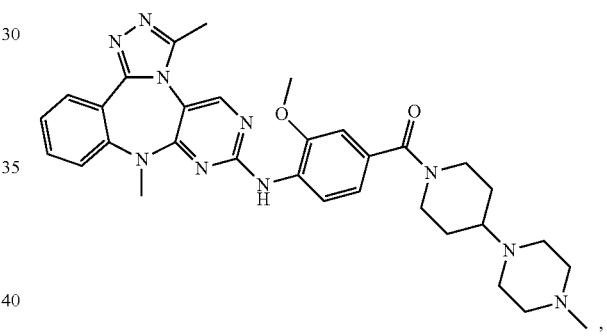

or a pharmaceutically acceptable salt, solvate, hydrate, polymorph, co-crystal, tautomer, stereoisomer, isotopically labeled derivative, or prodrug thereof.

In certain embodiments, the compounds described herein are compounds of any one of Formulae (I), (II-C), and (III), and pharmaceutically acceptable salts, solvates, hydrates, polymorphs, co-crystals, tautomers, stereoisomers, isotopically labeled derivatives, and prodrugs thereof. In certain embodiments, the compounds described herein are compounds of any one of Formulae (I), (II-C), and (III), and pharmaceutically acceptable salts, solvates, and hydrates thereof. In certain embodiments, the compounds described herein are compounds of any one of Formulae (I), (II-C), and (III), and pharmaceutically acceptable salts thereof. In certain embodiments, the compounds described herein are compounds of any one of Formulae (I), (II-C), and (III). In certain embodiments, the compounds described herein are compounds of any one of Formulae (I), (II), and (III), and pharmaceutically acceptable salts, solvates, hydrates, polymorphs, co-crystals, tautomers, stereoisomers, isotopically labeled derivatives, and prodrugs thereof (e.g., compounds of any one of Formulae (I), (II), and (III), and pharmaceutically acceptable salts thereof). In certain embodiments, a compound described herein is not compound 1, or a pharmaceutically acceptable salt, solvate, hydrate, polymorph, co-crystal, tautomer, stereoisomer, isotopically labeled derivative, or prodrug thereof. In certain embodiments, a compounds described herein is not compound 2, or a pharmaceutically acceptable salt, solvate, hydrate, polymorph, co-crystal, tautomer, stereoisomer, isotopically labeled derivative, or prodrug thereof. In certain embodiments, a compounds described herein is not compound 3, or a pharmaceutically acceptable salt, solvate, hydrate, polymorph, co-crystal, tautomer, stereoisomer, isotopically labeled derivative, or prodrug thereof. In certain embodiments, a compounds described herein is not compound 4, or a pharmaceutically acceptable salt, solvate, hydrate, polymorph, co-crystal, tautomer, stereoisomer, isotopically labeled derivative, or prodrug thereof. In certain embodiments, the compounds described herein is not any one of compounds 1 to 4, and pharmaceutically acceptable salts, solvates, hydrates, polymorphs, co-crystals, tautomers, stereoisomers, isotopically labeled derivatives, and prodrugs thereof.

Compounds described herein are binders of bromodomain-containing proteins. In certain embodiments, the compounds described herein bind to a bromodomain-containing protein. Without wishing to be bound by any particular theory, the compounds described herein are thought to bind in a binding pocket of a bromodomain of a bromodomain-containing protein. In certain embodiments, the compounds described herein bind to the binding pocket of the bromodomain by mimicking the contact between an acetyl-lysine residue of a second protein (e.g., a histone) and the binding pocket. In certain embodiments, the compounds described herein bind to the binding pocket of the bromodomain. In certain embodiments, the compounds described herein covalently bind to the bromodomain-containing protein. In certain embodiments, the compounds described herein non-covalently bind to the bromodomain-containing protein. In certain embodiments, the compounds described herein reversibly bind to the bromodomain-containing protein. In certain embodiments, the compounds described herein non-reversibly bind to the bromodomain-containing protein. In certain embodiments, the compounds described herein inhibit the activity of a bromodomain-containing protein. In certain embodiments, the compounds described herein inhibit the activity of a bromodomain-containing protein because of the binding of the compound to the bromodomain-containing protein. In certain embodiments, the compounds described herein inhibit the activity of a bromodomain-containing protein because of the binding of the compounds to a bromodomain of the bromodomain-containing protein. In certain embodiments, the compounds described herein inhibit the activity of a bromodomain. In certain embodiments, the activity of a bromodomain is the activity of bromodomain in binding an acetylated lysine residue (e.g., an acetylated lysine residue on the N-terminal tails of histones). In certain embodiments, the compounds described herein specifically bind to a bromodomain-containing protein. In certain embodiments, the compounds described herein specifically bind to a bromodomain of a bromodomain-containing protein. In certain embodiments, the compounds described herein that specifically bind to a bromodomain-containing protein show a greater binding affinity to the bromodomain-containing protein than to one or more other proteins or one or more other bromodomain-containing proteins. In certain embodiments, the compounds described herein non-specifically bind to a bromodomain-containing protein. In certain embodiments, the compounds described herein non-specifically bind to a bromodomain of a bromodomain-containing protein. In certain embodiments, the compounds described herein reduce transcriptional elongation. In certain embodiments, the compounds described herein disrupt the subcellular localization of a bromodomain-containing protein. In certain embodiments, the compounds described herein reduce chromatin binding. In certain embodiments, the compounds described herein inhibit the binding of Histone H4 Kac peptide to a bromodomain of a bromodomain-containing protein. In certain embodiments, the compounds described herein form one or more hydrogen bonds with an evolutionarily conserved asparagine in a bromodomain of a bromodomain-containing protein. In certain embodiments, the asparagine is Asn140 in BRD4(1) and Asn429 in BRD2(2). In certain embodiments, the bromodomain-containing protein is BRD4 or BRD2; and the asparagine is Asn140 in BRD4(1) and Asn429 in BRD2(2). In certain embodiments, the compounds described herein bind competitively with chromatin in a cellular environment. It is thus expected that the compounds described herein may be useful in the treatment of a disease associated with the activity a bromodomain-containing protein (e.g., a proliferative disease).

The bromodomain-containing proteins that may be bound, and/or whose activity may be inhibited, by the compounds described herein include, but are not limited to, the bromodomain-containing proteins described herein. In certain embodiments, the bromodomain-containing protein is a bromo and extra terminal (BET) protein. In certain embodiments, the bromodomain-containing protein is BRD2. In certain embodiments, the bromodomain-containing protein is BRD2(1). In certain embodiments, the bromodomain-containing protein is BRD2(2). In certain embodiments, the bromodomain-containing protein is BRD3. In certain embodiments, the bromodomain-containing protein is BRD3(1). In certain embodiments, the bromodomain-containing protein is BRD3(2). In certain embodiments, the bromodomain-containing protein is BRD4. In certain embodiments, the bromodomain-containing protein is BRD4(1). In certain embodiments, the bromodomain-containing protein is BRD4(2). In certain embodiments, the bromodomain-containing protein is BRDT. In certain embodiments, the bromodomain-containing protein is BRDT(1). In certain embodiments, the bromodomain-containing protein is BRDT(2). In certain embodiments, the bromodomain-containing protein is a TBP (TATA box binding protein)-associated factor protein (TAF). In certain embodiments, the bromodomain-containing protein is TAF1. In certain embodiments, the bromodomain-containing protein is TAF1L. In certain embodiments, the bromodomain-containing protein is CREB-binding protein (CBP). In certain embodiments, the bromodomain-containing protein is E1A binding protein p300 (EP300).

The binding affinity of a compound described herein to a bromodomain-containing protein may be measured by the dissociation constant ($K_d$) value of an adduct of the compound described herein and the bromodomain-containing protein using methods known in the art (e.g., isothermal titration calorimetry (ITC)). In certain embodiments, the adduct comprises the compound described herein and the bromodomain-containing protein, which are bound (e.g., covalently or non-covalently) to each other. In certain embodiments, the $K_d$ value of the adduct is at most about 100 µM, at most about 30 µM, at most about 10 µM, at most about 3 µM, at most about 1 µM, at most about 300 nM, at most about 100 nM, at most about 30 nM, at most about 10 nM, at most about 3 nM, or at most about 1 nM. In certain embodiments, the $K_d$ value of the adduct is at least about 1 nM, at least about 10 nM, at least about 100 nM, at least about 1 µM, at least about 10 µM, or at least about 100 µM.

Combinations of the above-referenced ranges (e.g., at most about 10 μM and at least about 1 nM) are also within the scope of the invention. Other ranges are also possible. In certain embodiments, the $K_d$ value of the adduct is at most about 10 μM. In certain embodiments, the $K_d$ value of the adduct is at most about 300 nM. In certain embodiments, the $K_d$ value of the adduct is at most about 100 nM.

In certain embodiments, the activity of the bromodomain-containing proteins described herein is inhibited by the compounds described herein. The inhibition of the activity of a bromodomain-containing protein by a compound described herein may be measured by the half maximal inhibitory concentration ($IC_{50}$) value of a compound described herein when the compound described herein, or a pharmaceutical composition thereof, is contacted, directly or indirectly, with the bromodomain-containing protein. The $IC_{50}$ values may be obtained using methods known in the art. In certain embodiments, $IC_{50}$ values are obtained by a competition binding assay. In certain embodiments, $IC_{50}$ values are obtained by a method described herein. In certain embodiments, the $IC_{50}$ value of a compound described herein is at most about 1 mM, at most about 300 μM, at most about 100 μM, at most about 30 μM, at most about 10 μM, at most about 3 μM, at most about 1 μM, at most about 300 nM, at most about 100 nM, at most about 30 nM, at most about 10 nM, at most about 3 nM, or at most about 1 nM. In certain embodiments, the $IC_{50}$ value of a compound described herein is at least about 1 nM, at least about 3 nM, at least about 10 nM, at least about 30 nM, at least about 100 nM, at least about 300 nM, at least about 1 μM, at least about 3 μM, at least about 10 μM, at least about 30 μM, at least about 100 μM, at least about 300 μM, or at least 1 mM. Combinations of the above-referenced ranges (e.g., at most about 300 μM and at least about 1 μM) are also within the scope of the invention. Other ranges are also possible. In certain embodiments, the $IC_{50}$ value of a compound described herein is at most about 300 μM. In certain embodiments, the $IC_{50}$ value of a compound described herein is at most about 30 μM. In certain embodiments, the $IC_{50}$ value of a compound described herein is at most about 10 μM.

The compounds described herein may selectively inhibit the activity of a bromodomain-containing protein. It is understood that, when a compound, pharmaceutical composition, method, use, or kit is referred to as "selectively" inhibiting the activity of a first protein, the compound, pharmaceutical composition, method, use, or kit inhibits the activity of the first protein to a greater extent than of at least a second protein that is different from the first protein. In certain embodiments, the compounds described herein selectively inhibit the activity of a bromodomain-containing protein, compared to a different bromodomain-containing protein. In certain embodiments, the compounds described herein selectively inhibit the activity of a bromodomain-containing protein, compared to a protein that is not a bromodomain-containing protein. In certain embodiments, the compounds described herein selectively inhibit the activity of a bromodomain-containing protein, compared to a kinase (e.g., a kinase described herein). In certain embodiments, the compounds described herein selectively inhibit the activity of a bromodomain-containing protein, compared to MPS1 (TTK), ERK5 (BMK1, MAPK7), a polo kinase (e.g., polo kinase 1, polo kinase 2, polo kinase 3, polo kinase 4), Ack1, Ack2, AbI, DCAMKL1, ABL1, an AbI mutant, DCAMKL2, ARK5, BRK, MKNK2, FGFR4, TNK1, PLK1, ULK2, PLK4, PRKD1, PRKD2, PRKD3, ROS 1, RPS6KA6, TAOK1, TAOK3, TNK2, Bcr-Ab1, GAK, cSrc, TPR-Met, Tie2, MET, FGFR3, Aurora, AxI, Bmx, BTK, c-kit, CHK2, Flt3, MST2, p70S6K, PDGFR, PKB, PKC, Raf, ROCK-H, Rsk1, SGK, TrkA, TrkB, and/or TrkC. In certain embodiments, the compounds described herein selectively inhibit the activity of a bromodomain-containing protein, compared to a MAP kinase. In certain embodiments, the compounds described herein selectively inhibit the activity of a bromodomain-containing protein, compared to a mitotic spindle kinase. In certain embodiments, the compounds described herein selectively inhibit the activity of a bromodomain-containing protein, compared to a polo kinase. In certain embodiments, the compounds described herein selectively inhibit a BET protein. In certain embodiments, the compounds described herein selectively inhibit BRD2. In certain embodiments, the compounds described herein selectively inhibit BRD3. In certain embodiments, the compounds described herein selectively inhibit BRD4. In certain embodiments, the compounds described herein selectively inhibit BRDT. In certain embodiments, the compounds described herein selectively inhibit a TAF protein (e.g., TAF1 or TAF1L), CBP, and/or EP300. In certain embodiments, a compound described herein is a non-selective inhibitor of two or more bromodomain-containing proteins. In certain embodiments, a compound described herein is a non-selective inhibitor of a bromodomain-containing protein and a protein that is not a bromodomain-containing protein.

The compounds described herein may also selectively bind to a bromodomain of a bromodomain-containing protein. It is understood that, when a compound is referred to as "selectively" binding to a bromodomain of a bromodomain-containing protein, the compound binds to the bromodomain of the bromodomain-containing protein with a great affinity than to a non-bromodomain of the bromodomain-containing protein.

The selectivity of a compound described herein in inhibiting the activity of a bromodomain-containing protein over a second protein (e.g., a kinase) that is different from the bromodomain-containing protein may be measured by the quotient of the $IC_{50}$ value of the compound described herein in inhibiting the activity of the second protein over the $IC_{50}$ value of the compound described herein in inhibiting the activity of the bromodomain-containing protein. The selectivity of a compound described herein for a bromodomain-containing protein over second protein may also be measured by the quotient of the $K_d$ value of an adduct of the compound described herein and the second protein over the $K_d$ value of an adduct of the compound described herein and the bromodomain-containing protein. In certain embodiments, the selectivity is at least about 1-fold, at least about 3-fold, at least about 5-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold. In certain embodiments, the selectivity is at most about 100,000-fold, at most about 10,000-fold, at most about 1,000-fold, at most about 100-fold, at most about 10-fold, or at most about 1-fold. Combinations of the above-referenced ranges (e.g., and at least about 2-fold and at most about 10,000-fold) are also within the scope of the invention. Other ranges are also possible. In certain embodiments, the selectivity is at least about 3-fold. In certain embodiments, the selectivity is at least about 10-fold. In certain embodiments, the selectivity is at least about 100-fold.

It is known in the art that a bromodomain-containing protein is implicated in a wide range of diseases. For example, BRD3 and BRD4 are related to BRD3 NUT midline carcinoma and BRD4 NUT midline carcinoma, respectively, BRDT is related to sperm formation, and CBP is related to mixed-lineage leukemia (MLL). Therefore, the compounds described herein are expected to be useful in treating and/or preventing diseases associated with bromodomain-containing proteins or as a male contraceptive.

Pharmaceutical Compositions, Kits, and Administration

The present invention provides pharmaceutical compositions comprising a compound described herein (e.g., a compound of any one of Formulae (I), (II-C), and (III), or a pharmaceutically acceptable salt, solvate, hydrate, polymorph, co-crystal, tautomer, stereoisomer, isotopically labeled derivative, or prodrug thereof), and optionally a pharmaceutically acceptable excipient. In certain embodiments, the pharmaceutical composition described herein comprises a compound of any one of Formulae (I), (II-C), and (III), or a pharmaceutically acceptable salt thereof, and optionally a pharmaceutically acceptable excipient. In certain embodiments, the pharmaceutical composition described herein comprises a compound of any one of Formulae (I), (II-C), and (III), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating and/or preventing a disease (e.g., a disease described herein) in a subject in need thereof. In certain embodiments, the effective amount is an amount effective for treating a disease in a subject in need thereof. In certain embodiments, the effective amount is an amount effective for preventing a disease in a subject in need thereof. In certain embodiments, the effective amount is an amount effective for reducing the risk of developing a disease in a subject in need thereof. In certain embodiments, the effective amount is an amount effective for contraception in a subject in need thereof. In certain embodiments, the effective amount is an amount effective for inhibiting the replication of a virus. In certain embodiments, the effective amount is an amount effective for kill a virus. In certain embodiments, the effective amount is an amount effective for inhibiting the activity (e.g., aberrant activity, such as increased activity) of a bromodomain-containing protein in a subject or cell. In certain embodiments, the effective amount is an amount effective for inhibiting the activity (e.g., aberrant activity, such as increased activity) of a bromodomain in a subject or cell. In certain embodiments, the effective amount is an amount effective for inhibiting the binding of a bromodomain of a bromodomain-containing protein to an acetyl-lysine residue of a second protein (e.g., a histone) in a subject or cell. In certain embodiments, the effective amount is an amount effective for modulating (e.g., inhibiting) transcriptional elongation in a subject or cell. In certain embodiments, the effective amount is an amount effective for modulating (e.g., down-regulating or inhibiting) the expression (e.g., transcription) of a gene that is regulated by a bromodomain-containing protein in a subject or cell. In certain embodiments, the effective amount is an amount effective for modulating (e.g., reducing) the level of a bromodomain-containing protein in a subject or cell.

An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the effective amount is an amount effective for inhibiting the activity of a bromodomain-containing protein, the activity of a bromodomain, the binding of a bromodomain of a bromodomain-containing protein to an acetyl-lysine residue of a second protein (e.g., a histone), the transcriptional elongation, and/or the expression (e.g., transcription) of a gene that is regulated by a bromodomain-containing protein by at least about 10%, at least about 20%, at least about 30%, at least about 40%, at least about 50%, at least about 60%, at least about 70%, at least about 80%, or at least about 90%. In certain embodiments, the effective amount is an amount effective for inhibiting the activity of a bromodomain-containing protein, the binding of a bromodomain of a bromodomain-containing protein to an acetyl-lysine residue of a second protein (e.g., a histone), and/or the expression (e.g., transcription) of a gene that is regulated by a bromodomain-containing protein by at most about 90%, at most about 80%, at most about 70%, at most about 60%, at most about 50%, at most about 40%, at most about 30%, at most about 20%, or at most about 10%. Combinations of the ranges described herein (e.g., at least about 20% and at most about 50%) are also within the scope of the invention. In certain embodiments, the activity of a bromodomain-containing protein, the binding of a bromodomain of a bromodomain-containing protein to an acetyl-lysine residue of a second protein (e.g., a histone), and/or the expression (e.g., transcription) of a gene that is regulated by a bromodomain-containing protein are inhibited by a percentage or a range of percentage described herein by an effective amount of a compound described herein.

In certain embodiments, the gene regulated by a bromodomain-containing protein is a gene regulated by a bromo and extra terminal protein (BET). In certain embodiments, the gene regulated by a bromodomain-containing protein is BRD2. In certain embodiments, the gene regulated by a bromodomain-containing protein is BRD2(1). In certain embodiments, the gene regulated by a bromodomain-containing protein is BRD2(2). In certain embodiments, the gene regulated by a bromodomain-containing protein is BRD3. In certain embodiments, the gene regulated by a bromodomain-containing protein is BRD3(1). In certain embodiments, the gene regulated by a bromodomain-containing protein is BRD3(2). In certain embodiments, the gene regulated by a bromodomain-containing protein is BRD4. In certain embodiments, the gene regulated by a bromodomain-containing protein is BRD4(1). In certain embodiments, the gene regulated by a bromodomain-containing protein is BRD4(2). In certain embodiments, the gene regulated by a bromodomain-containing protein is BRDT. In certain embodiments, the gene regulated by a bromodomain-containing protein is BRDT(1). In certain embodiments, the gene regulated by a bromodomain-containing protein is BRDT(2). In certain embodiments, the gene regulated by a bromodomain-containing protein is a gene regulated by a TBP (TATA box binding protein)-associated factor protein (TAF). In certain embodiments, the gene regulated by a bromodomain-containing protein is TAF1. In certain embodiments, the gene regulated by a bromodomain-containing protein is TAF1L. In certain embodiments, the gene regulated by a bromodomain-containing protein is a gene regulated by a CREB-binding protein (CBP). In certain embodiments, the gene regulated by a bromodomain-containing protein is a gene regulated by an E1A binding protein p300 (EP300).

Pharmaceutical compositions described herein can be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations). An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to have a disease in a subject in need thereof, in inhibiting the replication of a virus, in killing a virus, in inhibiting the activity of a bromodomain-containing protein in a subject or cell, in inhibiting the activity of a bromodomain in a subject or cell, in inhibiting the binding of a bromodomain of a bromodomain-containing protein to an acetyl-lysine residue of a second protein (e.g., a histone) in a subject or cell, in modulating (e.g., inhibiting) the transcription elongation, in modulating (e.g., inhibiting) the expression (e.g., transcription) of a gene that is regulated by a bromodomain-containing protein in a subject or cell), in modulating (e.g., reducing) the level of a bromodomain-containing protein in a subject or cell, bioavailability, and/or safety, reduce drug resistance, reduce and/or modify their metabolism, inhibit their excretion, and/or modify their distribution within the body of a subject. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZAL-TRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is an anti-viral agent. In certain embodiments, the additional pharmaceutical agent is a binder of a bromodomain-containing protein. In certain embodiments, the additional pharmaceutical agent is a binder of a bromodomain. In certain embodiments, the additional pharmaceutical agent is a binder or inhibitor of a bromodomain-containing protein. In certain embodiments, the additional pharmaceutical agent is an binder or inhibitor of a bromodomain. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy), and chemotherapy.

Also encompassed by the invention are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits are useful for treating and/or preventing a disease described herein in a subject in need thereof. In certain embodiments, the kits are useful for treating a disease described herein in a subject in need thereof. In certain embodiments, the kits are useful for preventing a disease described herein in a subject in need thereof. In certain embodiments, the kits are useful for reducing the risk of developing a disease described herein in a subject in need thereof. In certain embodiments, the kits are useful for contraception (e.g., male contraception). In certain embodiments, the kits are useful for in inhibiting the replication of a virus. In certain embodiments, the kits are useful for killing a virus. In certain embodiments, the kits are useful for inhibiting the activity (e.g., aberrant activity, such as increased activity) of a bromodomain-containing protein in a subject or cell. In certain embodiments, the kits are useful for inhibiting the activity (e.g., aberrant activity, such as increased activity) of a bromodomain in a subject or cell. In certain embodiments, the kits are useful for inhibiting the binding of a bromodomain of a bromodomain-containing protein to an acetyl-lysine residue of a second protein (e.g., a histone) in a subject or cell. In certain embodiments, the kits are useful for modulating (e.g., inhibiting) the transcriptional elongation in a subject or cell. In certain embodiments, the kits are useful for modulating (e.g., down-regulating or inhibiting) the expression (e.g., transcription) of a gene that is regulated by a bromodomain-containing protein in a subject or cell. In certain embodiments, the kits are useful for modulating (e.g., reducing) the level of a bromodomain-containing protein in a subject or cell.

In certain embodiments, the kits are useful for screening a library of compounds to identify a compound that is useful in a method of the invention.

In certain embodiments, a kit described herein further includes instructions for using the kit, such as instructions for using the kit in a method of the invention (e.g., instructions for administering a compound or pharmaceutical composition described herein to a subject). A kit described herein may also include information as required by a regulatory agency such as the U.S. Food and Drug Administration (FDA). In certain embodiments, the information included in the kits is prescribing information. In certain embodiments, the kits and instructions provide for treating and/or preventing a disease described herein in a subject in need thereof. In certain embodiments, the kits and instructions provide for treating a disease described herein in a subject in need thereof. In certain embodiments, the kits and instructions provide for preventing a disease described herein in a subject in need thereof. In certain embodiments, the kits and instructions provide for reducing the risk of developing a disease described herein in a subject in need thereof. In certain embodiments, the kits and instructions provide for contraception (e.g., male contraception). In certain embodiments, the kits and instructions provide for inhibiting the replication of a virus. In certain embodiments, the kits and instructions provide for killing a virus. In certain embodiments, the kits and instructions provide for inhibiting the activity (e.g., aberrant activity, such as increased activity) of a bromodomain-containing protein in a subject or cell. In certain embodiments, the kits and instructions provide for inhibiting the activity (e.g., aberrant activity, such as increased activity) of a bromodomain in a subject or cell. In certain embodiments, the kits and instructions provide for inhibiting the binding of a bromodomain of a bromodomain-containing protein to an acetyl-lysine residue of a second protein (e.g., a histone) in a subject or cell. In certain embodiments, the kits and instructions provide for modulating (e.g., inhibiting) the transcriptional elongation. In certain embodiments, the kits and instructions provide for modulating (e.g., down-regulating or inhibiting) the expression (e.g., transcription) of a gene that is regulated by a bromodomain-containing protein in a subject or cell. In certain embodiments, the kits and instructions provide for modulating (e.g., reducing) the level of a bromodomain-containing protein in a subject or cell. In certain embodiments, the kits and instructions provide for screening a library of compounds to identify a compound that is useful in a method of the invention. A kit described herein may include one or more additional pharmaceutical agents described herein as a separate composition.

Methods of Treatment and Uses

The present invention provides methods for the treatment of a wide range of diseases, such as diseases associated with bromodomains, diseases associated with the activity (e.g., aberrant activity) of bromodomains, diseases associated with bromodomain-containing proteins, and disease associated with the activity (e.g., aberrant activity) of bromodomain-containing proteins. Exemplary diseases include, but are not limited to, proliferative diseases, cardiovascular diseases, viral infections, fibrotic diseases, metabolic diseases, endocrine diseases, and radiation poisoning. Also provided by the present invention are methods for contraception (e.g., male contraception). The present invention further provides methods of inhibiting the activity (e.g., aberrant activity, such as increased activity) of a bromodomain or bromodomain-containing protein, methods of inhibiting the binding of a bromodomain of a bromodomain-containing protein to an acetyl-lysine residue of a second protein (e.g., a histone), methods of modulating (e.g., inhibiting) the transcriptional elongation, and methods of modulating (e.g., down-regulating or inhibiting) the expression (e.g., transcription) of a gene that is regulated by a bromodomain-containing protein.

Gene regulation is fundamentally governed by reversible, non-covalent assembly of macromolecules. Signal transduction to RNA polymerase requires higher-ordered protein complexes, spatially regulated by assembly factors capable of interpreting the post-translational modification states of chromatin. Epigenetic readers are structurally diverse proteins, and each of the epigenetic readers possesses one or more evolutionarily conserved effector modules, which recognize covalent modifications of proteins (e.g., histones) or DNA. The ε-N-acetylation of lysine residues (Kac) on histone tails is associated with an open chromatin architecture and transcriptional activation. Context-specific molecular recognition of acetyl-lysine is principally mediated by bromodomains.

Bromodomain-containing proteins are of substantial biological interest, as components of transcription factor complexes (e.g., TBP (TATA box binding protein)-associated factor 1 (TAF1), CREB-binding protein (CBP or CREBBP), P300/CBP-associated factor (PCAF), and Gcn5) and determinants of epigenetic memory. There are 41 human proteins containing a total of 57 diverse bromodomains. Despite large sequence variations, all bromodomains share a conserved fold comprising a left-handed bundle of four alpha helices ($α_Z$, $α_A$, $α_B$, and $α_C$), linked by diverse loop regions (ZA and BC loops) that determine substrate specificity. Co-crystal structures with peptidic substrates showed that the acetyl-lysine is recognized by a central hydrophobic cavity and is anchored by a hydrogen bond with an asparagine residue present in most bromodomains. The bromo and extra-terminal (BET) family (e.g., BRD2, BRD3, BRD4 and BRDT) shares a common domain architecture comprising two N-terminal bromodomains that exhibit high level of sequence conservation, and a more divergent C-terminal recruitment domain.

Recent research has established a compelling rationale for targeting BRD4 in cancer. BRD4 functions to facilitate cell cycle progression and knock-down in cultured cancer cell lines prompts G1 arrest. BRD4 is an important mediator of transcriptional elongation, functioning to recruit the positive transcription elongation factor complex (P-TEFb). Cyclin dependent kinase-9, a core component of P-TEFb, is a validated target in chronic lymphocytic leukemia, and has recently been linked to c-Myc dependent transcription. Bromodomains present in BRD4 recruit P-TEFb to mitotic chromosomes resulting in increased expression of growth promoting genes. BRD4 remains bound to transcriptional start sites of genes expressed during M/G1 but has not been found present at start sites that are expressed later in the cell cycle. Knockdown of BRD4 in proliferating cells has been shown to lead to G1 arrest and apoptosis by decreasing expression levels of genes important for mitotic progression and survival.

Importantly, BRD4 has recently been identified as a component of a recurrent t(15; 19) chromosomal translocation in an aggressive form of human squamous cell carcinoma. Such translocations express the tandem N-terminal bromodomains of BRD4 as an in-frame chimera with the nuclear protein in testis (NUT) protein, genetically defining the NUT midline carcinoma (NMC). Functional studies in patient-derived NMC cell lines have validated the essential role of the BRD4-NUT oncoprotein in maintaining the characteristic proliferation advantage and differentiation block of this malignancy. Notably, RNA silencing of BRD4-NUT gene expression arrests proliferation and prompts squamous differentiation with a marked increase in cytokeratin expression. A bromodomain may also down-regulates Myc and other transcripitional factors, such as interleukin 7 receptor (IL7R). These observations underscore the utility and therapeutic potential of an binder or inhibitor of bromodomain-containing proteins.

In another aspect, the present invention provides methods of inhibiting the activity of a bromodomain-containing protein in a subject or cell. In certain embodiments, the bromodomain-containing protein is a bromodomain-containing protein described herein (e.g., a BET protein, such as BRD2, BRD3, BRD4, or BRDT). In certain embodiments, the activity of a bromodomain-containing protein in a subject or cell is inhibited by the inventive methods. In certain embodiments, the activity of a bromodomain-containing protein in a subject or cell is inhibited by the inventive methods by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a bromodomain-containing protein in a subject or cell is inhibited by the inventive methods by at most about 90%, at most about 80%, at most about 70%, at most about 60%, at most about 50%, at most about 40%, at most about 30%, at most about 20%, at most about 10%, at most about 3%, or at most about 1%. Combinations of the above-referenced ranges (e.g., at least about 10% and at most about 50%) are also within the scope of the invention. Other ranges are also possible. In some embodiments, the activity of a bromodomain-containing protein in a subject or cell is selectively inhibited by the inventive methods. In some embodiments, the activity of a bromodomain-containing protein in a subject or cell is selectively inhibited by the inventive methods, compared to the activity of a kinase (e.g., a MAP kinase, a mitotic spindle kinase, a polo kinase). In other embodiments, the activity of a bromodomain-containing protein in a subject or cell is non-selectively inhibited by the inventive methods. In certain embodiments, the cytokine level and/or histamine release are reduced by the inventive methods.

In certain embodiments, the activity of a bromodomain-containing protein is an aberrant activity of the bromodomain-containing protein. In certain embodiments, the activity of a bromodomain-containing protein is an increased activity of the bromodomain-containing protein. In certain embodiments, the activity of a bromodomain-containing protein is reduced by a method of the invention.

In certain embodiments, the subject is an animal. The animal may be of either sex and may be at any stage of development. In certain embodiments, the subject is a male.

In certain embodiments, the subject is a female. In certain embodiments, the subject described herein is a human. In certain embodiments, the subject described herein is a human male. In certain embodiments, the subject described herein is a human female. In certain embodiments, the subject is a human diagnosed as having a disease described herein. In certain embodiments, the subject is a human diagnosed as being at a higher-than-normal risk to have a disease described herein. In certain embodiments, the subject is a human suspected of having a disease described herein. In certain embodiments, the subject is a non-human animal. In certain embodiments, the subject is a fish. In certain embodiments, the subject is a mammal. In certain embodiments, the subject is a non-human mammal. In certain embodiments, the subject is a human or non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs).

In certain embodiments, the cell described herein is present in vitro. In certain embodiments, the cell is present ex vivo. In certain embodiments, the cell is present in vivo.

In another aspect, the present invention provides methods of inhibiting the activity of a bromodomain in a subject or cell. In certain embodiments, the activity of a bromodomain is an aberrant activity of the bromodomain. In certain embodiments, the activity of a bromodomain is an increased activity of the bromodomain. In certain embodiments, the activity of a bromodomain is reduced by a method of the invention.

Another aspect of the present invention relates to methods of inhibiting the binding of a bromodomain of a bromodomain-containing protein to an acetyl-lysine residue of a second protein (e.g., a histone) in a subject or cell. In certain embodiments, the second protein is a protein including at least one acetyl-lysine residue. In certain embodiments, the second protein is not a bromodomain-containing protein. In certain embodiments, the second protein is a histone. In certain embodiments, the histone is selected from the group consisting of H1, H2A, H2B, H3, H4, and H5. In certain embodiments, the binding of a bromodomain of the bromodomain-containing protein to an acetyl-lysine residue of the second protein (e.g., a histone) is inhibited by the inventive methods.

In another aspect, the present invention provides methods of modulating (e.g., inhibiting) the transcription elongation. In certain embodiments, the transcription elongation is modulated (e.g., inhibited) by the inventive methods.

In another aspect, the present invention provides methods of modulating the expression (e.g., transcription) of a gene (e.g., a gene described herein) that is regulated by a bromodomain-containing protein in a subject or cell. In certain embodiments, the present invention provides methods of down-regulating or inhibiting the expression (e.g., transcription) of a gene that is regulated by a bromodomain-containing protein in a subject or cell. Without wishing to be bound by any particular theory, the compounds and pharmaceutical compositions described herein may be able to interfere with the binding of a bromodomain-containing protein to a transcriptional start site of the gene. In certain embodiments, the compounds and pharmaceutical compositions described herein interfere with the acetyl-lysine recognition during the expression (e.g., transcription) of the gene. In certain embodiments, the compounds and pharmaceutical compositions described herein interfere with the acetyl-lysine anchoring during the expression (e.g., transcription) of the gene. In certain embodiments, the expression (e.g., transcription) of a gene that is regulated by a bromodomain-containing protein in a subject or cell is modulated by the inventive methods. In certain embodiments, the expression (e.g., transcription) of a gene that is regulated by a bromodomain-containing protein in a subject or cell is down-regulated or inhibited by the inventive methods. In certain embodiments, the gene that is regulated by a bromodomain-containing protein is an oncogene.

Another aspect of the present invention relates to methods of treating a disease in a subject in need thereof. In certain embodiments, the disease is treated by the inventive methods.

In certain embodiments, the disease is a disease associated with a bromodomain-containing protein. In certain embodiments, the disease is a disease associated with the activity of a bromodomain-containing protein. In certain embodiments, the disease is a disease associated with the aberrant activity (e.g., increased activity) of a bromodomain-containing protein.

In certain embodiments, the disease is a disease associated with a bromodomain (e.g., a bromodomain of a bromodomain-containing protein). In certain embodiments, the disease is a disease associated with the activity of a bromodomain. In certain embodiments, the disease is a disease associated with the aberrant activity (e.g., increased activity) of a bromodomain. In certain embodiments, the disease is a disease associated with the function (e.g., dysfunction) of a bromodomain.

In certain embodiments, the disease described herein is driven by a transcriptional activator. In certain embodiments, the transcriptional activator is Myc. In certain embodiments, the disease is associated with a NUT rearrangement. In certain embodiments, the disease is a disease associated with aberrant Myc function. In certain embodiments, the disease is a disease associated with interleukin 7 receptor (IL7R).

In certain embodiments, the disease is a proliferative disease (e.g., a proliferative disease described herein). In certain embodiments, the disease is cancer (e.g., a cancer described herein). In certain embodiments, the disease is lung cancer. In certain embodiments, the disease is multiple myeloma. In certain embodiments, the disease is neuroblastoma. In certain embodiments, the disease is colon cancer. In certain embodiments, the disease is testicular cancer. In certain embodiments, the disease is ovarian cancer. In certain embodiments, the disease is lung cancer (e.g., small-cell lung cancer or non-small-cell lung cancer). In certain embodiments, the disease is NUT midline carcinoma (e.g., BRD3 NUT midline carcinoma or BRD4 NUT midline carcinoma). In certain embodiments, the disease is leukemia. In certain embodiments, the disease is mixed-lineage leukemia (MLL). In certain embodiments, the disease is acute myelocytic leukemia (AML), biphenotypic B myelomonocytic leukemia, or erythroleukemia. In certain embodiments, the disease is selected from the group consisting of Burkitt's lymphoma, breast cancer, colon cancer, neuroblastoma, glial blastoma multiforme, chronic lymphocytic leukemia, and squamous cell carcinoma.

In certain embodiments, the disease is a benign neoplasm (e.g., a benign neoplasm described herein).

In certain embodiments, the disease is an inflammatory disease (e.g., an inflammatory disease described herein). In certain embodiments, the disease is a disease that involves an inflammatory response to an infection with a bacterium, virus, fungus, parasite, and/or protozoon. In certain embodiments, the disease is selected from the group consisting of osteoarthritis, acute gout, multiple sclerosis, an inflammatory bowel disease (e.g., Crohn's disease and ulcerative colitis), neuroinflammation, asthma, a chronic obstructive airways disease, pneumonitis, myositis, eczema, dermatitis, acne, cellulitis, an occlusive disease, thrombosis, alopecia, nephritis, vasculitis, retinitis, uveitis, scleritis, sclerosing cholangitis, hypophysitis, thyroiditis, septic shock, systemic inflammatory response syndrome (SIRS), toxic shock syndrome, acute lung injury, ARDS (adult respiratory distress syndrome), acute renal failure, burns, pancreatitis (e.g., acute pancreatitis), post-surgical syndromes, sarcoidosis, Herxheimer reactions, encephalitis, myelitis, meningitis, and malaria. In certain embodiments, the disease is acute or chronic pancreatitis. In certain embodiments, the disease is burns. In certain embodiments, the disease is an inflammatory bowel disease. In certain embodiments, the disease is neuroinflammation. In certain embodiments, the disease is sepsis or sepsis syndrome. In certain embodiments, the disease is graft-versus-host disease (GVHD).

In certain embodiments, the disease is an autoimmune disease (e.g., an autoimmune disease described herein). In certain embodiments, the disease is rheumatoid arthritis. In certain embodiments, the disease is psoriasis, systemic lupus erythematosus, vitiligo, a bullous skin disease.

In certain embodiments, the disease is a cardiovascular disease. In certain embodiments, the disease is atherogenesis or atherosclerosis. In certain embodiments, the disease is arterial stent occlusion, heart failure (e.g., congestive heart failure), a coronary arterial disease, myocarditis, pericarditis, a cardiac valvular disease, stenosis, restenosis, in-stent-stenosis, angina pectoris, myocardial infarction, acute coronary syndromes, coronary artery bypass grafting, a cardiopulmonary bypass procedure, endotoxemia, ischemia-reperfusion injury, cerebrovascular ischemia (stroke), renal reperfusion injury, embolism (e.g., pulmonary, renal, hepatic, gastro-intestinal, or peripheral limb embolism), or myocardial ischemia.

In certain embodiments, the disease is a viral infection. In certain embodiments, the disease is a DNA virus infection. In certain embodiments, the disease is a dsDNA virus infection. In certain embodiments, the disease is an ssDNA virus infection. In certain embodiments, the disease is an RNA virus infection. In certain embodiments, the disease is a dsRNA virus infection. In certain embodiments, the disease is a (+)ssRNA virus infection. In certain embodiments, the disease is a (−)ssRNA virus infection. In certain embodiments, the disease is a reverse transcribing (RT) virus infection. In certain embodiments, the disease is an ssRNA-RT virus infection. In certain embodiments, the disease is a dsDNA-RT virus infection. In certain embodiments, the disease is human immunodeficiency virus (HIV) infection. In certain embodiments, the disease is acquired immunodeficiency syndrome (AIDS). In certain embodiments, the disease is human papillomavirus (HPV) infection. In certain embodiments, the disease is hepatitis C virus (HCV) infection. In certain embodiments, the disease is a herpes virus infection (e.g., herpes simplex virus (HSV) infection). In certain embodiments, the disease is Ebola virus infection. In certain embodiments, the disease is severe acute respiratory syndrome (SARS). In certain embodiments, the disease is influenza virus infection. In certain embodiments, the disease is an influenza virus infection. In certain embodiments, the disease is an influenza A virus infection. In certain embodiments, the disease is human flu (e.g., H1N1, H2N2, H3N2, H5N1, H7N7, H1N2, H9N2, H7N2, H7N3, or H10N7 virus infection). In certain embodiments, the disease is bird flu (e.g., H5N1 or H7N9 virus infection). In certain embodiments, the disease is swine influenza (e.g., H1N1, H1N2, H2N1, H3N1, H3N2, or H2N3 virus infection, or influenza C virus infection). In certain embodiments, the disease is equine influenza (e.g., H7N7 or H3N8 virus infection). In certain embodiments, the disease is canine influenza (e.g., H3N8 virus infection). In certain embodiments, the disease is an influenza B virus infection. In certain embodiments, the disease is an influenza C virus infection. In certain embodiments, the disease is Dengue fever, Dengue hemorrhagic fever (DHF), Dengue shock syndrome (DSS), hepatitis A, hepatitis B, hepatitis D, hepatitis E, hepatitis F, Coxsackie A virus infection, Coxsackie B virus infection, fulminant viral hepatitis, viral myocarditis, parainfluenza virus infection, an RS virus (RSV) infection (e.g., RSV bronchiolitis, RSV pneumonia, especially an infant and childhood RSV infection and RSV pneumonia in the patients with cardiopulmonary disorders), measles virus infection, vesicular stomatitis virus infection, rabies virus infection, Japanese encephalitis, Junin virus infection, human cytomegalovirus infection, varicellovirus infection, cytomegalovirus infection, muromegalovirus infection, proboscivirus infection, roseolovirus infection, lymphocryptovirus infection, macavirus infection, percavirus infection, rhadinovirus infection), poliovirus infection, Marburg virus infection, Lassa fever virus infection, Venezuelan equine encephalitis, Rift Valley Fever virus infection, Korean hemorrhagic fever virus infection, Crimean-Congo hemorrhagic fever virus infection, encephalitis, Saint Louise encephalitis, Kyasanur Forest disease, Murray Valley encephalitis, tick-borne encephalitis, West Nile encephalitis, yellow fever, adenovirus infection, poxvirus infection, or a viral infection in subjects with immune disorders.

In certain embodiments, the disease is a fibrotic condition. In certain embodiments, the disease is selected from the group consisting of renal fibrosis, post-operative stricture, keloid formation, hepatic cirrhosis, biliary cirrhosis, and cardiac fibrosis. In certain embodiments, the disease is scleroderma. In certain embodiments, the disease is idiopathic pulmonary fibrosis.

In certain embodiments, the disease is an endocrine disease. In certain embodiments, the disease is Addison's disease.

In certain embodiments, the disease is a metabolic disease. In certain embodiments, the disease is diabetes. In certain embodiments, the disease is type 1 diabetes. In certain embodiments, the disease is type 2 diabetes or gestational diabetes. In certain embodiments, the disease is obesity. In certain embodiments, the disease is fatty liver (NASH or otherwise), cachexia, hypercholesterolemia, or a disorder of lipid metabolism via the regulation of apolipoprotein A1 (APOA1).

In certain embodiments, the disease is radiation poisoning. In certain embodiments, the disease is radiation injury.

In certain embodiments, the disease is acute rejection of transplanted organs or multi-organ dysfunction syndrome.

In certain embodiments, the disease is Alzheimer's disease.

In still another aspect, the present invention provides methods of preventing a disease described herein in a subject in need thereof. In certain embodiments, the disease is prevented by the inventive methods.

In yet another aspect, the present invention provides methods of reducing the risk to have a disease described herein in a subject in need thereof. In certain embodiments, the risk to have the disease is reduced by the inventive methods.

In yet another aspect, the present invention provides methods for contraception in a subject in need thereof. In certain embodiments, the present invention provides methods of male contraception in a male subject in need thereof. In certain embodiments, the present invention provides methods of female contraception in a female subject in need thereof.

In yet another aspect, the present invention provides methods of inhibiting sperm formation in a subject in need thereof.

Another aspect of the present invention relates to methods of inhibiting the replication of a virus. In certain embodiments, the replication of the virus is inhibited by the inventive methods.

In certain embodiments, the virus is a virus described herein. In certain embodiments, the virus is the virus causing a viral infection described herein. In certain embodiments, the virus is human immunodeficiency virus (HIV), human papillomavirus (HPV), hepatitis C virus (HCV), herpes simplex virus (HSV), Ebola virus, or influenza virus.

In certain embodiments, the virus described herein is present in vitro. In certain embodiments, the virus is present ex vivo. In certain embodiments, the virus is present in vivo.

Another aspect of the present invention relates to methods of killing a virus. In certain embodiments, the virus is killed by the inventive methods.

Another aspect of the invention relates to methods of inhibiting the interaction between a bromodomain-containing protein and an immunoglobulin (Ig) regulatory element in a subject or cell.

In certain embodiments, the methods of the invention include administering to a subject in need thereof an effective amount of a compound or pharmaceutical composition described herein. In certain embodiments, the methods of the invention include administering to a subject in need thereof a therapeutically effective amount of a compound or pharmaceutical composition described herein. In certain embodiments, the methods of the invention include administering to a subject in need thereof a prophylactically effective amount of a compound or pharmaceutical composition described herein. In certain embodiments, the methods of the invention include contacting a cell with an effective amount of a compound or pharmaceutical composition described herein. In certain embodiments, the methods of the invention include contacting a virus with an effective amount of a compound or pharmaceutical composition described herein.

Another aspect of the invention relates to methods of modulating gene that is regulated by a bromodomain-containing protein expressing in a subject or cell.

Another aspect of the invention relates to methods of modulating the level of a bromodomain-containing protein in a subject or cell.

Another aspect of the invention relates to methods of screening a library of compounds, and pharmaceutical acceptable salts thereof, to identify a compound, or a pharmaceutical acceptable salt thereof, that is useful in the methods of the invention. In certain embodiments, the methods of screening a library include obtaining at least two different compounds described herein; and performing at least one assay using the different compounds described herein. In certain embodiments, at least one assay is useful in identifying a compound that is useful in the inventive methods.

Typically, the methods of screening a library of compounds involve at least one assay. In certain embodiments, the assay is performed to detect one or more characteristics associated with the treatment and/or prevention of a disease described herein, with the inhibition of the activity of a bromodomain-containing protein, with the inhibition of the activity of a bromodomain, with the inhibition of the binding of a bromodomain to an acetyl-lysine residue of a second protein (e.g., a histone), with the modulation (e.g., inhibition) of the transcriptional elongation, and/or with the modulation (e.g., inhibition) of the expression (e.g., transcription) of a gene that is regulated by a bromodomain-containing protein. The characteristics may be desired characteristics (e.g., a disease having been treated, a disease having been prevented, the risk to have a disease having been reduced, the replication of a virus having been inhibited, a virus having been killed, the activity of a bromodomain-containing protein having been inhibited, the activity of a bromodomain, the binding of a bromodomain to an acetyl-lysine residue of a second protein (e.g., a histone) having been inhibited, the transcriptional elongation having been modulated (e.g., having been inhibited), the level of a bromodomain-containing protein in a subject or cell having been modulated (e.g., reduced), or the expression (e.g., transcription) of a gene that is regulated by a bromodomain-containing protein having been modulated (e.g., having been inhibited)). The characteristics may be undesired characteristics (e.g., a disease having not been treated, a disease having not been prevented, the risk to have a disease having not been reduced, the replication of a virus having not been inhibited, a virus not having been killed, the activity of a bromodomain-containing protein having not been inhibited, the activity of a bromodomain having not been inhibited, the binding of a bromodomain to an acetyl-lysine residue of a second protein (e.g., a histone) having not been inhibited, the transcriptional elongation having not been modulated (e.g., having not been inhibited), the level of a bromodomain-containing protein in a subject or cell having not been modulated (e.g., having not been reduced), or the expression (e.g., transcription) of a gene that is regulated by a bromodomain-containing protein having not been modulated (e.g., having not been inhibited)). The assay may be an immunoassay, such as a sandwich-type assay, competitive binding assay, one-step direct test, two-step test, or blot assay. The step of performing at least one assay may be performed robotically or manually. In certain embodiments, the assay comprises (a) contacting a library of compounds with a bromodomain-containing protein; and (b) detecting the binding of the library of compounds to the bromodomain-containing protein. In certain embodiments, the assay comprises detecting the specific binding of the library of compounds to the bromodomain-containing protein. In certain embodiments, the assay comprises detecting the specific binding of the library of compounds to a bromodomain of the bromodomain-containing protein. In certain embodiments, the detected binding of the library of compounds to the bromodomain-containing protein is useful in identifying the compound that is useful in the methods of the invention. In certain embodiments, the step of detecting the binding comprises using differential scanning fluorimetry (DSF), isothermal titration calorimetry (ITC), and/or an amplified luminescence proximity homogeneous assay (ALPHA). The step of performing at least one assay may be performed in a cell (e.g., a cancer cell) in vitro, ex vivo, or in vivo. In certain embodiments, the step of performing at least one assay is performed in a cell (e.g., a cancer cell) in vitro. In certain embodiments, the assay comprises (a) contacting a library of compounds with a cell; and (b) detecting a decrease in cell proliferation, an increase in cell death, and/or an increase in cell differentiation. In certain embodiments, the cell death is apoptotic cell death. In certain embodiments, the cell differentiation is identified by detecting an increase in cytokeratin expression. In certain embodiments, the step of performing at least one assay further comprises detecting a reduction in transcriptional elongation.

In another aspect, the present invention provides the compounds described herein for use in a method of the invention.

In still another aspect, the present invention provides the pharmaceutical compositions described herein for use in a method of the invention.

In still another aspect, the present invention provides uses of the compounds described herein in a method of the invention.

In further another aspect, the present invention provides uses of the pharmaceutical compositions described herein in a method of the invention.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Preparation of Compounds

The compounds provided herein can be prepared from readily available starting materials using the following general methods and procedures or methods known in the art (e.g., methods reported in U.S. Patent Application Publication, US 2012/040961; Elkins et al., *Journal of Medicinal Chemistry* (2013), 56(11), 4413-4421; Kavanagh et al., *Bioorganic & Medicinal Chemistry Letters* (2013), 23(13), 3690-3696; Deng et al., *European Journal of Medicinal Chemistry* (2013), 70, 758-767; Delbroek et al., *Journal of Pharmaceutical and Biomedical Analysis* (2013), 76, 49-58; Choi et al., *ACS Medicinal Chemistry Letters* (2012), 3(8), 658-662; Deng et al., *Nature Chemical Biology* (2011), 7(4), 203-205; and Deng et al., *ACS Medicinal Chemistry Letters* (2011), 2(3), 195-200). It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Various established synthetic methods may be used to arrive at the inventive compounds described herein. In one embodiment, the inventive compounds can be prepared using the sequence provided in Scheme 1. Amine addition of S-1 into nitropyrimidines S-2 wherein $X^2$ and $X^3$ are each independently halide (e.g. fluoro, chloro, bromo, or iodo) provide intermediates S-3 wherein $R^{E1}$ is hydrogen or substituted or unsubstituted alkyl. In some embodiments, both $X^2$ and $X^3$ are chloro. Reduction of the nitro functionality in S-3 produces compounds S-4. In certain embodiments, the reduction conditions comprise a metal catalyst; e.g. palladium on carbon or Raney nickel. In certain embodiments, the reduction conditions comprise a metal at the (0) oxidation state; e.g. iron(0), tin(0), zinc(0). In certain embodiments, the reduction conditions comprise addition of an acid; e.g. acetic or hydrochloric acid. Cyclization of the free amino group leads to compounds S-5. In certain embodiments, the reduction and cyclization steps occur in one-pot.

In certain embodiments, the cyclization conditions comprise an amide coupling agent; e.g. HATU or EDC. Various leaving group conjugates of $R^E$ (i.e. LG-$R^E$, wherein LG is a leaving group as defined herein) can be contacted with compounds S-5 under appropriate conditions to afford intermediates S-6. In certain embodiments, the conditions comprise a base. In some embodiments, the conditions comprise an inorganic base; e.g. sodium hydride. In certain embodiments, the leaving group conjugate of $R^3$ is a halide; e.g. bromo or iodo. Subsequent linkage to the sidechain S-7 can be accomplished under aromatic substitution or coupling conditions to product compounds of any one of Formulae (I) to (III). In certain embodiments, the conditions comprise a base. In some embodiments, the conditions comprise an inorganic base; e.g. potassium or sodium carbonate. In certain embodiments, the conditions comprise a transition metal catalyst; e.g. a palladium or nickel catalyst. In certain embodiments, the conditions comprise a ligand; e.g. a phosphine ligand such as X-phos. In certain embodiments, compounds of S-6 can be alternatively modified by leaving group conjugates of $R^F$ (i.e. LG-$R^F$, wherein LG is a leaving group as defined herein) following cyclization. In certain embodiments, precursors to compounds of any one of Formulae (I) to (III) can be modified by leaving group conjugates of $R^C$ (i.e. LG-$R^C$, wherein LG is a leaving group as defined herein) as an alternative to introduction of $R^C$ through intermediate S-7. Alternative orders of assembly for the various synthetic intermediates into compounds of any one of Formulae (I) to (III) are contemplated.

Scheme 1

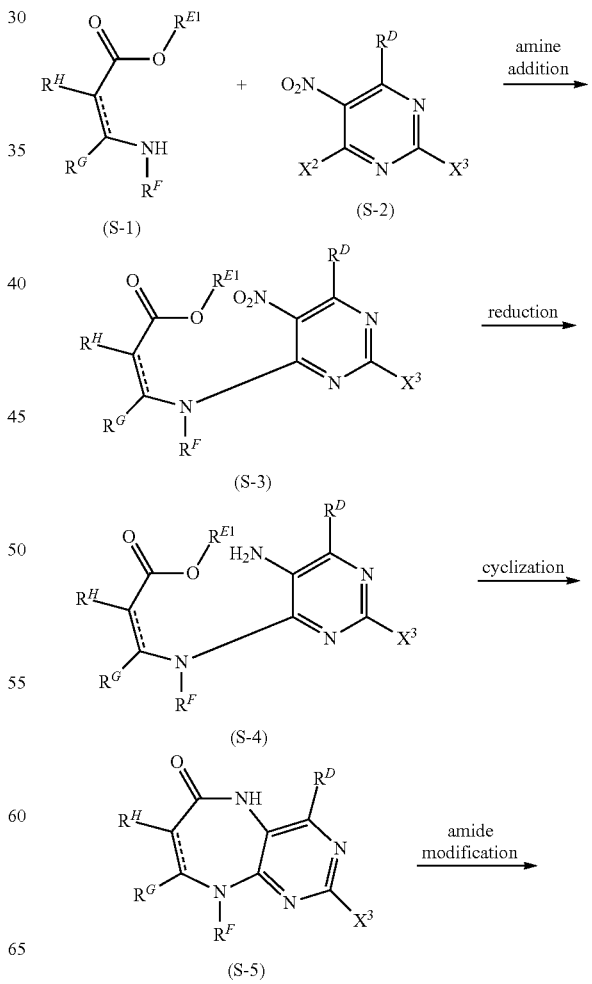

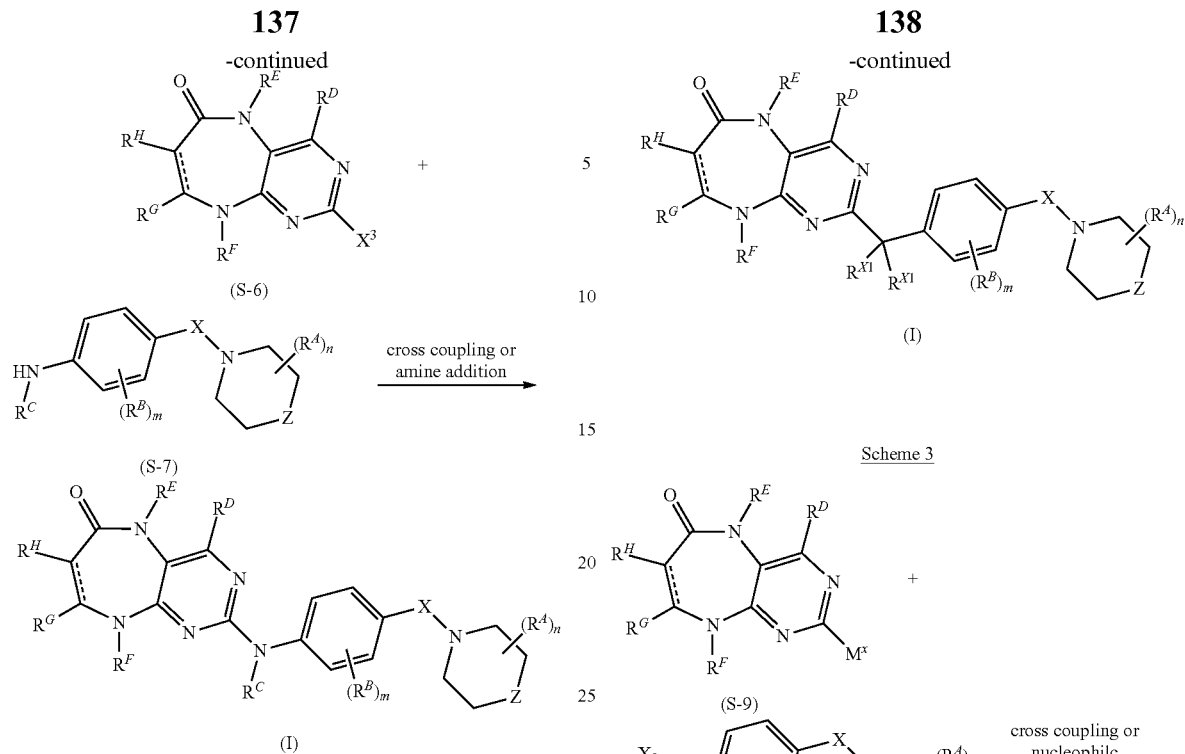

When linker of $X^1$ are alkyl, alternate methods of constructing the linkage to compounds S-6 are utilized (see Scheme 2. An organometal species S-8 wherein $M^X$ is a metal or metalloid (e.g. magnesium, lithium, zinc, boron, tin, or silicon) can be utilized to displace the halide $X^3$ of compounds S-6 to generate compounds of any one of Formulae (I) to (III). In certain embodiments, the reaction conditions may comprise a transition metal catalyst; e.g. palladium, nickel. In certain embodiments, the reaction conditions may comprise a ligand; e.g. a phosphine ligand such as X-phos. Alternatively, the metal species S-9 can be used to couple to or displace halides of S-10 (see Scheme 3). Alternative orders of assembly for the various synthetic intermediates into compounds of any one of Formulae (I) to (III) are contemplated. Compounds of Formula (II-C) can be prepared using methods similar to the methods of preparing the compounds of Formula (II). Non-limiting examples of the preparation of exemplary compounds described herein are illustrated in Examples 1 to 3.

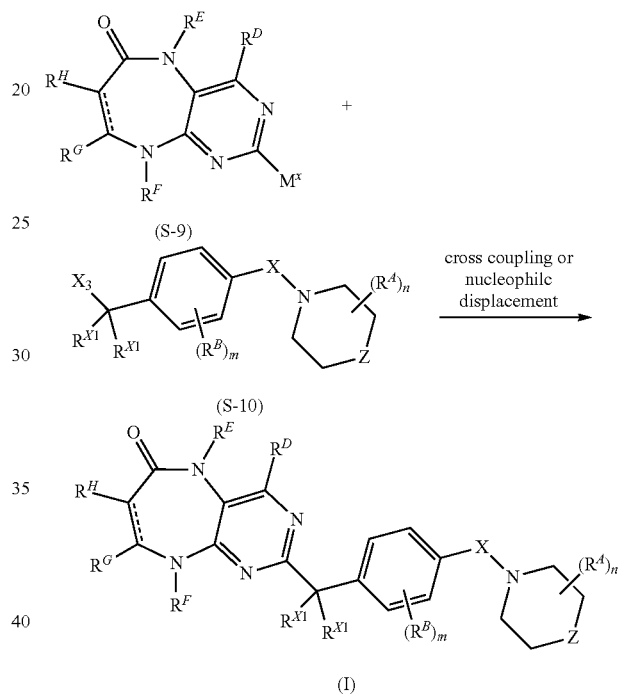

Example 1

Preparation of 2-((2-methoxy-4-(4-(4-methylpiperazin-1-yl)piperidine-1-carbonyl)phenyl)amino)-5,11-dimethyl-5H-benzo[e]pyrido[3, 2-b][1, 4]diazepin-6(11H)-one

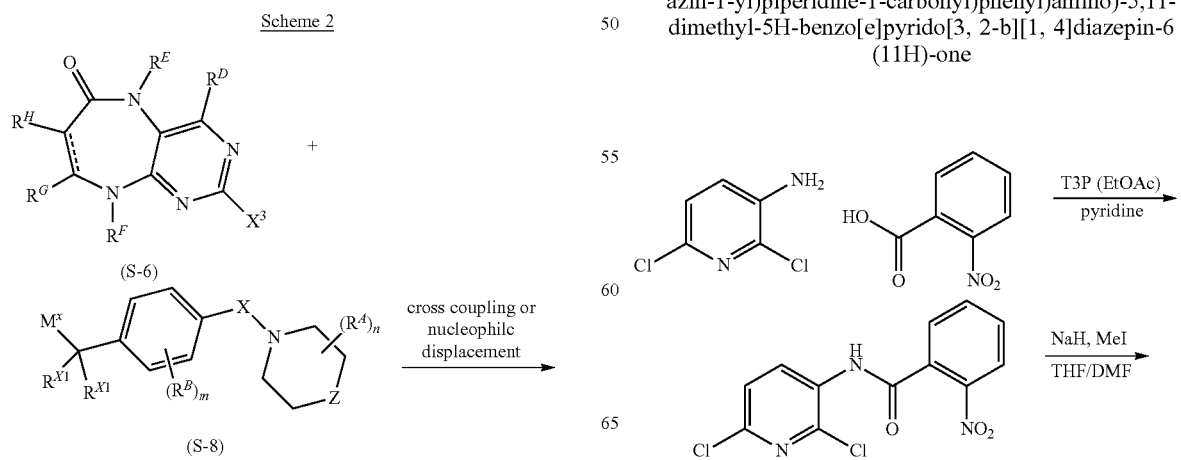

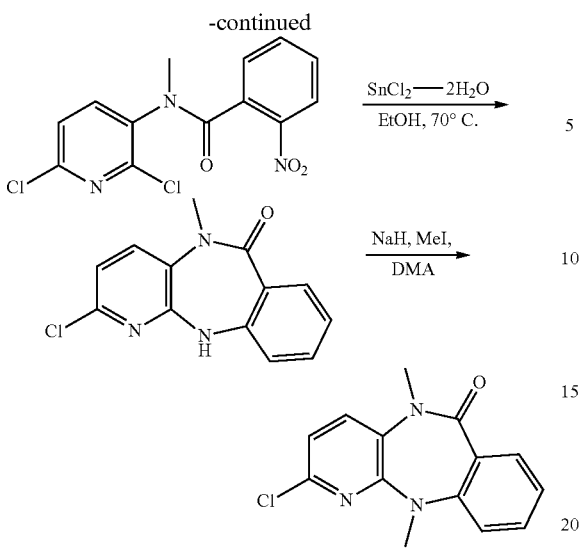

N-(2,6-dichloropyridin-3-yl)-2-nitrobenzamide

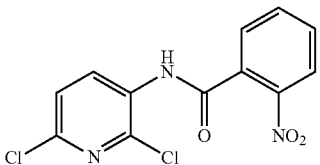 [SMILES: O=C(Nc1ccc(Cl)nc1Cl)c1ccccc1[N+](=O)[O-]]

2,6-Dichloropyridin-3-amine (0.50 g, 3.07 mmol, 1 eq) and 2-nitrobenzoic acid (0.564 g, 3.38 mmol, 1.1 eq) were dissolved in pyridine (20 mL, 0.75 M) at 0° C. A 50% solution of T3P in EtOAc (9.1 mL) was added slowly. The mixture was allowed to warm slowly to room temperature overnight. After 25 hours, the mixture was diluted with ice water and extracted three times with EtOAc. The combined organic layers were dried over sodium sulfate, filtered and concentrated under reduced pressure. Purification by column chromatography (ISCO, 40 g silica column, 0-40% EtOAc/hexanes, 25 minute gradient) gave a white solid (0.73 g, 2.34 mmol, 76%). $^1$H NMR (400 MHz, Chloroform-d) δ 8.82 (d, J=8.7 Hz, 1H), 8.22-8.15 (m, 1H), 7.88-7.64 (m, 4H), 7.38 (d, J=8.5 Hz, 1H). LCMS 312.22 (M+H).

N-(2,6-dichloropyridin-3-yl)-N-methyl-2-nitrobenzamide

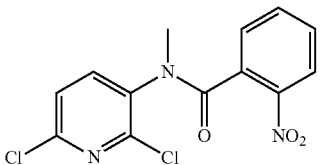 [SMILES: CN(C(=O)c1ccccc1[N+](=O)[O-])c1ccc(Cl)nc1Cl]

N-(2,6-dichloropyridin-3-yl)-2-nitrobenzamide (0.246 g, 0.789 mmol, 1 eq) was dissolved in THF (5.3 mL, 0.15 M) and cooled to 0° C. Sodium hydride (95%, dry) (37.9 mg, 1.578 mmol, 2 eq) was added, followed by MeI (0.147 mL, 2.368 mmol, 3 eq) and the mixture was warmed to room temperature. DMF (1 mL) was added to improve solubility. The mixture was stirred for 20 hours, then diluted with water and extracted twice with EtOAc. The aqueous mixture was then acidified to pH 3 with 2M HCl, then extracted twice more with EtOAc. The combined organic layer was dried over sodium sulfate, filtered and concentrated under reduced pressure. Purification by column chromatography (ISCO, 4 g silica column, 0-60% EtOAc/hexanes, 18 minute gradient) gave a yellow oil (0.12889 g, 0.3952 mmol, 50%). $^1$H NMR (400 MHz, Chloroform-d) δ 8.29 (d, J=8.3 Hz, 0H), 7.99 (d, J=7.9 Hz, 1H), 7.93 (d, J=8.1 Hz, 0H), 7.83 (td, J=7.5, 1.1 Hz, 0H), 7.70-7.64 (m, 1H), 7.60 (dd, J=7.6, 1.3 Hz, 0H), 7.56-7.51 (m, 1H), 7.47-7.41 (m, 2H), 7.10 (d, J=8.2 Hz, 1H), 3.44 (s, 3H), 3.11 (s, 1H) (mixture of rotamers). LCMS 326.18 (M+H).

2-Chloro-5-methyl-5H-benzo[e]pyrido[3,2-b][1,4]diazepin-6(11H)-one

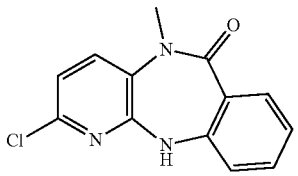 [SMILES: CN1C(=O)c2ccccc2Nc2nc(Cl)ccc21]

N-(2,6-dichloropyridin-3-yl)-N-methyl-2-nitrobenzamide (0.129 g, 0.395 mmol, 1 eq) was dissolved in EtOH. Tin(II) chloride dehydrate (0.446 g, 1.98 mmol, 5 eq) was added and the mixture was heated to 70° C. for 18 hours. The mixture was cooled to room temperature, diluted with half saturated sodium carbonate and extracted three times with chloroform. The combined organic layer was then washed with half saturated sodium carbonate, dried over sodium sulfate, filtered and condensed. Purification by column chromatography (ISCO, 12 g silica column, 0-60% EtOAc/hexanes, 20 minute gradient) gave the desired product as a light yellow solid (40.82 mg, 0.157 mmol, 40%). $^1$H NMR (400 MHz, Chloroform-d) δ 7.91 (dd, J=7.9, 1.6 Hz, 1H), 7.39 (d, J=8.2 Hz, 1H), 7.35 (ddd, J=8.0, 7.4, 1.6 Hz, 1H), 7.10-7.01 (m, 2H), 6.83 (dd, J=8.0, 0.9 Hz, 1H), 6.33 (s, 1H), 3.47 (s, 3H). $^{13}$C NMR (100 MHz, cdcl$_3$) δ 167.78, 154.02, 146.94, 144.29, 133.46, 133.30, 133.16, 128.46, 123.67, 123.26, 119.41, 119.26, 38.35. LCMS 260.29 (M+H).

A significant amount of the reduced, but non-cyclized product, 2-amino-N-(2,6-dichloropyridin-3-yl)-N-methylbenzamide was also isolated. Heating this intermediate in EtOH (0.1 M) at 70° C. for 24 hours led to formation of the desired product in 72% yield.

2-Chloro-5,11-dimethyl-5H-benzo[e]pyrido[3,2-b][1,4]diazepin-6(11H)-one

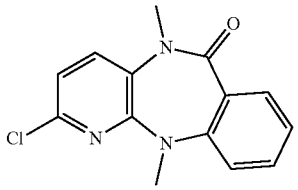 [SMILES: CN1C(=O)c2ccccc2N(C)c2nc(Cl)ccc21]

Sodium hydride (95%, dry) (7.5 mg, 0.314 mmol, 2 eq) was dissolved in DMA (0.79 mL, 0.2 M) at 0° C. 2-chloro-5-methyl-5H-benzo[e]pyrido[3,2-b][1,4]diazepin-6(11H)-one (40.82 mg, 0.157 mmol, 1 eq) was added as a solution in DMA (0.79 mL, 0.2 M). MeI (29.4 microliters, 0.472 mmol, 3 eq) was added and the mixture was warmed to room temperature. After 9 hours, the mixture was diluted with water and extracted three times with chloroform and once with EtOAc. The combined organic layer was dried over sodium sulfate, filtered and condensed. Purification by column chromatography (ISCO, 4 g column, 0-60% EtOAc/hexanes, 18 minute gradient) gave the desired product as a white solid (34.31 mg, 0.12498 mmol, 80%). ¹H NMR (400 MHz, Chloroform-d) δ 7.81 (dd, J=8.1, 1.7 Hz, 1H), 7.48-7.35 (m, 2H), 7.17-7.01 (m, 3H), 3.48 (s, 3H), 3.37 (s, 3H). ¹³C NMR (100 MHz, cdcl₃) δ 168.43, 156.81, 151.15, 144.40, 132.95, 132.75, 132.23, 130.51, 126.59, 123.64, 119.49, 117.38, 38.04, 36.29. LCMS 274.28 (M+H).

2-((2-Methoxy-4-(4-(4-methylpiperazin-1-yl)piperidine-1-carbonyl)phenyl)amino)-5,11-dimethyl-5H-benzo[e]pyrido[3,2-b][1,4]diazepin-6(11H)-one

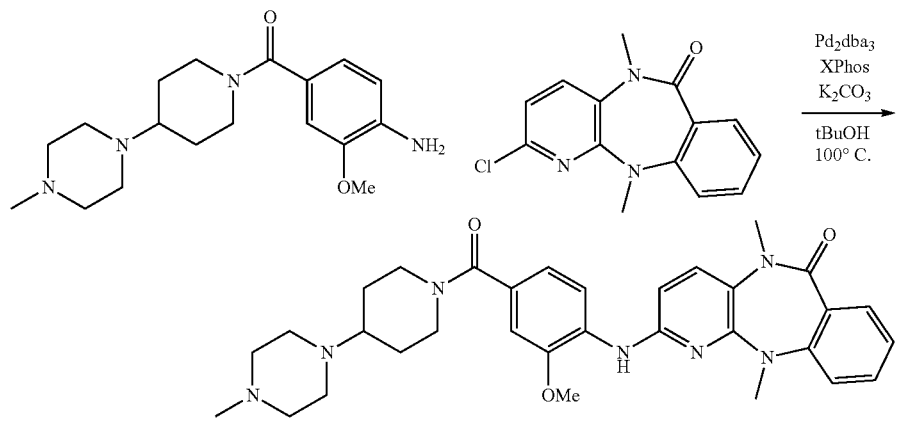

2-Chloro-5,11-dimethyl-5H-benzo[e]pyrido[3,2-b][1,4]diazepin-6(11H)-one (17.02 mg, 0.0622 mmol, 1 eq), (4-amino-3-methoxyphenyl)(4-(4-methylpiperazin-1-yl)piperidin-1-yl)methanone (24.8 mg, 0.0746 mmol, 1.2 eq), Pd₂dba₃ (2.8 mg, 0.00311 mmol, 5 mol %), XPhos (4.4 mg, 0.00933 mmol, 15 mol %) and potassium carbonate (34.4 mg, 0.251 mmol, 4 eq) were dissolved in tBuOH (0.62 mL, 0.1M) and heated to 100° C. for 23 hours. The mixture was filtered through CELITE, washed with DCM/MeOH/EtOAc and concentrated under reduced pressure. Purification by preparative HPLC, (followed by treatment with 3M NaOH, and extraction with chloroform) gave the desired product as a yellow solid (14.88 mg, 0.0261 mmol, 42%).

Example 2

Preparation of 4-((5,11-dimethyl-6-oxo-6,11-dihydro-5H-benzo[e]pyrido[3,2-b][1,4]diazepin-2-yl)amino)benzenesulfonamide N-(tert-butyl)-4-((5,11-dimethyl-6-oxo-6,11-dihydro-5H-benzo[e]pyrido[3,2-b][1,4]diazepin-2-yl)amino)benzenesulfonamide

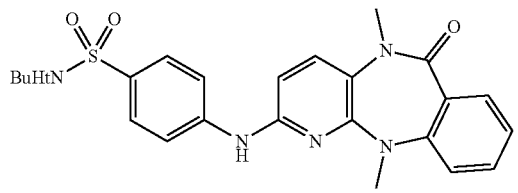

2-Chloro-5,11-dimethyl-5H-benzo[e]pyrido[3,2-b][1,4]diazepin-6(11H)-one (17.2 mg, 0.0628 mmol, 1 eq), 4-amino-N-(tert-butyl)benzenesulfonamide (17.2 mg, 0.0754 mmol, 1.2 eq), Pd₂dba₃ (2.9 mg, 0.00314 mmol, 5 mol %), XPhos (4.5 mg, 0.00942 mmol, 15 mol %) and potassium carbonate (34.7 mg, 0.251 mmol, 4 eq) were dissolved in tBuOH (0.63 mL, 0.1M) and heated to 100° C. for 23 hours. The mixture was filtered through CELITE, washed with DCM/MeOH and concentrated under reduced pressure. Purification by column chromatography (ISCO, 12 g column, 0-10% MeOH/DCM, 15 minute gradient) gave the desired product as a yellow solid (24.79 mg, 0.0532 mmol, 84%). ¹H NMR (400 MHz, Chloroform-d) δ 7.85-7.77 (m, 3H), 7.57 (d, J=8.8 Hz, 2H), 7.38 (t, J=8.5 Hz, 2H), 7.09 (dd, J=7.8, 2.1 Hz, 2H), 6.72 (s, 1H), 6.58 (d, J=8.5 Hz, 1H), 4.44 (s, 1H), 3.48 (s, 3H), 3.38 (s, 3H), 1.25 (s, 9H). ¹³C NMR (100 MHz, cdcl₃) δ 168.67, 155.72, 151.67, 149.25, 144.22, 134.99, 132.95, 132.20, 131.97, 128.49, 126.92, 123.89, 123.13, 117.15, 116.82, 105.58, 54.52, 37.66, 36.11, 30.20. LCMS 466.47 (M+H).

4-((5,11-Dimethyl-6-oxo-6,11-dihydro-5H-benzo[e]pyrido[3,2-b][1,4]diazepin-2-yl)amino)benzenesulfonamide

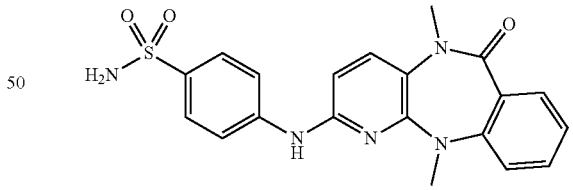

N-(tert-butyl)-4-((5,11-dimethyl-6-oxo-6,11-dihydro-5H-benzo[e]pyrido[3,2-b][1,4]diazepin-2-yl)amino)benzenesulfonamide (9.37 mg, 0.0201 mmol, 1 eq) was dissolved in TFA. Anisole (10 microliters) was added and the mixture was stirred for 24 hours at room temperature, then concentrated under reduced pressure. Purification by column chromatography (ISCO, 4 g silica column, 0-10% MeOH/DCM, 15 minute gradient) gave a white solid (4.04 mg, 0.00987 mmol, 49%). ¹H NMR (400 MHz, Methanol-d4) δ 7.87-7.77 (m, 4H), 7.68 (dd, J=7.8, 1.7 Hz, 1H), 7.57 (d, J=8.6 Hz, 1H), 7.46 (ddd, J=8.7, 7.4, 1.7 Hz, 1H), 7.21 (d, J=8.0 Hz, 1H), 7.13-7.07 (m, 1H), 6.65 (d, J=8.5 Hz, 1H), 3.45 (s, 3H), 3.41 (s, 3H). $^{13}$C NMR (100 MHz, cd$_3$od) δ 171.05, 156.71, 153.94, 152.37, 146.49, 135.73, 134.58, 133.65, 132.38, 128.28, 128.13, 124.14, 123.59, 118.11, 107.93, 37.90, 36.58. LCMS 410.36 (M+H).

Example 3

Preparation of 4-((5,11-dimethyl-6-oxo-6,11-dihydro-5H-benzo[e]pyrido[3,2-b][1,4]diazepin-2-yl)amino)-3-methoxy-N-(1-methylpiperidin-4-yl)benzamide

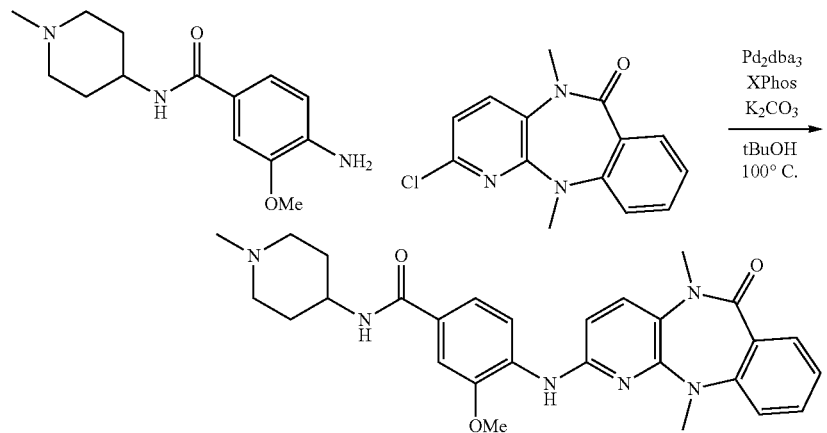

2-Chloro-5,11-dimethyl-5H-benzo[e]pyrido[3,2-b][1,4]diazepin-6(11H)-one (39.53 mg, 0.144 mmol, 1 eq), 4-amino-3-methoxy-n-(1-methylpiperidin-4-yl)benzamide (48.1 mg, 0.183 mmol, 1.2 eq), Pd$_2$dba$_3$ (7.0 mg, 0.0076 mmol, 5 mol %), XPhos (10.9 mg, 0.0228 mmol, 15 mol %) and potassium carbonate (84.0 mg, 0.608 mmol, 4 eq) were dissolved in tBuOH (1.5 mL, 0.1M) and heated to 100° C. for 17 hours. The mixture was filtered through CELITE, washed with DCM/MeOH/EtOAc and concentrated under reduced pressure. Purification by column chromatography (ISCO, 4 g column, 0-15% MeOH/DCM, 15 minute gradient) gave the desired product as a yellow solid (60.6 mg, 0.121 mmol, 84%). $^1$H NMR (400 MHz, Methanol-d$_4$) δ 8.52 (d, J=8.5 Hz, 1H), 7.66 (dd, J=7.8, 1.6 Hz, 1H), 7.55-7.45 (m, 3H), 7.44-7.38 (m, 1H), 7.14 (d, J=8.1 Hz, 1H), 7.06 (t, J=7.5 Hz, 1H), 6.74 (d, J=8.6 Hz, 1H), 4.06-3.97 (m, 1H), 3.95 (s, 3H), 3.41 (s, 3H), 3.35 (s, 3H), 3.14 (d, J=12.3 Hz, 2H), 2.55 (d, J=12.2 Hz, 2H), 2.50 (s, 3H), 2.04 (d, J=10.8 Hz, 2H), 1.87-1.74 (m, 2H). $^{13}$C NMR (100 MHz, cd$_3$od) δ 170.95, 169.52, 156.54, 153.88, 152.21, 148.93, 135.12, 134.41, 133.60, 132.39, 128.10, 127.07, 124.08, 123.41, 121.52, 118.01, 117.49, 110.11, 108.32, 56.45, 56.42, 55.22, 47.26, 45.17, 37.87, 37.85, 36.56, 31.46. LCMS 501.48 (M+H).

Example 4

Biochemical and Cellular Assays of the Compounds Acetyl-Histone Binding Assay

Assays were performed with minor modifications from the manufacturer's protocol (PerkinElmer, USA). All reagents were diluted in 50 mM HEPES, 150 mM NaCl, 0.1% w/v BSA, and 0.01% w/v Tween 20 at pH 7.5 and allowed to equilibrate to room temperature prior to addition to plates. After addition of Alpha beads to master solutions, all subsequent steps were performed in low light conditions. A 2× solution of components with final concentrations of BRD4.1 at 80 nM, Ni-coated Acceptor Bead at 25 μg/ml, and 80 nM biotinylated H4-tetra acetyl was added in 10 μL to 384-well plates (AlphaPlate—384, PerkinElmer, USA). Biotinylated peptide for BRD4.1 was synthesized in-house on a CEM Liberty 9008005 microwave peptide synthesizer: H4-tetra acetyl, biotin-PEG2-SGRGKacGGKacGLGKacG-GAKacRHRK—COOH. Addition to wells was performed with either a multichannel pipet (for optimization experiments) or a Biotek EL406 liquid handler. After a 1000-rpm spin-down for 1 minute, 100 nL of the solutions of the compounds of the invention from stock plates were added by pin transfer using a Janus Workstation (PerkinElmer, USA). The streptavidin-coated donor beads (25 μg/ml final) were added as with previous solution in a 2×, 10 μL volume. Following this addition, the plates were sealed with foil to block light exposure and to prevent evaporation. The plates were spun down again at 1000 rpm for 1 minute. Next, the plates were incubated in the room with the plate reader (for temperature equilibration) for 1.5 hour prior to reading the assay. AlphaScreen measurements were performed on an Envision 2104 (PerkinElmer, USA) utilizing the manufacturer's protocol.

Cellular Assay

The compounds of the invention are also evaluated in the BRD4 dependant cell line for the cellular activity to generate cellular IC$_{50}$ values.

Cells (e.g., BRD4 dependant cells) were counted and adjusted to 60,000 cells/mL. Using a Biotek EL406, 50 μL of the cells in media were distributed into 384 well white plates from Thermo. Immediately after plating, compounds of the invention in DMSO were distributed to plates. For large plate sets, cells were returned to a 37° C. incubator while not in use. The compounds were added to plates using a 100 nL 384 well pin transfer manifold on a Janus workstation. Stocks were arrayed in 10 point quadruplicate dose response in DMSO stock in 384-well Greiner compound plates. After addition of the compounds, plates were incubated for three days in a 37° C. incubator. Cell viability was read out using ATPlite from Perkin Elmer. Plates were removed from the incubator and brought to room temperature prior to use. Lyophilized powder was resuspended in lysis buffer and diluted 1:2 with DI water. 25 μL of this solution was added to each well using the Biotek liquid handler. Plates were sealed with adherent aluminum seals prior to vortexing and spinning down at 1000 g for 1 minute. Plates were incubated for 15 minutes at room temperature before signal was read on an Envision Plate Reader.

Isothermal Titration Calorimetery

ITC was performed using a ITC200 microcalorimeter from GE™ (Northampton, Mass.). All experiments were carried out at 25° C. while stirring at 1000 rpm, in ITC buffer (50 mM HEPES pH 7.4 at 25° C., 150 mM NaCl). The microsyringe was loaded with a solution of the protein sample (225 μM, in ITC buffer). The compound solution (22.5 μM, in ITC buffer) was titrated into the protein solution via syringe. All titrations were conducted using an initial injection of 0.2 μl, followed by 19 identical injections of 2 μl with a duration of 5 sec (per injection) and a spacing of 90 sec between injections. The heat of dilution was determined by independent titrations (protein into buffer) and was subtracted from the experimental data. The collected data were implicated in the MicroCal™ Origin software supplied with the instrument to yield enthalpies of binding (ΔH) and binding constants ($K_a$). The collected data were implicated in the MicroCal™ Origin software supplied with the instrument to yield enthalpies of binding (ΔH) and binding constants ($K_B$) as previously described by Wiseman and coworkers. Thermodynamic parameters were calculated (ΔG=ΔH−TΔS=−RTln$K_B$, where ΔG, ΔH and ΔS are the changes in free energy, enthalpy and entropy of binding respectively). A single binding site model was employed.

Cell Cycle Analysis by Flow Cytometry

797, MOLM-13, and HL60 cells were plated in T-75 flasks and grown in DMEM (797) or RPMI (MOLM-13 and HL60) containing 10% fetal bovine serum and 1% penicillin/streptomycin. Cells were treated with compound at 1 uM (797) or 500 nM (MOLM-13 and HL60), or the equivalent volume of DMSO for 24 hours. 2×106 cells were spun at 500×g for minutes at 4° C. and washed with PBS. Pellets were resuspended in 1 mL of cold PBS and added dropwise while gently vortexing to 9 mL 70% ethanol in a 15 mL polypropylene centrifuge tube. Fixed cells were then frozen at −20° C. overnight. The next day, cells were centrifuged at 500×g for 10 minutes at 4° C. and washed with 3 mL of cold PBS. Cells were resuspended in 500 μL of propidium iodide staining solution (0.2 mg/mL RNAse A, 0.2 mg/mL propidium iodide, 01.% Triton-X in PBS) and incubated for 20 min at 37° C. Samples were then transferred to ice and analyzed on a BD FACS Canto II. Histograms were generated and cell cycle analysis was performed using ModFit flow cytometry analysis software.

Results

Shown in Table 1 are the in vitro percent inhibition values of BRD4.1 at 2.5 μM compound concentration for exemplary compounds, where "uM" refers to micromolar, and "% INHIB" refers to % inhibition.

TABLE 1

| Structure | % INHIB (at 2.5 uM) |
|---|---|
| 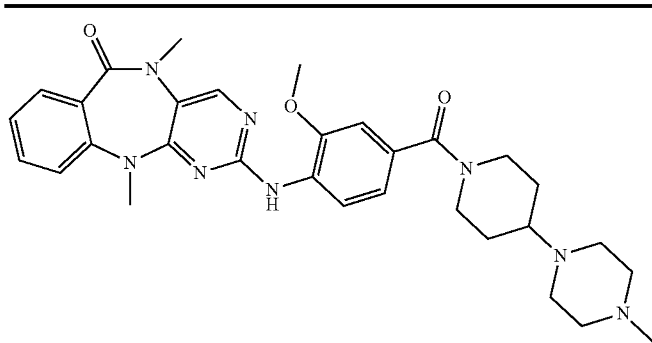 | 20.5 |
| 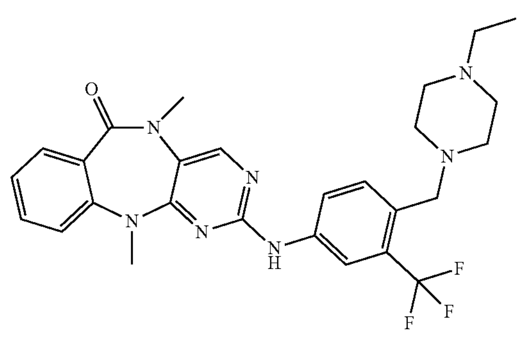 [SMILES: CCN1CCN(Cc2ccc(Nc3ncc4c(n3)N(C)c3ccccc3C(=O)N4C)cc2C(F)(F)F)CC1] | 45.8 |
| 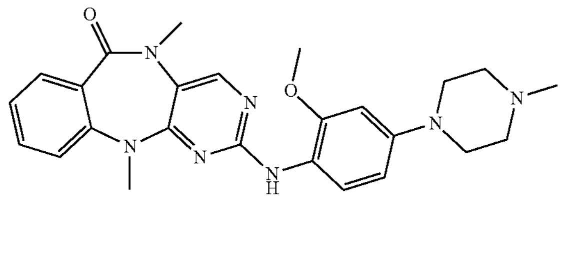 [SMILES: COc1cc(N2CCN(C)CC2)ccc1Nc1ncc2c(n1)N(C)c1ccccc1C(=O)N2C] | 36.1 |

TABLE 1-continued

| Structure | % INHIB (at 2.5 uM) |
|---|---|
| 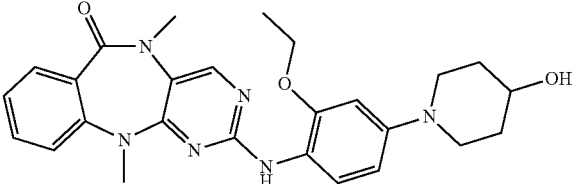 | 29.5 |
| 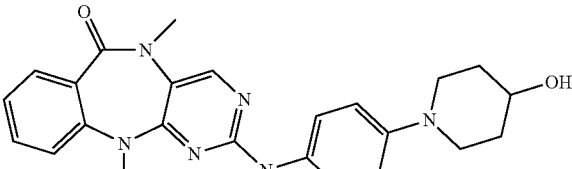 | 50.8 |

Shown in Table 2 are exemplary $IC_{50}$ values of select compounds described herein and compounds JQ1 and GSK461364 against select bromodomain-containing proteins, kinases, and cell lines. "uM": μM.

TABLE 2

| Compound | $IC_{50}$ |
|---|---|
| 3 | BRD4 $IC_{50}$ = 1,368 nM |
|   | BRDT $IC_{50}$ = 3,683 nM |
|   | BRD4 $IC_{50}$ = 813 nM |
|   | LRRK2 $IC_{50}$ = >10 uM |
|   | MV411 $IC_{50}$ = 1,424 nM |
|   | NOMO-1 $IC_{50}$ = 7,232 nM |
|   | MOLM-13 $IC_{50}$ = 2,916 nM |
|   | 797 $IC_{50}$ = 2,489 nM |
| 2-227 | BRD4 $IC_{50}$ = 2,139 nM |
|   | BRDT $IC_{50}$ = 5,410 nM |
|   | BRD4 $IC_{50}$ = 1,873 nM |
|   | LRRK2 $IC_{50}$ = >10 uM |
|   | MV411 $IC_{50}$ = 1,953 nM |
|   | NOMO-1 $IC_{50}$ = 6,361 nM |
|   | MOLM-13 $IC_{50}$ = 4,249 nM |
|   | 797 $IC_{50}$ = 5,765 nM |
| 2-221 | BRD4 $IC_{50}$ = 2,991 nM |
|   | BRDT $IC_{50}$ = 5,660 nM |
|   | BRD4 $IC_{50}$ = 3,266 nM |
|   | AURKA $IC_{50}$ >10 uM |
|   | AURKB $IC_{50}$ >10 uM |
|   | AURKC $IC_{50}$ >10 uM |
|   | MV411 $IC_{50}$ = 3,248 nM |
|   | NOMO-1 $IC_{50}$ >20 uM |
|   | MOLM-13 $IC_{50}$ = 10,920 nM |
|   | 797 $IC_{50}$ = 9,284 nM |
| 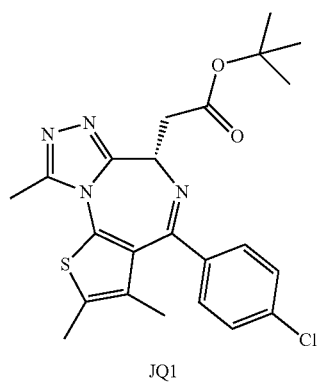 [SMILES: Cc1sc2c(c1C)C(c1ccc(Cl)cc1)=N[C@@H](CC(=O)OC(C)(C)C)c1nnc(C)n1-2] | BRD4 $IC_{50}$ = 44 nM |
|   | BRDT $IC_{50}$ = 147 nM |
|   | MV411 $IC_{50}$ = 65.6 nM |
|   | NOMO1 $IC_{50}$ = 172 nM |
|   | Kasumi-1 $IC_{50}$ = 48.8 nM |
|   | TF-1 $IC_{50}$ = 0.109 uM |
|   | MOLM-13 $IC_{50}$ = 89.2 nM |
|   | 797 $IC_{50}$ = 92 nM |

JQ1

TABLE 2-continued

| Compound | IC$_{50}$ |
|---|---|
| 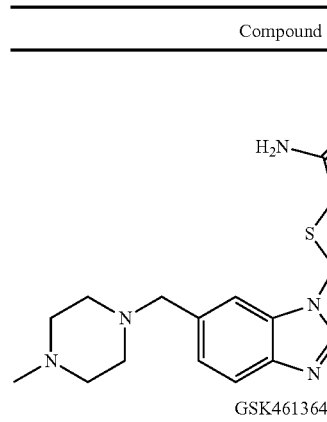<br>GSK461364 | BRD4 IC$_{50}$ >50 uM<br>BRDT IC$_{50}$ >50 uM<br>MV411 IC$_{50}$ = 7.1 nM<br>NOMO1 IC$_{50}$ = 5.91 nM<br>Kasumi-1 IC$_{50}$ = 7.8 nM<br>TF-1 IC$_{50}$ = poor convergence<br>MOLM-13 IC$_{50}$ = 6.93 nM<br>797 IC$_{50}$ = 8 nM |

What is claimed is:

1. A compound of Formula (I):

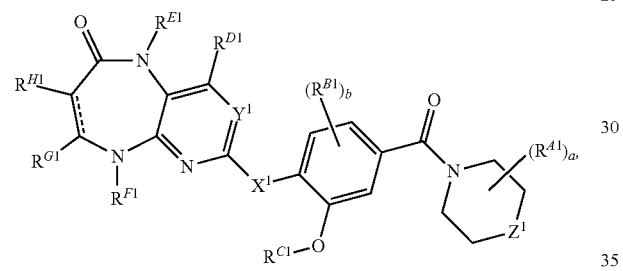

or a pharmaceutically acceptable salt thereof, wherein:
  ═══ is a single or double bond;
  $X^1$ is —O—, —S—, or —C($R^{X1}$)$_2$—, wherein each instance of $R^{X1}$ is independently hydrogen, halogen, or substituted or unsubstituted C$_{1-6}$ alkyl;
  $Y^1$ is N or CR$^{Y1}$, wherein R$^{Y1}$ is hydrogen, halogen, or substituted or unsubstituted C$_{1-6}$ alkyl;
  $Z^1$ is —O—, —N(R$^{Z1}$)— or —C(R$^{Z1}$)$_2$—, wherein each instance of R$^{Z1}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or two instances of R$^{Z1}$ are joined to form a substituted or unsubstituted carbocyclic or substituted or unsubstituted heterocyclic ring;
  each instance of R$^{A1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1a}$, —N(R$^{A1a}$)$_2$, —SR$^{A1a}$, —CN, —SCN, —C(═NR$^{A1a}$)R$^{A1a}$, —C(═NR$^{A1a}$)OR$^{A1a}$, —C(═NR$^{A1a}$)N(R$^{A1a}$)$_2$, —C(═O)R$^{A1a}$, —C(═O)OR$^{A1a}$, —C(═O)N(R$^{A1a}$)$_2$, —NO$_2$, —NR$^{A1a}$C(═O)R$^{A1a}$, —NR$^{A1a}$C(═O)OR$^{A1a}$, —NR$^{A1a}$C(═O)N(R$^{A1a}$)$_2$, —OC(═O)R$^{A1a}$, —OC(═O)OR$^{A1a}$, or —OC(═O)N(R$^{A1a}$)$_2$, wherein each instance of R$^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A1a}$ groups are joined to form a substituted or unsubstituted heterocyclic or substituted or unsubstituted heteroaryl ring;
  a is 0, 1, 2, 3, 4, 5, 6, 7, or 8;
  each instance of R$^{B1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1a}$, —N(R$^{B1a}$)$_2$, —SR$^{B1a}$, —CN, —SCN, —C(═NR$^{B1a}$)R$^{B1a}$, —C(═NR$^{B1a}$)OR$^{B1a}$, —C(═NR$^{B1a}$)N(R$^{B1a}$)$_2$, —C(═O)R$^{B1a}$, —C(═O)OR$^{B1a}$, —C(═O)N(R$^{B1a}$)$_2$, —NO$_2$, —NR$^{B1a}$C(═O)R$^{B1a}$, —NR$^{B1a}$C(═O)OR$^{B1a}$, —NR$^{B1a}$C(═O)N(R$^{B1a}$)$_2$, —OC(═O)R$^{B1a}$, —OC(═O)OR$^{B1a}$, or —OC(═O)N(R$^{B1a}$)$_2$, wherein each instance of R$^{B1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{B1a}$ groups are joined to form a substituted or unsubstituted heterocyclic or substituted or unsubstituted heteroaryl ring;
  b is 0, 1, 2, or 3;
  R$^{C1}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

$R^{D1}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D1a}$, —$N(R^{D1a})_2$, —$SR^{D1a}$, —CN, —SCN, —C(=$NR^{D1a}$)$R^{D1a}$, —C(=$NR^{D1a}$)$OR^{D1a}$, —C(=$NR^{D1a}$)N($R^{D1a}$)$_2$, —C(=O)$R^{D1a}$, —C(=O)$OR^{D1a}$, —C(=O)N($R^{D1a}$)$_2$, —$NO_2$, —$NR^{D1a}$C(=O)$R^{D1a}$, —$NR^{D1a}$C(=O)$OR^{D1a}$, —$NR^{D1a}$C(=O)N($R^{D1a}$)$_2$, —OC(=O)$R^{D1a}$, —OC(=O)$OR^{D1a}$, or —OC(=O)N($R^{D1a}$)$_2$, wherein each instance of $R^{D1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{D1a}$ groups are joined to form a substituted or unsubstituted heterocyclic or substituted or unsubstituted heteroaryl ring;

$R^{E1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{F1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{G1}$ is hydrogen, halogen, or substituted or unsubstituted $C_{1-6}$ alkyl; and $R^{H1}$ is hydrogen, halogen, or substituted or unsubstituted $C_{1-6}$ alkyl;

or $R^{G1}$ and $R^{H1}$ are joined to form a substituted or unsubstituted phenyl ring.

2. The compound of claim 1, wherein the compound is of the formula:

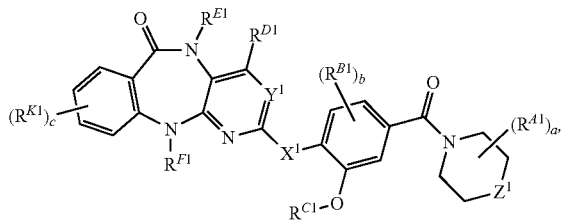

or a pharmaceutically acceptable salt thereof, wherein:
each instance of $R^{K1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{K1a}$, —$N(R^{K1a})_2$, —$SR^{K1a}$, —CN, —SCN, —C(=$NR^{K1a}$)$R^{K1a}$, —C(=$NR^{K1a}$)$OR^{K1a}$, —C(=$NR^{K1a}$)N($R^{K1a}$)$_2$, —C(=O)$R^{K1a}$, —C(=O)$OR^{K1a}$, —C(=O)N($R^{K1a}$)$_2$, —$NO_2$, —$NR^{K1a}$C(=O)$R^{K1a}$, —$NR^{K1a}$C(=O)$OR^{K1a}$, —$NR^{K1a}$C(=O)N($R^{K1a}$)$_2$, —OC(=O)$R^{K1a}$, —OC(=O)$OR^{K1a}$, or —OC(=O)N($R^{K1a}$)$_2$, wherein each instance of $R^{K1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{K1a}$ groups are joined to form a substituted or unsubstituted heterocyclic or substituted or unsubstituted heteroaryl ring; and c is 0, 1, 2, 3, or 4.

3. The compound of claim 1, wherein the compound is of the formula:

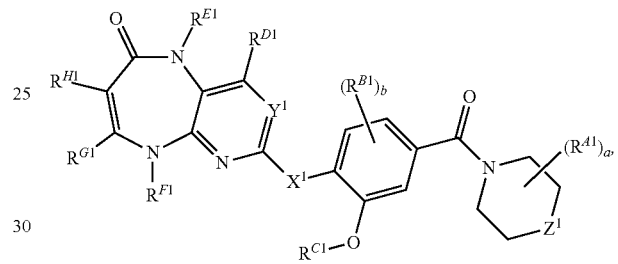

or a pharmaceutically acceptable salt thereof.

4. The compound of claim 1, or a pharmaceutically acceptable salt thereof, wherein a is 0.

5. The compound of claim 1, or a pharmaceutically acceptable salt thereof, wherein b is 0.

6. The compound of claim 1, or a pharmaceutically acceptable salt thereof, wherein $R^{G1}$ is hydrogen, or substituted or unsubstituted $C_{1-6}$ alkyl.

7. The compound of claim 1, or a pharmaceutically acceptable salt thereof, wherein $R^{H1}$ is hydrogen, or substituted or unsubstituted $C_{1-6}$ alkyl.

8. The compound of claim 1, or a pharmaceutically acceptable salt thereof, wherein $R^{G1}$ and $R^{H1}$ are joined to form a substituted or unsubstituted phenyl ring.

9. A compound of Formula (II-C):

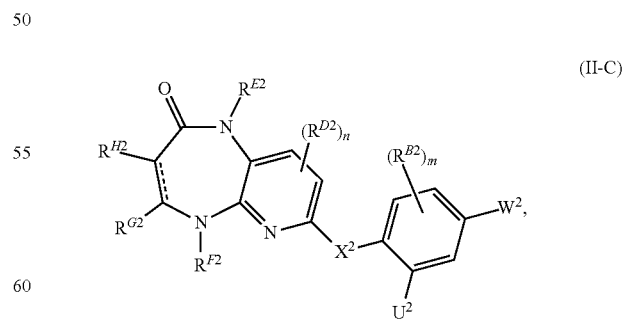

(II-C)

or a pharmaceutically acceptable salt thereof, wherein:
=== is a single or double bond;
$W^2$ is —S(=O)$OR^{W2}$, —S(=O)N($R^{W2}$)$_2$, —S(=O)$_2$$OR^{W2}$, —S(=O)$_2$N($R^{W2}$)$_2$,

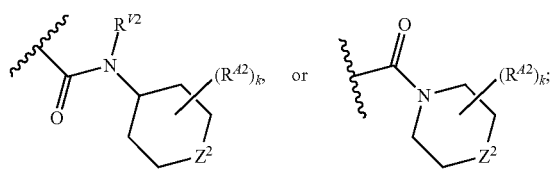

each instance of $R^{W2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two instances of $R^{W2}$ are joined to form a substituted or unsubstituted heterocyclic or substituted or unsubstituted heteroaryl ring; and $R^{V2}$ is hydrogen, substituted or unsubstituted $C_{1-6}$ alkyl, or a nitrogen protecting group;

$U^2$ is $R^{B2}$ or —$OR^{C2}$;

$X^2$ is —O—, —S—, —N($R^{X2}$)—, or —C($R^{X2}$)$_2$—, wherein each instance of $R^{X2}$ is independently hydrogen, halogen, substituted or unsubstituted $C_{1-6}$ alkyl, or a nitrogen protecting group when attached to a nitrogen atom;

$Z^2$ is —O—, —N($R^{Z2}$)— or —C($R^{Z2}$)$_2$—, wherein each instance of $R^{Z2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or two instances of $R^{Z2}$ are joined to form a substituted or unsubstituted carbocyclic or substituted or unsubstituted heterocyclic ring;

each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A2a}$, —N($R^{A2a}$)$_2$, —$SR^{A2a}$, —CN, —SCN, —C(=N$R^{A2a}$)$R^{A2a}$, —C(=N$R^{A2a}$)$OR^{A2a}$, —C(=N$R^{A2a}$)N($R^{A2a}$)$_2$, —C(=O)$R^{A2a}$, —C(=O)$OR^{A2a}$, —C(=O)N($R^{A2a}$)$_2$, —NO$_2$, —N$R^{A2a}$C(=O)$R^{A2a}$, —N$R^{A2a}$C(=O)$OR^{A2a}$, —N$R^{A2a}$C(=O)N($R^{A2a}$)$_2$, —OC(=O)$R^{A2a}$, —OC(=O)$OR^{A2a}$, or —OC(=O)N($R^{A2a}$)$_2$, wherein each instance of $R^{A2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2a}$ groups are joined to form a substituted or unsubstituted heterocyclic or substituted or unsubstituted heteroaryl ring;

k is 0, 1, 2, 3, 4, 5, 6, 7, 8, or 9;

each instance of $R^{B2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B2a}$, —N($R^{B2a}$)$_2$, —$SR^{B2a}$, —CN, —SCN, —C(=N$R^{B2a}$)$R^{B2a}$, —C(=N$R^{B2a}$)$OR^{B2a}$, —C(=N$R^{B2a}$)N($R^{B2a}$)$_2$, —C(=O)$R^{B2a}$, —C(=O)$OR^{B2a}$, —C(=O)N($R^{B2a}$)$_2$, —NO$_2$, —N$R^{B2a}$C(=O)$R^{B2a}$, —N$R^{B2a}$C(=O)$OR^{B2a}$, —N$R^{B2a}$C(=O)N($R^{B2a}$)$_2$, —OC(=O)$R^{B2a}$, —OC(=O)$OR^{B2a}$, or —OC(=O)N($R^{B2a}$)$_2$, wherein each instance of $R^{B2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B2a}$ groups are joined to form a substituted or unsubstituted heterocyclic or substituted or unsubstituted heteroaryl ring;

m is 0, 1, 2, or 3;

$R^{C2}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

each instance of $R^{D2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D2a}$, —N($R^{D2a}$)$_2$, —$SR^{D2a}$, —CN, —SCN, —C(=N$R^{D2a}$)$R^{D2a}$, —C(=N$R^{D2a}$)$OR^{D2a}$, —C(=N$R^{D2a}$)N($R^{D2a}$)$_2$, —C(=O)$R^{D2a}$, —C(=O)$OR^{D2a}$, —C(=O)N($R^{D2a}$)$_2$, —NO$_2$, —N$R^{D2a}$C(=O)$R^{D2a}$, —N$R^{D2a}$C(=O)$OR^{D2a}$, —N$R^{D2a}$C(=O)N($R^{D2a}$)$_2$, —OC(=O)$R^{D2a}$, —OC(=O)$OR^{D2a}$, or —OC(=O)N($R^{D2a}$)$_2$, wherein each instance of $R^{D2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{D2a}$ groups are joined to form a substituted or unsubstituted heterocyclic or substituted or unsubstituted heteroaryl ring;

n is 0, 1, or 2;

$R^{E2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{F2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{G2}$ is hydrogen, halogen, or substituted or unsubstituted $C_{1-6}$ alkyl; and $R^{H2}$ is hydrogen, halogen, or substituted or unsubstituted $C_{1-6}$ alkyl;

or $R^{G2}$ and $R^{H2}$ are joined to form a substituted or unsubstituted phenyl ring.

10. A compound of Formula (III):

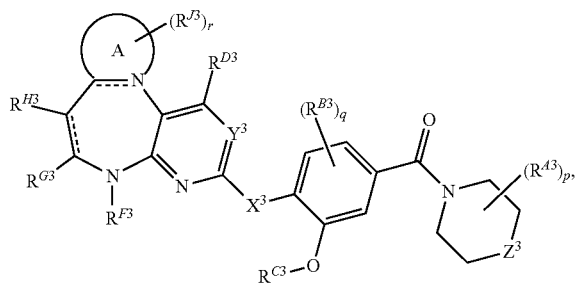

(III)

or a pharmaceutically acceptable salt thereof, wherein:
each instance of === is independently a single or double bond;

$X^3$ is —O—, —S—, —N($R^{X3}$)—, or —C($R^{X3}$)$_2$—, wherein each instance of $R^{X3}$ is independently hydrogen, halogen, substituted or unsubstituted $C_{1-6}$ alkyl, or a nitrogen protecting group when attached to a nitrogen atom;

$Y^3$ is N or $CR^{Y3}$, wherein $R^{Y3}$ is hydrogen, halogen, or substituted or unsubstituted $C_{1-6}$ alkyl;

$Z^3$ is —O—, —N($R^{Z3}$)— or —C($R^{Z3}$)$_2$—, wherein each instance of $R^{Z3}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or two instances of $R^{Z3}$ are joined to form a substituted or unsubstituted carbocyclic or substituted or unsubstituted heterocyclic ring;

each instance of $R^{A3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A3a}$, —N(R$^{A3a}$)$_2$, —SR$^{A3a}$, —CN, —SCN, —C(=NR$^{A3a}$)R$^{A3a}$, —C(=NR$^{A3a}$)OR$^{A3a}$, —C(=NR$^{A3a}$)N(R$^{A3a}$)$_2$, —C(=O)R$^{A3a}$, —C(=O)OR$^{A3a}$, —C(=O)N(R$^{A3a}$)$_2$, —NO$_2$, —NR$^{A3a}$C(=O)R$^{A3a}$, —NR$^{A3a}$C(=O)OR$^{A3a}$, —NR$^{A3a}$C(=O)N(R$^{A3a}$)$_2$, —OC(=O)R$^{A3a}$, —OC(=O)OR$^{A3a}$, or —OC(=O)N(R$^{A3a}$)$_2$, wherein each instance of R$^{A3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A3a}$ groups are joined to form a substituted or unsubstituted heterocyclic or substituted or unsubstituted heteroaryl ring;

p is 0, 1, 2, 3, 4, 5, 6, 7, or 8;

each instance of R$^{B3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B3a}$, —N(R$^{B3a}$)$_2$, —SR$^{B3a}$, —CN, —SCN, —C(=NR$^{B3a}$)R$^{B3a}$, —C(=NR$^{B3a}$)OR$^{B3a}$, —C(=NR$^{B3a}$)N(R$^{B3a}$)$_2$, —C(=O)R$^{B3a}$, —C(=O)OR$^{B3a}$, —C(=O)N(R$^{B3a}$)$_2$, —NO$_2$, —NR$^{B3a}$C(=O)R$^{B3a}$, —NR$^{B3a}$C(=O)OR$^{B3a}$, —NR$^{B3a}$C(=O)N(R$^{B3a}$)$_2$, —OC(=O)R$^{B3a}$, —OC(=O)OR$^{B3a}$, or —OC(=O)N(R$^{B3a}$)$_2$, wherein each instance of R$^{B3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{B3a}$ groups are joined to form a substituted or unsubstituted heterocyclic or substituted or unsubstituted heteroaryl ring;

q is 0, 1, 2, or 3;

R$^{C3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

R$^{D3}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D3a}$, —N(R$^{D3a}$)$_2$, —SR$^{D3a}$, —CN, —SCN, —C(=NR$^{D3a}$)R$^{D3a}$, —C(=NR$^{D3a}$)OR$^{D3a}$, —C(=NR$^{D3a}$)N(R$^{D3a}$)$_2$, —C(=O)R$^{D3a}$, —C(=O)OR$^{D3a}$, —C(=O)N(R$^{D3a}$)$_2$, —NO$_2$, —NR$^{D3a}$C(=O)R$^{D3a}$, —NR$^{D3a}$C(=O)OR$^{D3a}$, —NR$^{D3a}$C(=O)N(R$^{D3a}$)$_2$, —OC(=O)R$^{D3a}$, —OC(=O)OR$^{D3a}$, or —OC(=O)N(R$^{D3a}$)$_2$, wherein each instance of R$^{D3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{D3a}$ groups are joined to form a substituted or unsubstituted heterocyclic or substituted or unsubstituted heteroaryl ring;

Ring A is substituted or unsubstituted, 5- to 6-membered, monocyclic, heterocyclic or heteroaryl ring;

each instance of R$^{J3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{J3a}$, —N(R$^{J3a}$)$_2$, —SR$^{J3a}$, —CN, —SCN, —C(=NR$^{J3a}$)R$^{J3a}$, —C(=NR$^{J3a}$)OR$^{J3a}$, —C(=NR$^{J3a}$)N(R$^{J3a}$)$_2$, —C(=O)R$^{J3a}$, —C(=O)OR$^{J3a}$, —C(=O)N(R$^{J3a}$)$_2$, —NO$_2$, —NR$^{J3a}$C(=O)R$^{J3a}$, —NR$^{J3a}$C(=O)OR$^{J3a}$, —NR$^{J3a}$C(=O)N(R$^{J3a}$)$_2$, —OC(=O)R$^{J3a}$, —OC(=O)OR$^{J3a}$, —OC(=O)N(R$^{J3a}$)$_2$, or a nitrogen protecting group when attached to a nitrogen atom, wherein each instance of R$^{J3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{J3a}$ groups are joined to form a substituted or unsubstituted heterocyclic or substituted or unsubstituted heteroaryl ring;

r is 0, 1, 2, 3, 4, 5, 6, 7, or 8;

R$^{F3}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

R$^{G3}$ is hydrogen, halogen, or substituted or unsubstituted C$_{1-6}$ alkyl; and R$^{H3}$ is hydrogen, halogen, or substituted or unsubstituted C$_{1-6}$ alkyl;

or R$^{G3}$ and R$^{H3}$ are joined to form a substituted or unsubstituted phenyl ring.

11. A pharmaceutical composition comprising a compound of claim 1, or a pharmaceutically acceptable salt thereof, and optionally a pharmaceutically acceptable excipient.

12. A method of treating a disease associated with a bromodomain or bromodomain-containing protein or with aberrant activity of a bromodomain or bromodomain-containing protein in a subject in need thereof, the method comprising administering to the subject a therapeutically effective amount of a compound of claim 1, or a pharmaceutically acceptable salt thereof.

13. A method for male contraception, the method comprising administering to a subject in need thereof an effective amount of a compound of claim 1, or a pharmaceutically acceptable salt thereof.

14. A method of inhibiting the activity of a bromodomain or bromodomain-containing protein in a subject or cell, the method comprising administering to the subject or contacting the cell with an effective amount of a compound of claim 1, or a pharmaceutically acceptable salt thereof.

15. A method of inhibiting the binding of a bromodomain of a bromodomain-containing protein to an acetyl-lysine residue of a second protein in a subject or cell, the method comprising administering to the subject or contacting the cell with an effective amount of a compound of claim 1, or a pharmaceutically acceptable salt thereof, wherein the second protein is a protein that comprises at least one acetyl-lysine residue and is different from the bromodomain-containing protein.

16. A method of modulating or inhibiting the expression of a gene that is regulated by a bromodomain-containing protein in a subject or cell, the method comprising administering to the subject or contacting the cell with an effective amount of a compound of claim 1, or a pharmaceutically acceptable salt thereof.

17. The compound of claim 1, or a pharmaceutically acceptable salt thereof, wherein X is —O—.

18. The compound of claim 1, or a pharmaceutically acceptable salt thereof, wherein X$^1$ is —C(R$^{X1}$)$_2$—.

19. The compound of claim 1, or a pharmaceutically acceptable salt thereof, wherein Y$^1$ is N.

20. The compound of claim 1, or a pharmaceutically acceptable salt thereof, wherein Z$^1$ is —N(R$^{Z1}$)—.

21. The compound of claim 1, or a pharmaceutically acceptable salt thereof, wherein Z$^1$ is —C(R$^{Z1}$)$_2$—.

22. The compound of claim 21, or a pharmaceutically acceptable salt thereof, wherein at least one instance of R$^{Z1}$ is substituted or unsubstituted, 4- to 7-membered, monocyclic heterocyclyl, wherein one, two, or three atoms in the heterocyclic ring system are independently nitrogen, oxygen, or sulfur.

23. The compound of of claim 1, or a pharmaceutically acceptable salt thereof, wherein R$^{E1}$ is substituted or unsubstituted C$_{1-6}$ alkyl.

24. The compound of of claim 1, or a pharmaceutically acceptable salt thereof, wherein R$^{F1}$ is substituted or unsubstituted C$_{1-6}$ alkyl.

25. The compound of claim 1, wherein the compound is of the formula:

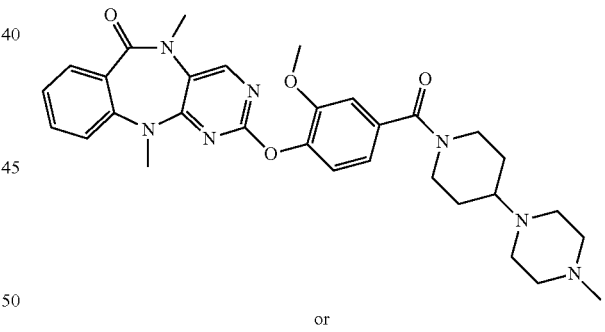

or

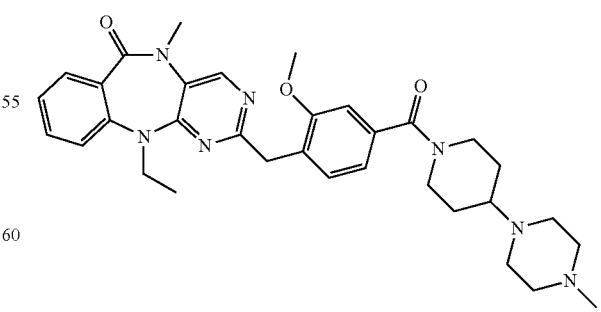

or a pharmaceutically acceptable salt thereof.

26. The compound of claim 9, wherein the compound is of Formula (II):

(II)

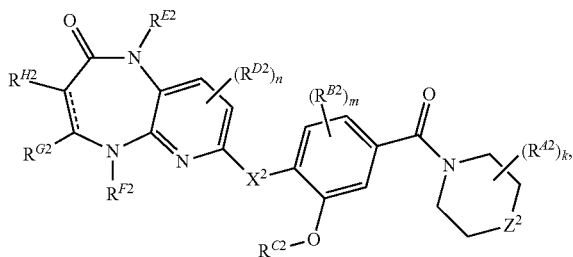

or a pharmaceutically acceptable salt thereof.

27. The compound of claim 9, wherein the compound is the formula:

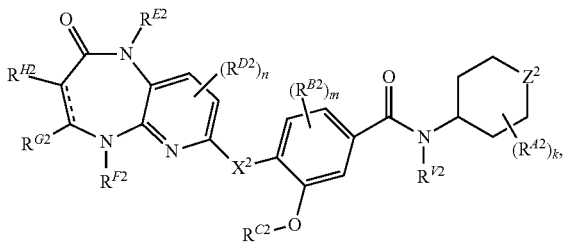

or a pharmaceutically acceptable salt thereof.

28. The compound of claim 9, wherein the compound is of the formula:

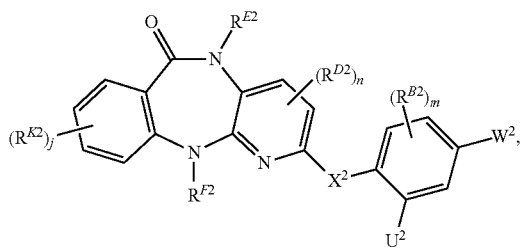

or a pharmaceutically acceptable salt thereof, wherein:
each instance of $R^{K2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{K2a}$, —$N(R^{K2a})_2$, —$SR^{K2a}$, —CN, —SCN, —C(=$NR^{K2a}$)$R^{K2a}$, —C(=$NR^{K2a}$)$OR^{K2a}$, —C(=$NR^{K2a}$)$N(R^{K2a})_2$, —C(=O)$R^{K2a}$, —C(=O)$OR^{K2a}$, —C(=O)$N(R^{K2a})_2$, —$NO_2$, —$NR^{K2a}$C(=O)$R^{K2a}$, —$NR^{K2a}$C(=O)$OR^{K2a}$, —$NR^{K2a}$C(=O)$N(R^{K2a})_2$, —OC(=O)$R^{K2a}$, —OC(=O)$OR^{K2a}$, or —OC(=O)$N(R^{K2a})_2$, wherein each instance of $R^{K2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{K2a}$ groups are joined to form a substituted or unsubstituted heterocyclic or substituted or unsubstituted heteroaryl ring; and
j is 0, 1, 2, 3, or 4.

29. The compound of claim 28, wherein the compound is of the formula:

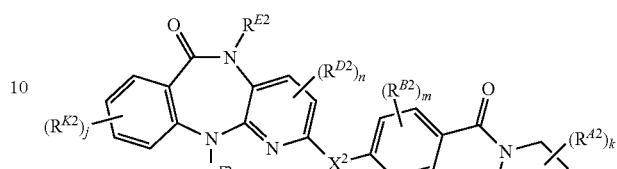

or

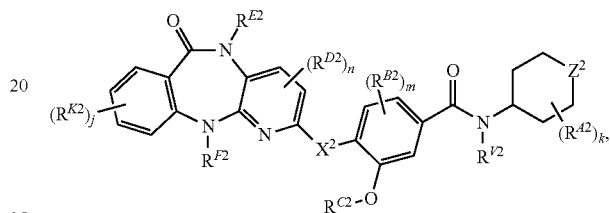

or a pharmaceutically acceptable salt thereof.

30. The compound of claim 9, or a pharmaceutically acceptable salt thereof, wherein $W^2$ is —S(=O)$_2$N(R$^{W2}$)$_2$.

31. The compound of claim 9, or a pharmaceutically acceptable salt thereof, wherein $W^2$ is

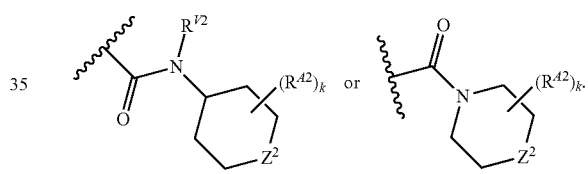

32. The compound of claim 9, or a pharmaceutically acceptable salt thereof, wherein $X^2$ is —N(R$^{X2}$)—.

33. The compound of claim 9, or a pharmaceutically acceptable salt thereof, wherein $R^{E2}$ is substituted or unsubstituted $C_{1-6}$ alkyl.

34. The compound of claim 9, or a pharmaceutically acceptable salt thereof, wherein $R^{F2}$ is substituted or unsubstituted $C_{1-6}$ alkyl.

35. The compound of claim 9, or a pharmaceutically acceptable salt thereof, wherein $R^{G2}$ and $R^{H2}$ are joined to form a substituted or unsubstituted phenyl ring.

36. The compound of claim 9, wherein the compound is of the formula:

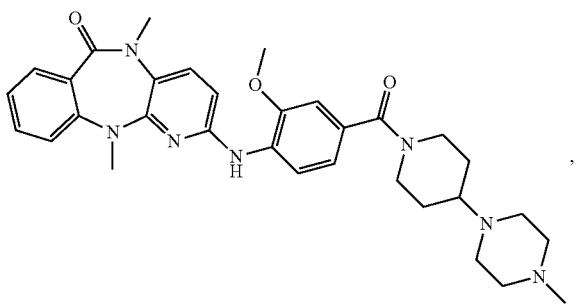 [SMILES: COc1cc(C(=O)N2CCC(N3CCN(C)CC3)CC2)ccc1Nc1ccc2c(n1)N(C)c1ccccc1C(=O)N2C]

or a pharmaceutically acceptable salt thereof.

37. The compound of claim 9, wherein the compound is of the formula:

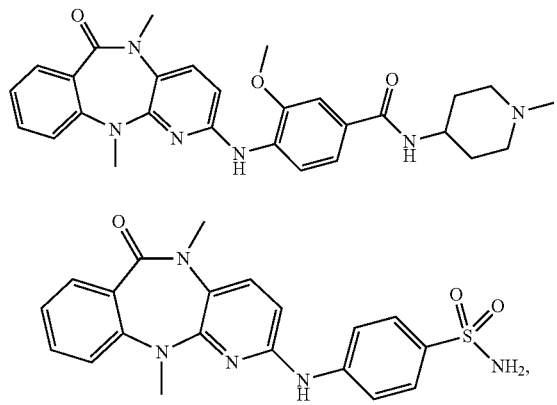

or a pharmaceutically acceptable salt thereof.

38. The compound of claim 10, wherein the compound is of the formula:

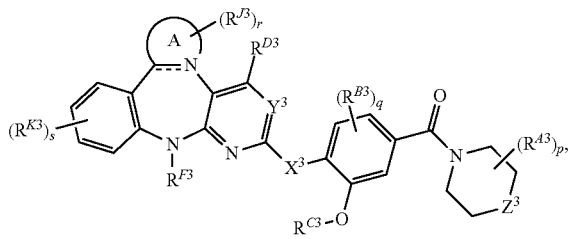

or a pharmaceutically acceptable salt thereof, wherein:

each instance of $R^{K3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{K3a}$, —$N(R^{K3a})_2$, —$SR^{K3a}$, —CN, —SCN, —C(=$NR^{K3a}$)$R^{K3a}$, —C(=$NR^{K3a}$)$OR^{K3a}$, —C(=$NR^{K3a}$)$N(R^{K3a})_2$, —C(=O)$R^{K3a}$, —C(=O)$OR^{K3a}$, —C(=O)$N(R^{K3a})_2$, —$NO_2$, —$NR^{K3a}$C(=O)$R^{K3a}$, —$NR^{K3a}$C(=O)$OR^{K3a}$, —$NR^{K3a}$C(=O)$N(R^{K3a})_2$, —OC(=O)$R^{K3a}$, —OC(=O)$OR^{K3a}$, or —OC(=O)$N(R^{K3a})_2$, wherein each instance of $R^{K3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{K3a}$ groups are joined to form a substituted or unsubstituted heterocyclic or substituted or unsubstituted heteroaryl ring; and s is 0, 1, 2, 3, or 4.

39. The compound of claim 10, wherein the compound is of the formula:

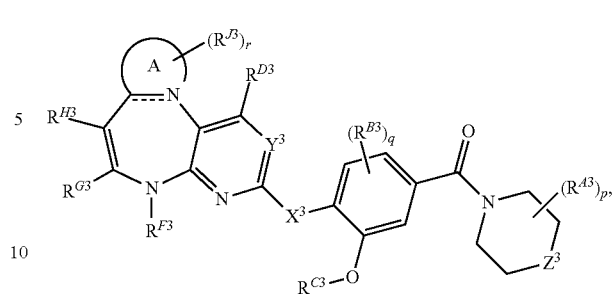

or a pharmaceutically acceptable salt thereof.

40. The compound of claim 10, wherein the compound is of the formula:

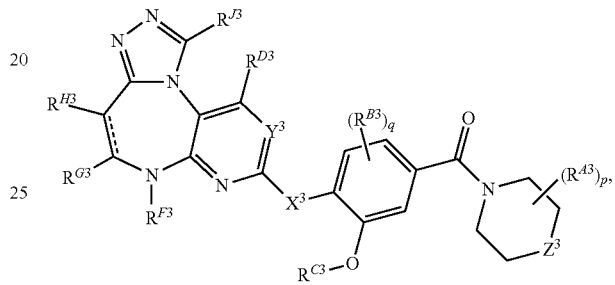

or a pharmaceutically acceptable salt thereof.

41. The compound of claim 10, or a pharmaceutically acceptable salt thereof, wherein $X^3$ is —$N(R^{X3})$—.

42. The compound of claim 10, or a pharmaceutically acceptable salt thereof, wherein $Y^3$ is N.

43. The compound of claim 10, or a pharmaceutically acceptable salt thereof, wherein $Z^3$ is —$C(R^{Z3})_2$—.

44. The compound of claim 10, or a pharmaceutically acceptable salt thereof, wherein Ring A is substituted or unsubstituted, 5- to 6-membered, monocyclic heteroaryl ring.

45. The compound of claim 10, or a pharmaceutically acceptable salt thereof, wherein $R^{F3}$ is substituted or unsubstituted $C_{1-6}$ alkyl.

46. The compound of claim 10, or a pharmaceutically acceptable salt thereof, wherein $R^{G3}$ and $R^{H3}$ are joined to form a substituted or unsubstituted phenyl ring.

47. The compound of claim 10, wherein the compound is of the formula:

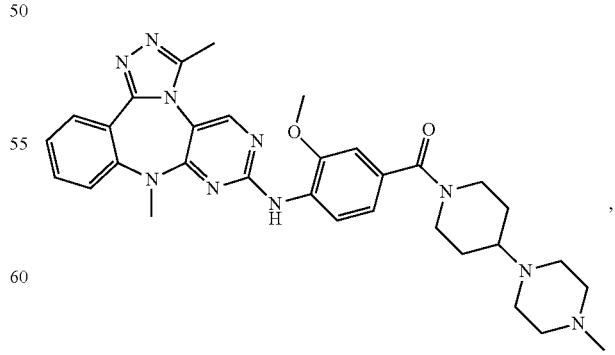

or a pharmaceutically acceptable salt thereof.

48. The method of claim 12, wherein the disease is a proliferative disease.

49. The method of claim 12, wherein the disease is cancer.

50. The method of claim 12, wherein the disease is lung cancer, multiple myeloma, neuroblastoma, colon cancer, testicular cancer, ovarian cancer, NUT midline carcinoma, or mixed-lineage leukemia (MLL).

51. The method of claim 12, wherein the disease is a benign neoplasm, pathological angiogenesis, inflammatory disease, cardiovascular disease, autoimmune disease, viral infection, fibrotic disease, metabolic disease, or endocrine disease.

52. The method of claim 12, wherein the disease is rheumatoid arthritis, sepsis, atherogenesis, atherosclerosis, human immunodeficiency virus (HIV) infection, acquired immunodeficiency syndrome (AIDS), human papillomavirus (HPV) infection, hepatitis C virus (HCV) infection, herpes simplex virus (HSV) infection, Ebola virus infection, severe acute respiratory syndrome (SARS), influenza, radiation poisoning, scleroderma, idiopathic pulmonary fibrosis, graft-versus-host disease (GVHD), diabetes, or obesity.

53. A pharmaceutical composition comprising a compound of claim 9, or a pharmaceutically acceptable salt thereof, and optionally a pharmaceutically acceptable excipient.

54. A method of treating a disease associated with a bromodomain or bromodomain-containing protein or with aberrant activity of a bromodomain or bromodomain-containing protein in a subject in need thereof, the method comprising administering to the subject a therapeutically effective amount of a compound of claim 9, or a pharmaceutically acceptable salt thereof.

55. The method of claim 54, wherein the disease is a proliferative disease.

56. The method of claim 54, wherein the disease is cancer.

57. The method of claim 54, wherein the disease is lung cancer, multiple myeloma, neuroblastoma, colon cancer, testicular cancer, ovarian cancer, NUT midline carcinoma, or mixed-lineage leukemia (MLL).

58. The method of claim 54, wherein the disease is a benign neoplasm, pathological angiogenesis, inflammatory disease, cardiovascular disease, autoimmune disease, viral infection, fibrotic disease, metabolic disease, or endocrine disease.

59. The method of claim 54, wherein the disease is rheumatoid arthritis, sepsis, atherogenesis, atherosclerosis, human immunodeficiency virus (HIV) infection, acquired immunodeficiency syndrome (AIDS), human papillomavirus (HPV) infection, hepatitis C virus (HCV) infection, herpes simplex virus (HSV) infection, Ebola virus infection, severe acute respiratory syndrome (SARS), influenza, radiation poisoning, scleroderma, idiopathic pulmonary fibrosis, graft-versus-host disease (GVHD), diabetes, or obesity.

60. A method for male contraception, the method comprising administering to a subject in need thereof an effective amount of a compound of claim 9, or a pharmaceutically acceptable salt thereof.

61. A method of inhibiting the activity of a bromodomain or bromodomain-containing protein in a subject or cell, the method comprising administering to the subject or contacting the cell with an effective amount of a compound of claim 9, or a pharmaceutically acceptable salt thereof.

62. A method of inhibiting the binding of a bromodomain of a bromodomain-containing protein to an acetyl-lysine residue of a second protein in a subject or cell, the method comprising administering to the subject or contacting the cell with an effective amount of a compound of claim 9, or a pharmaceutically acceptable salt thereof, wherein the second protein is a protein that comprises at least one acetyl-lysine residue and is different from the bromodomain-containing protein.

63. A method of modulating or inhibiting the expression of a gene that is regulated by a bromodomain-containing protein in a subject or cell, the method comprising administering to the subject or contacting the cell with an effective amount of a compound of claim 9, or a pharmaceutically acceptable salt thereof.

64. A pharmaceutical composition comprising a compound of claim 10, or a pharmaceutically acceptable salt thereof, and optionally a pharmaceutically acceptable excipient.

65. A method of treating a disease associated with a bromodomain or bromodomain-containing protein or with aberrant activity of a bromodomain or bromodomain-containing protein in a subject in need thereof, the method comprising administering to the subject a therapeutically effective amount of a compound of claim 10, or a pharmaceutically acceptable salt thereof.

66. The method of claim 65, wherein the disease is a proliferative disease.

67. The method of claim 65, wherein the disease is cancer.

68. The method of claim 65, wherein the disease is lung cancer, multiple myeloma, neuroblastoma, colon cancer, testicular cancer, ovarian cancer, NUT midline carcinoma, or mixed-lineage leukemia (MLL).

69. The method of claim 65, wherein the disease is a benign neoplasm, pathological angiogenesis, inflammatory disease, cardiovascular disease, autoimmune disease, viral infection, fibrotic disease, metabolic disease, or endocrine disease.

70. The method of claim 65, wherein the disease is rheumatoid arthritis, sepsis, atherogenesis, atherosclerosis, human immunodeficiency virus (HIV) infection, acquired immunodeficiency syndrome (AIDS), human papillomavirus (HPV) infection, hepatitis C virus (HCV) infection, herpes simplex virus (HSV) infection, Ebola virus infection, severe acute respiratory syndrome (SARS), influenza, radiation poisoning, scleroderma, idiopathic pulmonary fibrosis, graft-versus-host disease (GVHD), diabetes, or obesity.

71. A method for male contraception, the method comprising administering to a subject in need thereof an effective amount of a compound of claim 10, or a pharmaceutically acceptable salt thereof.

72. A method of inhibiting the activity of a bromodomain or bromodomain-containing protein in a subject or cell, the method comprising administering to the subject or contacting the cell with an effective amount of a compound of claim 10, or a pharmaceutically acceptable salt thereof.

73. A method of inhibiting the binding of a bromodomain of a bromodomain-containing protein to an acetyl-lysine residue of a second protein in a subject or cell, the method comprising administering to the subject or contacting the cell with an effective amount of a compound of claim 10, or a pharmaceutically acceptable salt thereof, wherein the second protein is a protein that comprises at least one acetyl-lysine residue and is different from the bromodomain-containing protein.

74. A method of modulating or inhibiting the expression of a gene that is regulated by a bromodomain-containing protein in a subject or cell, the method comprising administering to the subject or contacting the cell with an effective amount of a compound of claim 10, or a pharmaceutically acceptable salt thereof.

\* \* \* \* \*